(12) United States Patent
Islam

(10) Patent No.: US 12,268,475 B2
(45) Date of Patent: *Apr. 8, 2025

(54) WEARABLE DEVICE FOR DIFFERENTIAL MEASUREMENT ON PULSE RATE AND BLOOD FLOW

(71) Applicant: OMNI MEDSCI, INC., Ann Arbor, MI (US)

(72) Inventor: Mohammed N. Islam, Ann Arbor, MI (US)

(73) Assignee: OMNI MEDSCI, INC., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/927,698

(22) Filed: Oct. 25, 2024

(65) Prior Publication Data

US 2025/0049326 A1 Feb. 13, 2025

Related U.S. Application Data

(60) Continuation of application No. 18/899,012, filed on Sep. 27, 2024, which is a continuation of application
(Continued)

(51) Int. Cl.
*A61B 5/00* (2006.01)
*A61B 5/145* (2006.01)
(Continued)

(52) U.S. Cl.
CPC .......... *A61B 5/0088* (2013.01); *A61B 5/0013* (2013.01); *A61B 5/0022* (2013.01);
(Continued)

(58) Field of Classification Search
CPC ... A61B 5/0088; A61B 5/0013; A61B 5/0022; A61B 5/0075; A61B 5/0086;
(Continued)

(56) References Cited

U.S. PATENT DOCUMENTS

| 4,063,106 A | 12/1977 | Ashkin et al. |
| 4,158,750 A | 6/1979 | Sakoe et al. |

(Continued)

FOREIGN PATENT DOCUMENTS

| CA | 2458123 | 9/2004 |
| CN | 101849821 A | 10/2010 |

(Continued)

OTHER PUBLICATIONS

Aaviksoo, J., et al., "Observation of optical precursors at pulse propagation in GaAs", Physical Review A, vol. 44, No. 9, Nov. 1, 1991, pp. R5353-R5356.

(Continued)

*Primary Examiner* — Md M Rahman
(74) *Attorney, Agent, or Firm* — Brooks Kushman P.C.

(57) ABSTRACT

A wearable device to measure a user's physiological parameters comprising one or more biosensors, as well as a light source comprising light emitting diodes, lenses for directing light towards tissue of the user comprising blood vessels, and a detection system receiving reflected tissue light. The physiological parameters, for example hypertension, are measured with a differential measurement. For example, the physiological parameters may be associated with pulse rate and blood flow. The output signal is associated with the physiological parameters, and artificial intelligence may be used in making decisions regarding the output signal. Signal-to-noise ratio of the output signal may be improved by synchronizing the detection system to the light source, increasing light intensity, and detecting a change. The wearable device is configured to determine that is being worn by the user and may be configured to communicate with a smartphone or tablet.

20 Claims, 100 Drawing Sheets

Related U.S. Application Data

No. 18/891,970, filed on Sep. 20, 2024, which is a continuation of application No. 18/438,144, filed on Feb. 9, 2024, now Pat. No. 12,193,790, which is a continuation of application No. 18/103,408, filed on Jan. 30, 2023, now Pat. No. 11,896,346, which is a continuation of application No. 17/514,778, filed on Oct. 29, 2021, now Pat. No. 11,564,577, which is a continuation of application No. 17/078,771, filed on Oct. 23, 2020, now Pat. No. 11,160,455, which is a continuation of application No. 16/722,188, filed on Dec. 20, 2019, now Pat. No. 10,820,807, which is a continuation of application No. 16/506,885, filed on Jul. 9, 2019, now Pat. No. 10,517,484, which is a continuation of application No. 16/272,069, filed on Feb. 11, 2019, now abandoned, which is a continuation of application No. 16/029,611, filed on Jul. 8, 2018, now Pat. No. 10,201,283, which is a continuation of application No. 15/888,052, filed on Feb. 4, 2018, now Pat. No. 10,136,819, which is a continuation of application No. 15/212,549, filed on Jul. 18, 2016, now Pat. No. 9,885,698, which is a continuation of application No. 14/650,897, filed as application No. PCT/US2013/075700 on Dec. 17, 2013, now Pat. No. 9,494,567, said application No. 16/506,885 is a continuation of application No. 16/004,359, filed on Jun. 9, 2018, now Pat. No. 11,109,761, which is a continuation of application No. 14/109,007, filed on Dec. 17, 2013, now Pat. No. 9,993,159, said application No. 16/506,885 is a continuation of application No. 16/188,194, filed on Nov. 12, 2018, now Pat. No. 10,386,230, which is a continuation of application No. 16/004,154, filed on Jun. 8, 2018, now Pat. No. 10,126,283, which is a continuation of application No. 15/855,201, filed on Dec. 27, 2017, now Pat. No. 9,995,722, which is a continuation of application No. 15/711,907, filed on Sep. 21, 2017, now Pat. No. 9,897,584, which is a division of application No. 15/357,225, filed on Nov. 21, 2016, now Pat. No. 9,797,876, which is a continuation of application No. 14/650,981, filed on Jun. 10, 2015, now Pat. No. 9,500,634, said application No. 16/506,885 is a continuation of application No. 16/241,628, filed on Jan. 7, 2019, now Pat. No. 10,441,176, which is a continuation of application No. 16/015,737, filed on Jun. 22, 2018, now Pat. No. 10,172,523, which is a continuation of application No. 15/594,053, filed on May 12, 2017, now Pat. No. 10,188,299, which is a continuation of application No. 14/875,709, filed on Oct. 6, 2015, now Pat. No. 9,651,533, which is a continuation of application No. 14/108,986, filed on Dec. 17, 2013, now Pat. No. 9,164,032, said application No. 16/506,885 is a continuation of application No. 16/284,514, filed on Feb. 25, 2019, now abandoned, which is a continuation of application No. 16/016,649, filed on Jun. 24, 2018, now Pat. No. 10,213,113, which is a continuation of application No. 15/860,065, filed on Jan. 2, 2018, now Pat. No. 10,098,546, which is a continuation of application No. 15/686,198, filed on Aug. 25, 2017, now Pat. No. 9,861,286, which is a continuation of application No. 15/357,136, filed on Nov. 21, 2016, now Pat. No. 9,757,040, which is a continuation of application No. 14/651,367, filed as application No. PCT/US2013/075736 on Dec. 17, 2013, now Pat. No. 9,500,635.

(60) Provisional application No. 61/747,472, filed on Dec. 31, 2012, provisional application No. 61/747,553, filed on Dec. 31, 2012, provisional application No. 61/747,487, filed on Dec. 31, 2012, provisional application No. 61/747,477, filed on Dec. 31, 2012, provisional application No. 61/754,698, filed on Jan. 21, 2013.

(51) Int. Cl.
| | |
|---|---|
| *A61B 5/1455* | (2006.01) |
| *A61C 19/04* | (2006.01) |
| *G01J 3/02* | (2006.01) |
| *G01J 3/10* | (2006.01) |
| *G01J 3/14* | (2006.01) |
| *G01J 3/28* | (2006.01) |
| *G01J 3/42* | (2006.01) |
| *G01J 3/453* | (2006.01) |
| *G01N 21/35* | (2014.01) |
| *G01N 21/3504* | (2014.01) |
| *G01N 21/3563* | (2014.01) |
| *G01N 21/359* | (2014.01) |
| *G01N 21/39* | (2006.01) |
| *G01N 21/88* | (2006.01) |
| *G01N 33/02* | (2006.01) |
| *G01N 33/15* | (2006.01) |
| *G01N 33/44* | (2006.01) |
| *G01N 33/49* | (2006.01) |
| *G16H 40/67* | (2018.01) |
| *G16Z 99/00* | (2019.01) |
| *A61C 1/00* | (2006.01) |
| *G01J 3/12* | (2006.01) |
| *G01J 3/18* | (2006.01) |
| *G01M 3/38* | (2006.01) |
| *G01N 21/85* | (2006.01) |
| *G01N 21/95* | (2006.01) |
| *H01S 3/00* | (2006.01) |
| *H01S 3/067* | (2006.01) |
| *H01S 3/30* | (2006.01) |

(52) U.S. Cl.
CPC .......... *A61B 5/0075* (2013.01); *A61B 5/0086* (2013.01); *A61B 5/14532* (2013.01); *A61B 5/14546* (2013.01); *A61B 5/1455* (2013.01); *A61B 5/4547* (2013.01); *A61B 5/6801* (2013.01); *A61B 5/7203* (2013.01); *A61B 5/7257* (2013.01); *A61B 5/7405* (2013.01); *A61B 5/742* (2013.01); *A61C 19/04* (2013.01); *G01J 3/02* (2013.01); *G01J 3/0218* (2013.01); *G01J 3/108* (2013.01); *G01J 3/14* (2013.01); *G01J 3/28* (2013.01); *G01J 3/2823* (2013.01); *G01J 3/42* (2013.01); *G01J 3/453* (2013.01); *G01N 21/35* (2013.01); *G01N 21/3504* (2013.01); *G01N 21/3563* (2013.01); *G01N 21/359* (2013.01); *G01N 21/39* (2013.01); *G01N 21/88* (2013.01); *G01N 33/02* (2013.01); *G01N 33/025* (2013.01); *G01N 33/15* (2013.01); *G01N 33/442* (2013.01); *G01N 33/49* (2013.01); *G16H 40/67* (2018.01); *G16Z 99/00* (2019.02); *A61B 5/0024* (2013.01); *A61B 2562/0233* (2013.01); *A61B 2562/0238* (2013.01); *A61B 2562/146* (2013.01); *A61B 2576/02* (2013.01); *A61C 1/0046* (2013.01); *G01J 2003/104* (2013.01); *G01J 2003/1208* (2013.01); *G01J 3/1838*

(2013.01); *G01J 2003/2826* (2013.01); *G01M 3/38* (2013.01); *G01N 2021/3513* (2013.01); *G01N 2021/3595* (2013.01); *G01N 2021/399* (2013.01); *G01N 21/85* (2013.01); *G01N 21/9508* (2013.01); *G01N 2201/061* (2013.01); *G01N 2201/06113* (2013.01); *G01N 2201/062* (2013.01); *G01N 2201/08* (2013.01); *G01N 2201/12* (2013.01); *G01N 2201/129* (2013.01); *H01S 3/0092* (2013.01); *H01S 3/06758* (2013.01); *H01S 3/302* (2013.01); *Y02A 90/10* (2018.01)

(58) Field of Classification Search
CPC ............ A61B 5/14532; A61B 5/14546; A61B 5/1455; A61B 5/4547; A61B 5/6801; A61B 5/7203; A61B 5/7257; A61B 5/7405; A61B 5/742; A61B 5/0024; A61B 2562/0233; A61B 2562/0238; A61B 2562/146; A61B 2576/02; A61C 19/04; A61C 1/0046; G01J 3/02; G01J 3/0218; G01J 3/108; G01J 3/14; G01J 3/28; G01J 3/2823; G01J 3/42; G01J 3/453; G01J 3/1838; G01J 2003/104; G01J 2003/1208; G01J 2003/2826; G01N 21/35; G01N 21/3504; G01N 21/3563; G01N 21/359; G01N 21/39; G01N 21/88; G01N 33/02; G01N 33/025; G01N 33/15; G01N 33/442; G01N 33/49; G01N 21/85; G01N 21/9508; G01N 2021/3513; G01N 2021/3595; G01N 2021/399; G01N 2201/061; G01N 2201/06113; G01N 2201/062; G01N 2201/08; G01N 2201/12; G01N 2201/129; G16H 40/67; G16Z 99/00; G01M 3/38; H01S 3/0092; H01S 3/06758; H01S 3/302; Y02A 90/10
USPC ........................................................ 356/330
See application file for complete search history.

(56) References Cited

U.S. PATENT DOCUMENTS

| | | |
|---|---|---|
| 4,221,997 A | 9/1980 | Flemming |
| 4,275,266 A | 6/1981 | Lasar |
| 4,374,618 A | 2/1983 | Howard |
| 4,403,605 A | 9/1983 | Tanikawa |
| 4,462,080 A | 7/1984 | Johnstone et al. |
| 4,516,207 A | 5/1985 | Moriyama et al. |
| 4,523,884 A | 6/1985 | Clement et al. |
| 4,605,080 A | 8/1986 | Lemelson |
| 4,641,292 A | 2/1987 | Tunnell et al. |
| 4,704,696 A | 11/1987 | Reimer et al. |
| 4,728,974 A | 3/1988 | Nio et al. |
| 4,762,455 A | 8/1988 | Coughlan et al. |
| 4,776,016 A | 10/1988 | Hansen |
| 4,958,910 A | 9/1990 | Taylor et al. |
| 4,989,253 A | 1/1991 | Liang et al. |
| 5,078,140 A | 1/1992 | Kwoh |
| 5,084,880 A | 1/1992 | Esterowitz et al. |
| 5,086,401 A | 2/1992 | Glassman et al. |
| 5,134,620 A | 7/1992 | Huber |
| 5,142,930 A | 9/1992 | Allen et al. |
| 5,180,378 A | 1/1993 | Kung et al. |
| 5,191,628 A | 3/1993 | Byron |
| 5,218,655 A | 6/1993 | Mizrahi |
| 5,230,023 A | 7/1993 | Nakano |
| 5,246,004 A | 9/1993 | Clarke et al. |
| 5,267,152 A | 11/1993 | Yang et al. |
| 5,267,256 A | 11/1993 | Saruwatari et al. |
| 5,267,323 A | 11/1993 | Kimura |
| 5,300,097 A | 4/1994 | Lerner et al. |
| 5,303,148 A | 4/1994 | Mattson et al. |
| 5,305,427 A | 4/1994 | Nagata |
| 5,313,306 A | 5/1994 | Kuban et al. |
| 5,323,404 A | 6/1994 | Grubb |
| 5,345,538 A | 9/1994 | Narayannan et al. |
| 5,368,224 A | 11/1994 | Richardson et al. |
| 5,400,165 A | 3/1995 | Gnauck et al. |
| 5,408,409 A | 4/1995 | Glassman et al. |
| 5,458,122 A | 10/1995 | Hethuin |
| 5,497,769 A | 3/1996 | Gratton et al. |
| 5,544,654 A | 8/1996 | Murphy et al. |
| 5,563,710 A | 10/1996 | Webb et al. |
| 5,572,999 A | 11/1996 | Funda et al. |
| 5,617,871 A | 4/1997 | Burrows |
| 5,631,758 A | 5/1997 | Knox et al. |
| 5,687,734 A | 11/1997 | Dempsey et al. |
| 5,695,493 A | 12/1997 | Nakajima et al. |
| 5,696,778 A | 12/1997 | MacPherson |
| 5,704,351 A | 1/1998 | Mortara et al. |
| 5,718,234 A | 2/1998 | Warden et al. |
| 5,746,206 A | 5/1998 | Mannheimer |
| 5,747,806 A | 5/1998 | Khalil et al. |
| 5,748,103 A | 5/1998 | Flach et al. |
| 5,774,213 A | 6/1998 | Trebino et al. |
| 5,792,204 A | 8/1998 | Snell |
| 5,795,300 A | 8/1998 | Bryars |
| 5,812,978 A | 9/1998 | Nolan |
| 5,855,550 A | 1/1999 | Lai et al. |
| 5,862,803 A | 1/1999 | Besson et al. |
| 5,867,305 A | 2/1999 | Waarts et al. |
| 5,912,749 A | 6/1999 | Harstead et al. |
| 5,919,134 A | 7/1999 | Diab |
| 5,944,659 A | 8/1999 | Flach et al. |
| 5,950,629 A | 9/1999 | Taylor et al. |
| 5,957,854 A | 9/1999 | Besson et al. |
| 5,970,457 A | 10/1999 | Brant et al. |
| 6,014,249 A | 1/2000 | Fermann et al. |
| 6,031,603 A | 2/2000 | Fine et al. |
| 6,043,927 A | 3/2000 | Islam |
| 6,044,283 A | 3/2000 | Fein et al. |
| 6,078,833 A | 6/2000 | Hueber |
| 6,115,673 A | 9/2000 | Malin et al. |
| 6,181,414 B1 | 1/2001 | Raz et al. |
| 6,185,535 B1 | 2/2001 | Hedin et al. |
| 6,200,309 B1 | 3/2001 | Rice et al. |
| 6,212,310 B1 | 4/2001 | Waarts et al. |
| 6,224,542 B1 | 5/2001 | Chang et al. |
| 6,246,707 B1 | 6/2001 | Yin et al. |
| 6,246,896 B1 | 6/2001 | Dumoulin et al. |
| 6,273,858 B1 | 8/2001 | Fox et al. |
| 6,278,975 B1 | 8/2001 | Brant et al. |
| 6,281,471 B1 | 8/2001 | Smart |
| 6,285,897 B1 | 9/2001 | Kilcoyne et al. |
| 6,289,238 B1 | 9/2001 | Besson et al. |
| 6,301,271 B1 | 10/2001 | Sanders et al. |
| 6,301,273 B1 | 10/2001 | Sanders et al. |
| 6,325,978 B1 | 12/2001 | Labuda et al. |
| 6,333,803 B1 | 12/2001 | Kurotori et al. |
| 6,337,462 B1 | 1/2002 | Smart |
| 6,340,806 B1 | 1/2002 | Smart et al. |
| 6,350,261 B1 | 2/2002 | Domankevitz et al. |
| 6,364,834 B1 | 4/2002 | Reuss et al. |
| 6,374,006 B1 | 4/2002 | Islam et al. |
| 6,381,391 B1 | 4/2002 | Islam et al. |
| 6,402,691 B1 | 6/2002 | Peddicord et al. |
| 6,407,853 B1 | 6/2002 | Samson et al. |
| 6,436,107 B1 | 8/2002 | Wang et al. |
| 6,441,747 B1 | 8/2002 | Khair et al. |
| 6,442,430 B1 | 8/2002 | Ferek-Petric |
| 6,443,890 B1 | 9/2002 | Schulze et al. |
| 6,450,172 B1 | 9/2002 | Hartlaub et al. |
| 6,453,201 B1 | 9/2002 | Daum et al. |
| 6,454,705 B1 | 9/2002 | Cosentino et al. |
| 6,458,120 B1 | 10/2002 | Shen et al. |
| 6,462,500 B1 | 10/2002 | L'Hegarat et al. |
| 6,463,361 B1 | 10/2002 | Wang et al. |
| 6,480,656 B1 | 11/2002 | Islam et al. |
| 6,505,133 B1 | 1/2003 | Hanna et al. |
| 6,509,566 B1 | 1/2003 | Wamsley et al. |
| 6,512,936 B1 | 1/2003 | Monfre et al. |

(56) References Cited

U.S. PATENT DOCUMENTS

| | | |
|---|---|---|
| 6,534,012 B1 | 3/2003 | Hazen et al. |
| 6,549,702 B2 | 4/2003 | Islam et al. |
| 6,567,431 B2 | 5/2003 | Tabirian et al. |
| 6,587,702 B1 | 7/2003 | Ruchti et al. |
| 6,603,910 B2 | 8/2003 | Islam et al. |
| 6,605,080 B1 | 8/2003 | Altshuler et al. |
| 6,611,643 B2 | 8/2003 | Birk et al. |
| 6,619,835 B2 | 9/2003 | Kita |
| 6,625,180 B2 | 9/2003 | Bufetov et al. |
| 6,631,025 B2 | 10/2003 | Islam et al. |
| 6,640,117 B2 | 10/2003 | Makarewicz et al. |
| 6,659,947 B1 | 12/2003 | Carter et al. |
| 6,659,999 B1 | 12/2003 | Anderson et al. |
| 6,701,170 B2 | 3/2004 | Stetson |
| 6,708,048 B1 | 3/2004 | Chance |
| 6,731,967 B1 | 5/2004 | Turcott |
| 6,738,652 B2 | 5/2004 | Mattu et al. |
| 6,760,148 B2 | 7/2004 | Islam |
| 6,773,922 B2 | 8/2004 | Jeng et al. |
| 6,788,965 B2 | 9/2004 | Ruchti et al. |
| 6,802,811 B1 | 10/2004 | Slepian |
| 6,816,241 B2 | 11/2004 | Grubisic |
| 6,847,336 B1 | 1/2005 | Lemelson et al. |
| 6,864,978 B1 | 3/2005 | Hazen et al. |
| 6,885,498 B2 | 4/2005 | Islam |
| 6,885,683 B1 | 4/2005 | Fermann et al. |
| 6,898,451 B2 | 5/2005 | Wuori |
| 6,916,096 B2 | 7/2005 | Eberl et al. |
| 6,943,936 B2 | 9/2005 | Islam et al. |
| 6,990,364 B2 | 1/2006 | Ruchti et al. |
| 7,010,336 B2 | 3/2006 | Lorenz et al. |
| 7,027,467 B2 | 4/2006 | Baev et al. |
| 7,060,061 B2 | 6/2006 | Altshuler et al. |
| 7,105,823 B2 | 9/2006 | Abrahamsson et al. |
| 7,133,710 B2 | 11/2006 | Acosta et al. |
| 7,167,300 B2 | 1/2007 | Fermann et al. |
| 7,184,148 B2 | 2/2007 | Alphonse |
| 7,209,657 B1 | 4/2007 | Islam |
| 7,233,816 B2 | 6/2007 | Blank et al. |
| 7,259,906 B1 | 8/2007 | Islam |
| 7,263,288 B1 | 8/2007 | Islam |
| 7,278,966 B2 | 10/2007 | Hjelt et al. |
| 7,294,105 B1 | 11/2007 | Islam |
| 7,299,080 B2 | 11/2007 | Acosta et al. |
| 7,317,938 B2 | 1/2008 | Lorenz et al. |
| 7,318,909 B2 | 1/2008 | Lehmann et al. |
| 7,332,784 B2 | 2/2008 | Mills et al. |
| 7,356,364 B1 | 4/2008 | Bullock et al. |
| 7,395,158 B2 | 7/2008 | Monfre et al. |
| 7,433,116 B1 | 10/2008 | Islam |
| 7,468,036 B1 | 12/2008 | Rulkov et al. |
| 7,519,253 B2 | 4/2009 | Islam |
| 7,519,406 B2 | 4/2009 | Blank et al. |
| 7,620,674 B2 | 11/2009 | Ruchti et al. |
| 7,648,463 B1 | 1/2010 | Elhag et al. |
| 7,697,966 B2 | 4/2010 | Monfre et al. |
| 7,771,320 B2 | 8/2010 | Riley et al. |
| 7,787,503 B2 | 8/2010 | Wadsworth |
| 7,787,924 B2 | 8/2010 | Acosta et al. |
| 7,800,818 B2 | 9/2010 | Mattsson |
| 7,807,718 B2 | 10/2010 | Hashim et al. |
| 7,847,234 B2 | 12/2010 | Meyers et al. |
| 7,848,605 B2 | 12/2010 | Ridder et al. |
| 7,890,158 B2 | 2/2011 | Rowe et al. |
| 8,000,574 B2 | 8/2011 | Buchter et al. |
| 8,108,036 B2 | 1/2012 | Tran |
| 8,145,286 B2 | 3/2012 | Arai et al. |
| 8,157,730 B2 | 4/2012 | LeBoeuf et al. |
| 8,158,175 B2 | 4/2012 | Bourg, Jr. |
| 8,158,493 B2 | 4/2012 | Shah et al. |
| 8,172,761 B1 | 5/2012 | Rulkov et al. |
| 8,180,422 B2 | 5/2012 | Rebec |
| 8,180,591 B2 | 5/2012 | Yuen et al. |
| 8,198,589 B2 | 6/2012 | Tolton et al. |
| 8,213,007 B2 | 7/2012 | Wang et al. |
| 8,310,336 B2 | 11/2012 | Muhsin et al. |
| 8,315,682 B2 | 11/2012 | Such et al. |
| 8,320,621 B2 | 11/2012 | McEldowney |
| 8,430,310 B1 | 4/2013 | Ho et al. |
| 8,463,576 B2 | 6/2013 | Yuen et al. |
| 8,472,108 B2 | 6/2013 | Islam |
| 8,475,367 B2 | 7/2013 | Yuen et al. |
| 8,509,882 B2 | 8/2013 | Albert et al. |
| 8,587,771 B2 | 11/2013 | Xu et al. |
| 8,649,838 B2 | 2/2014 | Chen et al. |
| RE44,875 E | 4/2014 | Kiani et al. |
| 8,725,226 B2 | 5/2014 | Isaacson |
| 8,749,796 B2 | 6/2014 | Pesach et al. |
| 8,755,871 B2 | 6/2014 | Weng et al. |
| 8,767,190 B2 | 7/2014 | Hall |
| 8,788,002 B2 | 7/2014 | LeBoeuf et al. |
| 8,928,893 B2 | 1/2015 | Findlay et al. |
| 8,945,017 B2 | 2/2015 | Venkatraman et al. |
| 8,948,832 B2 | 2/2015 | Hong et al. |
| 8,954,135 B2 | 2/2015 | Yuen et al. |
| 9,110,163 B2 | 8/2015 | Rogan |
| 9,142,117 B2 | 9/2015 | Muhsin et al. |
| 9,151,829 B2 | 10/2015 | Campbell |
| 9,164,032 B2 | 10/2015 | Islam |
| 9,171,985 B2 | 10/2015 | Dutton et al. |
| 9,179,876 B2 | 11/2015 | Ochs et al. |
| 9,192,329 B2 | 11/2015 | Al-Ali |
| 9,207,121 B2 | 12/2015 | Adler |
| 9,236,519 B2 | 1/2016 | Mazzillo et al. |
| 9,241,676 B2 | 1/2016 | Lisogurski et al. |
| 9,265,456 B2 | 2/2016 | Kirenko et al. |
| 9,273,846 B1 | 3/2016 | Rossi et al. |
| 9,316,735 B2 | 4/2016 | Baxter |
| 9,326,712 B1 | 5/2016 | Kiani |
| 9,417,734 B2 | 8/2016 | Raynor et al. |
| 9,430,093 B2 | 8/2016 | Harrison et al. |
| 9,596,990 B2 | 3/2017 | Park et al. |
| 9,651,533 B2 | 5/2017 | Islam |
| 9,675,250 B2 | 6/2017 | Tverskoy |
| 9,723,993 B2 | 8/2017 | Vermeulen |
| 9,757,040 B2 | 9/2017 | Islam |
| 9,770,213 B2 | 9/2017 | Kirenko et al. |
| 9,820,658 B2 | 11/2017 | Tran |
| 9,860,522 B1 | 1/2018 | Lapstun |
| 9,861,286 B1 | 1/2018 | Islam |
| 9,885,698 B2 | 2/2018 | Islam |
| 9,891,309 B2 | 2/2018 | Hudman et al. |
| 9,915,726 B2 | 3/2018 | Bailey et al. |
| 10,117,588 B2 | 11/2018 | Lee et al. |
| 10,188,299 B2 | 1/2019 | Islam |
| 10,213,113 B2 | 2/2019 | Islam |
| 10,359,505 B2 | 7/2019 | Buettgen et al. |
| 10,376,192 B2 | 8/2019 | Lee et al. |
| 10,441,173 B2 | 11/2019 | Shan et al. |
| 10,517,484 B2 | 12/2019 | Islam |
| 10,646,167 B2 | 5/2020 | De Haan |
| 10,694,988 B2 | 6/2020 | Lee et al. |
| 10,705,191 B2 | 7/2020 | Ryu et al. |
| 10,806,354 B2 | 10/2020 | Hutchinson et al. |
| 10,824,837 B2 | 11/2020 | Yeke Yazdandoost et al. |
| 10,838,206 B2 | 11/2020 | Fortin-Deschenes et al. |
| 10,922,395 B2 | 2/2021 | Morestin et al. |
| 10,952,683 B2 | 3/2021 | Jones et al. |
| 11,403,754 B2 | 8/2022 | Hutchinson et al. |
| 11,625,098 B2 | 4/2023 | Beyhs |
| 2002/0013518 A1 | 1/2002 | West et al. |
| 2002/0019584 A1 | 2/2002 | Schulze et al. |
| 2002/0032468 A1 | 3/2002 | Hill et al. |
| 2002/0082612 A1 | 6/2002 | Moll et al. |
| 2002/0109621 A1 | 8/2002 | Khair et al. |
| 2002/0115914 A1 | 8/2002 | Russ |
| 2002/0128846 A1 | 9/2002 | Miller |
| 2002/0178003 A1 | 11/2002 | Gehrke et al. |
| 2003/0022126 A1 | 1/2003 | Buchalla et al. |
| 2003/0107739 A1 | 6/2003 | Lehmann et al. |
| 2003/0109055 A1 | 6/2003 | Lehmann et al. |
| 2003/0152307 A1 | 8/2003 | Drasek et al. |
| 2004/0174914 A1 | 9/2004 | Fukatsu |
| 2004/0240037 A1 | 12/2004 | Harter |

(56) References Cited

U.S. PATENT DOCUMENTS

| | | |
|---|---|---|
| 2005/0049468 A1 | 3/2005 | Carlson et al. |
| 2005/0111500 A1 | 5/2005 | Harter et al. |
| 2005/0133691 A1 | 6/2005 | Doppke et al. |
| 2005/0209516 A1 | 9/2005 | Fraden |
| 2006/0058683 A1 | 3/2006 | Chance |
| 2006/0198397 A1 | 9/2006 | Korolev et al. |
| 2006/0223032 A1 | 10/2006 | Fried et al. |
| 2006/0245461 A1 | 11/2006 | Islam |
| 2006/0268393 A1 | 11/2006 | Islam |
| 2006/0281982 A1 | 12/2006 | Grata et al. |
| 2006/0283931 A1 | 12/2006 | Polli et al. |
| 2007/0021670 A1 | 1/2007 | Mandelis et al. |
| 2007/0078348 A1 | 4/2007 | Holman |
| 2008/0086318 A1 | 4/2008 | Gilley et al. |
| 2008/0105665 A1 | 5/2008 | Kondo |
| 2008/0240502 A1 | 10/2008 | Freedman et al. |
| 2009/0028193 A1 | 1/2009 | Islam |
| 2009/0105605 A1 | 4/2009 | Abreu |
| 2009/0156932 A1 | 6/2009 | Zharov |
| 2009/0185274 A1 | 7/2009 | Shpunt |
| 2009/0204110 A1 | 8/2009 | Islam |
| 2009/0244288 A1 | 10/2009 | Fujimoto et al. |
| 2009/0287067 A1 | 11/2009 | Dorogusker et al. |
| 2010/0007717 A1 | 1/2010 | Spektor et al. |
| 2010/0046067 A1 | 2/2010 | Fermann et al. |
| 2010/0118123 A1 | 5/2010 | Freedman et al. |
| 2010/0160794 A1 | 6/2010 | Banet et al. |
| 2010/0160798 A1 | 6/2010 | Banet et al. |
| 2010/0217099 A1 | 8/2010 | LeBoeuf et al. |
| 2010/0217102 A1 | 8/2010 | LeBoeuf et al. |
| 2010/0284082 A1 | 11/2010 | Shpunt et al. |
| 2010/0322490 A1 | 12/2010 | Pan et al. |
| 2010/0331637 A1 | 12/2010 | Ting et al. |
| 2011/0040197 A1 | 2/2011 | Welch et al. |
| 2011/0143364 A1 | 6/2011 | Kim et al. |
| 2011/0188054 A1 | 8/2011 | Petronius et al. |
| 2011/0208015 A1 | 8/2011 | Welch et al. |
| 2011/0237911 A1 | 9/2011 | Lamego et al. |
| 2011/0267688 A1 | 11/2011 | Kleppe et al. |
| 2011/0282167 A1 | 11/2011 | Ridder et al. |
| 2011/0292376 A1 | 12/2011 | Kukushkin et al. |
| 2012/0013722 A1 | 1/2012 | Wong et al. |
| 2012/0041767 A1 | 2/2012 | Hoffman et al. |
| 2012/0075432 A1 | 3/2012 | Bilbrey et al. |
| 2012/0197093 A1 | 8/2012 | LeBoeuf et al. |
| 2012/0203077 A1 | 8/2012 | He et al. |
| 2012/0239013 A1 | 9/2012 | Islam |
| 2012/0245439 A1 | 9/2012 | Andre et al. |
| 2012/0310062 A1 | 12/2012 | Li et al. |
| 2012/0316455 A1 | 12/2012 | Rahman et al. |
| 2013/0274569 A1 | 10/2013 | Islam |
| 2013/0281795 A1 | 10/2013 | Varadan |
| 2013/0303921 A1 | 11/2013 | Chu et al. |
| 2013/0327966 A1 | 12/2013 | Fidler et al. |
| 2014/0078510 A1 | 3/2014 | Rubio Guivernau et al. |
| 2014/0081100 A1 | 3/2014 | Muhsin et al. |
| 2014/0236021 A1 | 8/2014 | Islam |
| 2014/0249427 A1 | 9/2014 | Liu |
| 2014/0275852 A1 | 9/2014 | Hong et al. |
| 2014/0275854 A1 | 9/2014 | Venkatraman et al. |
| 2015/0011851 A1 | 1/2015 | Mehta et al. |
| 2015/0338509 A1 | 11/2015 | Lange |
| 2016/0045118 A1 | 2/2016 | Kiani |
| 2016/0181325 A1 | 6/2016 | Johnson et al. |
| 2016/0327476 A1 | 11/2016 | Islam |
| 2018/0231373 A1 | 8/2018 | Pesach et al. |
| 2019/0294868 A1 | 9/2019 | Martinez |
| 2021/0096726 A1 | 4/2021 | Faulkner et al. |
| 2022/0225006 A1 | 7/2022 | Allec et al. |
| 2023/0000376 A1 | 1/2023 | Maman et al. |

FOREIGN PATENT DOCUMENTS

| | | |
|---|---|---|
| DE | 102010012987 A1 | 10/2010 |
| EP | 1148666 A2 | 10/2001 |
| JP | 2005270544 A | 10/2005 |
| WO | 1997015240 A1 | 5/1997 |
| WO | 1997049340 A1 | 12/1997 |
| WO | 2001050959 A1 | 7/2001 |
| WO | 2001089362 A2 | 11/2001 |
| WO | 2002027640 A2 | 4/2002 |
| WO | 2002028123 A2 | 4/2002 |
| WO | 2005013843 A2 | 2/2005 |
| WO | 2007061772 A1 | 5/2007 |
| WO | 2009130464 A1 | 10/2009 |
| WO | 2012135952 A1 | 10/2012 |
| WO | 2013012938 A1 | 1/2013 |
| WO | 2015084376 A1 | 6/2015 |
| WO | WO2021149048 A1 | 7/2021 |
| WO | WO2022074652 A1 | 4/2022 |
| WO | WO2022084991 A1 | 4/2022 |

OTHER PUBLICATIONS

Abeeluck, Akheelesh K., et al., "Continuous-wave pumping in the anomalous- and normal dispersion regimes of nonlinear fibers for supercontinuum generaffon", Optics Letters, vol. 30, No. 1, Jan. 1, 2005, pp. 61-63.

Absorption Coefficient and Penetration Depth, The Science of Solar, available at https://photon.libretexts.org/The_Science_of_Solar/Solar_Basics/C._Semico-nductors_and_Solar_Interactions/III._Absorption_of_Light_and_Generation/1.-Absorption Coefficient and Penetration Depth (Last Updated Nov. 3, 2018).

Akbari, H. K. Uto, Y. Kosugi, K. Kojima, N. Tanaka, "Cancer detection using infrared hyperspectral imaging," Cancer Science, vol. 102, No. 4, pp. 852-857 (Apr. 2011).

Amended Joint Claim Construction and Prehearing Statement filed in Case No. 2:18-cv-134-RWS (Dkt. #102) (Jan. 11, 2019).

Analysis of Edible Oils Using FT-NIR Spectroscopy. Bruker Optics, www.azom.com/article.aspx?ArticleID=5981, Mar. 10, 2012.

Andreoli, G. B. Bulgarelli, B. Hosgood, D. Tarchi, "Hyperspectral analysis of oil and oil-impacted soils for remote sensing purposes," Institute for the Protection and Security of the Citizen, European Commission Joint Research Centre, EUR 22739 EN (Mar. 2007).

Apple Inc.'s Preliminary Claim Constructions and Extrinsic Evidence Pursuant to Patent Local Rule 4-2 served in Case No. 2:18-cv-134-RWS (Nov. 1, 2018).

Application Brief the role of infrared microprobe analysis in forensic drug analysis, www.smithsdetection.com, Jun. 27, 2005.

Aris, Ishak Bin, "An Internet-Based Blood Pressure Monitoring System for Patients"; Journal of Telemedicine and Telecare 2001; pp. 51-53.

Arnold, T., M. De Biasio, R. Leitner, "Near-Infrared Imaging Spectroscopy for Counterfeit Drug Detection," Next Generation Spectroscopic Technologies IV, edited by M. A. Druy, R.A. Crocombe, Proceedings of SPIE, vol. 8032, 80320Y-1 to 7, (2011).

Asada et al., Mobile Monitoring with Wearable Photoplethysmographic Biosensors, Technical and Clinical Aspects of a Ring Sensor for Ambulatory, Telemetric, Continuous Health Monitoring in the Field, in the Hospital, and in the Home, IEEE Engineering in Medicine and Biology Magazine, (May/Jun. 2003) 13 pages.

Asada et al., The MIT Ring: History, Technology, and Challenges of Wearable Health Monitoring, MIT Industrial Liaison Program (2010) R&D Conference, MA, 72 pages.

Asada; Charts 1-3: Asada-533; U.S. Pat. No. 9,651,533 vs. *Asada; Omni MedSci, Inc.* v. *Apple Inc.*, pp. 1-188; May 22, 2019.

Asare et al., Analysis of Multi-Spectral Photoplethysmograph Biosensors, Proc. SPIE 8801, Novel Biophotonic Techniques and Applications II, 880106 (Jun. 2013), European Conferences on Biomedical Optics, Munich, Germany, 7 pages.

Asobe, Masaki, "Nonlinear Optical Properties of Chalcogenide Glass Fibers and Their Application to All-Optical Switching", Optical Fiber Technology, vol. 3, Article No. OF970214, 1997, pp. 142-148.

Asobe, Masaki, et al., "Third-order nonlinear spectroscopy in As2S3 chalcogenide glass fibers", J. Appl. Phys. 77 (11), Jun. 1, 1995, pp. 5518-5523.

(56) References Cited

OTHER PUBLICATIONS

Avdokhin, A. V., et al., "Continuous-wave, high-power, Raman continuum generation in holey fibers", Optics Letters, vol. 28, No. 15, Aug. 1, 2003, pp. 1353-1355.

Ayvaz, Huseyin, et al. "Application of infrared microspectroscopy and chemometric analysis for screening the acrylamide content in potato chips." Analytical Methods 5.8 (2013): 2020-2027.

B. Rigas, P.T.T. Wong, "Human Colon Adenocarcinoma Cell Lines Display Infrared Spectroscopic Features," Cancer Research, Jan. 1, 1992, pp. 84-88.

Barolet, Daniel, Light-Emitting Diodes (LEDs) in Dermatology, Seminars in Cutaneous Medicine and Surgery 27:227-238 (2008).

Bashkatov, A., et al., Optical properties of human skin, subcutaneous and mucous tissues in the wavelength range from 400 to 2000 nm, Journal of Physics D: Applied Physics 38 (2005) 2543-2555.

Baum P., et al., Strategic Intelligence Monitor on Personal Health Systems, Phase 2: Market Developments—Remote Patient Monitoring and Treatment, Telecare, Fitness/Wellness and mHealth, JRC Scientific and Policy Reports of European Commission (2013).

Beck, Mattias, et al., "Continuous Wave Operation of a Mid-Infrared Semiconductor Laser at Room Temperature," Science vol. 295, www.sciencemag.org, Jan. 11, 2002, pp. 301-305.

Belikov, A.V., A. V. Skripnik, K. V. Shatilova, "Study of the dynamics of the absorption spectra of human tooth enamel and dentine under heating and ablation by submillisecond pulse radiation of an erbium laser with a generation wavelength of 2.79 um," Optics and Spectroscopy, vol. 109, No. 2, pp. 211-216 (2010).

Bellisola, G. C. Sorio, "Infrared spectroscopy and microscopy in cancer research and diagnosis," American Journal of Cancer Research, vol. 2, No. 1, pp. 1-21 (2012).

Bizheva, K, et al., "Compact, broad-bandwidth fiberlaserforsub-2-pm axial resolution optical coherence tomography in the 1300-nm wavelength region," Optics Letters, vol. 28, No. 9, May 1, 2003, pp. 707-709.

Blank, T.B., T.L. Ruchti, A.D. Lorenz, S.L. Monfre, M.R. Makarewicz, M. Mattu, K.H. Hazen, "Clinical results from a non-invasive blood glucose monitor," Optical Diagnostics and Sensing of Biological Fluids and Glucose and Cholesterol Monitoring II, A.V. Priezzhev and G.L. Cote, Editors, Proceedings of SPIE, vol. 4624, pp. 1019 (2002).

Boppart, Stephen A., et al., "Imaging developing neural morphology using optical coherence tomography", Journal of Neuroscience Methods 70, 1996, pp. 65-72.

Boppart, Stephen A., et al., "Noninvasive assessment of the developing Xenopus cardiovascular system using optical coherence tomography", Prec. Natl. Acad. Sci. USA, vol. 94, Apr. 1997, pp. 4256-4261.

Borlinghaus, R., "Colours Count: how the challenge of fluorescence was solved in confocal microscopy," in Modern Research and Educational Topics in Microscopy, A. Mendez-Vilas and J. Diaz, eds, pp. 890-899, Formatex (2007).

Borlinghaus, R., "The White Confocal: Continuous Spectral Tuning in Excitation and Emission," in Optical Fluorescence Microscopy, A. Diaspro (Ed), Chapter 2, pp. 37-54, ISBN 978-3-642-15174-3, Springer-Verlag, Berlin (2011).

Borlinghaus, R.T., L. Kuschel, "White Light Laser: The Ultimate Source for Confocal Microscopy," http://www.leica-microsystems.com/science-lab/white-light-laser (Jun. 27, 2012).

Borrelli, N. F., et al., "Resonant and non-resonant effects in photonic glasses", Journal of Non-Crystalline Solids 185, 1995, pp. 109-122.

Boult, Maggi, et al., "Percutaneous Endoscopic Laser Discectomy", Systematic Review, Aust. N.Z.J. Surg., vol. 70, Apr. 7, 2000, pp. 475-479.

Boult, Maggi, et al., "Systematic Review of Percutaneous Endoscopic Laser Discectomy: Update and Re-appraisal", Australian Safety and Efficacy Register of New Interventional Procedures—Surgical Report No. 5, Feb. 2000, 49 pages.

Branche et al., Signal Quality and Power Consumption of a New Prototype Reflectance Pulse Oximeter Sensor, Proceedings of the IEEE 31st Annual Northeast Bioengineering Conference (2005), Hoboken, NJ, 2 pages.

Bronzino, Joseph D.; "The Biomedical Engineering Handbook", (1995).

Büning-Pfaue, Hans. "Analysis of water in food by near infrared spectroscopy." Food Chemistry 82.1 (2003): 107-115.

Burmen, M. P. Usenik, A. Fidler, F. Pernus, B. Likar, "A construction of standardized near infrared hyper-spectral teeth database-a first step in the development of reliable diagnostic tool for quantification and early detection of caries," Lasers in Dentistry XVII, edited by P. Rechmann, D. Fried, Proceedings of SPIE, vol. 7884, Paper 78840E (2011).

Busse, Lynda E., et al., "Design Parameters for Fluoride Multimode Fibers", Journal of Lightwave Technology, vol. 9, No. 7, Jul. 1991, pp. 828-831.

Buttussi, F., et al., Mopet: A context-aware and user-adaptive wearable system for fitness training, Artificial Intelligence in Medicine (2008) 42, 153-163.

Cai et al., Implementation of a Wireless Pulse Oximeter Based on Wrist Band Sensor, College of Biological Science and Medical Engineering Southeast University, (2010) 3rd International Conference on Biomedical Engineering and Informatics, Nanjing, China, 4 pages.

Camacho, Nancy P., et al., "FTIR Microscopic Imaging of Collagen and Proteoglycan in Bovine Cartilage," Biopolymers (Biospectroscopy), vol. 62, 2001, pp. 1-8.

Cardinal, T., et al., "Non-linear optical properties of chalcogenide glasses in the system As—S—Se", Journal of Non-Crystalline Solids 256 & 257, 1999, pp. 353-360.

Champert, Pierre-Alain, et al., "White-light supercontinuum generation in normally dispersive optical fiber using original multi-wavelength pumping system", Optics Express, vol. 12, No. 19, Sep. 20, 2004, pp. 4366-4371.

Choi, Joon Y., et al., "Thermal, Mechanical, Optical, and Morphologic Changes in Bovine Nucleus Pulposus Induced by Nd:YAG ($\lambda$=1.32 um) Laser Irradiation", Lasers in Surgery and Medicine, vol. 28, 2001, pp. 248-254.

Choi, Seung-Ho, et al., "Observation of Optical Precursors in Water", Physical Review Letters, vol. 92, No. 19, May 14, 2004, pp. 193903-1-193903-.3.

Chung, S., D. Fried, M. Staninec, C.L. Darling, "Multispectral near-IR reflectance and transillumination imaging of teeth," Biomedical Optics Express, vol. 2, No. 10, pp. 2804-2814 (2011).

Chung, S., D. Fried, M. Staninec, C.L. Darling, "Near infrared imaging of teeth at wavelengths between 1200 and 1600nm," Proceedings of the Society of Photo Optical Instrument Engineering, paper 7884 (2011).

Clark, R.N., J.M. Curchin, T. M. Hoefen, G.A. Swayze, "Reflectance Spectroscopy of organic compounds: 1. Alkanes," Journal of Geophysical Research, vol. 114, pp. E03001 1 to E03001 19, (2009).

Coen, Stephane, et al., "Supercontinuum generation by stimulated Raman scattering and parametric four-wave mixing in photonic crystal fibers", J. Opt. Soc. Am. B, vol. 19, No. 4, Apr. 2002, pp. 753-764.

Compendium of Chemical Terminology Gold Book, International Union of Pure and Applied Chemistry, Version 2.3.3 (Feb. 24, 2014).

Computer Motion, Inc. "HERMES™ O.R. Control Center-510(k) Summary of Safety and Effectiveness," Oct. 11, 2002, 5 pages.

Computer Motion, Inc., "501(k) Summary-ZEUS® MicroWrist™M Surgical System and Accessories," Sep. 24, 2002, 6 pages.

Curriculum Vitae of Brian W. Anthony, PhD (Nov. 18, 2018).

D'Amico, Anthony V., et al., "Optical Coherence Tomography as a Method for Identifying Benign and Malignant Microscopic Structures in the Prostate Gland", Basic Science, Urology 55 (5), 2000, pp. 783-787.

De Boer, Johannes F., et al., "Determination of the depth-resolved Stokes parameters of light backscattered from turbid media by use of polarization-sensitive optical coherence omography", Optics Letters, vol. 24, No. 5; Mar. 1, 1999, pp. 300-302.

(56) References Cited

OTHER PUBLICATIONS

De Boer, Johannes F., et al., "Imaging thermally damaged tissue by polarization sensitive optical coherence tomography", Optics Express 212, vol. 3, No. 6, Sep. 14, 1998, pp. 212-218.

Demircan, Ayhan, et al., "Supercontinuum generation by the modulation instability", Optics Communications 244, 2005, pp. 181-185.

Desthieux, B., et al., "111 ?W (0. 5 mJ) pulse amplification at 1.5 um using a gated cascade of three erbium-doped fiber amplifiers," Appl. Phys. Lett. vol. 63, Aug. 2, 1993, pp. 586-588.

District Court Preliminary Claim Constructions in Case No. 2:18-cv-134-RWS from Court at Markman hearing.

Dr. Mohammed Islam, Faculty Profile, University of Michigan, College of Engineering (available at https://islam.engin.umich.edu) (2019 The Regents of the University of Michigan).

Drexler, C., Hirmer, M., Danilov, S., Giglberger, S., Putzger, J., Niklas, A., Jager, A., Hiller, K., Loffler, S., Schmalz, G., Redlich, B., Schulz, I., Monkman, G., Ganichev, S. "Infrared spectroscopy for clinical diagnosis of dental pulp vitality." Infrared, Millimeter, and Terahertz Waves (IRMMW-THz), 2012 37th International Conference on. IEEE (2012).

Drexler, Wolfgang, "Ultrahigh-resolution optical coherence tomography", Journal of Biomedical Optics, vol. 9, No. 1, Jan./Feb. 2004, pp. 47-74.

Dubois, A., et al., "Three-dimensional cellular-level imaging using full-field optical coherence tomography", Physics in Medicine and Biology, Phys. Med. Biol. 49, 2004, pp. 1227-1234.

Dudley, John M., et al., "Supercontinuum generation in air-silica microstructured fibers with nanosecond and femtosecond pulse pumping", J. Opt. Soc. Am. B, vol. 19, No. 4, Apr. 2002, pp. 765-771.

Edwards, Glenn S., et al., "Advantage of the Mark-III FEL for biophysical research and biomedical applications", J. Synchrotron Rad. vol. 10, 2003, pp. 354-357.

Edwards, Glenn, et al., Tissue ablation by a free-electron laser tuned to the amide II band, Nature, vol. 371, Sep. 29, 1994, pp. 416-419.

Embedded-Lab, Introducing Easy Pulse: A DIY Photoplethysmographic Sensor for Measuring Hearth Rate, posted on www.Embedded-Lab.com Sep. 12, 2012, by R-B, 10 pages.

Enejder, A.M.K., T.G. Scecina, J. Oh, M. Hunter, W.C. Shih, S. Sasic, G.L. Horowitz, M.S. Feld, "Raman spectroscopy for noninvasive glucose measurements," Journal of Biomedical Optics, vol. 10, No. 3, 031114 (2005).

Evers, D.J., B.H.W. Hendriks, G.W. Lucassen, T.J.M. Ruers, "Optical spectroscopy: current advances and future applications in cancer diagnosis and therapy," Future Oncology, vol. 8, No. 3, pp. 307-320 (2012).

Evers, D.J., R. Nachabe, H.M. Klomp, J.W. van Sandick, M.W. Wouters, G. W. Lucassen, B.H.W. Hendriks, J. Wesseling, T.J.M. Ruers, "Diffuse reflectance spectroscopy: a new guidance tool for improvement of biopsy procedures in lung malignancies," Clinical Lung Cancer, article identifier 10.1016/j.clc.2012.02.001, 8 pages, (2012).

Excerpt from Claim Construction Markman Hearing Transcript filed in Case No. 2:18-cv-134-RWS (Feb. 6, 2019) vol. 1, pp. 1, 2, 21, 22.

Excerpts from Merriam-Webster's Collegiate Dictionary Eleventh Edition (2011).

Excerpts from the American Heritage Dictionary, 5th Edition (Jul. 2012).

Extended European Search Report for European Application No. 13867874.3 dated Jul. 15, 2016.

Extended European Search Report for European Application No. 13867892.5 dated Jul. 22, 2016.

Extended European Search Report for European Application No. 17155541.0 dated May 24, 2017.

Extended European Search Report for European Application No. 17156625.0 dated Mar. 20, 2017.

F. Kuhn, K. Oppermann, B. Horig, "Hydrocarbon Index-and algorithm for hyperspectral detection of hydrocarbons," International Journal of Remote Sensing, vol. 25, No. 12, pp. 2467-2473 (Jun. 20, 2004).

Falk, Peter, et al., "Supercontinuum generation in a photonic crystal fiber with two zero-dispersion wavelengths tapered to normal dispersion at all wavelengths", Optics Express, vol. 13, No. 19, Sep. 19, 2005, pp. 7535-7540.

Fantini, S. A. Sassaroli, "Near-infrared optical mammography for breast cancer detection with intrinsic contrast," Annals of Biomedical Engineering, vol. 40, No. 2, pp. 398-407 (Feb. 2012).

Faralli, S., et al., "Impact of Double Rayleigh Scattering Noise in Distributed Higher Order Raman Pumping Schemes", IEEE Photonics Technology Letters, vol. 15, No. 6, Jun. 2003, pp. 804-806.

Fedotova, O., et al., "Supercontinuum generation in planar rib waveguides enabled by anomalous dispersion", Optics Express, vol. 14, No. 4, Feb. 20, 2006, pp. 1512-1517.

File History for U.S. Pat. No. 9,651,533 issued May 16, 2017.

File History for U.S. Pat. No. 9,757,040 issued Sep. 12, 2017.

File History for U.S. Pat. No. 9,861,286 issued Jan. 9, 2018.

File History for U.S. Pat. No. 9,885,698 issued Feb. 6, 2018.

Final Office Action dated Oct. 21, 2016 for U.S. Appl. No. 14/875,709.

Fried, D. M. Staninec, C.L. Darling, "Near-infrared imaging of dental decay at 1310nm," Journal of Laser Dentistry, vol. 18, No. 1, pp. 8-16 (2010).

G. Edwards, et al., "Comparison of OPA and Mark-III FEL for Tissue Ablation at 6.45 Microns," Department of Physics and Free Electron Laser Laboratory, Duke University, 2002, 7 pages.

G.S. Edwards et al., "Free-electron-laser-based biophysical and biomedical instrumentation," American Institute of Physics, vol. 74, No. 7, Jul. 2003, pp. 3207-3245.

Galvis-Sánchez, Andrea C., et al. "Fourier transform near-infrared spectroscopy application for sea salt quality evaluation." Journal of agricultural and food chemistry 59.20 (2011): 11109-11116.

GE Healthcare, GE Ohmeda TufSat Oximeter for Clinicians on the go, (2012), A General Electric Co., www.gehealthcare.com, GE, Finland, 4 pages.

GE Healthcare, TuffSat User's Guide and Service Manual Electromagnetic Compatibility (EMC), (Mar. 2005) Helsinki, Finland, 43 pages.

Genty, G., et al., "Enhanced bandwidth of supercontinuum generated m microstructured fibers", Optics Express, vol. 12, No. 15, Jul. 26, 2004, pp. 3471-3480.

Genty, G., et al., "Supercontinuum generation in large mode-area microstructured fibers", Optics Express, vol. 13, No. 21, Oct. 17, 2005, pp. 8625-8633.

Glenn Edwards, "Biomedical and potential clinical applications for pulsed lasers operating near 6.45 um, " Society of Photo-Optical Instrumentation Engineers, 1995, 2 pages.

H. Harry Asada et al.; Mobile Monitoring With Wearable Photoplethysmographic Biosensors; IEEE Engineering in Medicine and Biology Magazine, Jun. 2003; 13 pps.

Haase, Norbert U. "Prediction of potato processing quality by near infrared reflectance spectroscopy of ground raw tubers" Journal of Near Infrared Spectroscopy 19.1 (2011): 37-45.

Hafez, M. I., et al., "The Effect of Irrigation on Peak Temperatures in Nerve Root, Dura, and Intervertebral Disc During Laser-Assisted Foraminoplasty", Lasers in Surgery and Medicine, vol. 29, 2001, pp. 33-37.

Hagen, C. L., et al., "Generation of a Continuum Extending to the Midinfrared by Pumping ZBLAN Fiber With an Ultrafast 1550-nm Source", IEEE Photonics Technology Letters, vol. 18, No. 1, Jan. 1, 2006, pp. 91-93.

Hamilton, James D., et al., "High Frequency Optoacoustic Arrays Using Etalon Detection", IEEE Transactions on Ultrasonics, Ferroelectrics, and Frequency Control, vol. 47, No. 1, Jan. 2000, pp. 160-169.

Hamilton, James D., et al., "High Frequency Ultrasound Imaging Using an Active Optical Detector", IEEE Transactions on Ultrasonics, Ferroelectrics, and Frequency Control, vol. 45, No. 3, May 1998, pp. 719-727.

(56) References Cited

OTHER PUBLICATIONS

Hamilton, James D., et al., "High Frequency Ultrasound Imaging with Optical Arrays", IEEE Transactions on Ultrasonics, Ferroelectrics, and Frequency Control, vol. 45, No. 1, Jan. 1998, pp. 216-235.

Harbold, J. M., et al., "Highly nonlinear As—S—Se glasses for all-optical switching", Optics Letters, vol. 27, No. 2, Jan. 15, 2002, pp. 119-121.

Harbold, Jeffrey M., et al., "Highly Nonlinear Ge—As—Se and Ge—As—S—Se Glasses for All-Optical Switching", IEEE Photonics Technology Letters, vol. 14, No. 6, Jun. 2002, pp. 822-824.

Harman-Boehm, I. A. Gal, A.M. Raykhman, J.D. Zahn, E. Naidis, Y. Mayzel, "Noninvasive glucose monitoring: a novel approach," Journal of Diabetes Science and Technology, vol. 3, No. 2 pp. 253-260 (2009).

Harrington, James A., "Infrared Fiber Optics", OSA Handbook, vol. III, white paper, to be published by McGraw Hill, Undated, 13 pages.

Hartmann, R., and H. Büning-Pfaue. "NIR determination of potato constituents." Potato research 41.4 (1998): 327-334.

Hazen, K.H., M.A. Arnold, G.W. Small, "Measurement of glucose and other analytes in undiluted human serum with near-infrared transmission spectroscopy," Analytica Chimica Acta, vol. 371, pp. 255-267 (1998).

Herranz, M., A. Ruibal, "Optical imaging in breast cancer diagnosis: the next evolution," Journal of Oncology, vol. 2012, article ID 863747, 10 pages, (2012).

Hilligsoe, Karen Marie, et al., "Supercontinuum generation in a photonic crystal fiber with two zero dispersion wavelengths", Optics Express, vol. 12, No. 6, Mar. 22, 2004, pp. 1045-1054.

Hirmer, Marion, Danilov, Sergey, Giglberger, Stephan, Putzger, Jurgen, Niklas, Andreas, Jager, Andreas, Hiller, Karl-Anton, Loffler, Susanne, Schmalz, Gottfried, Redlich, Britta, Schulz, Irene, Monkman, Gareth, Ganichev, Sergey. "Spectroscopic Study of Human Teeth and Blood from Visible to Terahertz Frequencies for Clinical Diagnosis of Dental Pulp Vitality." Journal of Infrared, Millimeter, and Terahertz Waves 33.3 (2012): 366-375.

Hirosawa, N. Y. Sakamoto, H. Katayama, S. Tonooka, K. Yano, "In vivo investigation of progressive alternations in rat mammary gland tumors by near-infrared spectroscopy," Analytical Biochemistry, vol. 305, pp. 156-165 (2002).

Hori, Takashi, et al., "Experimental and numerical analysis of widely broadened supercontinuum generation in highly nonlinear dispersion-shifted fiber with a femtosecond pulse", J. Opt. Soc. Am. B, vol. 21, No. 11, Nov. 2004, pp. 1969-1980.

Hori, Takashi, et al., "Flatly broadened, wideband and low noise supercontinuum generation in highly nonlinear hybrid fiber", Optics Express, vol. 12, No. 2, Jan. 26, 2004, pp. 317-324.

Humphreys et al., Noncontact Simultaneous Dual Wavelength Photoplethysmography: A Further Step Toward Noncontact Pulse Oximetry, (2007) Review of Scientific Instruments 78, 044304, American Institute of Physics, 6 pages.

Husakou, Anton V., et al., "Supercontinuum generation, four-wave mixing, and fission of higher-order solitons in photonic-crystal fibers", J. Opt. Soc. Am. B, vol. 19, No. 9, Sep. 2002, pp. 2171-2182.

I.B. Ads, A.A.E. Wagie, N.B. Mariun, A.B.E. Jammal, "An Internet-based blood pressure monitoring system for patients," Journal of Telemedicine and Telecare, 2001, pp. 51-53.

Iatridis, James C., et al., "Is the Nucleus Pulposus a Solid or a Fluid? Mechanical Behaviors of the Nucleus Pulposus of the Human Intervertebral Disc", Spine, vol. 21(10), May 15, 1996, pp. 1174-1184.

Inoue, H., et al., "Computer simulation of the vibrational spectra and properties of fluoride glasses based on $ZrF4$", Journal of Non-Crystalline Solids, vol. 161, 1993, pp. 118-122.

Inter Partes Review No. IPR2019-00910; Petition for Inter Partes Review of U.S. Pat. No. 9,757,040; *Apple Inc.* v. *Omni Medsci, Inc.*; pp. 1-96; dated Apr. 10, 2019.

Inter Partes Review No. IPR2019-00911; Petition for Inter Partes Review of U.S. Pat. No. 9,861,286; *Apple Inc.* v. *Omni Medsci, Inc.*; pp. 1-83; dated Apr. 10, 2019.

Inter Partes Review No. IPR2019-00912; Petition for Inter Partes Review of U.S. Pat. No. 9,885,698; *Apple Inc.* v. *Omni Medsci, Inc.*; pp. 1-94; dated Apr. 10, 2019.

Inter Partes Review No. IPR2019-00913; Petition for Inter Partes Review of U.S. Pat. No. 9,651,533; *Apple Inc.* v. *Omni Medsci, Inc.*; pp. 1-96; dated Apr. 10, 2019.

Inter Partes Review No. IPR2019-00914; Petition for Inter Partes Review of U.S. Pat. No. 9,861,286; *Apple Inc.* v. *Omni Medsci, Inc.*; pp. 1-90; dated Apr. 10, 2019.

Inter Partes Review No. IPR2019-00915; Petition for Inter Partes Review of U.S. Pat. No. 9,885,698; *Apple Inc.* v. *Omni Medsci, Inc.*; pp. 1-91; dated Apr. 10, 2019.

Inter Partes Review No. IPR2019-00916; Petition for Inter Partes Review of U.S. Pat. No. 9,651,533; *Apple Inc.* v. *Omni Medsci, Inc.*; pp. 1-90; dated Apr. 10, 2019.

Inter Partes Review No. IPR2019-00917; Petition for Inter Partes Review of U.S. Pat. No. 9,757,040; *Apple Inc.* v. *Omni Medsci, Inc.*; pp. 1-93; dated Apr. 10, 2019.

International Preliminary Report on Patentability for International Application No. PCT/US2013/07567 dated Jul. 9, 2015.

International Preliminary Report on Patentability for International Application No. PCT/US2013/075700 dated Jul. 9, 2015.

International Preliminary Report on Patentability for International Application No. PCT/US2013/075736 dated Jul. 9, 2015.

International Search Report and Written Opinion for International Application No. PCT/US2013/075700 dated Apr. 24, 2014.

International Search Report and Written Opinion for International Application No. PCT/US2013/075736 dated Apr. 7, 2014.

International Search Report and Written Opinion for International Application No. PCT/US2013/075767 dated Oct. 14, 2014.

Islam, M. N., et al., "Broad bandwidths from frequency-shifting solitons in fibers", Optics Letters, vol. 14, No. 7, Apr. 1, 1989, pp. 370-372.

Islam, M. N., et al., "Femtosecond distributed soliton spectrum in fibers", J. Opt. Soc. Am. B, vol. 6, No. 6, Jun. 1989, pp. 1149-1158.

Istepanian, Robert H., "The Comparative Performance of Mobile Telemedical Systems based on the IS-54 and GSM Cellular Telephone Standards"; Journal of Telemedicine and Telecare 1999; pp. 97-104.

J. Sanghera, I. Aggarwal, "IR Fiber Optics at NRL," undated, 10 pages.

J. Sanghera, L.B. Shaw, I.D. Aggarwal, "Applications of chalcogenide glass optical fibers," Academic of Science, 2003, pp. 1-11.

J.G. Webster; Design of Pulse Oximeters; Medical Science Series; Taylor & Francis Group; CRC Press; Oct. 23, 1997; 260 pps.

Jackson, Stuart D., et al., "Theory and numerical simulation of nth-order cascaded Raman fiber lasers", J. Opt. Soc. Am. B, vol. 18, No. 9, Sep. 2001, pp. 1297-1306.

Jarman, Richard H., "Novel optical fiber lasers", Current Opinion in Solid State and Materials Science, 1996, pp. 199-203.

Jasco Application Note No. 200DR0188-E, "Rapid Identification of illegal drug using NIR (identification of MDMA tablet)", Sep. 4, 2008.

Jung et al., Design of a Low-Power Consumption Wearable Reflectance Pulse Oximetry for Ubiquitous Healthcare System, International Conference on Control, Automation and Systems (Oct. 2008), in COEX, Seoul, Korea, 4 pages.

K.M. Joos, et al. "Optic Nerve Sheath Fenestration with a Novel Wavelength Produced by the Free Electron Laser (FEL), " Lasers in Surgery and Medicine, 27: 2000,191-205.

Karlsson, L. "Caries detection methods based on changes in optical properties between healthy and carious tissue, " International Journal of Dentistry, vol. 2010, Article ID 270729, 9 pages (2010).

Kays, Sandra E., William R. Windham, and Franklin E. Barton. "Prediction of total dietary fiber in cereal products using near-infrared reflectance spectroscopy." Journal of Agricultural and food chemistry 44.8 (1996): 2266-2271.

(56) References Cited

OTHER PUBLICATIONS

Kim-K.D., G.S. Son, S.S. Lim, S.S. Lee, "Measurement of glucose level exploiting a relative optical absorption at discrete probe wavelengths," Japanese Journal of Applied Physics, vol. 48, 077001 (2009).

Kobtsev, Serguei M., et al., "Modelling of high-power supercontinuum generation in highly nonlinear, dispersion shifted fibers at CW pump", Optics Express, vol. 13, No. 18, Sep. 5, 2005, pp. 6912-6918.

Konderpati, V.R., H.M. Heise, J. Backhaus, "Recent applications of near-infrared spectroscopy in cancer diagnosis and therapy," Annals of Bioanalytic Chemistry, vol. 390, pp. 125-139 (2008).

Kowalevicz, Andrew M., et al., "Ultrahigh resolution optical coherence tomography using a superluminescent light source" Optics Express 349, vol. 10, No. 7, Apr. 8, 2002, pp. 349-353.

Krantz, M., et al., The mobile fitness coach: Towards individualized skill assessment using personalized mobile devices, Pervasive and Mobile Computing (Jun. 2012).

Kumar, V.V. Ravi Kanth, et al., "Extruded soft glass photonic crystal fiber for ultrabroad supercontinuum generation", Optics Express, vol. 10, No. 25, Dec. 16, 2002, pp. 1520-1525.

Kurylyak et al., Smartphone-Based Photoplethysmogram Measurement, Department of Electronics, Computer and System Sciences, (2012) River Publishers, University of Calabria, Italy, 30 pages.

Kutz, J. Nathan, et al., Enhanced Supercontinuum Generation through Dispersion-Management, Optics Express, vol. 13, No. 11, May 30, 2005, pp. 3989-3998.

Lee, Ju Han, et al., "Continuous-wave supercontinuum laser based on an erbium-doped fiber ring cavity incorporating a highly non-linear optical fiber", Optics Letters, vol. 30, No. 19, Oct. 1, 2005, pp. 2599-2601.

Lee, Ju Han, et al., "Experimental performance comparison for various continuous-wave supercontinuum schemes: ring cavity and single pass structures", Optics Express, vol. 13, No. 13, Jun. 27, 2005, pp. 4848-4853.

Leff, D.R., O.J. Warren, L.C. Enfield, A. Gibson, T. Athanasion, D.K. Patten, J. Hebden, G.Z. Yang, A. Darzi, "Diffuse optical imaging of the healthy and diseased breast: a systematic review," Breast Cancer Research Treatment, vol. 108, pp. 9-22 (2008).

Leon-Saval, S. G., et al., "Supercontinuum generation in submicron fibre waveguides", Optics Express, vol. 12, No. 13, Jun. 28, 2004, pp. 2864-2869.

Li et al., A Wireless Reflective Pulse Oximeter with Digital Baseline Control for Unfiltered Photoplethysmograms, (Jun. 2012) IEEE Transactions on Biomedical Circuits and Systems, vol. 6, No. 3, 10 pages.

Li Xingde, et al., "Imaging needle for optical coherence tomography", Optics Letters, vol. 25, No. 20, Oct. 15, 2000, pp. 1520-1522.

Lisogurski; Charts 1-3: Lisogurski-533; U.S. Pat. No. 9,651,533 vs. Lisogurski; *Omni MedSci, Inc.* v. *Apple Inc.*, pp. 1-84; May 22, 2019.

Lucas, Jacques, "Infrared glasses", Current Opinion in Solid State & Materials Science 4, 1999. pp. 181-187.

Luo et al., A Non-Invasive Dual-Channel Oximeter Based on Near-Infrared Spectroscopy (NIRS), Biophotonics Lab, Center of Advanced Research in Photonics (2007), The Chinese University of Hong Kong, China, 2 pages.

Lussi, A., R. Hibst, R. Paulus, "Diagnodent: An optical method for caries detection," Journal of Dental Research, vol. 83, special issue C, pp. C80-C83 (2004).

M. Kumar, M.N. Islam, F.L. Terry, M.J. Freeman, A. Chan, M. Neelakandan, T. Manzur, "Stand-off detection of solid targets with diffuse reflection spectroscopy using a high-power mid-infrared supercontinuum source," Applied Optics, vol. 51, No. 15, pp. 2794-2807 (May 20, 2012).

Maia, A., L. Karlsson, W. Margulis, A. Gomes, "Evaluation of two imaging techniques: near-infrared transillumination and dental radiographs for the detection of early approximal enamel canes," Dentomaxillofacial Radiology, vol. 40, pp. 429-433 (2011).

Malin, S.F., T.L. Ruchti, T.B. Blank, S.N. Thennadil, S.L. Monfre, "Noninvasive prediction of glucose by near-infrared diffuse reflectance spectroscopy," Clinical Chemistry, vol. 45, No. 9, pp. 1651-1658 (1999).

Marbach, R., T. Koschinsky, F.A. Gries, H.M. Heise, "Noninvasive blood glucose assay by near-infrared diffuse reflectance spectroscopy of the human inner lip," Applied Spectroscopy, vol. 47, No. 7, pp. 875-881 (1993).

McCoy, R.M., J.G. Blake, K.L. Andrews, "Detecting hydrocarbon microseepage," Oil and Gas Journal, pp. 40-45 (May 28, 2001).

Mehrotra, R. A. Gupta, A. Kaushik, N. Prakash, H. Kandpal, "Infrared spectroscopic analysis of tumor pathology, " Indian Journal of Experimental Biology, vol. 45, pp. 71-76 (Jan. 2007).

Mendelson et al., A Wearable Reflectance Pulse Oximeter for Remote Physiological Monitoring, (Aug./Sep. 2006) Proceedings of the 28th IEEE EMBS Annual International Conference New York City, NY, 4 pages.

Michaels, C.A., T. Masiello, p. M. Chu, "Fourier transform spectrometry with a near-infrared supercontinuum source," Applied Spectroscopy, vol. 63, No. 5, pp. 538-543 (2009).

Mizunami, Toru, et al., "Gain saturation characteristics of Raman amplification in silica and fluoride glass optical fibers", Optics Communications 97, 1993, pp. 74-78.

Moon, Sucbei, et al., "Generation of octave-spanning supercontinuum with 1550-nm amplified diode-laser pulses and a dispersion-shifted fiber", Optics Express, vol. 14, No. 1, Jan. 9, 2006, pp. 270-278.

Morón et al., A Wireless Monitoring System for Pulse-Oximetry Sensors, (2005) Electronic Technology Department, University of Malaga, Spain, 6 pages.

Moros, J. N. Gallpienso, R. Vilches, S. Garrigues, M. DeLa Guardia, "Nondestructive direct determination of heroin in seized illicit street drugs by diffuse reflectance near-infrared spectroscopy," Analytical Chemistry, vol. 80, No. 19, pp. 7257-7265 (Oct. 1, 2008).

Moros,J., J. Kuligowski, G. Quintas, S. Garrigues, M. DeLa Guardia, "New cut-off criterion for uninformative variable elimination in multivariate calibration of near-infrared spectra for the determination of heroin in illicit street drugs," Analytica Chimica Acta, vol. 630, pp. 150-160 (2008).

Mussot, Arnaud, et al., "Generation of a broadband single-mode supercontinuum in a conventional dispersion-shifted fiber by use of a subnanosecond microchip laser", Optics Letters, vol. 28, No. 19, Oct. 1, 2003, pp. 1820-1822.

Na, J, J.H. Baek, S.Y. Ryu, C. Lee, B.H. Lee, "Tomographic imaging of incipient dental-caries using optical coherence tomography and comparison with various modalities," Optical Review, vol. 16, No. 4, pp. 426-431 (2009).

Nachabe, R., D.J. Evers, B.H.W. Hendriks, G.W. Lucassen, M.van der Voort, E.J. Rutgers, M.J.V. Peeters, J.A. Van der Hage, H.S. Oldenburg, J. Wesseling, T.J.M. Ruers, "Diagnosis of breast cancer using diffuse optical spectroscopy from 500 to 1600nm: comparison of classification methods," Journal of Biomedical Optics, vol. 16, No. 8, article 087010, 12 pages (Aug. 2011).

Nang, Yimin, et al., "Ultrahigh-resolution optical coherence tomography by broadband continuum generation from a photonic crystal fiber", Optics Letters, vol. 28, No. 3, Feb. 1, 2003, pp. 182-184.

Nassif, N. A., et al., "In vivo high-resolution video-rate spectral-domain optical coherence tomography of the human retina and optic nerve", Optics Express, vol. 12, No. 3, Feb. 9, 2004, pp. 367-375.

Nellcor; Charts 1-3: Nellcor-533; U.S. Pat. No. 9,651,533 vs. Nellcor; *Omni MedSci, Inc.* v. *Apple Inc.*, pp. 1-155; May 22, 2019.

New and Emerging Techniques-Surgical, Rapid Review, Laser Discectomy, Australian Safety and Efficacy Register of New Interventional Procedures-Surgical, Jun. 2003, 12 pages.

Ng, Choo Lum, Randy L. Wehling, and Susan L Cuppett. "Method for determining frying oil degradation by near-infrared spectroscopy." Journal of agricultural and food chemistry 55.3 (2007): 593-597.

Ni, Yongnian, Minghua Mei, and Serge Kokot. "Analysis of complex, processed substances with the use of NIR spectroscopy and chemometrics: Classification and prediction of properties-The potato crisps example." Chemometrics and Intelligent Laboratory Systems 105.2 (2011): 147-156.

(56) References Cited

OTHER PUBLICATIONS

Nicholson, J. W., "Supercontinuum generation in ultraviolet-irradiated fibers", Optics Letters, vol. 29, No. 20, Oct. 15, 2004, pp. 2363-2365.
Nicholson, J. W., et al., "All-fiber, octave-spanning supercontinuum", Optics Letters, vol. 28, No. 8, Apr. 15, 2003, pp. 643-645.
Nicholson, J. W., et al., "High power, single mode, all-fiber source of femtosecond pulses at 1550 nm and its use in supercontinuum generation", Optics Express, vol. 12, No. 13, Jun. 28, 2004, pp. 3025-3034.
Nicholson, J. W., et al., "Pulsed and continuous-wave supercontinuum generation in highly nonlinear, dispersion-shifted fibers", Applied Physics B 77, 2003, pp. 211-218.
Nishida, Yoshiki, et al., "Reliability of Fluoride Fiber Module for Optical Amplifier Use", IEEE Photonics Technology Letters, vol. 11, No. 12, Dec. 1999, pp. 1596-1598.
Nishizawa, N., "Generation and application of high-quality supercontinuum sources," Optical Fiber Technology, vol. 18, pp. 394-402 (2012).
Non-Final Office Action for U.S. Appl. No. 14/875,709 dated May 26, 2016.
Noreen, R., C.C. Chien, M. Delugin, S. Yao, R. Pineau, Y. Hwu, M. Moenner, C. Petibois, "Detection of collagens in brain tumors based on FTIR imaging and chemometrics," Annals of Bioanalytic Chemistry, vol. 401, pp. 845-852 (2011).
Notice of Allowance for U.S. Appl. No. 14/875,709 dated Jan. 10, 2017.
Nowak, G. A., et al., "Low-power high-efficiency wavelength conversion based on modulational instability in high-nonlinearity fiber," Optics Letters, vol. 23, No. 12, Jun. 15, 1998, pp. 936-938.
Nowak, George A., et al., "Stable supercontinuum generation in short lengths of conventional dispersion-shifted fiber", Applied Optics, vol. 38, No. 36, Dec. 20, 1999, pp. 7364-7369.
Nunnally, W.C., S.K. Holland, G. Laufer, "Wide field of view solar occultation gas filter correlation radiometer for stratospheric methane measurements from a sounding rocket," Thermosense XXV, K.E. Elliot, X.P. Maldague, Editors, Proceedings of SPIE, vol. 5073, pp. 122-130 (2003).
Olesberg, J.T., L. Liu, V.V. Zee, M.A. Arnold, "In vivo near-infrared spectroscopy of rat skin tissue with varying blood glucose levels," Analytic Chemistry, vol. 78, No. 1, pp. 215-223 (2006).
Olesberg, J.T., M.A. Arnold, C. Mermelstein, J. Schmitz, J. Wagner, "Tunable laser diode system for noninvasive blood glucose measurements," Applied Spectroscopy, vol. 59, No. 12, pp. 1480-1484 (2005).
Olsen, B.A., M.W. Borer, F.M. Perry, R.A. Forbes, "Screening for counterfeit drugs using near-infrared spectroscopy," Pharmaceutical Technology, pp. 62-71 (Jun. 2002).
Omni MedSci Inc.'s Opening Claim Construction Brief filed in Case No. 2:18-cv-134-RWS (Dkt. #85) (Dec. 20, 2018).
*Omni Medsci, Inc.* v. *Apple Inc.*; Case No. 2:18-cv-134-RWS (E.D. Tex.); Defendant's Invalidity Contentions, Aug. 28, 2018 (Exhibit A), 66 pps.
*Omni Medsci, Inc.* v. *Apple Inc.*; Case No. 2:18-cv-134-RWS (E.D. Tex.); Defendants Invalidity Contentions, Aug. 28, 2018 (Exhibit AA), 75 pps.
*Omni Medsci, Inc.* v. *Apple Inc.*; Case No. 2:18-cv-134-RWS (E.D. Tex.); Defendant's Invalidity Contentions, Aug. 28, 2018 (Exhibit B), 73 pps.
*Omni Medsci, Inc.* v. *Apple Inc.*; Case No. 2:18-cv-134-RWS (E.D. Tex.); Defendants Invalidity Contentions, Aug. 28, 2018 (Exhibit BB), 65 pps.
*Omni Medsci, Inc.* v. *Apple Inc.*; Case No. 2:18-cv-134-RWS (E.D. Tex.); Defendant's Invalidity Contentions, Aug. 28, 2018 (Exhibit C), 85 pps.
*Omni Medsci, Inc.* v. *Apple Inc.*; Case No. 2:18-cv-134-RWS (E.D. Tex.); Defendants Invalidity Contentions, Aug. 28, 2018 (Exhibit CC), 320 pps.
*Omni Medsci, Inc.* v. *Apple Inc.*; Case No. 2:18-cv-134-RWS (E.D. Tex.); Defendant's Invalidity Contentions, Aug. 28, 2018 (Exhibit D), 38 pps.
*Omni Medsci, Inc.* v. *Apple Inc.*; Case No. 2:18-cv-134-RWS (E.D. Tex.); Defendants Invalidity Contentions, Aug. 28, 2018 (Exhibit DD), 240 pps.
*Omni Medsci, Inc.* v. *Apple Inc.*; Case No. 2:18-cv-134-RWS (E.D. Tex.); Defendants Invalidity Contentions, Aug. 28, 2018 (Exhibit E), 120 pps.
*Omni Medsci, Inc.* v. *Apple Inc.*; Case No. 2:18-cv-134-RWS (E.D. Tex.); Defendants Invalidity Contentions, Aug. 28, 2018 (Exhibit F), 40 pps.
*Omni Medsci, Inc.* v. *Apple Inc.*; Case No. 2:18-cv-134-RWS (E.D. Tex.); Defendants Invalidity Contentions, Aug. 28, 2018 (Exhibit G), 66 pps.
*Omni Medsci, Inc.* v. *Apple Inc.*; Case No. 2:18-cv-134-RWS (E.D. Tex.); Defendants Invalidity Contentions, Aug. 28, 2018 (Exhibit H), 74 pps.
*Omni Medsci, Inc.* v. *Apple Inc.*; Case No. 2:18-cv-134-RWS (E.D. Tex.); Defendants Invalidity Contentions, Aug. 28, 2018 (Exhibit I), 102 pps.
*Omni Medsci, Inc.* v. *Apple Inc.*; Case No. 2:18-cv-134-RWS (E.D. Tex.); Defendants Invalidity Contentions, Aug. 28, 2018 (Exhibit J), 64 pps.
*Omni Medsci, Inc.* v. *Apple Inc.*; Case No. 2:18-cv-134-RWS (E.D. Tex.); Defendants Invalidity Contentions, Aug. 28, 2018 (Exhibit K), 77 pps.
*Omni Medsci, Inc.* v. *Apple Inc.*; Case No. 2:18-cv-134-RWS (E.D. Tex.); Defendants Invalidity Contentions, Aug. 28, 2018 (Exhibit L), 64 pps.
*Omni Medsci, Inc.* v. *Apple Inc.*; Case No. 2:18-cv-134-RWS (E.D. Tex.); Defendants Invalidity Contentions, Aug. 28, 2018 (Exhibit M), 119 pps.
*Omni Medsci, Inc.* v. *Apple Inc.*; Case No. 2:18-cv-134-RWS (E.D. Tex.); Defendants Invalidity Contentions, Aug. 28, 2018 (Exhibit N), 50 pps.
*Omni Medsci, Inc.* v. *Apple Inc.*; Case No. 2:18-cv-134-RWS (E.D. Tex.); Defendants Invalidity Contentions, Aug. 28, 2018 (Exhibit O), 63 pps.
*Omni Medsci, Inc.* v. *Apple Inc.*; Case No. 2:18-cv-134-RWS (E.D. Tex.); Defendants Invalidity Contentions, Aug. 28, 2018 (Exhibit P), 78 pps.
*Omni Medsci, Inc.* v. *Apple Inc.*; Case No. 2:18-cv-134-RWS (E.D. Tex.); Defendants Invalidity Contentions, Aug. 28, 2018 (Exhibit Q), 69 pps.
*Omni Medsci, Inc.* v. *Apple Inc.*; Case No. 2:18-cv-134-RWS (E.D. Tex.); Defendants Invalidity Contentions, Aug. 28, 2018 (Exhibit R), 61 pps.
*Omni Medsci, Inc.* v. *Apple Inc.*; Case No. 2:18-cv-134-RWS (E.D. Tex.); Defendants Invalidity Contentions, Aug. 28, 2018 (Exhibit S), 50 pps.
*Omni Medsci, Inc.* v. *Apple Inc.*; Case No. 2:18-cv-134-RWS (E.D. Tex.); Defendants Invalidity Contentions, Aug. 28, 2018 (Exhibit T), 174 pps.
*Omni Medsci, Inc.* v. *Apple Inc.*; Case No. 2:18-cv-134-RWS (E.D. Tex.); Defendants Invalidity Contentions, Aug. 28, 2018 (Exhibit U), 334 pps.
*Omni Medsci, Inc.* v. *Apple Inc.*; Case No. 2:18-cv-134-RWS (E.D. Tex.); Defendants Invalidity Contentions, Aug. 28, 2018 (Exhibit V), 137 pps.
*Omni Medsci, Inc.* v. *Apple Inc.*; Case No. 2:18-cv-134-RWS (E.D. Tex.); Defendants Invalidity Contentions, Aug. 28, 2018 (Exhibit W), 384 pps.
*Omni Medsci, Inc.* v. *Apple Inc.*; Case No. 2:18-cv-134-RWS (E.D. Tex.); Defendants Invalidity Contentions, Aug. 28, 2018 (Exhibit X), 291 pps.
*Omni Medsci, Inc.* v. *Apple Inc.*; Case No. 2:18-cv-134-RWS (E.D. Tex.); Defendants Invalidity Contentions, Aug. 28, 2018 (Exhibit Y), 120 pps.
*Omni Medsci, Inc.* v. *Apple Inc.*; Case No. 2:18-cv-134-RWS (E.D. Tex.); Defendants Invalidity Contentions, Aug. 28, 2018 (Exhibit Z), 53 pps.

(56) References Cited

OTHER PUBLICATIONS

Omre, A., Bluetooth Low Energy: Wireless Connectivity for Medical Monitoring, Journal of Diabetes Science & Technology, vol. 4, Issue 2 (Mar. 2010).

Ooen, Stephane, et al., "Supercontinuum generation by stimulated Raman scattering and Darametric four-wave mixing in photonic crystal fibers", J. Opt. Soc. Am. B, vol. 19, No. 4, Apr. 2002, pp. 753-764.

Ooi ET, Zhang XQ, Chen JH, Soh PH, Ng K, Yeo JH, "Non-invasive glucose measurement using multiple laser diodes," Optical Diagnostic and Sensing VII, edited by Gerard L. Cote, Alexander V. Priezzhev, Proc. of SPIE vol. 6445, 64450K, (2007).

Oughstun, Kurt E., "Influence of precursor fields on ultrashort pulse autocorrelation measurements and pulse width evolution", Optics Express, vol. 8, No. 8, Apr. 9, 2001, pp. 481-491.

P.A. Thielen and L.B. Shaw, et al., "Small-core As—Se fiber for Raman amplification," Optics Leti-ers, vol. 28, No. 16, Aug. 15, 2003, 3 pages.

Palou, A. J. Cruz, M. Blanco, J. Tomas, J. De Los Rios, M. Alcala, "Determination of drug, excipients and coating distribution in pharmaceutical tablets using NIR-CI," Journal of Pharmaceutical Analysis, vol. 2, No. 2, pp. 90-97 (2012).

Pan, Yingtian, et al., "Hand-held arthroscopic optical coherence tomography for in vivo high-resolution imaging of articular cartilage", Journal of Biomedical Optics 8(4), Oct. 2003, pp. 648-654.

Papemyi, S. B., et al., "Sixth-Order Cascaded Raman Amplification", OFC/NFOEC, 2005, 3 pages.

Parawira, S. "Classification of hyperspectral breast images for cancer detection," Dec. 4, 2009, downloaded from WWW, 5 pages.

Park, Jesung, et al., "Analysis of birefringent image in the retinal nerve fiber layer by polarization sensitive optical coherence tomography", Ophthalmic Technologies XIV, Proceedings of SPIE, vol. 5314, 2004, pp. 188-194.

Park; Charts 1-3: Park-533; U.S. Pat. No. 9,651,533 vs. Park; *Omni MedSci, Inc. v. Apple Inc.*, pp. 1-171; May 22, 2019.

Passat, "Solid-State Lasers and Optical Components," Jul. 14, 2003, 5 pages.

Patel, S., et al., A review of wearable sensors and systems with application rehabilitation, Journal of Neuroengineering & Rehabilitation 2012 9:21.

Patterson et al., Ratiometric Artifact Reduction in Low Power Reflective Photoplethysmography, (Aug. 2011) IEEE Transactions on Biomedical Circuits and Systems, vol. 5, No. 4, 9 pages.

PCT/US06/44451, Notification of Transmittal of the International Search Report and the Written Opinion of the International Searching Authority, or the Declaration, dated Nov. 29, 2007, 12 pages.

Pedreschi, F., V. H. Segtnan, and S. H. Knutsen. "On-line monitoring of fat, dry matter and acrylamide contents in potato chips using near infrared interactance and visual reflectance imaging." Food Chemistry 121.2 (2010): 616-620.

Peláez, LED Power Reduction Trade-Offs for Ambulatory Pulse Oximetry, Conference Proceedings of the 29th Annual International Conference of the IEEE EMBS (Aug. 2007) Lyon, France, 4 pages.

U.S. Appl. No. 12/206,432, "System and Method for Voice Control of Medical Devices," by Mohammed N. Islam, filed Sep. 8, 2008.

Pezzaniti, J.L., T.W. Jeng, L. McDowell, G.M. Oosta, "Preliminary investigation of near-infrared spectroscopic measurements of urea, creatinine, glucose, protein and ketone in urine," Clinical Biochemistry, vol. 34, pp. 239-246 (2001).

Pierce, Mark C., et al., "Advances in Optical Coherence Tomography imaging for Dermatology", Optical Coherence Tomography Advances, The Journal of Investigative Dermatology, Sep. 3, 2004, pp. 458-463.

Pojic, M. J. Mastilovic, N. Majcen, "The application of near infrared spectroscopy in wheat quality control," Infrared Spectroscopy-Life and Biomedical Sciences, pp. 167-184 (2012).

Povazay, B., et al., "Submicrometer axial resolution optical coherence tomography", Optical Letters, vol. 27, No. 20, Oct. 15, 2002, pp. 1800-1802.

Proof of Service of Summons in *Omni MedSci, Inc. v. Apple Inc.*, No. 2:18-cv-134 (E.D. Tex.) (Dkt. #12) (Apr. 13, 2018).

R.H. Istepanian, B. Woodward, p. A. Bales, S. Chen, B. Luk, "The comparative performance of mobile telemediCal systems based on the IS-54 and GSM cellular telephone standards," Journal of Telemedicine and Telecare, 1999, pp. 97-104.

R.Rox Anderson, et al., "Selective Photothermolysis: Precise Microsurgery by Selective Absorption of Pulsed Radiation," Department of Dermatology, Harvard Medical School, Science, vol. 220, Apr. 29, 1983, 4 pages.

Rambla, F.J., S. Garrigues, M. DeLa Guardia, "PLS-NIR determination of total sugar, glucose, fructose and sucrose in aqueous solutions of fruit juices," Analytica Chimica Acta, vol. 344, pp. 41-53 (1997).

Ranka, Jinendra K., et al., "Visible continuum generation in air-silica microstructure optical fibers with anomalous dispersion at 800 nm", Optics Letters, vol. 25, No. 1, Jan. 1, 2000, pp. 25-27.

Rauf Adil, "The Usage of Tablets in the HealthCare Industry," available at https://www.healthcareitnews.com/blog/usage-tablets-healthcare-industry (Aug. 2, 2012).

Reese, E.L, E.E. Fisher, D.A. Horowitz, "Photoelectric densitometry of the circulation of the human dental pulp," The Journal of the Baltimore College of Dental Surgery, vol. 26, No. 1, pp. 6-18 (1971).

Reich, G. "Near-infrared spectroscopy and imaging: basic principles and pharmaceutical applications," Advanced Drug Delivery Reviews, vol. 57, pp. 1109-1143 (2005).

Rein, Alan, and Luis Rodriguez-Saona. "Measurement of Acrylamide in Potato Chips by Portable FTIR Analyzers." (2013).

Rhee et al., Artifact-Resistant Power-Efficient Design of Finger-Ring Plethysmographic Sensors, IEEE Transactions on Biomedical Engineering (Jul. 2001), vol. 48, No. 7, Cambridge, MA, 11 pages.

Robert S. Jones et al.; Near-Infrared Transillumination at 1310-nm for the Imaging of Early Dental Decay; vol. 11; No. 18; Optics Express 2259; Sep. 8, 2003.

Rodionova, O.Y., L.P. Houmoller, A.L. Pomerantsev, P. Geladi, J. Burger, V.L. Dorofeyev, A.P. Arzamastsev, "NIR spectrometry for counterfeit drug detection: a feasibility study," Analytica Chimica Acta, vol. 549, pp. 151-158 (2005).

Roggan, Andre, et al., "Optical Properties of Circulating Human Blood in the Wavelength Range 400-2500 NM", Journal of Biomedical Optics, vol. 4, No. 1, Jan. 1999, pp. 36-46.

Roggo, Y. P. Chalus, L. Maurer, C. Lema-Martinez, A. Edmond, N. Jent, "A review of near infrared spectroscopy and chemometrics in pharmaceutical technologies," Journal of Pharmaceutical and Biomedical Analysis, vol. 44, pp. 683-700 (2007).

Rollins, Andrew M., et al., "Real-time in vivo imaging of human gastrointestinal ultrastructure by use of endoscopic optical coherence tomography with a novel efficient interferometer design", Optics Letters, vol. 24, No. 19, Oct. 1, 1999, pp. 1358-1360.

S.D. Khan, S. Jacobson, "Remote sensing and geochemistry for detecting hydrocarbon microseepages," GSA Bulletin, vol. 120, No. 1/2, pp. 96-105 (Jan./Feb. 2008).

Saliminia, A., et al., "Ultra-broad and coherent white light generation in silica glass by focused femtosecond pulses at 1.5pm", Optics Express, vol. 13, No. 15, Jul. 25, 2005, pp. 5731-5738.

Sanghera, J. S., et al., Active and passive chalcogenide glass optical fibers for IR applications: a review, Journal of Non-Crystalline Solids 256 & 257, 1999, pp. 6-16.

Scafi, S.H.F., C. Pasquini, "Identification of counterfeit drugs using near-infrared spectroscopy," Analyst, vol. 126, pp. 2218-2224 (2001).

Schmitt, Joseph, et al., "Intravascular Optical Coherence Tomography Opens a Window Onto Coronary Artery Disease", Optics & Photonics News, Feb. 2004, pp. 20-25.

Schneider, R.C., K.A. Kovar, "Analysis of ecstasy tablets: comparison of reflectance and transmittance near infrared spectroscopy," Forensic Science International, vol. 134, pp. 187-195 (2003).

Schreiber, T., et al., "Supercontinuum generation by femtosecond single and dual wavelength pumping in photonic crystal fibers with two zero dispersion wavelengths", Optics Express, vol. 13, No. 23, Nov. 14, 2005, pp. 9556-9569.

(56) References Cited

OTHER PUBLICATIONS

Schreiner et al., Blood Oxygen Level Measurement with a Chest-Based Pulse Oximetry Prototype System, Computing in Cardiology (2010) NIBEC, University of Ulster, Newtownabbey, Northern Ireland, 4 pages.
Schubert, E.F., Light-Emitting Diodes (Cambridge Univ. Press, 2nd ed. Reprinted 2014).
Schulz, I., J. Putzger, A. Niklas, M. Brandt, A. Jager, A. Hardt, S. Knorzer, K.A. Hiller, S. Loffler, G. Schmalz, S.N. Danilov, S. Giglberger, M. Hirmer, S.D. Ganichev, G. Monkman, "PPG signal acquisition and analysis on in vitro tooth model for dental pulp vitality assessment," ARC Submission 16, (2012).
Seefeldt, Michael, et al., "Compact white-light source with an average output power of 2.4 W and 900 nm spectral bandwidth", Optics Communications 216, pp. 199-202.
Segtnan, Vegard H., et al. "Screening of acrylamide contents in potato crisps using process variable settings and near-infrared spectroscopy." Molecular nutrition & food research 50.9 (2006): 811-817.
September, Danwille Jacqwin Franco. Detection and quantification of spice adulteration by near infrared hyperspectral imaging. Diss. Stellenbosch: University of Stellenbosch, 2011.
Shaw, et al., IR Supercontinuum Generation in As—Se Photonic Crystal Fiber, Optical Society of America, Copyright 2005, 3 pages.
Shiroma, Cecilia, and Luis Rodriguez-Saona. "Application of NIR and MIR spectroscopy in quality control of potato chips." Journal of Food Composition and Analysis 22.6 (2009): 596-605.
Shiroma, Cecilia. "Rapid quality control of potato chips using near and mid-infrared spectroscopy." (2007).
Shu-Fang, T. C. Jian-Ping, Z. Mi, "The information of oil and gas micro-seepage in Dongsheng Region of Inner Mongolia extraction based on the airborne hyperspectral remote sensing image," Remote Sensing of the Environment, 16th National Symposium on Remote Sensing of China, edited by Q. Tong, Proceedings of SPIE, vol. 7123, 71230K-1 to 8, (2008).
Slusher, Richard, et al., "Highly nonlinear composite chalcogenide/polymer fibers", OSA 2004, 1 page.
Slusher, Richart E., et al., "Large Raman gain and nonlinear phase shills in high-purity As2So3 chalcogenide fibers", J. Opt. Soc. Am. B, vol. 21, No. 6, Jun. 2004, pp. 1146-1155.
Smektala, F., et al., "Chalcogenide glasses with large non-linear refractive indices", Journal of Non-Crystalline Solids 239, 1998, pp. 139-142.
Smith, J.L., "The Pursuit of Noninvasive Glucose: Hunting the Deceitful Turkey," 2nd Edition, pp. 1-141 (2011).
Sobol, Emil, et al., "Time-resolved, light scattering measurements of cartilage and cornea denaturation due to free electron laser radiation", Journal of Biomedical Optics, vol. 8, No. 2, Apr. 2003, pp. 216-222.
Sondermann, N., K.A. Kovar, "Identification of ecstasy in complex matrices using near-infrared spectroscopy," Forensic Science International, vol. 102, pp. 133-147 (1999).
Staninec, M., S.M. Douglas, C.L. Darling, K. Chan, H. Kang, R. C. Lee, D. Fried, "Nondestructive clinical assessment of occlusal caries lesions using near-IR imaging methods," Lasers in Surgery and Medicine, vol. 43, No. 10, pp. 951-959 (2011).
State-Specific Trends in Chronic Kidney Failure-United States, 1990-2001, Morbidity and Mortality Weekly Report, Department of Health and Human Services Centers for Disease Control and Prevention, vol. 53, No. 39, copied from internet: file://C:\Documents and Settings\eturlo\Desktop\State-Specific Trends in Chronic Kidney . . . Feb. 12, 2010, Oct. 8, 2004, pp. 918-920.
Sun, Y., C.F. Booker, S. Kumari, R.N. Day, M. Davidson, A. Periasamy, "Characterization of an orange acceptor fluorescent protein for sensitized spectral fluorescence resonant energy transfer microscopy using a white-light laser," Journal of Biomedical Optics, vol. 14, No. 5, paper 054009 (2009).
Swan, M., Sensor Mania! The Internet of Things, Wearable Computing, Objective Metrics, and the Quantified Self 2.0, Journal of Sensor and Actuator Networks (2012).

Takushima, Yuichi, High average power, depolarized supercontinuum generation using a 1.55-um ASE noise source, Optics Express, vol. 13, No. 15, Jul. 25, 2005, pp. 5871.-5877.
Tanaka, Keiji, "Optical nonlinearity in photonic glasses", Journal of Materials Science: Materials in Electronics 16, 2005, pp. 633-643.
Taos, Inc., Infrared Light-to-Voltage Optical Sensors, (2006) Texas Advanced Optoelectronic Solutions Inc., The Lumenology Company, TX, 14 pages.
Taroni, P. D. Cornelli, A. Giusto, A. Pifferi, N. Shah, L. Spinelli, A. Torricelli, R. Cubeddu, "Assessment of collagen absorption and related potential diagnostic applications," Diffuse Optical Imaging of Tissue, edited by B.W. Pogue, R. Cubeddu, Proceedings of SPIE-OSA Biomedical Optics, SPIE vol. 6629, paper 66290D, 5 pages, (2007).
Taroni, P., "Diffuse optical imaging and spectroscopy of the breast: a brief outline of history and perspectives," Photochemical Photobiological Science, vol. 11, pp. 241-250 (2012).
Tearney, Guillermo J., et al., "In vivo Endoscopic Optical Biopsy with Optical Coherence Tomography", Science, New Series, vol. 276, Jun. 27, 1997, pp. 2037-2039.
Technology Transfer Policy, Office of Technology Transfer—University of Michigan (available at https://techtransfer.umich.edu/for-inventors/policies/technology-transfer- - policy/) (revision effective Jun. 1, 2009).
The Bylaws of the University of Michigan Board of Regents, (available at http://www.regents.umich.edu/bylaws/bylawsrevised_09-18.pdf) (last updated Sep. 20, 2018).
Thennadil, S.N., J.L. Rennert, B.J. Wenzel, K.H. Hazen, T.L. Ruchti, M.B. Block, "Comparison of glucose concentration in interstitial fluid, and capillary and venous blood during rapid changes in blood glucose levels," Diabetes Technology & Therapeutics, vol. 3, No. 3, pp. 357-365 (2001).
Thongtrangan, Issada, et al., "Minimally invasive spinal surgery: a historical perspective", Neurosurg. Focus, vol. 16, Article 13, Jan. 2004, pp. 1-10.
Thybo, Anette Kistrup, et al. "Prediction of sensory texture of cooked potatoes using uniaxial compression, near infrared spectroscopy and low field1H NMR spectroscopy." LWT-Food Science and Technology 33.2 (2000): 103-111.
Tolton, B.T., "A concept for a gas-filter correlation radiometer to remotely sense the atmospheric carbon dioxide col. from space," Notes and Correspondence, Journal of Atmospheric and Oceanic Technology, vol. 21, pp. 837-852, (May 2004).
Tombelaine, Vincent, et al., "Ultra wide band supercontinuum generation in air-silica holey fibers by SHG-induced modulation instabilities", Optics Express, vol. 13, No. 19, Sep. 19, 2005, pp. 7399-7404.
Travers, J. C., et al., "Extended blue supercontinuum generation in cascaded holey fibers", Optics Letters, vol. 30, No. 23, Dec. 1, 2005, pp. 3132-3134.
Travers, J. C., et al., "Extended continuous-wave supercontinuum generation in a low-water-loss holey fiber", Optics Letters, vol. 30, No. 15, Aug. 1, 2005, pp. 1938-1940.
Troy, T.L., S.N. Thennadil, "Optical properties of human skin in the near infrared wavelength range of 1000 to 2200nm," Journal of Biomedical Optics, vol. 6, No. 2, pp. 167-176, (2001).
U.S. Appl. No. 10/652,276, "System and Method for Voice Control of Medical devices," by Mohammed N. Islam, abandoned filed Aug. 29, 2003.
U.S. Appl. No. 10/757,341, "System and Method for Voice Control of Medical devices," by Mohammed N. Islam, filed Jan. 13, 2004.
U.S. Appl. No. 12/206,432, "System and Method for Voice Control of Medical Devices," by Mohammed N. Islam, pending filed Sep. 8, 2008.
U.S. Appl. No. 61/350,673; titled: Opticoustic Sensor; Inventor: Massi Joe E. Kiani; filed Jun. 2, 2010.
U.S. Appl. No. 61/747,472, filed Dec. 31, 2012.
U.S. Appl. No. 61/747,477, filed Dec. 31, 2012.
U.S. Appl. No. 61/747,487, filed Dec. 31, 2012.
U.S. Appl. No. 61/754,698, filed Jan. 21, 2013.
U.S. Patent and Trademark Office, Notice of Allowance and Fee(s) Due for U.S. Appl. No. 12/206,432, filed Sep. 8, 2008, Mohammed N. Islam, Date filed: Aug. 28, 2009.

(56) References Cited

OTHER PUBLICATIONS

U.S. Patent and Trademark Office, Office Action for U.S. Appl. No. 12/206,432, filed Sep. 8, 2008, Mohammed N, Islam, Date Filed: Mar. 12, 2009.

United States District Court Eastern District of Texas Marshall Division; Defendant and Counter Claimant Apple Inc.'s Amended Answer, Affirmative Defenses, and Counterclaims to Complaint of Plaintiff and Counter Defendant Omni Medsci, Inc.; Document 38; Jul. 19, 2018; 32 pps.

United States District Court Eastern District of Texas Marshall Division; *Omni Medsci, Inc.* vs. *Apple Inc.*; Civil Action No. 2:18-cv-00134 Jury Trial Demanded; Defendant's Invalidity Contentions; Aug. 28, 2018; 33 pps.

Unterhuber, A., et al., "Advances in broad bandwidth light sources for ultrahigh resolution optical coherence tomography", Physics in Medicine and Biology, Phys. Med. Biol. 49, 2004, pp. 1235-1246.

Urban, J. P. G., et al., "The Nucleus of the Intervertebral Disc from Development to Degeneration" Amer. Zool., vol. 40, 2000, pp. 53-61.

Urbas, A., M.W. Manning, A. Daugherty, L.A. Cassis, R.A. Lodder, "Near-infrared spectrometry of abdominal aortic aneurysm in the ApoE Mouse," Analytical Chemistry, vol. 75, No. 15, pp. 3650-3655 (Jul. 15, 2003).

Valencell; Charts 1-3: Valencell-533; U.S. Pat. No. 9,651,533 vs. Valencell; *Omni MedSci, Inc. v. Apple Inc.*, pp. 1-122; May 22, 2019.

Van Der Meer, F. P. Van Dijk, H. Van Der Werff, H. Yang, "Remote sensing and petroleum seepage: a review and case study, " Terra Nova, vol. 14, No. 1, pp. 1-17 (2002).

Van Der Meer, F., P. Van Dijk, S. Kroonenberg, Y. Hong, H. Lang, "Hyperspectral hydrocarbon microseepage detection and monitoring: potentials and limitations," Second EARSEI workshop on imaging spectroscopy, pp. 1-9 (2000).

Venugopalan, V., "Optical Society of America BIOMED Topical Meeting Tutorial on Tissue Optics", Apr. 27, 2004, pp. 1-32.

Vinay V. Alexander et al; Modulation Instability High Power All-Fiber Supercontinuum Lasers and Their Applications; Optical Fiber Technology 18; 2012; pp. 349-374.

Wadsworth, W. J., et al., "Supercontinuum and four-wave mixing with Q-switched pulses in endlessly single-mode photonic crystal fibres", Optics Express, vol. 12, No. 2, Jan. 26, 2004, pp. 299-309.

Wadsworth, William J., et al., "Supercontinuum generation in photonic crystal fibers and Optical fiber tapers: a novel light source", J. Opt. Soc. Am. B, vol. 19, No. 9, Sep. 2002, pp. 2148-2155.

Walsh, M.J., R.K. Reddy, R. Bhargava, "Label-free biomedical imaging with mid-IR spectroscopy," IEEE Journal of Selected Topics in Quantum Electronics, article identifier 10.1109/JSTQE. 2011.2182635, 12 pages, (2011).

Wang et al., Multichannel Reflective PPG Earpiece Sensor with Passive Motion Cancellation, (Dec. 2007) IEEE Transactions on Biomedical Circuits and Systems, vol. 1, No. 4, 7 pages.

Wang, Lihong V., Multiscale photoacoustic microscopy and computed tomography, Sep. 2009, Nature Photonics, vol. 3, pp. 503-509.

Wang, Yimin, et al., "Ultrahigh-resolution optical coherence tomography by broadband continuum generation from a photonic crystal fiber", Optics Letters, vol. 28, No. 3, Feb. 1, 2003, pp. 182-184.

Watari, M., H. Migashiyama, N. Mitsui, M. Tomo, Y. Ozaki, "On-line monitoring of the density of linear low-density polyethylene in a real plant by near-infrared spectroscopy and chemometrics," Applied Spectroscopy, vol. 58, No. 2, pp. 248-255 (2004).

Webster, Design of Pulse Oximeters, Medical Science Series (1997), Department of Electrical and Computer Engineering, University of Wisconsin-Madison, Institute of Physics Publishing, Bristol and Philadelphia, 267 pages.

Wedding, B.B., C. Wright, S. Grauf, R.D. White, "The application of near infrared spectroscopy for the assessment of avocado quality attributes," Infrared Spectroscopy-Life and Biomedical Sciences, pp. 211-230 (2011).

Werle, Peter, et al., "Near- and mid-infrared laser-optical sensors for gas analysis", Optics and Lasers in Engineering 37, 2002, pp. 101-114.

Westbrook, Paul S., "Improved Supercontinuum Generation Through UV Processing of Highly Nonlinear Fibers", Journal of Lightwave Technology, vol. 23, No. 1, Jan. 2005, pp. 13-18.

Williams, Phil. "Near-Infrared Spectroscopy of Cereals." Handbook of vibrational spectroscopy (2006).

Wuthrich, Stefan, et al., "Optical damage thresholds at 2.94 um in fluoride glass fibers", Applied Optics, vol. 31, No. 27, Sep. 20, 1992, pp. 5833-5837.

Xiao, J. Q. Tian, Y. Lu, L. Wang, X. Qi, B. Wen, "Extraction of hydrocarbon content information by using hyperspectral image at Liaodong Bay, China," downloaded from world wide web on Apr. 6, 2012.

Xie, T.-Q., et al., "Detection of tumorigenesis in urinary bladder with optical coherence tomography: optical characterization of morphological changes", Optics Express, vol. 10, No. 24, Dec. 2, 2002, 2003, pp. 1431-1443.

Xie, Tuqiang, et al., "Endoscopic optical coherence tomography with a modified microelectromechanical systems mirror for detection of bladder cancers", Applied Optics, vol. 42, No. 31, Nov. 1, 2003, pp. 6422-6426.

Xu, D., G. Ni, T. Jiang, L. Jiang, M. Chi, "Integration of field work and hyperspectral data for oil and gas exploration, " IEEE 1-4244-1212-9/07, pp. 3194-3197 (2007).

Xu, D-Q, G-Q Ni, L-L Jiang, Y-T Shen, T. Li, S-L Ge, X-B Shu, "Exploring for natural gas using reflectance spectra of surface soils," Advances in Space Research, vol. 41, pp. 1800-1817 (2008).

Yamaha, BODiBEAT, Body, Music, in Sync., BF-1 Quick Guide, Player/Heart Rate Monitor: Quick Manual, 120 pages.

Yeh, S-J, C.F. Hanna, O.S. Khalil, "Monitoring blood glucose changes in cutaneous tissue by temperature-modulated localized reflectance measurements," Clinical Chemistry, vol. 49, No. 6, pp. 924-934 (2003).

Zakian, C. I. Pretty, R. Ellwood, "Near-infrared hyperspectral imaging of teeth for dental canes detection, " Journal of Biomedical Optics, vol. 16, No. 6, 064047 (2009).

Ziegler, U., A.G. Bittermann, M. Hoechli, "Introduction to Confocal Laser Scanning Microscopy (LEICA)," www.zmb.unizh.ch, May 29, 2013.

Carlos F. Benitez-Quiroz, Ramprakah Srinivasan, and Aleix M. Martinez, "Facial color is an efficient mechanism to visually transmit emotion," Proceedings of the National Academy of Science PNAS, Apr. 3, 2018, vol. 115, No. 14, pp. 3581-3586.

Kaiwen Guo, Tianqu Zhai, Elton Pashollari, Christopher J. Varlamos, Aymaan Ahmed, and Mohammed N. Islam, "Contactless Vital Sign Monitoring System for Heart and Respiratory Rate Measurements with Motion Compensation Using a Near-Infrared Time-of-Flight Camera," Applied Sciences, 2021, 11, 10913. https://doi.org/10.3390/app112210913.

Kaiwen Guo, Tianqu Zhai, Manoj H. Purushothama, Alexander Dobre, Shawn Meah, Elton Pashollari, Aabhaas Vaish, Carl DeWilde and Mohammed N. Islam, "Contactless Vital Sign Monitoring System for In-Vehicle Driver Monitoring Using a Near-Infrared Time-of-Flight Camera," Applied Sciences, 2022, 12, 4416. https://doi.org/10.3390/app12094416.

"The 6 best LiDAR Apps and Games for iphone 12," http://www.mickeysworkshop.com/product-design/2021/1/23 (printed from web on Aug. 8, 2022).

Samuel Kim, Irfan Wisanggeni, Ryan Ros, Rania Hussein, "Detecting Fatigue Driving through Perclos: A Review," International Journal of Image Processing (IJIP), vol. 14, Issue 1, 2020, pp. 1-7.

Tereza Soukupova and Jan Cech, "Real-Time Eye Blink Detection using Facial Landmarks," 21st Computer Vision Winter Workshop, Luka Cehovin, Rok Mandeljc, Vitormir Struc (eds), Rimske Toplice, Slovenia, Feb. 3-5, 2016.

C. Fabian Benitez-Quiroz, Ramprakash Srinivasan and Aleix M. Martinez, "Discriminant Functional Learning of Color Features for the Recognition of Facial Action Units and Their Intensities," IEEE Transactions on Pattern Analysis and Machine Intelligence, vol. 41, No. 12, Dec. 2019, pp. 2835-2845.

(56) References Cited

OTHER PUBLICATIONS

Ramprakash Srinivasan, Julie D. Golomb and Aleix M. Martinez, "A Neural Basis of Facial Action Recognition in Humans," The Journal of Neuroscience, Apr. 20, 2016, vol. 36, No. 16, pp. 4434-4442.
Suhandi Junaedi and Habibullah Akbar, "Driver Drowsiness Detection Based on Face Feature and PERCLOS," Journal of Physics: Conference Series, 1090, 012037 (2018).
"Camera Phone," on Wikipedia, https://en.wikipedia.org/wiki/Camera_Phone, printed Aug. 19, 2022.
Preethi Padmanabhan, Chao Zhang, and Edoardo Charbon, "Modeling and Analysis of a Direct Time-of-Flight Sensor Architecture for LiDAR Applications," Sensors, 2019, 19, 5464; doi: 10.3390/s19245464, www.mdpi.com/journal/sensors.
Application Note: Time-of-flight Basics, Melexis, AUH-2022, pp. 1-14.
Dingkang Wang, Connor Watkins and Huikai Xie, "MEMS Mirrors for LiDAR: A Review," Micromachines 2020, 11, 456; doi:10.3390/mi11050456, www.mdpi.com/journal/micromachines.
Karl Joachim Ebeling, Rainer Michalzik and Holger Moench, "Vertical-cavity surface-emitting laser technology applications with focus on sensor and three-dimensional imaging," Japanese Journal of Applied Physics, 57, 08PA02 (2018), pp. 1-11.
Stella C. Gerdemann, Katherine McAuliffe, Peter R. Blake, Daniel B.M. Haun and Robert Hepach, "the ontogeny of children's social emotions in response to (un)fairness," 2022. Royal Society Open Science 9:191456. https://doi.org/10.1098/rsos.191456.
Robert Hepach, Amrisha Vaish and Michael Tomasello, "Novel paradigms to measure variability of behavior in early childhood: posture, gaze and pupil dilation," (2015), Frontiers in Psychology 6:858. doi: 10.3389/fpsyg.2015.00858, www.frontiersin.org.
Andrew Barszczyk and Kang Lee, "Measuring Blood Pressure: from Cuff to Smartphone," Current Hypertension Reports. (2019) 21:84 https://doi.org/10.1007/s11906-019-0990-3.
Deye Yang, Guomin Xiao, Jing Wei and Hong Luo, "Preliminary assessment of video-based blood pressure measurement according to ANSI/AAMI/ISO81060-2:2013 guideline accuracy criteria: Anura smartphone app with transdermal optimal imaging technology," Brief Report in Blood Pressure Monitoring. (2020) 25: 295-298.
Andrew Barszczyk, Weihong Zhou and Kang Lee, "Aim and Transdermal Optical Imaging," Springer Nature Switzerland AG 2021, N. Lidstromer, H. Ashrafian (eds.), Artificial Intelligence in Medicine, https://doi.org/10.1007/978-3-030-58080-3_250-1.
Hudda Salih, Si Jia Wu, Evgueni Kabakov, Kang Lee and Weihong Zhou, "Smartphone-based identification of critical levels of glycated hemoglobin A1c using transdermal optical imaging," Primary Research Article published in Journal of Natural Sciences, published Mar. 30, 2021, vol. 2, No. 1; doi: https://doi.org/10.33137/jns.v2i1.34645.
"Effects of diabetes on the body and organs," https://www.medicalnewstoday.com/articles/317483#faq (printed from the web Oct. 13, 2022).
Jiehui Sun, Keqin Han, Miao Xu, Lujuan Li, Jin Qian, Li Li and Xuejin Li, "Blood viscosity in subjects with type 2 diabetes Mellitus: Roles of hyperglycemia and elevated plasma fibrinogen," 2022, Frontiers in Physiology. 13:827428. doi: 10.3389/fphys.2022.827428. www.frontiersin.org.
Ying Li, Xiu-Xia Tian, Tiemin Liu, Rui-Tao Wang, "Association between whole blood viscosity and arterial stiffness in patients with type 2 diabetes mellitus," Springer published on-line Oct. 14, 2014, Endocrine, DOI: 10.1007/s12020-014-0451-3.
G.E. McVeigh, "Arterial Compliance in Hypertension and Diabetes mellitus," American Journal of Nephrology. 1996; 16:217-222.
"Compliance (physiology)," from Wikipedia, https://en.wikipedia.org/wiki/Compliance_(physiology), printed from web Jan. 10, 2023.
Chenguang Zhao, Dongwei Li, Yuanjun Kong, Hongyu Liu, Yiqing Hu, Haijing Niu, Ole Jensen, Xiaoli Li, Hanli Liu, Yan Song, "Transcranial photobiomodulation enhances visual working memory capacity in humans," Scientific Advances. 8, eqbq3211, pp. 1-12 (2022).
Fabrizio Dos Santos Cardoso, Farzad Salehpour, Norberto Cysne Coimbra, Francisco Gonzalez-Lima and Sergio Gomes Da Silva, "Photobiomodulation for the treatment of neuroinflammation: A systematic review of controlled laboratory animal studies," Frontiers in Neuroscience. (2022) 16:1006031. doi: 10.3389/fnins.2022.1006031.
Fabrizio Dos Santos Cardoso, Douglas W. Barrett, Zachary Wade, Sergio Gomes Da Silva and F. Gonzalez-Lima, "Photobiomodulation for the aging brain," Ageing Research Reviews. 70 (2021) 101415.
Fabrizio Dos Santos Cardoso, Farzad Salehpour, Norberto Cysne Coimbra, Francisco Gonzalez-Lima and Sergio Gomes Da Silva, "Photobiomodulation of cytochrome c oxidase by chronic transcranial laser in young and aged brains," Frontiers in Neuroscience. (2022) 16:818005. doi: 10.3389/fnins.2022.818005.
Agnes S. Chan, Tsz-Lok Lee, Michael R. Hamblin, Mei-Chun Cheung, "Photoneuromodulation makes a difficult cognitive task less arduous," www.nature.com/scientificreports. Science Reports (2021) 11:13688; https://doi.org/10.1038/s41598-021-93228-2.
Celeste L. Saucedo, Emily C. Courtois, Zachary S. Wade, Meghan N. Kelley, Nusha Kheradbin, Douglas W. Barrett, F. Gonzalez-Lima, "Transcranial laser simulation: Mitochondrial and cerebrovascular effects in younger and older healthy adults." Brain Stimulation, 14 (2021) 440-449; http://www.journals.elsevier.com/brain-stimulation.
"The science behind how laser therapy works." https://lightforcemedical.com/photobiomodulation-therapy-pbm/, printed from the web Jan. 18, 2023.
Meeri Kim, "Can low-power light improve working memory?" https://www.optica-opn.org/home/newsroom/2022/december/can_low-power_light_improve_working_memory/, printed from web Jan. 18, 2023.
Christoph F. Geissler, Jorn Schneider, Christian Frings, "Shedding light on the prefrontal correlates of mental workload in simulated driving: a functional near-infrared spectroscopy study," www.nature.com/scientificreports. Scientific Reports (2021) 11:705; https://doi.org/10.1038/s41598-020-80477-w.
Marie Cheour, "Parts of the brain used while driving," written Dec. 5, 2018, https://healthfully.com/parts-of-the-brain-involved-with-hearing-4113334.html, printed from web Jan. 22, 2023.
Hannah J. Foy, Patrick Runham, Peter Chapman, "Prefrontal cortex activation and young driver behavior: a fNIRS study," (2016) PLoS One 11 (5): e0156512. doi: 10.1371/journal.pone.0156512.
Kayoko Yoshino, Noriyuki Oka, Kouji Yamamoto, Hideki Takahashi, and Toshinori Kato, "Correlation of prefrontal cortical activation with changing vehicle speeds in actual driving: a vector-based functional near-infrared spectroscopy study," Frontiers in Human Neuroscience, www.frontiersin.org, Dec. 2013, vol. 7, Article 895; doi: 10.3389/fnhum.2013.00895.
Fangqing Zhengren, George Chernyshov, Dingding Zheng, "Cognitive load assessment from facial temperature using smart eyewear," MDR, Keio University (2020).
Naomi P. Friedman and Trevor W. Robbins, "The role of prefrontal cortex in cognitive control and execution function," Neuropsychopharmacology (2022) 47:72-89; https://doi.org/10.1038/s441386-021-01132-0.
Kanji Matsukawa, Ryota Asahara, Miho Yoshikawa and Kana Endo, "Deactivation of the prefrontal cortex during exposure to pleasantly-charged emotional challenge," www.nature.com/scientificreports. (2018) 8:14540; doi: 10.1038/s41598-018-32752-0.
Hugo Mitre-Hernandez, Jorge Sanchez-Rodriguez, Sergio Nava-Munoz and Carlos Lara-Alvarez, "Classifying the difficulty levels of working memory tasks by using pupillary response," PeerJ 10:e12864; http://doi.org/10.7717/peerj.12864.
Krzysztof Krejtz, Andrew T. Duchowski, Anna Niedzielska, Cezary Biele, Izabela Krejtz, "Eye tracking cognitive load using pupil diameter and microsaccades with fixed gaze," (2018) PLoS One 13 (9): e0203629. https://doi.org/10.1371/journal.pone.0203629.
Hamidur Rahmah, Mobyen Uddin Ahmed, Shaibal Barua, Peter Funk and Shahina Begum, "Vision-based driver's cognitive load classification considering eye movement using machine learning and deep learning," Sensors, 2021, 21, 8019. https://doi.org/10.3390/s21238019.

(56) References Cited

OTHER PUBLICATIONS

Product Document by Ams Osram on "Belago 1.1 Dot-Pattern Infrared Illuminator" Datasheet DS000676, Apr. 21, 2021.
Inter Partes Review No. 2021-00453; Decision Granting Institution of Inter Partes Review of U.S. Pat. No. 10,517,484, *Apple, Inc.* v. *Omni Medsci, Inc.*; pp. 1-50, dated Aug. 6, 2021.
Inter Partes Review No. IPR2020-00175; Judgement Final Written Decision of U.S. Pat. No. 10,188,299; *Apple, Inc.* v. *Omni Medsci, Inc.*; pp. 1-71; dated Jun. 14, 2021.
Inter Partes Review No. IPR2020-00175; Petition for Inter Partes Review of U.S. Pat. No. 10,188,299; *Apple Inc.* v. *Omni Medsci, Inc.*; pp. 1-91; dated Dec. 11, 2019.
Inter Partes Review No. IPR2020-00209; Petition for Inter Partes Review of U.S. Pat. No. 10,213,113; *Apple Inc.* v. *Omni Medsci, Inc.*; pp. 1-91; dated Dec. 11, 2019.
File History for U.S. Pat. No. 10,213,113 issued Feb. 26, 2019, 686 pps.
Declaration of Brian W. Anthony, PhD, regarding U.S. Pat. No. 10,213,113 in IPR2020-00209, Dec. 11, 2019, 101 pps.
United States District Court Eastern District of Texas Marshall Division; *Omni Medsci, Inc.* vs. *Apple Inc.*; Civil Action No. 2:18-cv-00429; Second Amended Complaint; Feb. 26, 2019; 274 pps.
United States District Court Northern District of California Oakland Division; *Omni Medsci, Inc.* vs. *Apple Inc.*; Civil Action No. 19-cv-05673-YGR; Order staying the case; Nov. 20, 2019, 5 pps.
File History for U.S. Pat. No. 10,188,299 issued Jan. 29, 2019, 787 pps.
Declaration of Brian W. Anthony, PhD, regarding U.S. Pat. No. 10188,299 in IPR2020-00175, Dec. 11, 2019, 119 pps.
United States District Court Eastern District of Texas Marshall Division; *Omni Medsci, Inc.* vs. *Apple Inc.*; Civil Action No. 2:18-cv-429; Amended Complaint; Jan. 28, 2019; 169 pps.
Inter Partes Review No. IPR2019-00916; Final Written Decision of U.S. Pat. No. 9,651,533 *Apple Inc.* v. *Omni Medsci, Inc.*; pp. 1-67; dated Oct. 14, 2020.
Miles et al., "Time of Flight Cameras: Principles, Methods, and Applications", Springer, pp. 1-95, Nov. 2012, SpringerBriefs in Computer Science.
Dal Mutto C. et al., "Time-of-Flight Cameras and Microsoft Kinect TM, A user perspective on technology and applications", pp. 1-116, Jan. 24, 2013, published by Springer.
Blum, Robert et al., "GaAs lasers eye multiple targets", www.compoundsemiconductor.net, Jan./Feb. 2013, pp. 61-64, Angel Business Communications.
Inter Partes Review No. IPR2021-00453; Petition for Inter Partes Review of U.S. Pat. No. 10,517,484; *Apple Inc.* v. *Omni Medsci, Inc.*; pp. 1-103; dated Jan. 22, 2021.
File History for U.S. Pat. No. 10,517,484 issued Dec. 24, 2019, 1223 pages.
Declaration of Brian Anthony regarding U.S. Pat. No. 10,517,484 in IPR2021-00453, Jan. 22, 2021, 138 pages.
Affidavit of Process Server, *Omni MedSci, Inc.* v. *Apple Inc.*, No. 3:20-cv-00563-KAW (N.D. Cal.), Jan. 29, 2020, 1 page.
Deposition Transcript of Duncan Leo MacFarlane, Ph.D., P.E., *Apple Inc.* v. *Omni MedSci, Inc.*, IPR2019-00916 (PTAB Apr. 16, 2020), 102 pages.
Omni Preliminary Proposed Claim Constructions, Nov. 1, 2018. Case No. 2:18-cv-134-RWS, 1 page.
Order Granting Motion to Stay Pending Interlocutory Appeal Related to Standing Question, *Omni MedSci, Inc.* v. *Apple Inc.*, No. 20-cv-00563-YGR (N.D. Cal. Apr. 28, 2020), 2 pages.
Claim Construction Memorandum Opinion and Order. Case No. 2:18-CV-000134-RWS (Jun. 24, 2019).
Claim Construction Memorandum Opinion and Order. Case No. 2:18-CV-000429-RWS (Aug. 14, 2019).
Declaration of Brian W. Anthony, PhD regarding U.S. Pat. No. 10,098,546 filed in IPR2020-00029 (Oct. 17, 2019).
Declaration of Brian W. Anthony, PhD regarding U.S. Pat. No. 9,651,533 filed in IPR2019-00913 (Apr. 10, 2019).
Declaration of Brian W. Anthony, PhD regarding U.S. Pat. No. 9,651,533 filed in IPR2019-00916 (Apr. 10, 2019).
Declaration of Brian W. Anthony, PhD regarding U.S. Pat. No. 9,757,040 filed in IPR2019-00910 (Apr. 10, 2019).
Declaration of Brian W. Anthony, PhD regarding U.S. Pat. No. 9,757,040 filed in IPR2019-00917 (Apr. 10, 2019).
Declaration of Brian W. Anthony, PhD regarding U.S. Pat. No. 9,861,286 filed in IPR2019-00911 (Apr. 10, 2019).
Declaration of Brian W. Anthony, PhD regarding U.S. Pat. No. 9,861,286 filed in IPR2019-00914 (Apr. 10, 2019).
Declaration of Brian W. Anthony, PhD regarding U.S. Pat. No. 9,885,698 filed in IPR2019-00912 (Apr. 10, 2019).
Declaration of Brian W. Anthony, PhD regarding U.S. Pat. No. 9,885,698 filed in IPR2019-00915 (Apr. 10, 2019).
File History for U.S. Pat. No. 10,098,546, issued Oct. 16, 2018.
Inter Partes Review No. IPR2020-00029; Petition for Inter Partes Review of U.S. Pat. No. 10,098,546; *Apple Inc.* v. *Omni Medsci, Inc.*; dated Oct. 17, 2019.
Lister et al., Optical properties of human skin (Journal of Biomedical Optics 2012).
Mark Nelson & Jean-Loup Gailly, The Data Compression Book (Cary Sullivan et al. eds.) (2nd ed. 1996).
Newton, H., Newton's Telecom Dictionary (18th ed. 2002).
*Order, Omni MedSci, Inc.* v. *Apple Inc.*, No. 2:18-cv-134-RWS in the United States District Court for the Eastern District of Texas Marshall Division (Aug. 16, 2019), ECF No. 283.
Proof of Service of Summons in *Omni MedSci, Inc.* v. *Apple Inc.*, No. 2:18-cv-429 (E.D. Tex.).

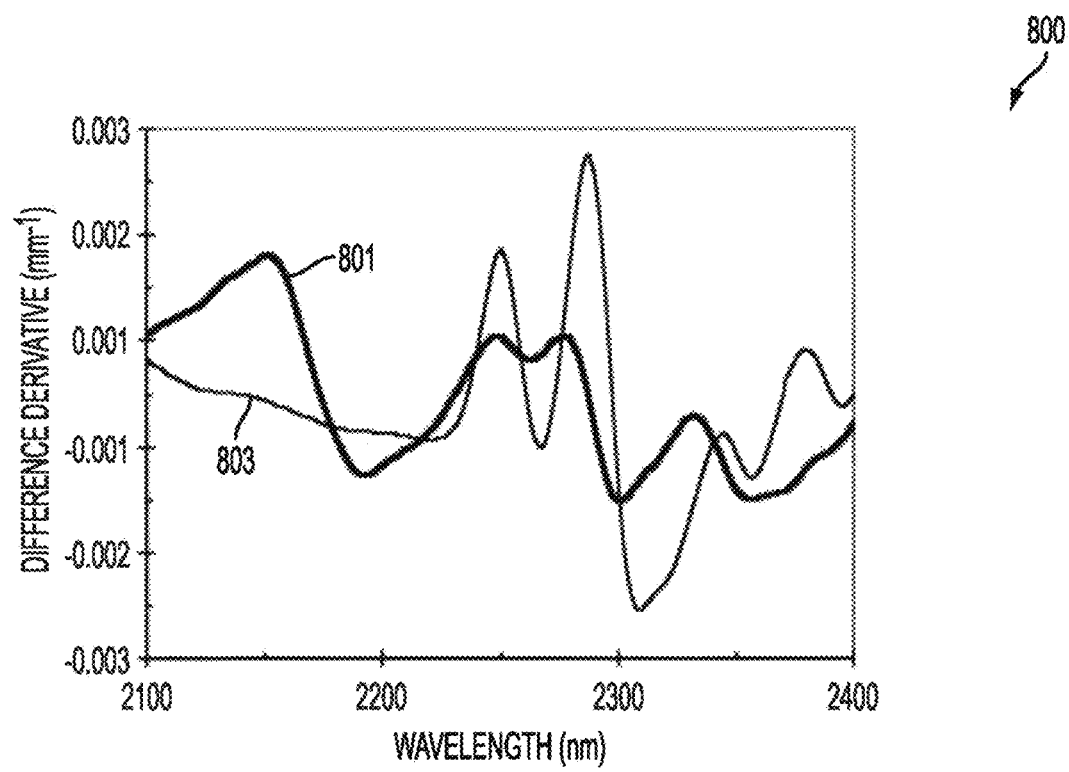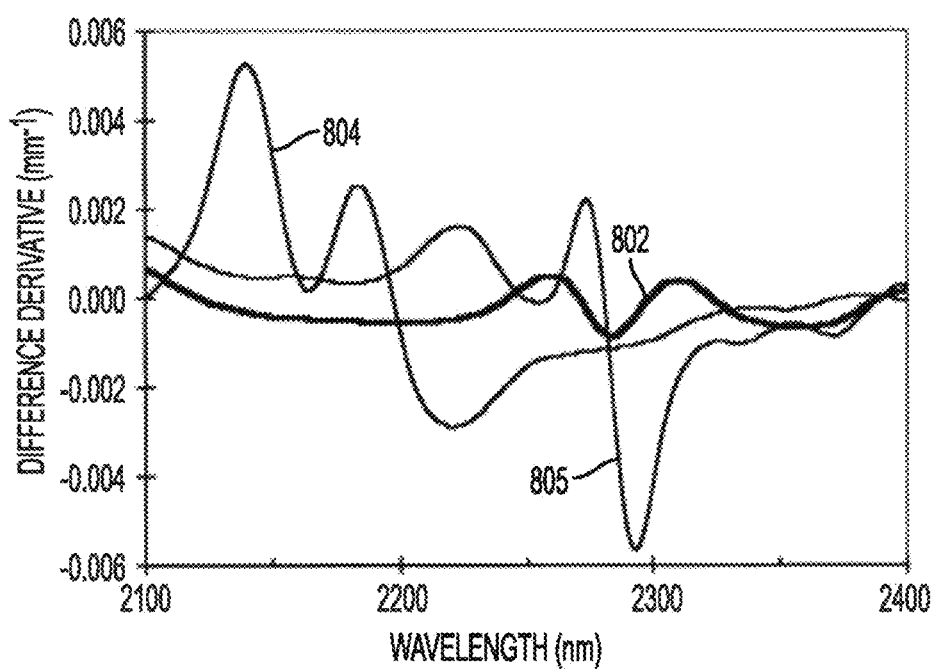
FIG. 8A

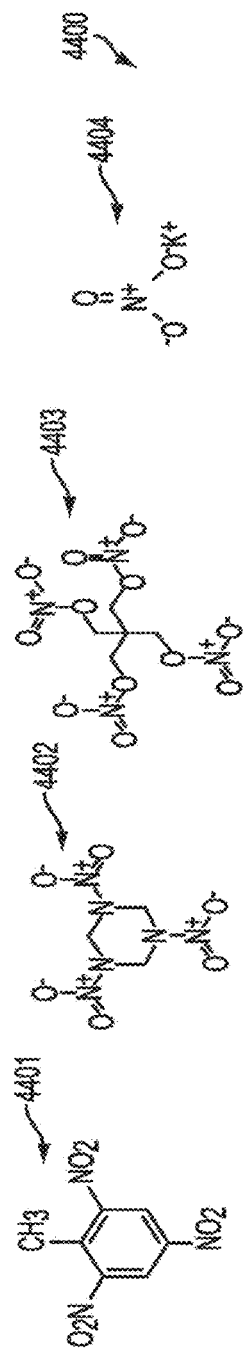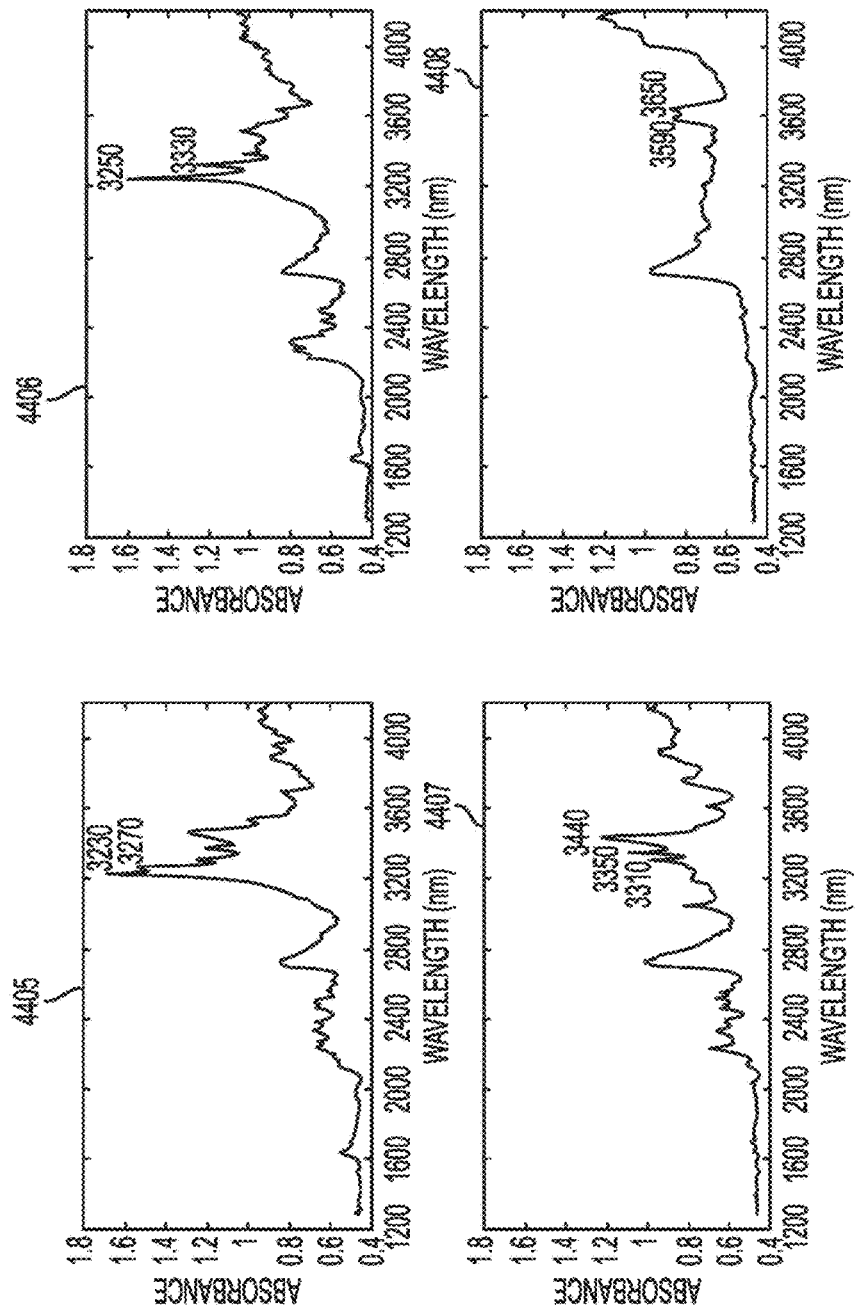
FIG. 44

| TENTATIVE FREQUENCIES OF HEROIN BANDS (nm) | ACTUALLY MEASURED PEAK FREQUENCIES (nm) | FORMS OF MODES OF VIBRATION ASSIGNMENT |
|---|---|---|
| 1160 | 1157 | C—O STRETCH FOURTH OVERTONE |
| 1195 | 1190 | C—H SECOND OVERTONE |
|  | 1200 | C—H SECOND OVERTONE |
| 1360 | 1357 | C—H COMBINATION |
| 1395 | 1391 | C—H COMBINATION |
| 1420 | 1425 | O—H FIRST OVERTONE |
| 1570 | 1570 | N—H STRETCH FIRST OVERTONE |
| 1685 | 1684 | C—H STRETCH FIRST OVERTONE |
| 1705 | 1709 | C—H STRETCH FIRST OVERTONE |
| 1725 | 1727 | C—H STRETCH FIRST OVERTONE |
| 1765 | 1767 | C—H STRETCH FIRST OVERTONE |
| 1780 | 1780 | C—H STRETCH FIRST OVERTONE |
| 1920 | 1914 | C—O STRETCH SECOND OVERTONE |
| 1950 | 1936 | C—O STRETCH SECOND OVERTONE |
| 1990 | 2000 | N—H STRETCH/N—H BEND COMBINATION |
| 2070 | 2074 | N—H DEFORMATION OVERTONE |
| 2090 | 2100 | C—H COMBINATION |
| 2140 | 2135 | C—H STRETCH/C—O STRETCH COMBINATION OR SYM C—H DEFORMATION |
|  | 2144 | C—H STRETCH/C—O STRETCH COMBINATION OR SYM C—H DEFORMATION |

FROM FIG. 58A

| | | |
|---|---|---|
| 2170 | 2172 | ASYMMETRIC C—H STRETCH/C—H DEFORMATION COMBINATION |
| 2180 | 2178 | N—H BEND SECOND OVERTONE OR C—H STRETCH/C—O STRETCH COMBINATION, OR C—O STRETCH C—N STRETCH; N—H IN-PLANE BEND. |
| 2200 | 2194 | CH STRETCH/C—O STRETCH COMBINATION |
| 2280 | 2284 | C—H STRETCH/CH$_2$ DEFORMATION |
| 2300 | 2300 | C—H BEND SECOND OVERTONE |
| 2325 | 2320 | CH STRETCH/CH$_2$ DEFORMATION COMBINATION |
| 2352 | 2352 | CH$_2$ BEND SECOND OVERTONE |
| 2380 | 2384 | C—H STRETCH/C—C STRETCH COMBINATION |
| 2470 | 2454 | C—H COMBINATION OR SYM C—N—C STRETCH OVERTONE |
| 2488 | 2485 | C—H STRETCH/C—C STRETCH COMBINATION |
| 2530 | 2524 | ASYMMETRIC C—N—C STRETCH FIRST OVERTONE |
| 2530 | 2537 | ASYMMETRIC C—N—C STRETCH FIRST OVERTONE |

FIG. 58B

WEARABLE DEVICE FOR DIFFERENTIAL MEASUREMENT ON PULSE RATE AND BLOOD FLOW

CROSS-REFERENCE TO RELATED APPLICATIONS

This application is a continuation of U.S. application Ser. No. 18/899,012 filed Sep. 27, 2024, which is a continuation of U.S. application Ser. No. 18/891,970 filed Sep. 20, 2024, which is a continuation of U.S. application Ser. No. 18/438,144 filed Feb. 9, 2024, now U.S. Pat. No. 12,193,790, which is a continuation of U.S. application Ser. No. 18/103,408 filed Jan. 30, 2023, now U.S. Pat. No. 11,896,346, which is a continuation of U.S. application Ser. No. 17/514,778 filed Oct. 29, 2021, now U.S. Pat. No. 11,564,577, which is a continuation of U.S. application Ser. No. 17/078,771 filed Oct. 23, 2020, now U.S. Pat. No. 11,160,455, which is a continuation of U.S. application Ser. No. 16/722,188 filed Dec. 20, 2019, now U.S. Pat. No. 10,820,807, which is a continuation of U.S. application Ser. No. 16/506,885 filed Jul. 9, 2019, now U.S. Pat. No. 10,517,484, which is a continuation of U.S. application Ser. No. 16/272,069 filed Feb. 11, 2019, now abandoned, which is a continuation of U.S. application Ser. No. 16/029,611 filed Jul. 8, 2018, now U.S. Pat. No. 10,201,283, which is a continuation of U.S. application Ser. No. 15/888,052 filed Feb. 4, 2018 (U.S. Pat. No. 10,136,819), now abandoned, which is a continuation of U.S. application Ser. No. 15/212,549 filed Jul. 18, 2016 (U.S. Pat. No. 9,885,698), now abandoned, which is a continuation of U.S. application Ser. No. 14/650,897 filed Jun. 10, 2015, now U.S. Pat. No. 9,494,567, which is a U.S. National Phase of PCT/US2013/075700 filed Dec. 17, 2013, which claims the benefit of U.S. provisional application Ser. No. 61/747,472 filed Dec. 31, 2012, the disclosures of all of which are hereby incorporated in their entirety by reference herein.

U.S. application Ser. No. 16/506,885, now U.S. Pat. No. 10,517,484, is also a continuation of U.S. application Ser. No. 16/004,359 filed Jun. 9, 2018, now U.S. Pat. No. 11,109,761, which is a continuation of U.S. application Ser. No. 14/109,007 filed Dec. 17, 2013 (now U.S. Pat. No. 9,993,159), which claims the benefit of U.S. provisional application Ser. No. 61/747,553 filed Dec. 31, 2012, the disclosures of all of which are hereby incorporated in their entirety by reference herein.

U.S. application Ser. No. 16/506,885, now U.S. Pat. No. 10,517,484, is also a continuation of U.S. application Ser. No. 16/188,194 filed Nov. 12, 2018 (U.S. Pat. No. 10,386,230), now abandoned, which is a continuation of U.S. application Ser. No. 16/004,154 filed Jun. 8, 2018 (now U.S. Pat. No. 10,126,283), which is a continuation of U.S. application Ser. No. 15/855,201 filed Dec. 27, 2017 (U.S. Pat. No. 9,995,722), now abandoned, which is a continuation of U.S. application Ser. No. 15/711,907 filed Sep. 21, 2017 (U.S. Pat. No. 9,897,584), now abandoned, which is a divisional of U.S. application Ser. No. 15/357,225 filed Nov. 21, 2016 (U.S. Pat. No. 9,797,876), now abandoned, which is a continuation of U.S. application Ser. No. 14/650,981 filed Jun. 10, 2015 (now U.S. Pat. No. 9,500,634), which is the U.S. national phase of PCT Application No. PCT/US2013/075767 filed Dec. 17, 2013, which claims the benefit of U.S. provisional application Ser. No. 61/747,485 filed Dec. 31, 2012, the disclosures of all of which are hereby incorporated by reference in their entirety.

U.S. application Ser. No. 16/506,885, now U.S. Pat. No. 10,517,484, is also a continuation of U.S. application Ser. No. 16/241,628 filed Jan. 7, 2019, now U.S. Pat. No. 10,441,176, which is a continuation of U.S. Ser. No. 16/015,737 filed Jun. 22, 2018 (U.S. Pat. No. 10,172,523), now abandoned, which is a continuation of U.S. Ser. No. 15/594,053 filed May 12, 2017 (U.S. Pat. No. 10,188,299), now abandoned, which is a continuation of U.S. application Ser. No. 14/875,709 filed Oct. 6, 2015 (now U.S. Pat. No. 9,651,533), which is a continuation of U.S. application Ser. No. 14/108,986 filed Dec. 17, 2013 (U.S. Pat. No. 9,164,032), now abandoned, which claims the benefit of U.S. provisional application Ser. No. 61/747,487 filed Dec. 31, 2012, the disclosures of all of which are hereby incorporated in their entirety by reference herein.

U.S. application Ser. No. 16/506,885, now U.S. Pat. No. 10,517,484, is also a continuation of U.S. application Ser. No. 16/284,514 filed Feb. 25, 2019, now abandoned, which is a continuation of U.S. application Ser. No. 16/016,649 filed Jun. 24, 2018 (U.S. Pat. No. 10,213,113), now abandoned, which is a continuation of U.S. application Ser. No. 15/860,065 filed Jan. 2, 2018 (U.S. Pat. No. 10,098,546), now abandoned, which is a continuation of U.S. application Ser. No. 15/686,198 filed Aug. 25, 2017 (U.S. Pat. No. 9,861,286), now abandoned, which is a continuation of U.S. application Ser. No. 15/357,136 filed Nov. 21, 2016 (U.S. Pat. No. 9,757,040), now abandoned, which is a continuation of U.S. application Ser. No. 14/651,367 filed Jun. 11, 2015 (now U.S. Pat. No. 9,500,635), which is the U.S. national phase of PCT Application No. PCT/US2013/075736 filed Dec. 17, 2013, which claims the benefit of U.S. provisional application Ser. No. 61/747,477 filed Dec. 31, 2012 and U.S. provisional application Ser. No. 61/754,698 filed Jan. 21, 2013, the disclosures of all of which are hereby incorporated by reference in their entirety.

This application is related to U.S. provisional application Ser. No. 61/747,477 filed Dec. 31, 2012; Ser. No. 61/747,481 filed Dec. 31, 2012; Ser. No. 61/747,485 filed Dec. 31, 2012; Ser. No. 61/747,487 filed Dec. 31, 2012; Ser. No. 61/747,492 filed Dec. 31, 2012; Ser. No. 61/747,553 filed Dec. 31, 2012; and Ser. No. 61/754,698 filed Jan. 21, 2013, the disclosures of all of which are hereby incorporated in their entirety by reference herein.

This application is also related to International Application PCT/US2013/075736 entitled Short-Wave Infrared Super-Continuum Lasers For Early Detection Of Dental Caries; U.S. application Ser. No. 14/108,995 filed Dec. 17, 2013 entitled Focused Near-Infrared Lasers For Non-Invasive Vasectomy And Other Thermal Coagulation Or Occlusion Procedures (U.S. Pat. App. Pub. No. US2014/0188092A1); International Application PCT/US2013/075767 entitled Short-Wave Infrared Super-Continuum Lasers For Natural Gas Leak Detection, Exploration, And Other Active Remote Sensing Applications; U.S. application Ser. No. 14/108,986 filed Dec. 17, 2013 (U.S. Pat. No. 9,164,032) entitled Short-Wave Infrared Super-Continuum Lasers For Detecting Counterfeit Or Illicit Drugs And Pharmaceutical Process Control; U.S. application Ser. No. 14/108,974 filed Dec. 17, 2013 entitled Non-Invasive Treatment Of Varicose Veins (U.S. Pat. App. Pub. No. US2014/018894A1); and U.S. application Ser. No. 14/109,007 filed Dec. 17, 2013 entitled Near-Infrared Super-Continuum Lasers For Early Detection Of Breast And Other Cancers (now U.S. Pat. No. 9,993,159), the disclosures of all of which are hereby incorporated in their entirety by reference herein.

BACKGROUND

With the growing obesity epidemic, the number of individuals with diabetes is also increasing dramatically. For example, there are over 200 million people who have diabetes. Diabetes control requires monitoring of the glucose level, and most glucose measuring systems available commercially require drawing of blood. Depending on the severity of the diabetes, a patient may have to draw blood and measure glucose four to six times a day. This may be extremely painful and inconvenient for many people. In addition, for some groups, such as soldiers in the battlefield, it may be dangerous to have to measure periodically their glucose level with finger pricks.

Thus, there is an unmet need for non-invasive glucose monitoring (e.g., monitoring glucose without drawing blood). The challenge has been that a non-invasive system requires adequate sensitivity and selectivity, along with repeatability of the results. Yet, this is a very large market, with an estimated annual market of over $10B in 2011 for self-monitoring of glucose levels.

One approach to non-invasive monitoring of blood constituents or blood analytes is to use near-infrared spectroscopy, such as absorption spectroscopy or near-infrared diffuse reflection or transmission spectroscopy. Some attempts have been made to use broadband light sources, such as tungsten lamps, to perform the spectroscopy. However, several challenges have arisen in these efforts. First, many other constituents in the blood also have signatures in the near-infrared, so spectroscopy and pattern matching, often called spectral fingerprinting, is required to distinguish the glucose with sufficient confidence. Second, the non-invasive procedures have often transmitted or reflected light through the skin, but skin has many spectral artifacts in the near-infrared that may mask the glucose signatures. Moreover, the skin may have significant water and blood content. These difficulties become particularly complicated when a weak light source is used, such as a lamp. More light intensity can help to increase the signal levels, and, hence, the signal-to-noise ratio.

As described in this disclosure, by using brighter light sources, such as fiber-based supercontinuum lasers, superluminescent laser diodes, light-emitting diodes or a number of laser diodes, the near-infrared signal level from blood constituents may be increased. By shining light through the teeth, which have fewer spectral artifacts than skin in the near-infrared, the blood constituents may be measured with less interfering artifacts. Also, by using pattern matching in spectral fingerprinting and various software techniques, the signatures from different constituents in the blood may be identified. Moreover, value-add services may be provided by wirelessly communicating the monitored data to a handheld device such as a smart phone, and then wirelessly communicating the processed data to the cloud for storing, processing, and transmitting to several locations.

Dental care and the prevention of dental decay or dental caries has changed in the United States over the past several decades, due to the introduction of fluoride to drinking water, the use of fluoride dentifrices and rinses, application of topical fluoride in the dental office, and improved dental hygiene. Despite these advances, dental decay continues to be the leading cause of tooth loss. With the improvements over the past several decades, the majority of newly discovered carious lesions tend to be localized to the occlusal pits and fissures of the posterior dentition and the proximal contact sites. These early carious lesions may be often obscured in the complex and convoluted topography of the pits and fissures or may be concealed by debris that frequently accumulates in those regions of the posterior teeth. Moreover, such lesions are difficult to detect in the early stages of development.

Dental caries may be a dynamic disease that is characterized by tooth demineralization leading to an increase in the porosity of the enamel surface. Leaving these lesions untreated may potentially lead to cavities reaching the dentine and pulp and perhaps eventually causing tooth loss. Occlusal surfaces (bite surfaces) and approximal surfaces (between the teeth) are among the most susceptible sites of demineralization due to acid attack from bacterial by-products in the biofilm. Therefore, there is a need for detection of lesions at an early stage, so that preventive agents may be used to inhibit or reverse the demineralization.

Traditional methods for caries detection include visual examination and tactile probing with a sharp dental exploration tool, often assisted by radiographic (x-ray) imaging. However, detection using these methods may be somewhat subjective; and, by the time that caries are evident under visual and tactile examination, the disease may have already progressed to an advanced stage. Also, because of the ionizing nature of x-rays, they are dangerous to use (limited use with adults, and even less used with children). Although x-ray methods are suitable for approximal surface lesion detection, they offer reduced utility for screening early caries in occlusal surfaces due to their lack of sensitivity at very early stages of the disease.

Some of the current imaging methods are based on the observation of the changes of the light transport within the tooth, namely absorption, scattering, transmission, reflection and/or fluorescence of light. Porous media may scatter light more than uniform media. Taking advantage of this effect, the Fiber-optic trans-illumination is a qualitative method used to highlight the lesions within teeth by observing the patterns formed when white light, pumped from one side of the tooth, is scattered away and/or absorbed by the lesion. This technique may be difficult to quantify due to an uneven light distribution inside the tooth.

Another method called quantitative light-induced fluorescence-QLF-relies on different fluorescence from solid teeth and caries regions when excited with bright light in the visible. For example, when excited by relatively high intensity blue light, healthy tooth enamel yields a higher intensity of fluorescence than does demineralized enamel that has been damaged by caries infection or any other cause. On the other hand, for excitation by relatively high intensity of red light, the opposite magnitude change occurs, since this is the region of the spectrum for which bacteria and bacterial by-products in carious regions absorb and fluoresce more pronouncedly than do healthy areas. However, the image provided by QLF may be difficult to assess due to relatively poor contrast between healthy and infected areas. Moreover, QLF may have difficulty discriminating between white spots and stains because both produce similar effects. Stains on teeth are commonly observed in the occlusal sites of teeth, and this obscures the detection of caries using visible light.

As described in this disclosure, the near-infrared region of the spectrum offers a novel approach to imaging carious regions because scattering is reduced and absorption by stains is low. For example, it has been demonstrated that the scattering by enamel tissues reduces in the form of $1/(\text{wavelength})^3$, e.g., inversely as the cube of wavelength. By using a broadband light source in the short-wave infrared (SWIR) part of the spectrum, which corresponds approximately to 1400 nm to 2500 nm, lesions in the enamel and dentine may be observed. In one embodiment, intact teeth have low reflection over the SWIR wavelength range. In the presence of caries, the scattering increases, and the scattering is a function of wavelength; hence, the reflected signal decreases with increasing wavelength. Moreover, particularly when caries exist in the dentine region, water build up may occur, and dips in the SWIR spectrum corresponding to the water absorption lines may be observed. The scattering and water absorption as a function of wavelength may thus be used for early detection of caries and for quantifying the degree of demineralization.

SWIR light may be generated by light sources such as lamps, light emitting diodes, one or more laser diodes, super-luminescent laser diodes, and fiber-based super-continuum sources. The SWIR super-continuum light sources advantageously may produce high intensity and power, as well as being a nearly transform-limited beam that may also be modulated. Also, apparatuses for caries detection may include C-clamps over teeth, a handheld device with light input and light detection, which may also be attached to other dental equipment such as drills. Alternatively, a mouth-guard type apparatus may be used to simultaneously illuminate one or more teeth. Fiber optics may be conveniently used to guide the light to the patient as well as to transport the signal back to one or more detectors and receivers.

Remote sensing or hyper-spectral imaging often uses the sun for illumination, and the short-wave infrared (SWIR) windows of about 1.5-1.8 microns and about 2-2.5 microns may be attractive because the atmosphere transmits in these wavelength ranges. Although the sun can be a bright and stable light source, its illumination may be affected by the time-of-day variations in the sun angle as well as weather conditions. For example, the sun may be advantageously used for applications such as hyper-spectral imaging only between about 9 am to 3 μm, and it may be difficult to use the sun during cloudy days or during inclement weather. In one embodiment, the hyper-spectral sensors measure the reflected solar signal at hundreds (e.g., 100 to 200+) contiguous and narrow wavelength bands (e.g., bandwidth between 5 nm and 10 nm). Hyper-spectral images may provide spectral information to identify and distinguish between spectrally similar materials, providing the ability to make proper distinctions among materials with only subtle signature differences. In the SWIR wavelength range, numerous gases, liquids and solids have unique chemical signatures, particularly materials comprising hydro-carbon bonds, O—H bonds, N—H bonds, etc. Therefore, spectroscopy in the SWIR may be attractive for stand-off or remote sensing of materials based on their chemical signature, which may complement other imaging information.

A SWIR super-continuum (SC) source may be able to replace at least in part the sun as an illumination source for active remote sensing, spectroscopy, or hyper-spectral imaging. In one embodiment, reflected light spectroscopy may be implemented using the SWIR light source, where the spectral reflectance can be the ratio of reflected energy to incident energy as a function of wavelength. Reflectance varies with wavelength for most materials because energy at certain wavelengths may be scattered or absorbed to different degrees. Using a SWIR light source may permit 24/7 detection of solids, liquids, or gases based on their chemical signatures. As an example, natural gas leak detection and exploration may require the detection of methane and ethane, whose primary constituents include hydro-carbons. In the SWIR, for instance, methane and ethane exhibit various overtone and combination bands for vibrational and rotational resonances of hydro-carbons. In one embodiment, diffuse reflection spectroscopy or absorption spectroscopy may be used to detect the presence of natural gas. The detection system may include a gas filter correlation radiometer, in a particular embodiment. Also, one embodiment of the SWIR light source may be an all-fiber integrated SWIR SC source, which leverages the mature technologies from the telecommunications and fiber optics industry. Beyond natural gas, active remote sensing in the SWIR may also be used to identify other materials such as vegetation, greenhouse gases or environmental pollutants, soils and rocks, plastics, illicit drugs, counterfeit drugs, firearms and explosives, paints, and various building materials.

Counterfeiting of pharmaceuticals is a significant issue in the healthcare community as well as for the pharmaceutical industry worldwide. For example, according to the World Health Organization, in 2006 the market for counterfeit drugs worldwide was estimated at around $43 Billion. Moreover, the use of counterfeit medicines may result in treatment failure or even death. For instance, in 1995 dozens of children in Haiti and Nigeria died after taking counterfeit medicinal syrups that contained diethylene glycol, an industrial solvent. As another example, in Asia one report estimated that 90% of Viagra sold in Shanghai, China, was counterfeit. With more pharmaceuticals being purchased through the internet, the problem of counterfeit drugs coming from across the borders into the United States has been growing rapidly.

A rapid, non-destructive, non-contact optical method for screening or identification of counterfeit pharmaceuticals is needed. Spectroscopy using near-infrared or short-wave infrared (SWIR) light may provide such a method, because most pharmaceuticals comprise organic compounds that have overtone or combination absorption bands in this wavelength range (e.g., between approximately 1-2.5 microns). Moreover, most drug packaging materials are at least partially transparent in the near-infrared or SWIR, so that drug compositions may be detected and identified through the packaging non-destructively. Also, using a near-infrared or SWIR light source with a spatially coherent beam permits screening at stand-off or remote distances. Beyond identifying counterfeit drugs, the near-infrared or SWIR spectroscopy may have many other beneficial applications. For example, spectroscopy may be used for rapid screening of illicit drugs or to implement process analytical technology in pharmaceutical manufacturing. There are also a wide array of applications in assessment of quality in the food industry, including screening of fruit, vegetables, grains and meats.

In one embodiment, a near-infrared or SWIR super-continuum (SC) source may be used as the light source for spectroscopy, active remote sensing, or hyper-spectral imaging. One embodiment of the SWIR light source may be an all-fiber integrated SWIR SC source, which leverages the mature technologies from the telecommunications and fiber optics industry. Exemplary fiber-based super-continuum sources may emit light in the near-infrared or SWIR between approximately 1.4-1.8 microns, 2-2.5 microns, 1.4-2.4 microns, 1-1.8 microns, or any number of other bands. In particular embodiments, the detection system may be a dispersive spectrometer, a Fourier transform infrared spectrometer, or a hyper-spectral imaging detector or camera. In addition, reflection or diffuse reflection light spectroscopy may be implemented using the SWIR light source, where the spectral reflectance can be the ratio of reflected energy to incident energy as a function of wavelength.

Breast cancer is considered to be the most common cancer among women in industrialized countries. It is believed that early diagnosis and consequent therapy could significantly reduce mortality. Mammography is considered the gold standard among imaging techniques in diagnosing breast pathologies. However, the use of ionizing radiation in mammography may have adverse effects and lead to other complications. Moreover, screening x-ray mammography may be limited by false positives and negatives, leading to unnecessary physical and psychological morbidity. Although breast cancer is one of the focuses of this disclosure, the same techniques may also be applied to other cancer types, including, for example, skin, prostate, brain, pancreatic, and colorectal cancer.

Diagnostic methods for assessment and therapy follow-up of breast cancer include mammography, ultrasound, and magnetic resonance imaging. The most effective screening technique at this time is x-ray mammography, with an overall sensitivity for breast cancer detection around 75%, which is even further reduced in women with dense breasts to around 62%. Moreover, x-ray mammography has a 22% false positive rate in women under 50, and the method cannot accurately distinguish between benign and malignant tumors. Magnetic resonance imaging and ultrasound are sometimes used to augment x-ray mammography, but they have limitations such as high cost, low throughput, limited specificity and low sensitivity. Thus, there is a continued need to detect cancers earlier for treatment, missed by mammography, and to add specificity to the procedures.

Optical breast imaging may be an attractive technique for breast cancer to screen early, augment with mammography, or use in follow-on treatments. Also, optical breast imaging may be performed by intrinsic tissue contrast alone (e.g., hemoglobin, water, collagen, and lipid content), or with the use of exogenous fluorescent probes that target specific molecules. For example, near-infrared (NIR) light may be used to assess optical properties, where the absorption and scattering by the tissue components may change with carcinoma. For most of the studies conducted to date, NIR light in the wavelength range of 600-1000 nm has been used for sufficient tissue penetration; these wavelengths have permitted imaging up to several centimeters deep in soft tissue. Optical breast imaging using fluorescent contrast agents may improve lesion contrast and may potentially permit detection of changes in breast tissue earlier. In one embodiment, the fluorescent probes may either bind specifically to certain targets associated with cancer or may non-specifically accumulate at the tumor site.

Optical methods of imaging and spectroscopy can be non-invasive using non-ionizing electromagnetic radiation, and these techniques could be exploited for screening of wide populations and for therapy monitoring. "Optical mammography" may be a diffuse optical imaging technique that aims at detecting breast cancer, characterizing its physiological and pathological state, and possibly monitoring the efficacy of the therapeutic treatment. The main constituents of breast tissue may be lipid, collagen, water, blood, and other structural proteins. These constituents may exhibit marked and characteristic absorption features in the NIR wavelength range. Thus, diffuse optical imaging and spectroscopy in the NIR may be helpful for diagnosing and monitoring breast cancer. Another advantage of such imaging is that optical instruments tend to be portable and more cost effective as compared to other instrumentation that is conventionally used for medical diagnosis. This can be particularly true, if the mature technologies for telecommunications and fiber optics are exploited.

Spectroscopy using NIR or short-wave infrared (SWIR) light may be beneficial, because most tissue has organic compounds that have overtone or combination absorption bands in this wavelength range (e.g., between approximately 0.8-2.5 microns). In one embodiment, a NIR or SWIR super-continuum (SC) laser that is an all-fiber integrated source may be used as the light source for diagnosing cancerous tissue. Exemplary fiber-based super-continuum sources may emit light in the NIR or SWIR between approximately 1.4-1.8 microns, 2-2.5 microns, 1.4-2.4 microns, 1-1.8 microns, or any number of other bands. In particular embodiments, the detection system may be one or more photo-detectors, a dispersive spectrometer, a Fourier transform infrared spectrometer, or a hyper-spectral imaging detector or camera. In addition, reflection or diffuse reflection light spectroscopy may be implemented using the SWIR light source, where the spectral reflectance can be the ratio of reflected energy to incident energy as a function of wavelength.

For breast cancer, experiments have shown that with growing cancer the collagen content increases while the lipid content decreases. Therefore, early breast cancer detection may involve the monitoring of absorption or scattering features from collagen and lipids. In addition, NIR spectroscopy may be used to determine the concentrations of hemoglobin, water, as well as oxygen saturation of hemoglobin and optical scattering properties in normal and cancerous breast tissue. For optical imaging to be effective, it may also be desirable to select the wavelength range that leads to relatively high penetration depths into the tissue. In one embodiment, it may be advantageous to use optical wavelengths in the range of about 1000-1400 nm. In another embodiment, it may be advantageous to use optical wavelengths in the range of about 1600-1800 nm. Higher optical power densities may be used to increase the signal-to-noise ratio of the detected light through the diffuse scattering tissue, and surface cooling or focused light may be beneficial for preventing pain or damage to the skin and outer layer surrounding the breast tissue. Since optical energy may be non-ionizing, different exposure times may be used without danger or harmful radiation.

SUMMARY

According to one aspect of this disclosure, an apparatus is disclosed that is adapted to be worn by a user. The apparatus comprises one or more biosensors adapted to be placed on the user, wherein one or more physiological parameters are measured, wherein measuring of the one or more physiological parameters comprises a differential measurement, and wherein the one or more physiological parameters comprises a pulse rate monitoring and a blood flow measurement. The apparatus also comprises a light source comprising a plurality of light emitting diodes that are configured to generate an output optical light having one or more optical wavelengths. The apparatus also comprises one or more lenses configured to receive at least a portion of the output optical light and to deliver a lens output light to tissue comprising skin. The apparatus further comprises a detection system configured to receive at least a portion of the lens output light reflected from the tissue and to generate an output signal is indicative of the one or more physiological parameters that has a signal-to-noise ratio. The detection system is configured to be synchronized to the light source, comprises a plurality of detectors that are spatially separated from each other, and at least one analog to digital converter is coupled to at least one of the plurality of detectors. The apparatus is configured to increase the signal-to-noise ratio by increasing light intensity of at least one of the plurality of light emitting diodes from an initial light intensity. The detection system further configured to generate a first signal responsive to light received while the light emitting diodes are off, generate a second signal responsive to light received while at least one of the light emitting diodes is on, and increase the signal-to-noise ratio by comparing the first signal and the second signal. The apparatus is at least in part configured to determine, based at least in part on the output signal, that the apparatus is being worn by the user.

According to another aspect of this disclosure, a wearable device configured to be worn by a user. The wearable device comprises a light source configured to be on or off, responsive to the light source being on, the light source generates an output light, a lens positioned to direct at least a portion of the output light towards a bodily tissue of the user, a detector; and The processor is configured to be responsive to (1) the light source being on and the detector receiving at least a portion of the output light that is reflected from the bodily tissue of the user, generate a first output signal having a first signal-to-noise ratio; (2) responsive to the light source being off and the detector receiving ambient light, generate a second output signal having a second signal-to-noise ratio; (3) generate a third output signal using at least a portion of the first output signal and at least a portion of the second output signal, the third output signal having a third signal-to-noise ratio that is greater than the first signal-to-noise ratio and greater than the second signal-to-noise ratio, the third output signal being associated with a physiological parameter of the user; and (4) determine, based at least in part on the third output signal, that the wearable device is being worn by the user.

According to a further aspect of this disclosure, a system is disclosed for a device worn by a user. The system comprises a light source comprising a plurality of light emitting diodes that are configured to generate an output optical light having one or more optical wavelengths. One or more lenses configured to receive at least a portion of the output optical light and to direct a lens output light towards a bodily tissue of the user. A detection system configured to receive at least a portion of the lens output light reflected from the bodily tissue and to generate an output signal having a signal-to-noise ratio. The detection system is configured to be synchronized to the light source. The signal-to-noise ratio of the output signal is increased by increasing light intensity of at least one of the plurality of light emitting diodes from an initial light intensity. The detection system comprises a plurality of detectors that are spatially separated from each other. At least one analog to digital converter is coupled to at least one of the plurality of detectors. The output signal is associated with one or more physiological parameters. The detection system is configured to generate a first signal responsive to light received while the light emitting diodes are off The detection system is configured to generate a second signal responsive to light received while at least one of the light emitting diodes is on. The detection system is configured to increase the signal-to-noise ratio by comparing the first signal and the second signal. The detection system is configured to measure the one or more physiological parameters when worn by the user. One or more physiological parameters change in response to stretching of a hand of the user, movement of a finger of the user, or movement of a thumb of the user, and wherein the device is at least in part configured to determine, based at least in part on the output signal, that the device is being worn by the user.

BRIEF DESCRIPTION OF THE DRAWINGS

For a more complete understanding of the present disclosure, and for further features and advantages thereof, reference is now made to the following description taken in conjunction with the accompanying drawings, in which:

FIG. 8A shows the first derivative spectra of ketone and protein at concentrations of 10 g/L (left). In addition, the first derivative spectra of urea, creatinine, and glucose are shown on the right at concentrations of 10 g/L.

FIG. 44 illustrates the chemical structure and molecular formula for various explosives, along with the absorbance spectra obtained using a super-continuum source.

FIG. 58A lists possible band assignments for the various spectral features in pure heroin.

FIG. 58B also lists possible band assignments for the various spectral features in pure heroin.

DETAILED DESCRIPTION

Figure 1:
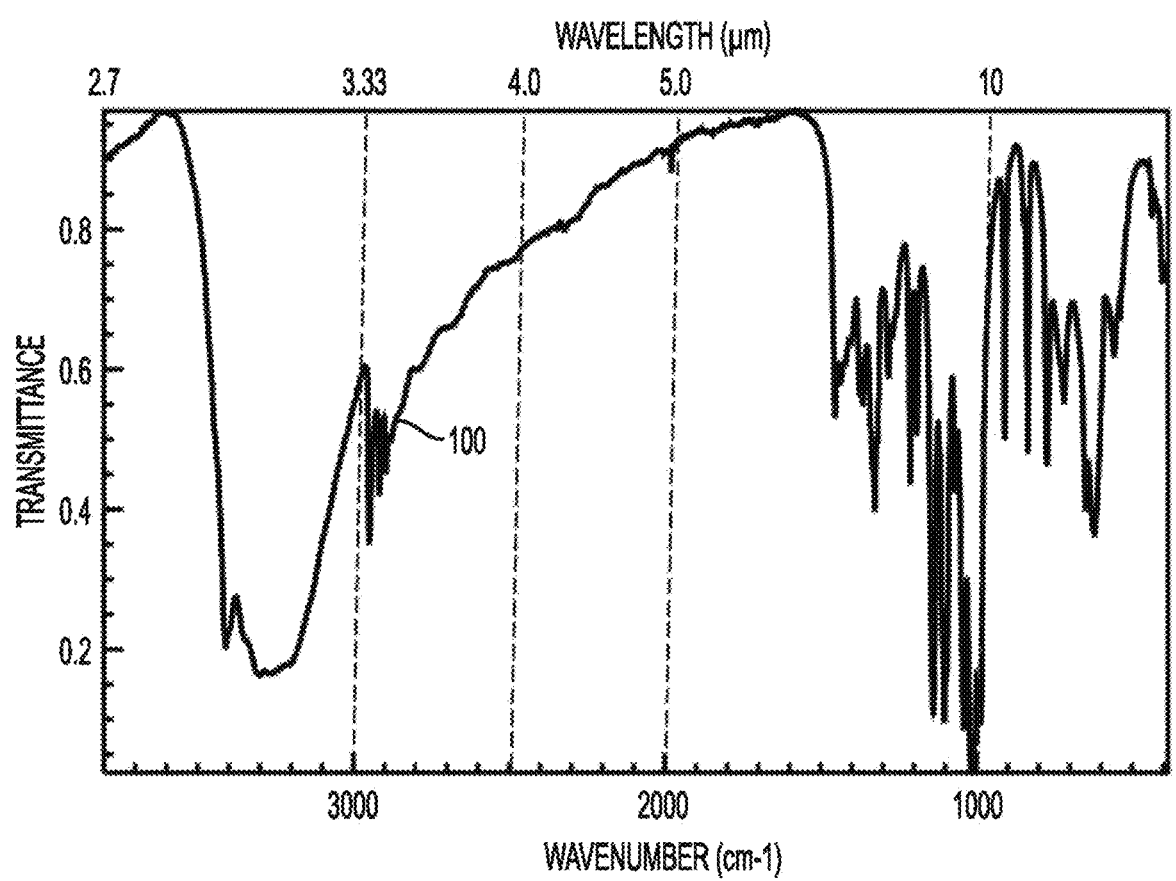
FIG. 1 plots the transmittance versus wavenumber for glucose in the mid-wave and long-wave infrared wavelengths between approximately 2.7 to 12 microns.

Section 1: Near-Infrared Lasers for Non-Invasive Monitoring of Glucose, Ketones, HbA1C, and Other Blood Constituents As required, detailed embodiments of the present disclosure are described herein; however, it is to be understood that the disclosed embodiments are merely exemplary of the disclosure that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present disclosure.

Various ailments or diseases may require measurement of the concentration of one or more blood constituents. For example, diabetes may require measurement of the blood glucose and HbA1c levels. On the other hand, diseases or disorders characterized by impaired glucose metabolism may require the measurement of ketone bodies in the blood. Examples of impaired glucose metabolism diseases include Alzheimer's, Parkinson's, Huntington's, and Lou Gehrig's or amyotrophic lateral sclerosis (ALS). Techniques related to near-infrared spectroscopy or hyper-spectral imaging may be particularly advantageous for non-invasive monitoring of some of these blood constituents.

As used throughout this document, the term "couple" and or "coupled" refers to any direct or indirect communication between two or more elements, whether or not those elements are physically connected to one another. As used throughout this disclosure, the term "spectroscopy" means that a tissue or sample is inspected by comparing different features, such as wavelength (or frequency), spatial location, transmission, absorption, reflectivity, scattering, refractive index, or opacity. In one embodiment, "spectroscopy" may mean that the wavelength of the light source is varied, and the transmission, absorption or reflectivity of the tissue or sample is measured as a function of wavelength. In another embodiment, "spectroscopy" may mean that the wavelength dependence of the transmission, absorption or reflectivity is compared between different spatial locations on a tissue or sample. As an illustration, the "spectroscopy" may be performed by varying the wavelength of the light source, or by using a broadband light source and analyzing the signal using a spectrometer, wavemeter, or optical spectrum analyzer.

As used throughout this document, the term "fiber laser" refers to a laser or oscillator that has as an output light or an optical beam, wherein at least a part of the laser comprises an optical fiber. For instance, the fiber in the "fiber laser" may comprise one of or a combination of a single mode fiber, a multi-mode fiber, a mid-infrared fiber, a photonic crystal fiber, a doped fiber, a gain fiber, or, more generally, an approximately cylindrically shaped waveguide or light-pipe. In one embodiment, the gain fiber may be doped with rare earth material, such as ytterbium, erbium, and/or thulium. In another embodiment, the mid-infrared fiber may comprise one or a combination of fluoride fiber, ZBLAN fiber, chalcogenide fiber, tellurite fiber, or germanium doped fiber. In yet another embodiment, the single mode fiber may include standard single-mode fiber, dispersion shifted fiber, non-zero dispersion shifted fiber, high-nonlinearity fiber, and small core size fibers.

As used throughout this disclosure, the term "pump laser" refers to a laser or oscillator that has as an output light or an optical beam, wherein the output light or optical beam is coupled to a gain medium to excite the gain medium, which in turn may amplify another input optical signal or beam. In one particular example, the gain medium may be a doped fiber, such as a fiber doped with ytterbium, erbium or thulium. In one embodiment, the "pump laser" may be a fiber laser, a solid state laser, a laser involving a nonlinear crystal, an optical parametric oscillator, a semiconductor laser, or a plurality of semiconductor lasers that may be multiplexed together. In another embodiment, the "pump laser" may be coupled to the gain medium by using a fiber coupler, a dichroic mirror, a multiplexer, a wavelength division multiplexer, a grating, or a fused fiber coupler.

As used throughout this document, the term "super-continuum" and or "supercontinuum" and or "SC" refers to a broadband light beam or output that comprises a plurality of wavelengths. In a particular example, the plurality of wavelengths may be adjacent to one-another, so that the spectrum of the light beam or output appears as a continuous band when measured with a spectrometer. In one embodiment, the broadband light beam may have a bandwidth of at least 10 nm. In another embodiment, the "super-continuum" may be generated through nonlinear optical interactions in a medium, such as an optical fiber or nonlinear crystal. For example, the "super-continuum" may be generated through one or a combination of nonlinear activities such as four-wave mixing, the Raman effect, modulational instability, and self-phase modulation.

As used throughout this disclosure, the terms "optical light" and or "optical beam" and or "light beam" refer to photons or light transmitted to a particular location in space. The "optical light" and or "optical beam" and or "light beam" may be modulated or unmodulated, which also means that they may or may not contain information. In one embodiment, the "optical light" and or "optical beam" and or "light beam" may originate from a fiber, a fiber laser, a laser, a light emitting diode, a lamp, a pump laser, or a light source.

Spectrum for Glucose

One molecule of interest is glucose. The glucose molecule has the chemical formula C6H12O6, so it has a number of hydro-carbon bonds. An example of the infrared transmittance of glucose 100 is illustrated in FIG. 1. The vibrational spectroscopy shows that the strongest lines for bending and stretching modes of C—H and O—H bonds lie in the wavelength range of approximately 6-12 microns. However, light sources and detectors are more difficult in the mid-wave infrared and long-wave infrared, and there is also strongly increasing water absorption in the human body beyond about 2.5 microns. Although weaker, there are also non-linear combinations of stretching and bending modes between about 2 to 2.5 microns, and first overtone of C—H stretching modes between approximately 1.5-1.8 microns. These signatures may fall in valleys of water absorption, permitting non-invasive detection through the body. In addition, there are yet weaker features from the second overtones and higher-order combinations between about 0.8-1.2 microns; in addition to being weaker, these features may also be masked by absorption in the hemoglobin. Hence, the short-wave infrared (SWIR) wavelength range of approximately 1.4 to 2.5 microns may be an attractive window for near-infrared spectroscopy of blood constituents.

Figure 2:
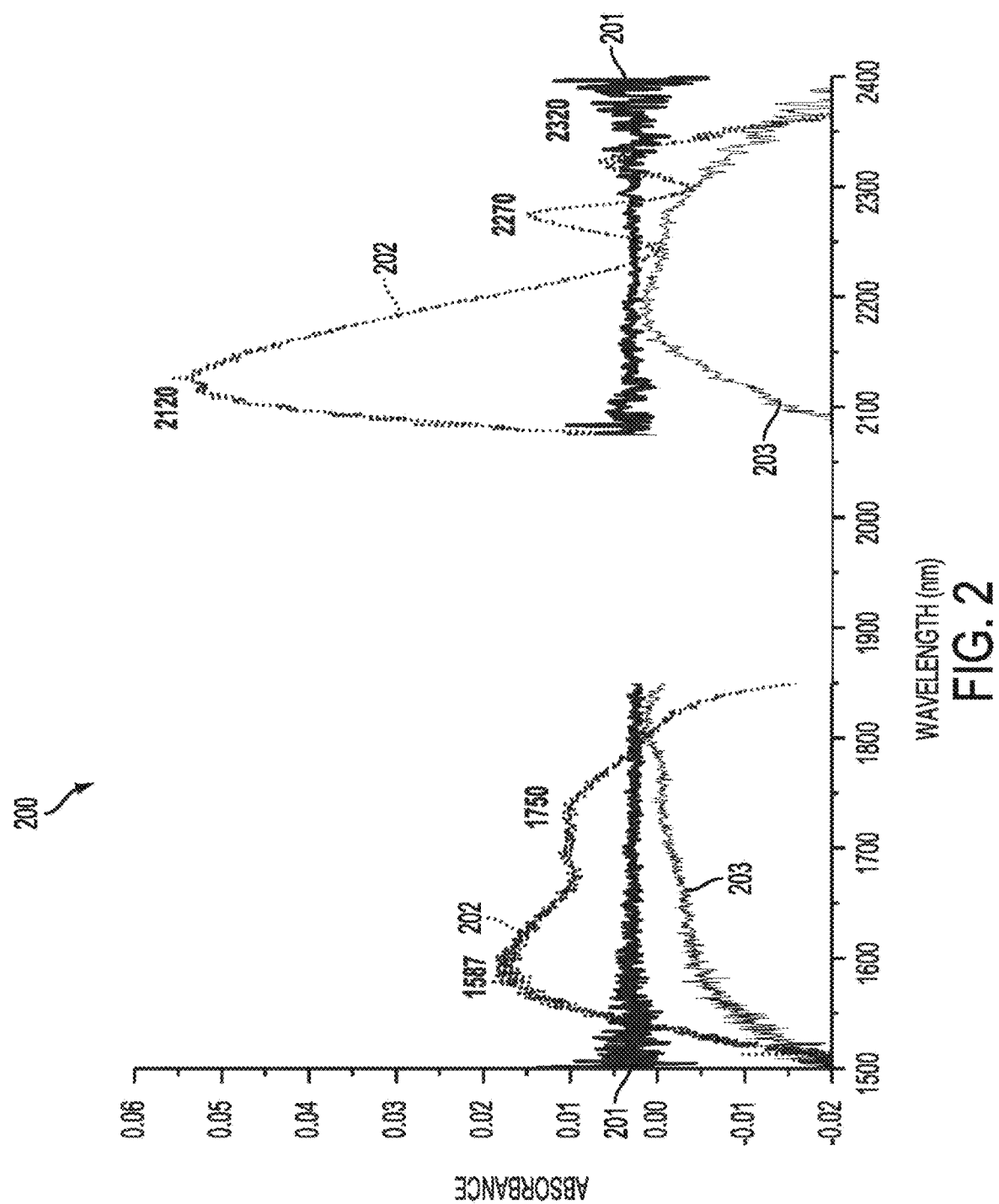
FIG. 2 illustrates measurements of the absorbance of different blood constituents, such as glucose, hemoglobin, and hemoglobin A1c. The measurements are done using an FTIR spectrometer in samples with a 1 mm path length.

As an example, measurements of the optical absorbance 200 of hemoglobin, glucose and HbA1c have been performed using a Fourier-Transform Infrared Spectrometer-FTIR. As FIG. 2 shows, in the SWIR wavelength range hemoglobin is nearly flat in spectrum 201 (the noise at the edges is due to the weaker light signal in the measurements). On the other hand, the glucose absorbance 202 has at least five distinct peaks near 1587 nm, 1750 nm, 2120 nm, 2270 nm and 2320 nm.

Figure 3A:
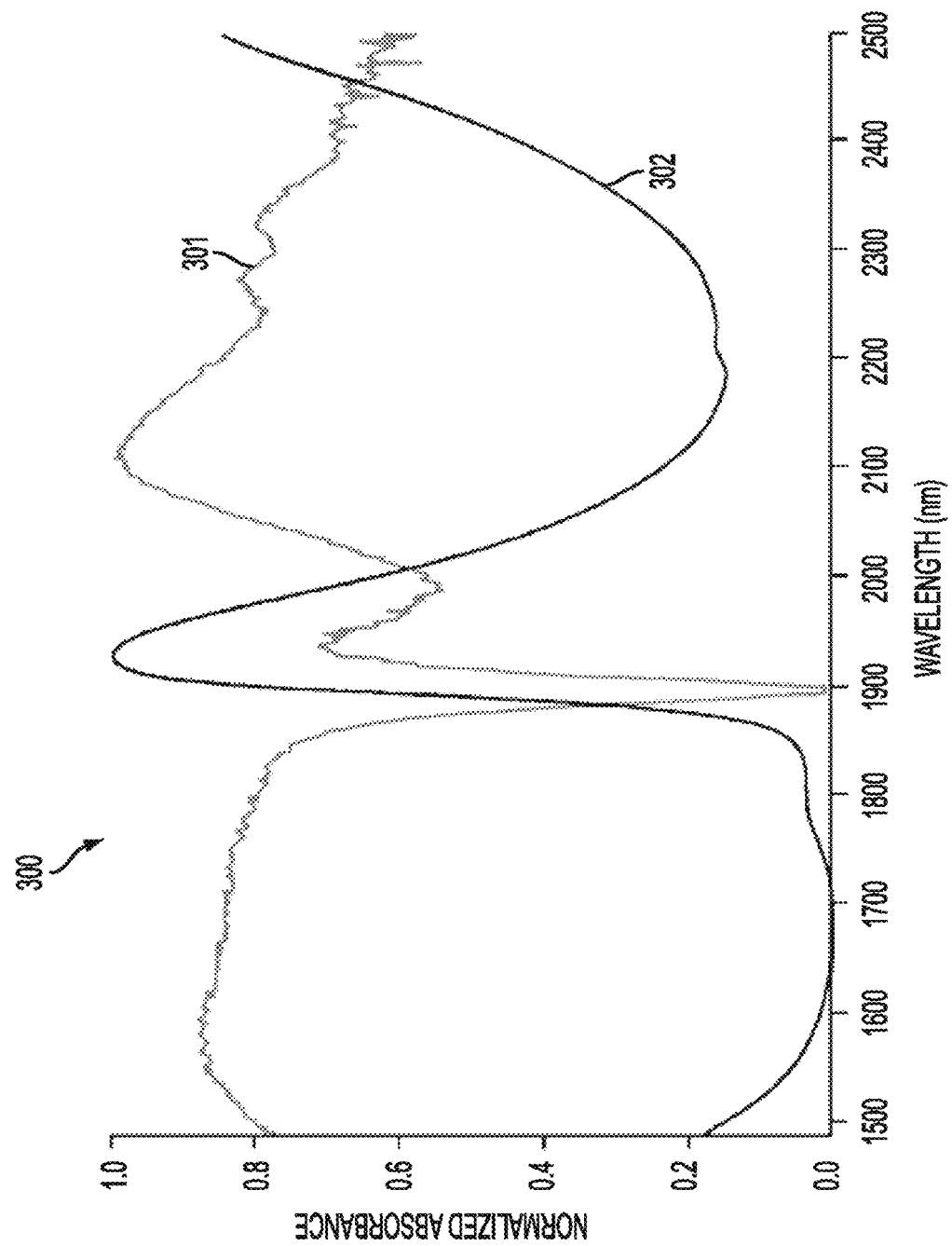
FIG. 3A shows the normalized absorbance of water and glucose (not drawn to scale). Water shows transmission windows between about 1500-1850 nm and 2050-2500 nm.
Figure 3B:
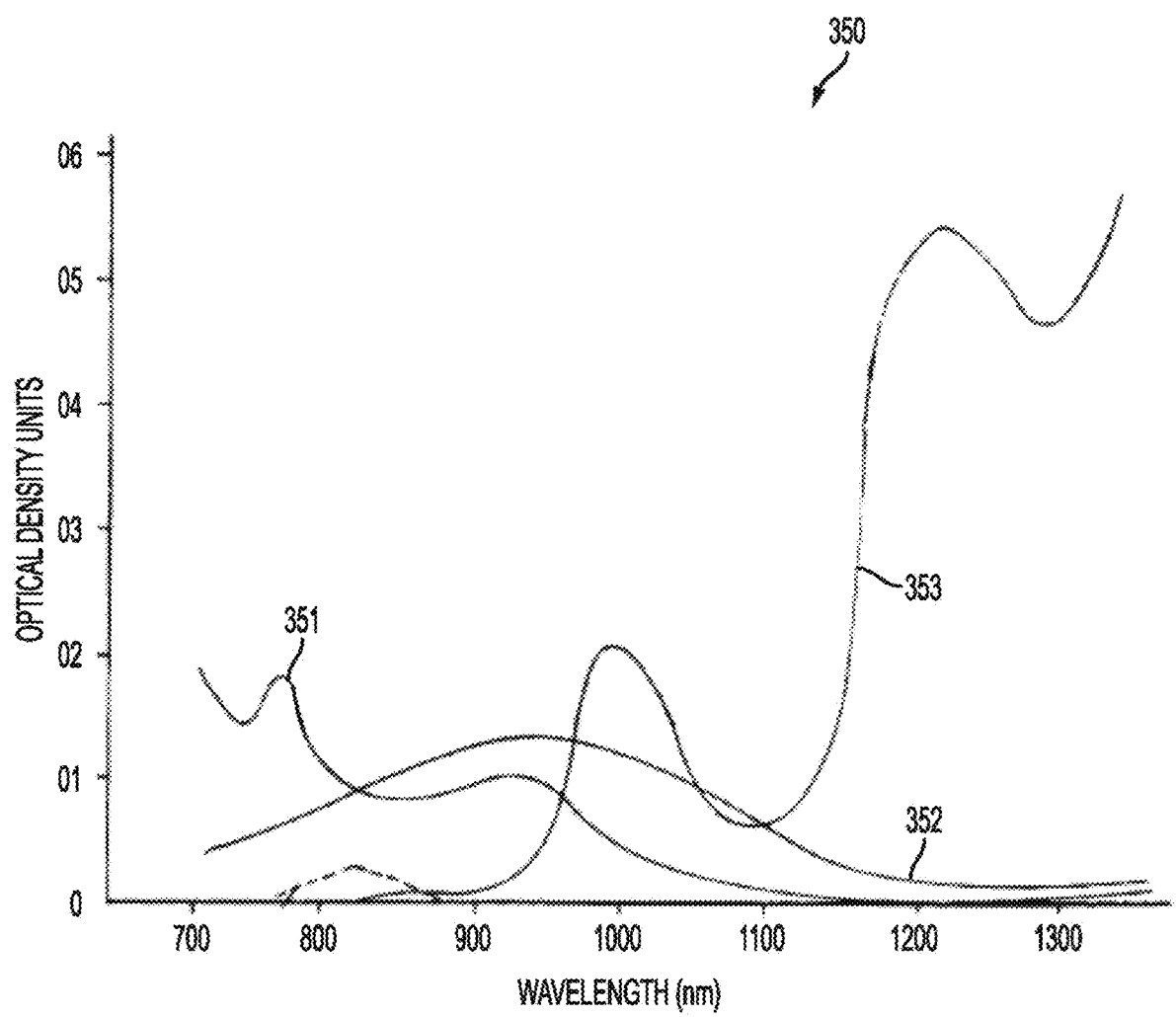
FIG. 3B illustrates the absorbance of hemoglobin and oxygenated hemoglobin overlapped with water.

FIG. 3A overlaps 300 the normalized absorbance of glucose 301 with the absorbance of water 302 (not drawn to scale). It may be seen that water has an absorbance feature between approximately 1850 nm and 2050 nm, but water 302 also has a nice transmission window between approximately 1500-1850 nm and 2050 to 2500 nm. For wavelengths less than about 1100 nm, the absorption of hemoglobin 351 and oxygenated hemoglobin 352 in FIG. 3B has a number of features 350, which may make it more difficult to measure blood constituents. Also, beyond 2500 nm the water absorption becomes considerably stronger over a wide wavelength range. Therefore, an advantageous window for measuring glucose and other blood constituents may be in the SWIR between 1500 and 1850 nm and 2050 to 2500 nm. These are exemplary wavelength ranges, and other ranges can be used that would still fall within the scope of this disclosure.

One further consideration in choosing the laser wavelength is known as the "eye safe" window for wavelengths longer than about 1400 nm. In particular, wavelengths in the eye safe window may not transmit down to the retina of the eye, and therefore, these wavelengths may be less likely to create permanent eye damage. The near-infrared wavelengths have the potential to be dangerous, because the eye cannot see the wavelengths (as it can in the visible), yet they can penetrate and cause damage to the eye. Even if a practitioner is not looking directly at the laser beam, the practitioner's eyes may receive stray light from a reflection or scattering from some surface. Hence, it can always be a good practice to use eye protection when working around lasers. Since wavelengths longer than about 1400 nm are substantially not transmitted to the retina or substantially absorbed in the retina, this wavelength range is known as the eye safe window. For wavelengths longer than 1400 nm, in general only the cornea of the eye may receive or absorb the light radiation.

Figure 4A:
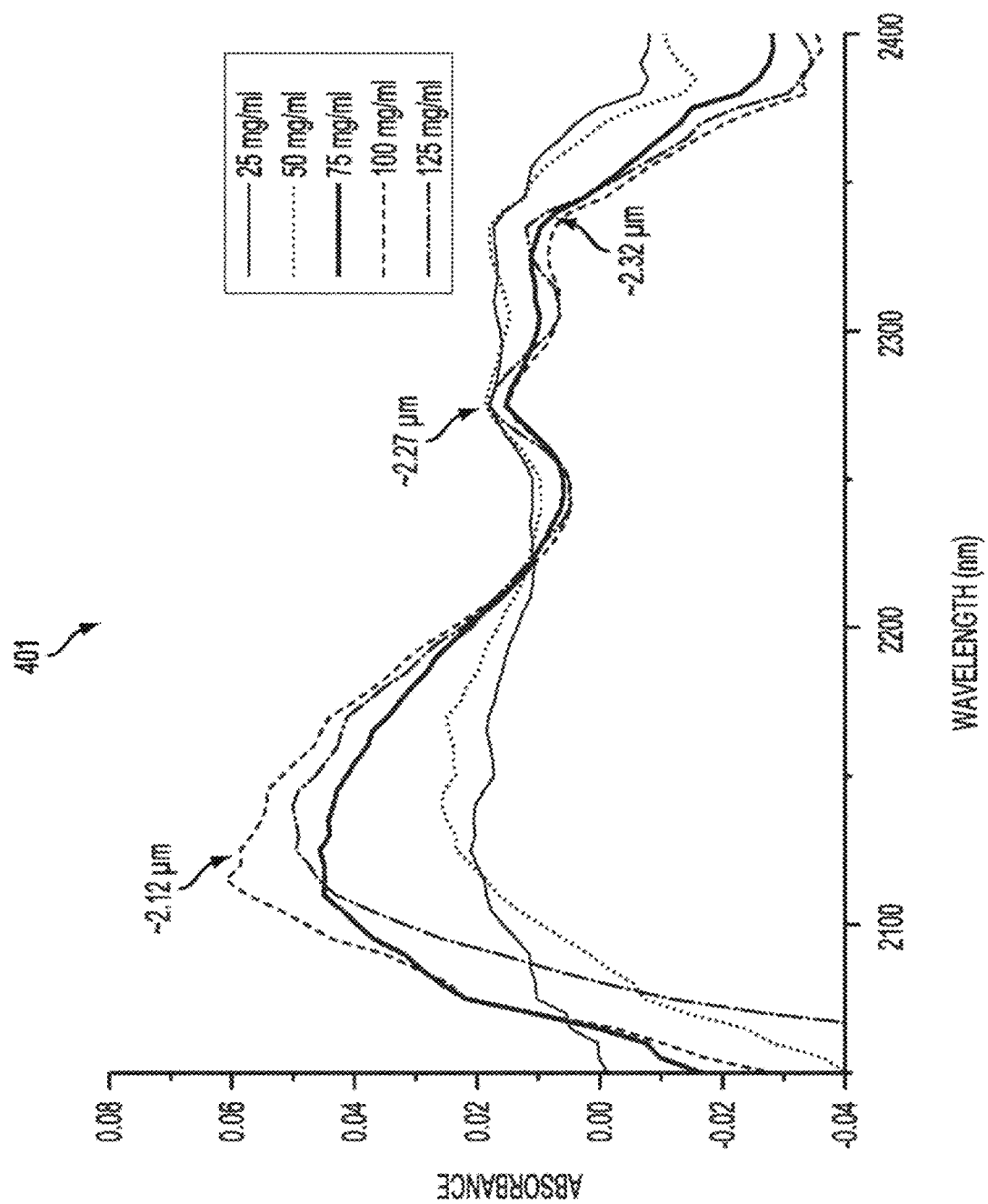
FIG. 4A shows measured absorbance in different concentrations of glucose solution over the wavelength range of about 2000 to 2400 nm. This data is collected using a SWIR super-continuum laser with the sample path length of about 1.1 mm.
Figure 4B:
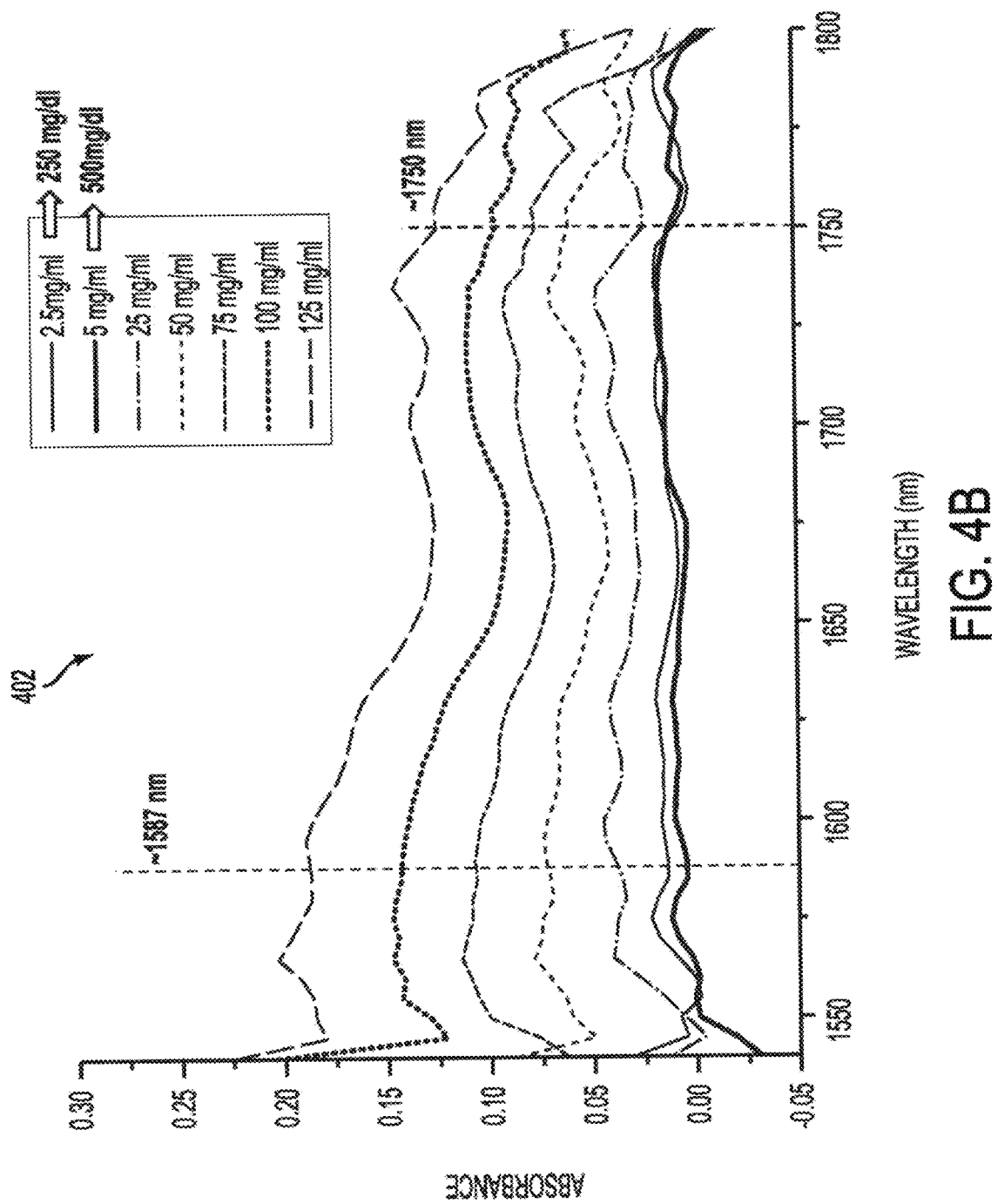
FIG. 4B illustrates measured absorbance in different concentrations of glucose solution over the wavelength range of about 1550 to 1800 nm. The data is collected using a SWIR super-continuum laser with a sample path length of about 10 mm.

Beyond measuring blood constituents such as glucose using FTIR spectrometers, measurements have also been conducted in another embodiment using super-continuum lasers, which will be described later in this disclosure. In this particular embodiment, some of the exemplary preliminary data for glucose absorbance are illustrated in FIGS. 4A and 4B. The optical spectra 401 in FIG. 4A for different levels of glucose concentration in the wavelength range between 2000 and 2400 nm show the three absorption peaks near 2120 nm (2.12 µm), 2270 nm (2.27 µm) and 2320 nm (2.32 µm). Moreover, the optical spectra 402 in FIG. 4B for different levels of glucose concentration in the wavelength range between 1500 and 1800 nm show the two broader absorption peaks near 1587 nm and 1750 nm. It should be appreciated that although data measured with FTIR spectrometers or super-continuum lasers have been illustrated, other light sources can also be used to obtain the data, such as super-luminescent laser diodes, light emitting diodes, a plurality of laser diodes, or even bright lamp sources that generate adequate light in the SWIR.

Figure 5:
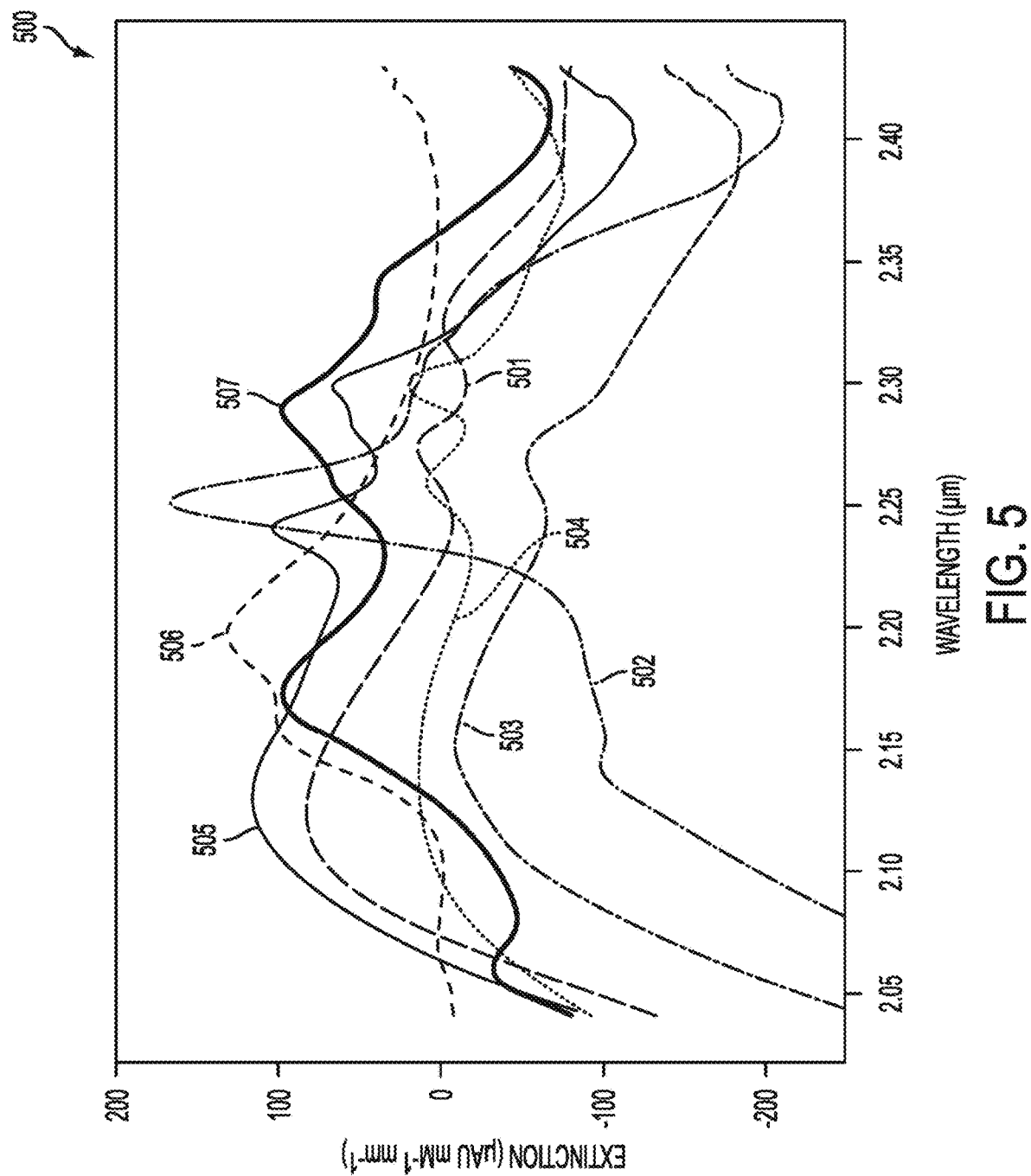
FIG. 5 illustrates the spectrum for different blood constituents in the wavelength range of about 2 to 2.45 microns (2000 to 2450 nm).

Although glucose has a distinctive signature in the SWIR wavelength range, one problem of non-invasive glucose monitoring is that many other blood constituents also have hydro-carbon bonds. Consequently, there can be interfering signals from other constituents in the blood. As an example, FIG. 5 illustrates the spectrum 500 for different blood constituents in the wavelength range of 2 to 2.45 microns. The glucose absorption spectrum 501 can be unique with its three peaks in this wavelength range. However, other blood constituents such as triacetin 502, ascorbate 503, lactate 504, alanine 505, urea 506, and BSA 507 also have spectral features in this wavelength range. To distinguish the glucose 501 from these overlapping spectra, it may be advantageous to have information at multiple wavelengths. In addition, it may be advantageous to use pattern matching algorithms and other software and mathematical methods to identify the blood constituents of interest. In one embodiment, the spectrum may be correlated with a library of known spectra to determine the overlap integrals, and a threshold function may be used to quantify the concentration of different constituents. This is just one way to perform the signal processing, and many other techniques, algorithms, and software may be used and would fall within the scope of this disclosure.

Ketone Bodies Monitoring

Beyond glucose, there are many other blood constituents that may also be of interest for health or disease monitoring. In another embodiment, it may be desirous to monitor the level of ketone bodies in the blood stream. Ketone bodies are three water-soluble compounds that are produced as by-products when fatty acids are broken down for energy in the liver. Two of the three are used as a source of energy in the heart and brain, while the third is a waste product excreted from the body. In particular, the three endogenous ketone bodies are acetone, acetoacetic acid, and beta-hydroxybutyrate or 3-hydroxybutyrate, and the waste product ketone body is acetone.

Ketone bodies may be used for energy, where they are transported from the liver to other tissues. The brain may utilize ketone bodies when sufficient glucose is not available for energy. For instance, this may occur during fasting, strenuous exercise, low carbohydrate, ketogenic diet and in neonates. Unlike most other tissues that have additional energy sources such as fatty acids during periods of low blood glucose, the brain cannot break down fatty acids and relies instead on ketones. In one embodiment, these ketone bodies are detected.

Ketone bodies may also be used for reducing or eliminating symptoms of diseases or disorders characterized by impaired glucose metabolism. For example, diseases associated with reduced neuronal metabolism of glucose include Parkinson's disease, Alzheimer's disease, amyotrophic lateral sclerosis (ALS, also called Lou Gehrig's disease), Huntington's disease and epilepsy. In one embodiment, monitoring of alternate sources of ketone bodies that may be administered orally as a dietary supplement or in a nutritional composition to counteract some of the glucose metabolism impairments is performed. However, if ketone bodies supplements are provided, there is also a need to monitor the ketone level in the blood stream. For instance, if elevated levels of ketone bodies are present in the body, this may lead to ketosis; hyperketonemia is also an elevated level of ketone bodies in the blood. In addition, both acetoacetic acid and beta-hydroxybutyric acid are acidic, and, if levels of these ketone bodies are too high, the pH of the blood may drop, resulting in ketoacidosis.

The general formula for ketones is $C_nH_{2n}O$. In organic chemistry, a ketone is an organic compound with the structure $RC(=O)R'$, where R and R' can be a variety of carbon-containing substituents. It features a carbonyl group (C=O) bonded to two other carbon atoms. Because the ketones contain the hydrocarbon bonds, there might be expected to be features in the SWIR, similar in structure to those found for glucose.

Figure 6:
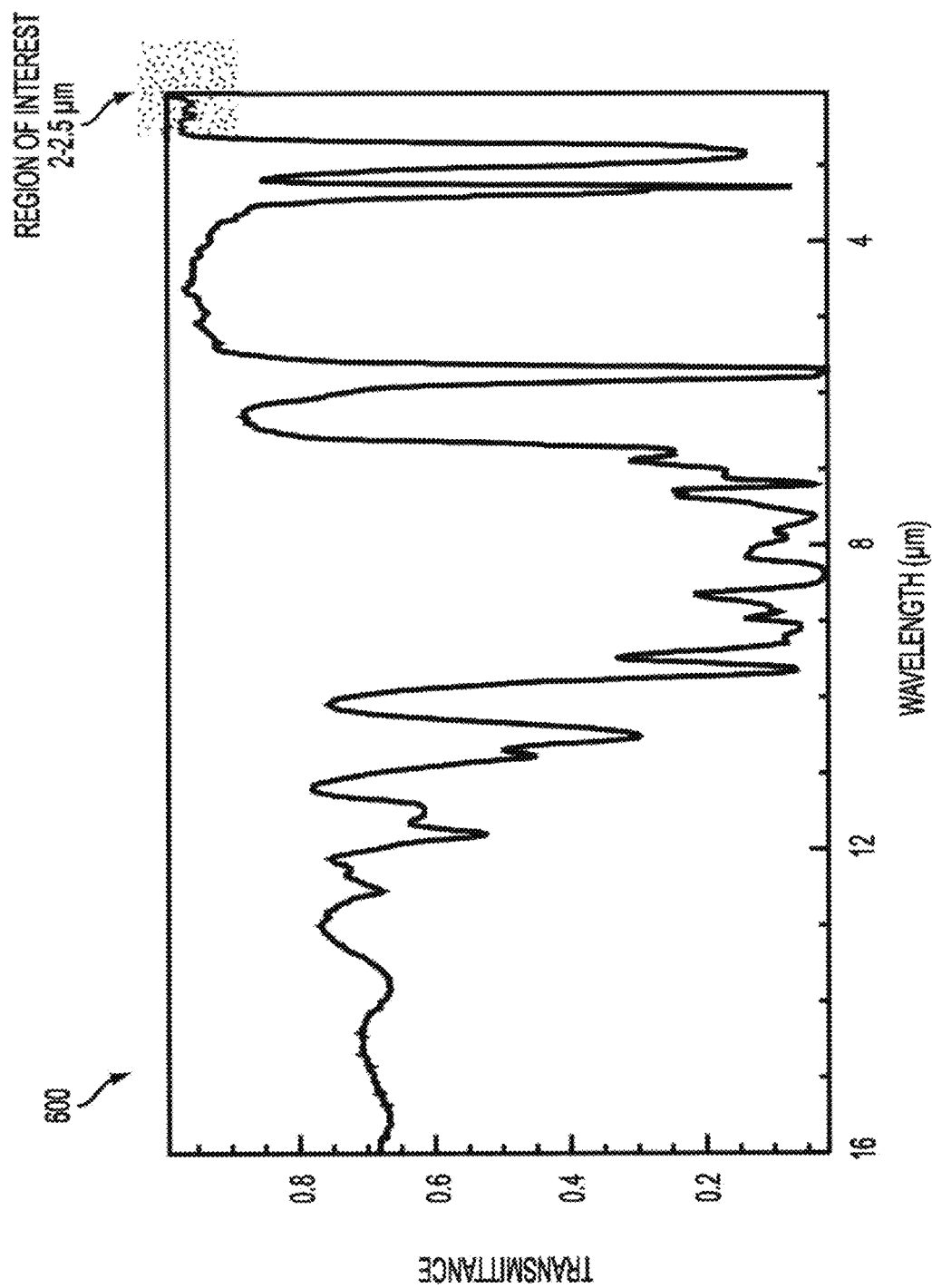
FIG. 6 shows the transmittance versus wavelength in microns for the ketone 3-hydroxybutyrate. The wavelength range is approximately 2 to 16 microns.

The infrared spectrum 600 for the ketone 3-hydroxybutyrate is illustrated in FIG. 6. Just as in glucose, there are significant features in the mid- and long-wave infrared between 6 to 12 microns, but these may be difficult to observe non-invasively. On the other hand, there are some features in the SWIR that may be weaker, but they could potentially be observed non-invasively, perhaps through blood and water.

Figure 7:
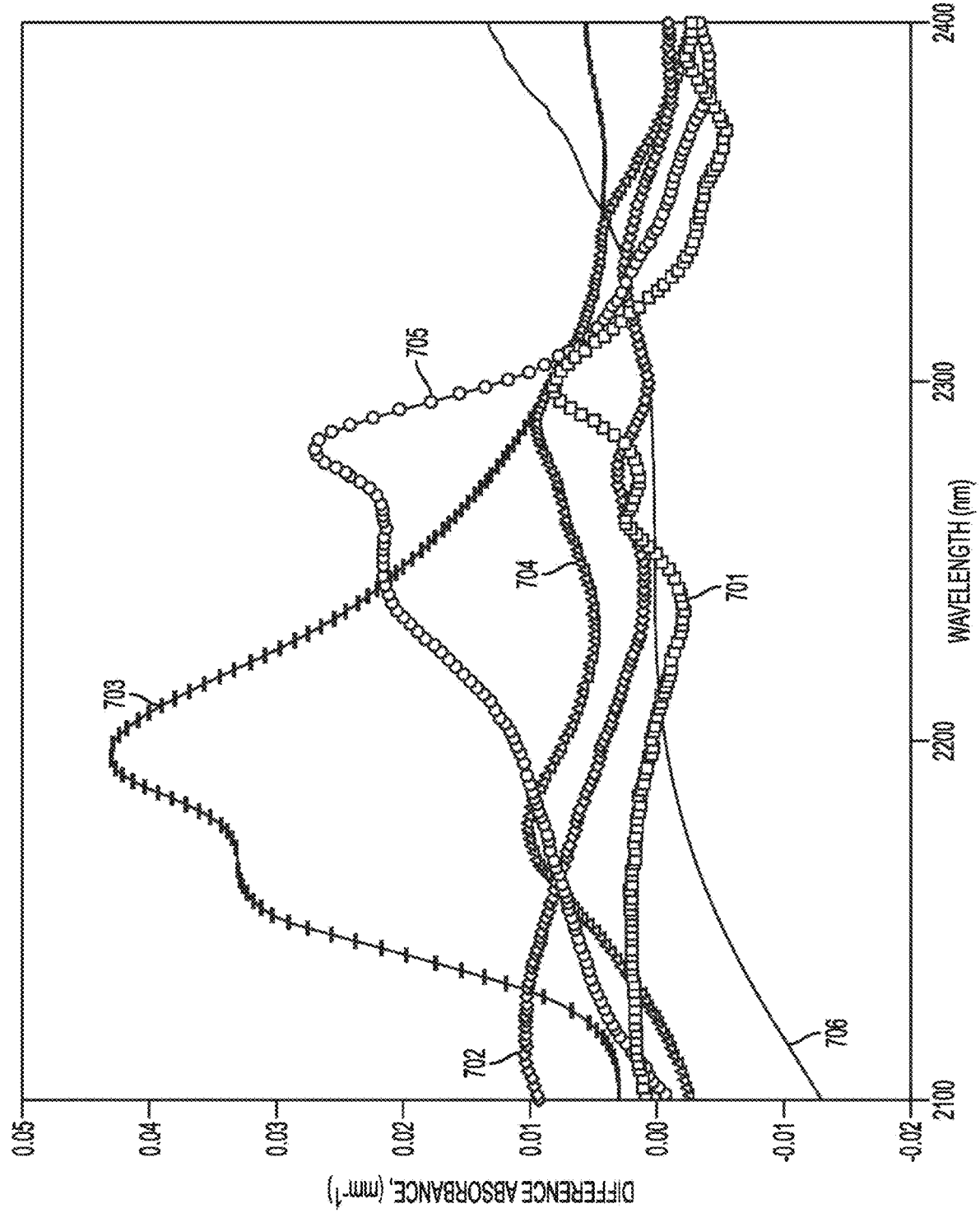
FIG. 7 illustrates the optical absorbance for ketones as well as some other blood constituents in the wavelength range of about 2100 to 2400 nm.

The optical spectra 700 for ketones as well as some other blood constituents are exemplified in FIG. 7 in the wavelength range of 2100 nm to 2400 nm. In this embodiment, the absorbance for ketones is 701, while the absorbance for glucose is 702. However, there are also features in this wavelength range for other blood constituents, such as urea 703, albumin or blood protein 704, creatinine 705, and nitrite 706. In this wavelength range of 2100 to 2400 nm, the features for ketone 701 seem more spectrally pronounced than even glucose.

Different signal processing techniques can be used to enhance the spectral differences between different constituents. In one embodiment, the first or second derivatives of the spectra may enable better discrimination between substances. The first derivative may help remove any flat offset or background, while the second derivative may help to remove any sloped offset or background. In some instances, the first or second derivative may be applied after curve fitting or smoothing the reflectance, transmittance, or absorbance. For example, FIG. 8A illustrates the derivative spectra for ketone 801 and glucose 802, which can be distinguished from the derivative spectra for protein 803, urea 804 and creatinine 805. Based on FIG. 8A, it appears that ketones 801 may have a more pronounced difference than even glucose 802 in the wavelength range between 2100 and 2400 nm. Therefore, ketone bodies should also be capable of being monitored using a non-invasive optical technique in the SWIR, and a different pattern matching library could be used for glucose and ketones.

Hemoglobin A1c Monitoring

Another blood constituent that may be of interest for monitoring of health or diseases is hemoglobin A1c, also known as HbA1c or glycated hemoglobin (glycol-hemoglobin or glycosylated hemoglobin). HbA1c is a form of hemoglobin that is measured primarily to identify the average plasma glucose concentration over prolonged periods of time. Thus, HbA1c may serve as a marker for average blood glucose levels over the previous months prior to the measurements.

In one embodiment, when a physician suspects that a patient may be diabetic, the measurement of HbA1c may be one of the first tests that are conducted. An HbA1c level less than approximately 6% may be considered normal. On the other hand, an HbA1c level greater than approximately 6.5% may be considered to be diabetic. In diabetes mellitus, higher amounts of HbA1c indicate poorer control of blood glucose levels. Thus, monitoring the HbA1c in diabetic patients may improve treatment. Current techniques for measuring HbA1c require drawing blood, which may be inconvenient and painful. The point-of-care devices use immunoassay or boronate affinity chromatography, as an example. Thus, there is also an unmet need for non-invasive monitoring of HbA1c.

FIG. 2 illustrates the FTIR measurements of HbA1c absorbance 203 over the wavelength range between 1500 and 2400 nm for a concentration of approximately 1 mg/ml. Whereas the absorbance of hemoglobin 201 over this wavelength range is approximately flat, the HbA1c absorbance 203 shows broad features and distinct curvature. Although the HbA1c absorbance 203 does not appear to exhibit as pronounced features as glucose 202, the non-invasive SWIR measurement should be able to detect HbA1c with appropriate pattern matching algorithms. Moreover, the spectrum for HbA1c may be further enhanced by using first or second derivative data, as seen for ketones in FIG. 8A. Beyond absorption, reflectance, or transmission spectroscopy, it may also be possible to detect blood constituents such as HbA1c using Raman spectroscopy or surface-enhanced Raman spectroscopy. In general, Raman spectroscopy may require higher optical power levels.

As an illustration, non-invasive measurement of blood constituents such as glucose, ketone bodies, and HbA1c has been discussed thus far. However, other blood constituents can also be measured using similar techniques, and these are also intended to be covered by this disclosure. In other embodiments, blood constituents such as proteins, albumin, urea, creatinine or nitrites could also be measured. For instance, the same type of SWIR optical techniques might be used, but the pattern matching algorithms and software could use different library features or functions for the different constituents.

Figure 8B:
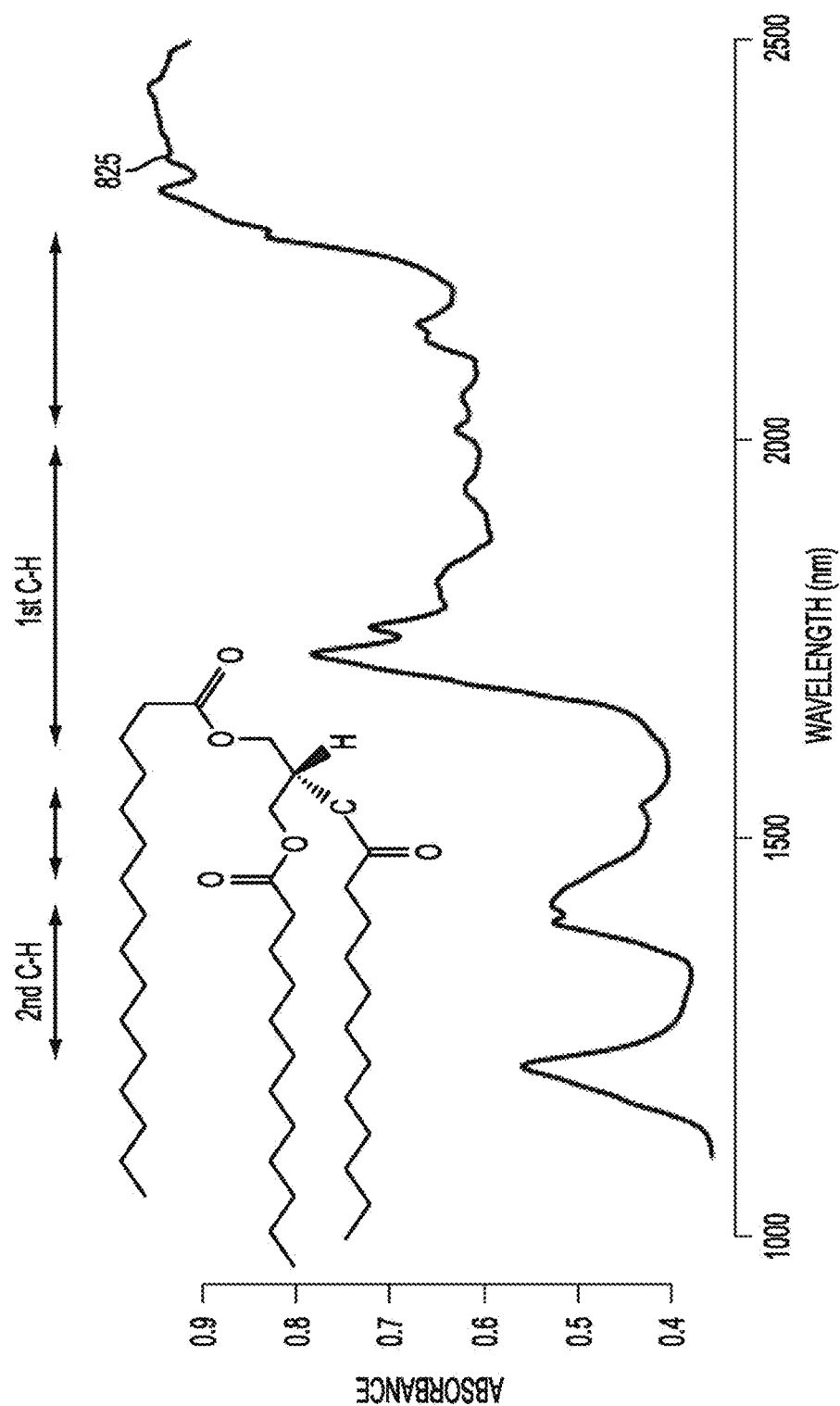
FIG. 8B illustrates the near infrared absorbance for triglyceride.

In yet another embodiment, the optical techniques described in this disclosure could also be used to measure levels of triglycerides. Triglycerides are bundles of fats that may be found in the blood stream, particularly after ingesting meals. The body manufactures triglycerides from carbohydrates and fatty foods that are eaten. In other words, triglycerides are the body's storage form of fat. Triglycerides are comprised of three fatty acids attached to a glycerol molecule, and measuring the level of triglycerides may be important for diabetics. The triglyceride levels or concentrations in blood may be rated as follows: desirable or normal may be less than 150 mg/dl; borderline high may be 150-199 mg/dl; high may be 200-499 mg/dl; and very high may be 500 mg/dl or greater. FIG. 8B illustrates one example of the near-infrared absorbance 825 for triglycerides. There are distinct absorbance peaks in the spectrum that should be measurable. The characteristic absorption bands may be assigned as follows: (a) the first overtones of C—H stretching vibrations (1600-1900 nm); (b) the region of second overtones of C—H stretching vibrations (1100-1250 nm); and, (c) two regions (2000-2200 nm and 1350-1500 nm) that comprise bands due to combinations of C—H stretching vibrations and other vibrational modes.

Figure 8C:
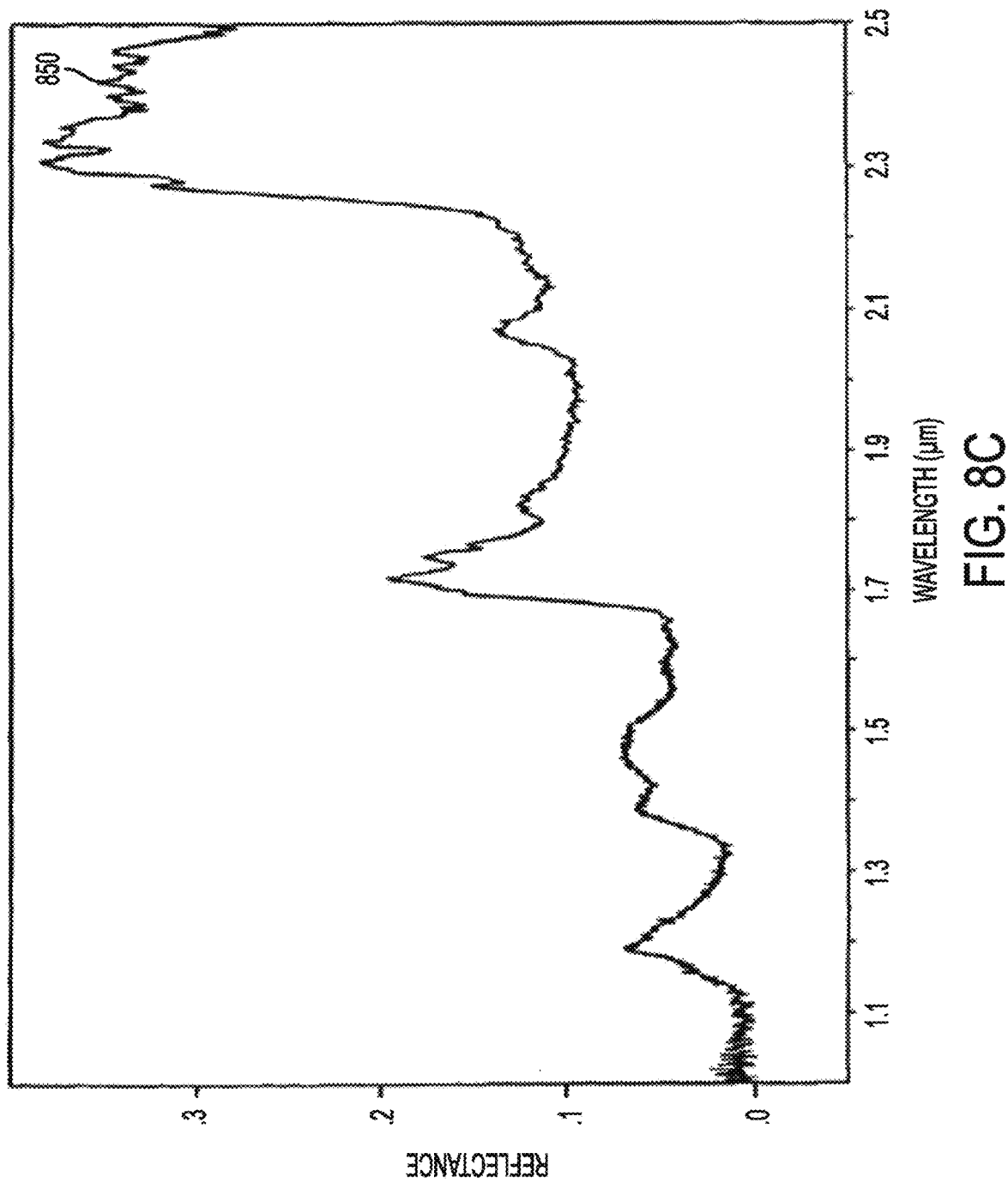
FIG. 8C shows the near-infrared reflectance spectrum for cholesterol.
Figure 8D:
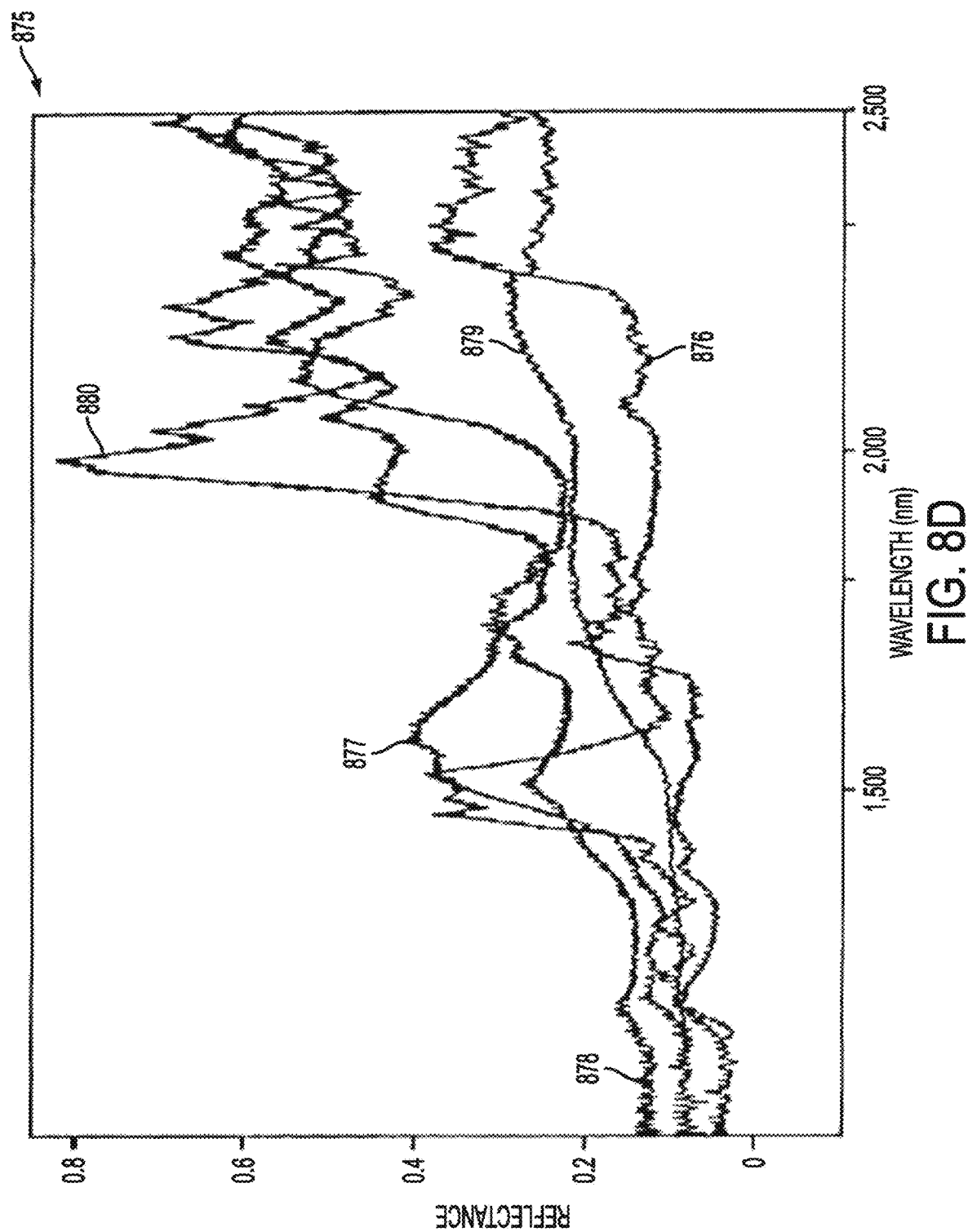
FIG. 8D illustrates the near-infrared reflectance versus wavelength for various blood constituents, including cholesterol, glucose, albumin, uric acid, and urea.

A further example of blood compositions that can be detected or measured using near-infrared light includes cholesterol monitoring. For example, FIG. 8C shows the near-infrared reflectance spectrum for cholesterol 850 with wavelength in microns (μm). Distinct absorption peaks are observable near 1210 nm (1.21 μm), 1720 nm (1.72 μm), and between 2300-2500 nm (2.3-2.5 μm). Also, there are other features near 1450 nm (1.45 μm) and 2050 nm (2.05 μm). In FIG. 8D the near-infrared reflectances 875 are displayed versus wavelength (nm) for various blood constituents. The spectrum for cholesterol 876 is overlaid with glucose 877, albumin 878, uric acid 879, and urea 880. As may be noted from FIG. 8D, at about 1720 nm and 2300 nm, cholesterol 876 reaches approximate reflectance peaks, while some of the other analytes are in a more gradual mode. Various signal processing methods may be used to identify and quantify the concentration of cholesterol 876 and/or glucose 877, or some of the other blood constituents.

As illustrated by FIGS. 5 and 7, one of the issues in measuring a particular blood constituent is the interfering and overlapping signal from other blood constituents. The selection of the constituent of interest may be improved using a number of techniques. For example, a higher light level or intensity may improve the signal-to-noise ratio for the measurement. Second, mathematical modeling and signal processing methodologies may help to reduce the interference, such as multivariate techniques, multiple linear regression, and factor-based algorithms, for example. For instance, a number of mathematical approaches include multiple linear regression, partial least squares, and principal component regression (PCR). Also, as illustrated in FIG. 8A, various mathematical derivatives, including the first and second derivatives, may help to accentuate differences between spectra. In addition, by using a wider wavelength range and using more sampling wavelengths may improve the ability to discriminate one signal from another. These are just examples of some of the methods of improving the ability to discriminate between different constituents, but other techniques may also be used and are intended to be covered by this disclosure.

Interference from Skin

Several proposed non-invasive glucose monitoring techniques rely on transmission, absorption, and/or diffuse reflection through the skin to measure blood constituents or blood analytes in veins, arteries, capillaries or in the tissue itself. However, on top of the interference from other blood constituents or analytes, the skin also introduces significant interference. For example, chemical, structural, and physiological variations occur that may produce relatively large and nonlinear changes in the optical properties of the tissue sample. In one embodiment, the near-infrared reflectance or absorbance spectrum may be a complex combination of the tissue scattering properties that result from the concentration and characteristics of a multiplicity of tissue components including water, fat, protein, collagen, elastin, and/or glucose. Moreover, the optical properties of the skin may also change with environmental factors such as humidity, temperature and pressure. Physiological variation may also cause changes in the tissue measurement over time and may vary based on lifestyle, health, aging, etc. The structure and composition of skin may also vary widely among individuals, between different sites within an individual, and over time on the same individual. Thus, the skin introduces a dynamic interference signal that may have a wide variation due to a number of parameters.

Figure 9:
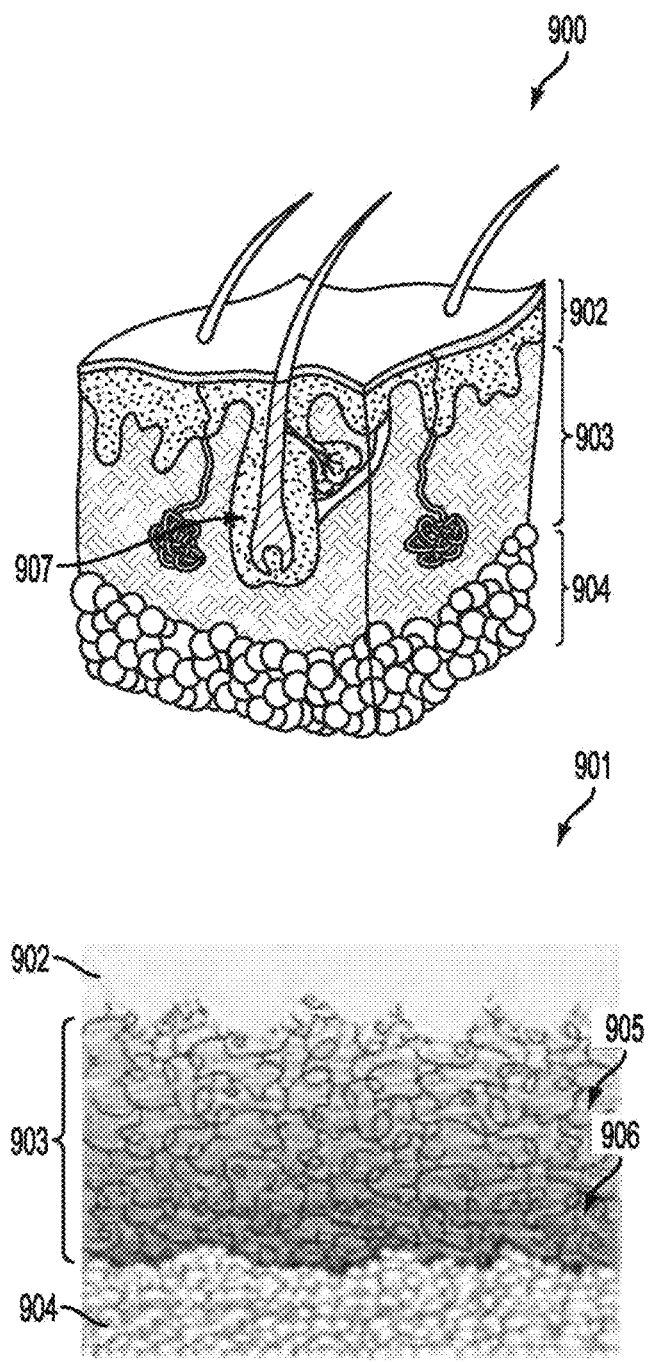
FIG. 9 shows a schematic of the human skin. In particular, the dermis may comprise significant amounts of collagen, elastin, lipids, and water.

FIG. 9 shows a schematic cross-section of human skin 900, 901. The top layer of the skin is epidermis 902, followed by a layer of dermis 903 and then subcutaneous fat 904 below the dermis. The epidermis 902, with a thickness of approximately 10-150 microns, may provide a barrier to infection and loss of moisture and other body constituents. The dermis 903 ranges in thickness from approximately 0.5 mm to 4 mm (averages approximately 1.2 mm over most of the body) and may provide the mechanical strength and elasticity of skin.

In the dermis 903, water may account for approximately 70% of the volume. The next most abundant constituent in the dermis 903 may be collagen 905, a fibrous protein comprising 70-75% of the dry weight of the dermis 903. Elastin fibers 906, also a protein, may also be plentiful in the dermis 903, although they constitute a smaller portion of the bulk. In addition, the dermis 903 may contain a variety of structures (e.g., sweat glands, hair follicles with adipose rich sebaceous glands 907 near their roots, and blood vessels) and other cellular constituents.

Below the dermis 903 lies the subcutaneous layer 904 comprising mostly adipose tissue. The subcutaneous layer 904 may be by volume approximately 10% water and may be comprised primarily of cells rich in triglycerides or fat. With this complicated structure of the skin 900,901, the concentration of glucose may vary in each layer according to a variety of factors including the water content, the relative sizes of the fluid compartments, the distribution of capillaries, the perfusion of blood, the glucose uptake of cells, the concentration of glucose in blood, and the driving forces (e.g., osmotic pressure) behind diffusion.

Figure 10:
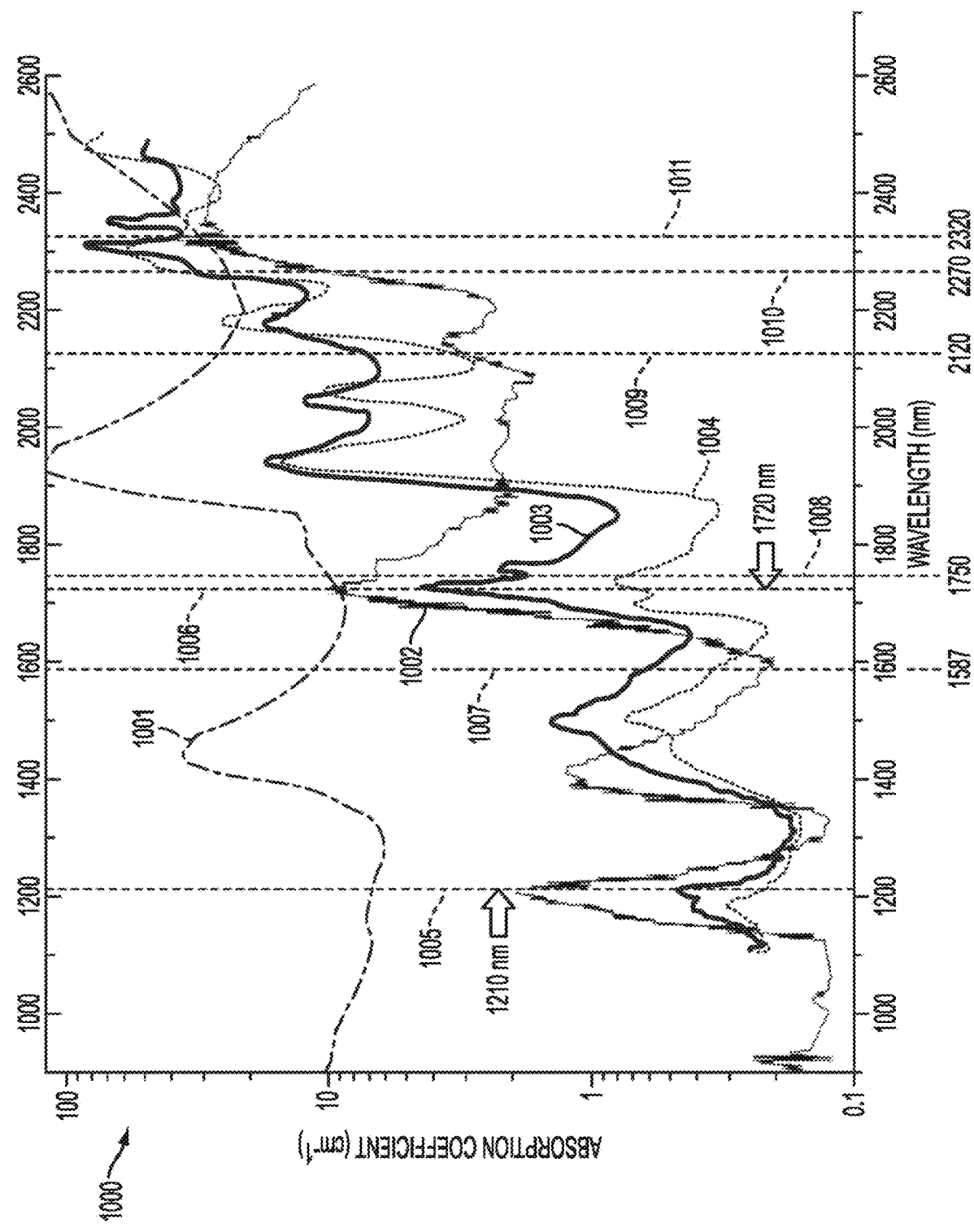
FIG. 10 illustrates the absorption coefficients for water (including scattering), adipose, collagen, and elastin.

To better understand the interference that the skin introduces when attempting to measure glucose, the absorption coefficient for the various skin constituents should be examined. For example, FIG. 10 illustrates 1000 the absorption coefficients for water (including scattering) 1001, adipose 1002, collagen 1003 and elastin 1004. Note that the absorption curves for water 1001 and adipose 1002 are calibrated, whereas the absorption curves for collagen 1003 and elastin 1004 are in arbitrary units. Also shown are vertical lines demarcating the wavelengths near 1210 nm 1005 and 1720 nm 1006. In general, the water absorption increases with increasing wavelength. With the increasing absorption beyond about 2000 nm, it may be difficult to achieve deeper penetration into biological tissue in the infrared wavelengths beyond approximately 2500 nm.

Although the absorption coefficient may be useful for determining the material in which light of a certain infrared wavelength will be absorbed, to determine the penetration depth of the light of a certain wavelength may also require the addition of scattering loss to the curves. For example, the water curve 1001 includes the scattering loss curve in addition to the water absorption. In particular, the scattering loss can be significantly higher at shorter wavelengths. In one embodiment, near the wavelength of 1720 nm (vertical line 1006 shown in FIG. 10), the adipose absorption 1002 can still be higher than the water plus scattering loss 1001. For tissue that contains adipose, collagen and elastin, such as the dermis of the skin, the total absorption can exceed the light energy lost to water absorption and light scattering at 1720 nm. On the other hand, at 1210 nm the adipose absorption 1002 can be considerably lower than the water plus scattering loss 1001, particularly since the scattering loss can be dominant at these shorter wavelengths.

The interference for glucose lines observed through skin may be illustrated by overlaying the glucose lines over the absorption curves 1000 for the skin constituents. For example, FIG. 2 illustrated that the glucose absorption 202 included features centered around 1587 nm, 1750 nm, 2120 nm, 2270 nm and 2320 nm. On FIG. 10 vertical lines have been drawn at the glucose line wavelengths of 1587 nm 1007, 1750 nm 1008, 2120 nm 1009, 2270 nm 1010 and 2320 nm 1011. In one embodiment, it may be difficult to detect the glucose lines near 1750 nm 1008, 2270 nm 1010 and 2320 nm 1011 due to significant spectral interference from other skin constituents. On the other hand, the glucose line near 1587 m 1007 may be more easily detected because it peaks while most of the other skin constituents are sloped downward toward an absorption valley. Moreover, the glucose line near 2120 nm 1009 may also be detectable for similar reasons, although adipose may have conflicting behavior due to local absorption minimum and maximum nearby in wavelength.

Thus, beyond the problem of other blood constituents or analytes having overlapping spectral features (e.g., FIG. 5), it may be difficult to observe glucose spectral signatures through the skin and its constituents of water, adipose, collagen and elastin. One approach to overcoming this difficulty may be to try to measure the blood constituents in veins that are located at relatively shallow distances below the skin. Veins may be more beneficial for the measurement than arteries, since arteries tend to be located at deeper levels below the skin. Also, in one embodiment it may be advantageous to use a differential measurement to subtract out some of the interfering absorption lines from the skin. For example, an instrument head may be designed to place one probe above a region of skin over a blood vein, while a second probe may be placed at a region of the skin without a noticeable blood vein below it. Then, by differencing the signals from the two probes, at least part of the skin interference may be cancelled out.

Figure 11:
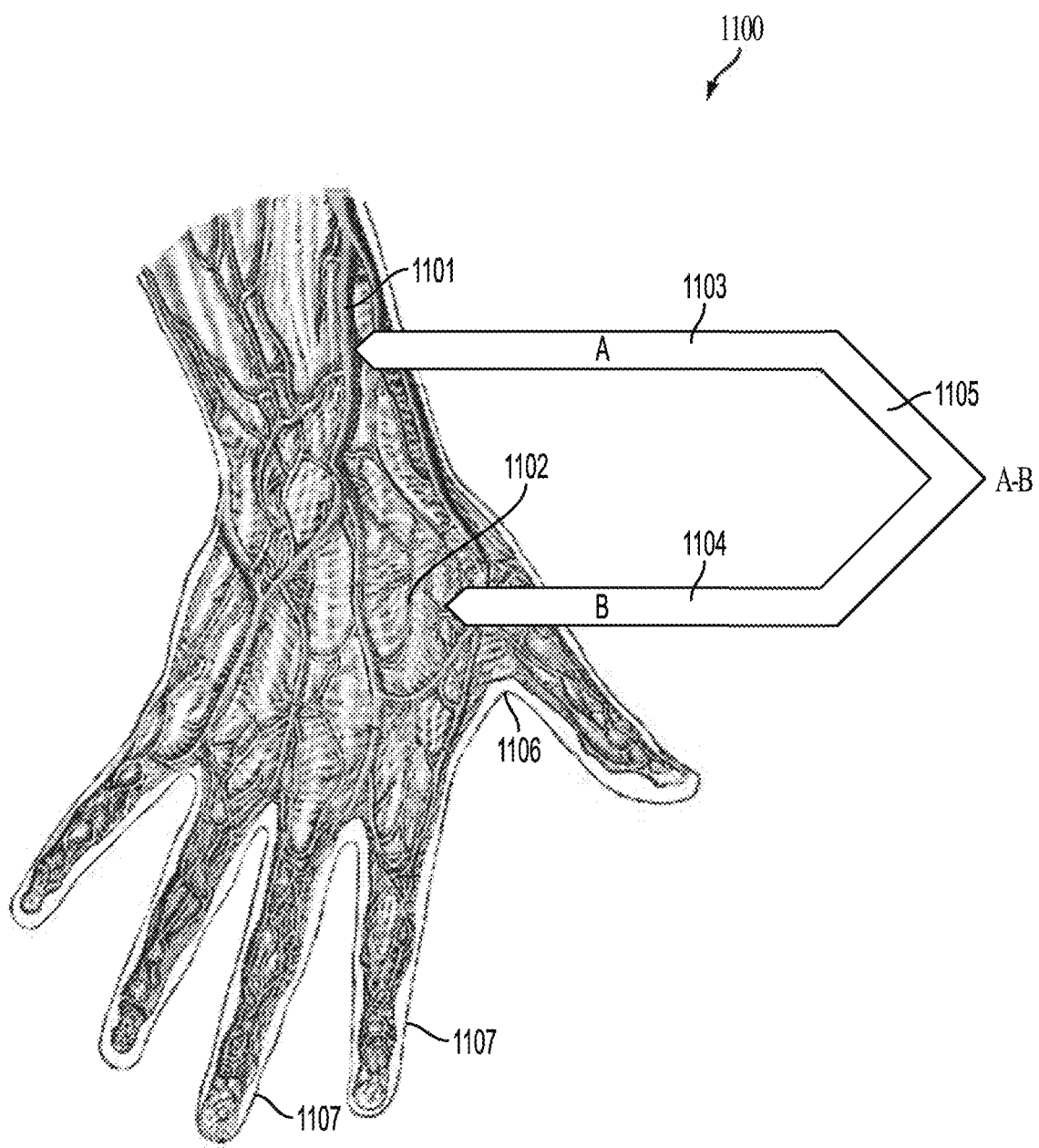
FIG. 11 shows the dorsal of the hand, where a differential measurement may be made to at least partially compensate for or subtract out the skin interference.
Figure 12:
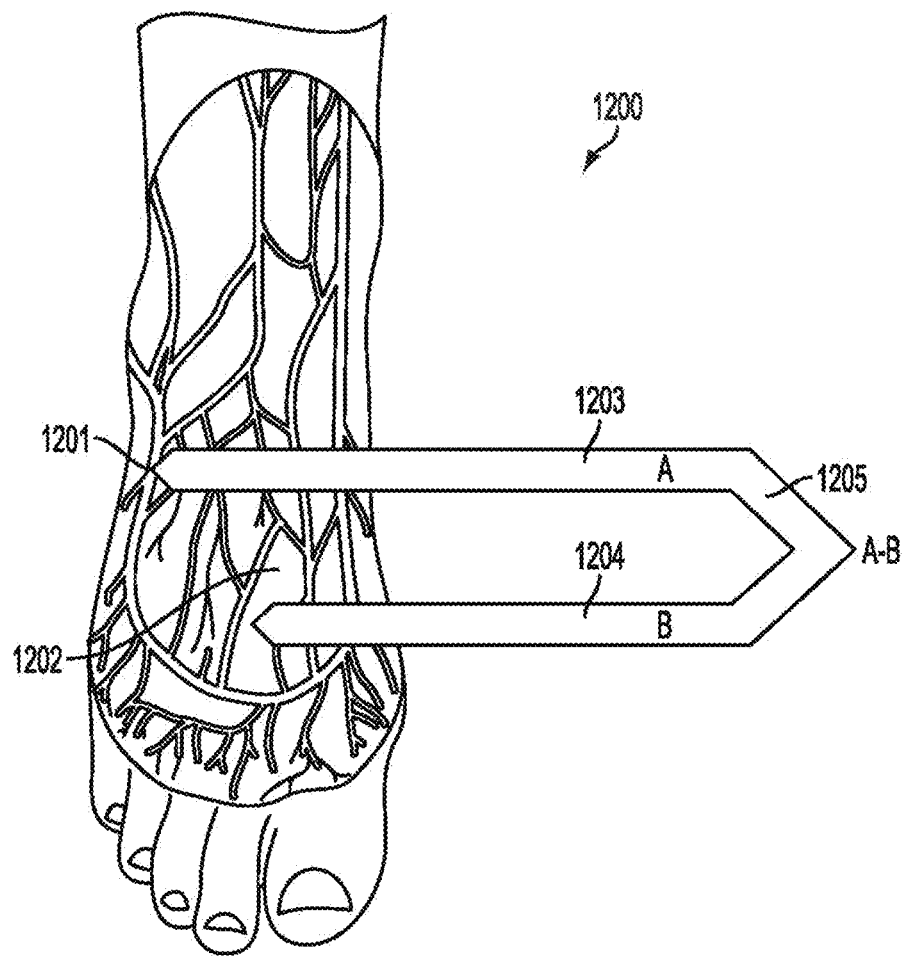
FIG. 12 shows the dorsal of the foot, where a differential measurement may be made to at least partially compensate for or subtract out the skin interference.

Two representative embodiments for performing such a differential measurement are illustrated in FIG. 11 and FIG. 12. In one embodiment shown in FIG. 11, the dorsal of the hand 1100 may be used for measuring blood constituents or analytes. The dorsal of the hand 1100 may have regions that have distinct veins 1101 as well as regions where the veins are not as shallow or pronounced 1102. By stretching the hand and leaning it backwards, the veins 1101 may be accentuated in some cases. A near-infrared diffuse reflectance measurement may be performed by placing one probe 1103 above the vein-rich region 1101. To turn this into a differential measurement, a second probe 1104 may be placed above a region without distinct veins 1102. Then, the outputs from the two probes may be subtracted 1105 to at least partially cancel out the features from the skin. The subtraction may be done preferably in the electrical domain, although it can also be performed in the optical domain or digitally/mathematically using sampled data based on the electrical and/or optical signals. Although one example of using the dorsal of the hand 1100 is shown, many other parts of the hand can be used within the scope of this disclosure. For example, alternate methods may use transmission through the webbing between the thumb and the fingers 1106, or transmission or diffuse reflection through the tips of the fingers 1107.

In another embodiment, the dorsal of the foot 1200 may be used instead of the hand. One advantage of such a configuration may be that for self-testing by a user, the foot may be easier to position the instrument using both hands. One probe 1203 may be placed over regions where there are more distinct veins 1201, and a near-infrared diffuse reflectance measurement may be made. For a differential measurement, a second probe 1204 may be placed over a region with less prominent veins 1202, and then the two probe signals may be subtracted, either electronically or optically, or may be digitized/sampled and processed mathematically depending on the particular application and implementation. As with the hand, the differential measurements may be intended to compensate for or subtract out (at least in part) the interference from the skin. Since two regions are used in close proximity on the same body part, this may also aid in removing some variability in the skin from environmental effects such as temperature, humidity, or pressure. In addition, it may be advantageous to first treat the skin before the measurement, by perhaps wiping with a cloth or treated cotton ball, applying some sort of cream, or placing an ice cube or chilled bag over the region of interest.

Although two embodiments have been described, many other locations on the body may be used using a single or differential probe within the scope of this disclosure. In yet another embodiment, the wrist may be advantageously used, particularly where a pulse rate is typically monitored. Since the pulse may be easily felt on the wrist, there is underlying the region a distinct blood flow. Other embodiments may use other parts of the body, such as the ear lobes, the tongue, the inner lip, the nails, the eye, or the teeth. Some of these embodiments will be further described below. The ear lobes or the tip of the tongue may be advantageous because they are thinner skin regions, thus permitting transmission rather than diffuse reflection. However, the interference from the skin is still a problem in these embodiments. Other regions such as the inner lip or the bottom of the tongue may be contemplated because distinct veins are observable, but still the interference from the skin may be problematic in these embodiments. The eye may seem as a viable alternative because it is more transparent than skin. However, there are still issues with scattering in the eye. For example, the anterior chamber of the eye (the space between the cornea and the iris) comprises a fluid known as aqueous humor. However, the glucose level in the eye chamber may have a significant temporal lag on changes in the glucose level compared to the blood glucose level.

Figure 13:
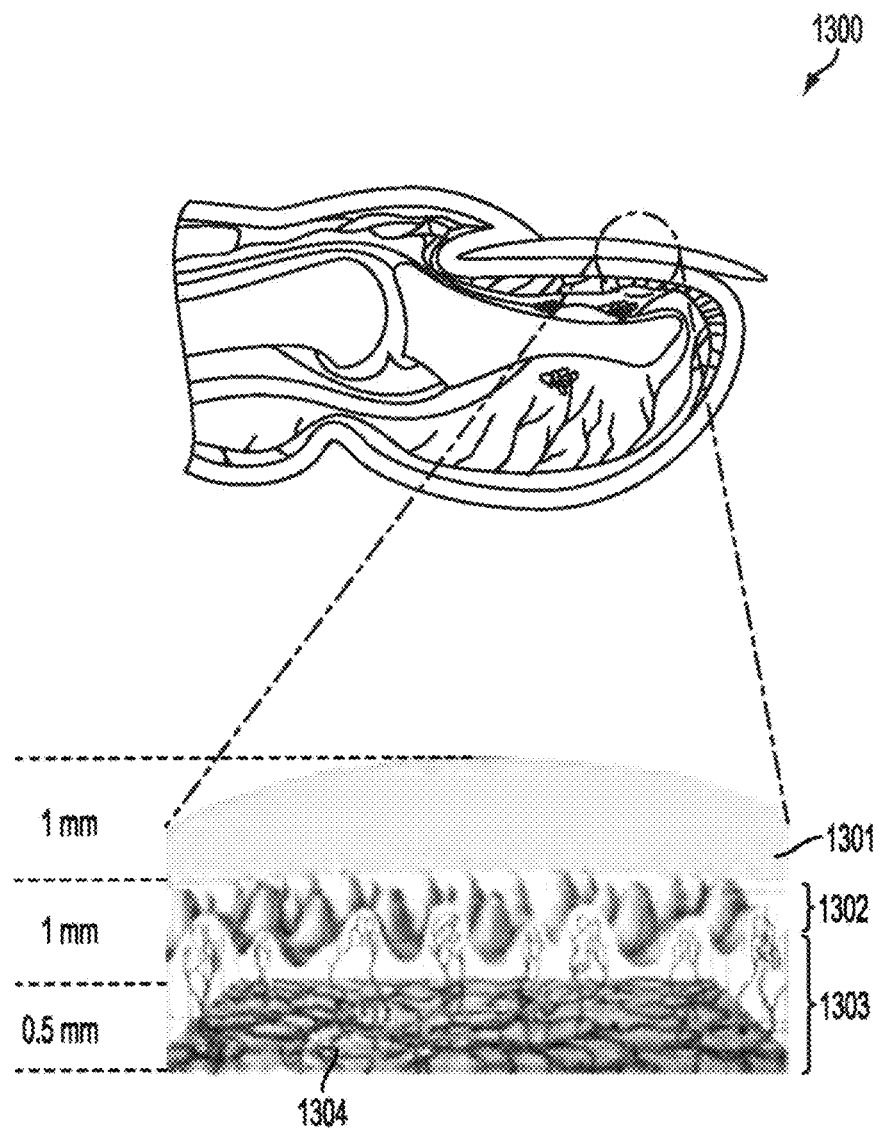
FIG. 13 illustrates a typical human nail tissue structure and the capillary vessels below it.

Because of the complexity of the interference from skin in non-invasive glucose monitoring (e.g., FIG. 10), other parts of the body without skin above blood vessels or capillaries may be alternative candidates for measuring blood constituents. One embodiment may involve transmission or reflection through human nails. As an example, FIG. 13 illustrates a typical human nail tissue structure 1300 and the capillary vessels below it. The fingernail 1301 is approximately 1 mm thick, and below this resides a layer of epidermis 1302 with a thickness of approximately 1 mm. The dermis 1304 is also shown, and within particularly the top about 0.5 mm of dermis are a significant number of capillary vessels. To measure the blood constituents, the light exposed on the top of the fingernail must penetrate about 2-2.5 mm or more, and the reflected light (round trip passage) should be sufficiently strong to measure. In one embodiment, the distance required to penetrate could be reduced by drilling a hole in the fingernail 1301.

Figure 14:
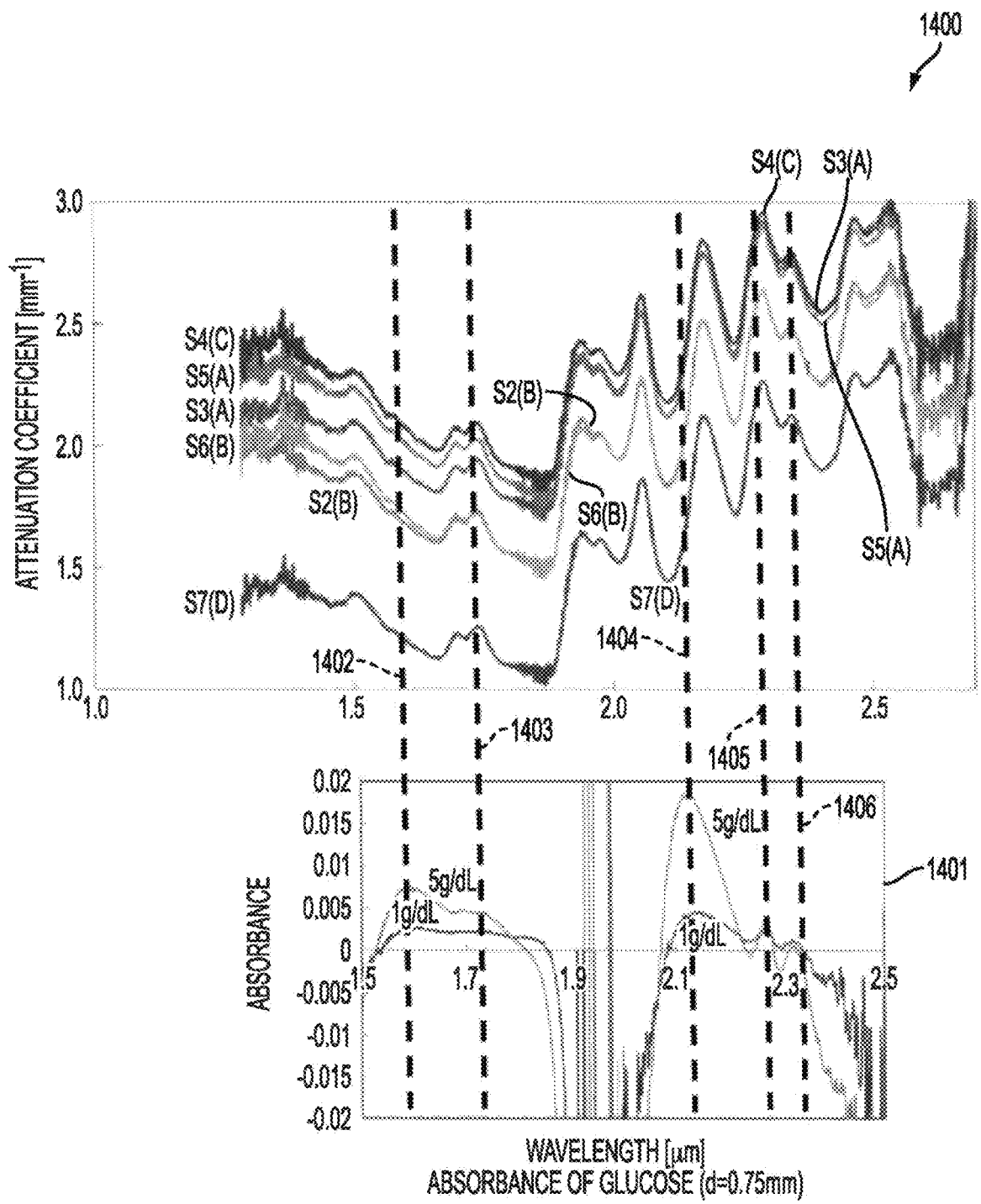
FIG. 14 shows the attenuation coefficient for seven nail samples that are allowed to stand in an environment with a humidity level of 14%. These coefficients are measured using an FTIR spectrometer over the near-infrared wavelength range of approximately 1 to 2.5 microns. Below is also included the spectrum of glucose.

In this alternative embodiment using the fingernail, there may still be interference from the nail's spectral features. For example, FIG. 14 illustrates the attenuation coefficient 1400 for seven nail samples that are allowed to stand in an environment with a humidity level of 14%. These coefficients are measured using an FTIR spectrometer over the near-infrared wavelength range of approximately 1 to 2.5 microns. These spectra are believed to correspond to the spectra of keratin contained in the nail plate. The base lines for the different samples are believed to differ because of the influence of scattering. Several of the absorption peaks observed correspond to peaks of keratin absorption, while other features may appear from the underlying epidermis and dermis. It should also be noted that the attenuation coefficients 1400 also vary considerably depending on humidity level or water content as well as temperature and other environmental factors. Moreover, the attenuation coefficient may also change in the presence of nail polish of various sorts.

Similar to skin, the large variations in attenuation coefficient for fingernails also may interfere with the absorption peaks of glucose. As an example, in FIG. 14 below the fingernail spectrum is also shown the glucose spectrum 1401 for two different glucose concentrations. The vertical lines 1402, 1403, 1404, 1405 and 1406 are drawn to illustrate the glucose absorption peaks and where they lie on the fingernail spectra 1400. As is apparent, the nail has interfering features that may be similar to skin, particularly since both have spectra that vary not only in wavelength but also with environmental factors. In one embodiment, it may be possible to see the glucose peaks 1402 and 1404 through the fingernail, but it may be much more difficult to observe the glucose peaks near 1403, 1405 and 1406.

Transmission or Reflection Through Teeth

Figure 15:
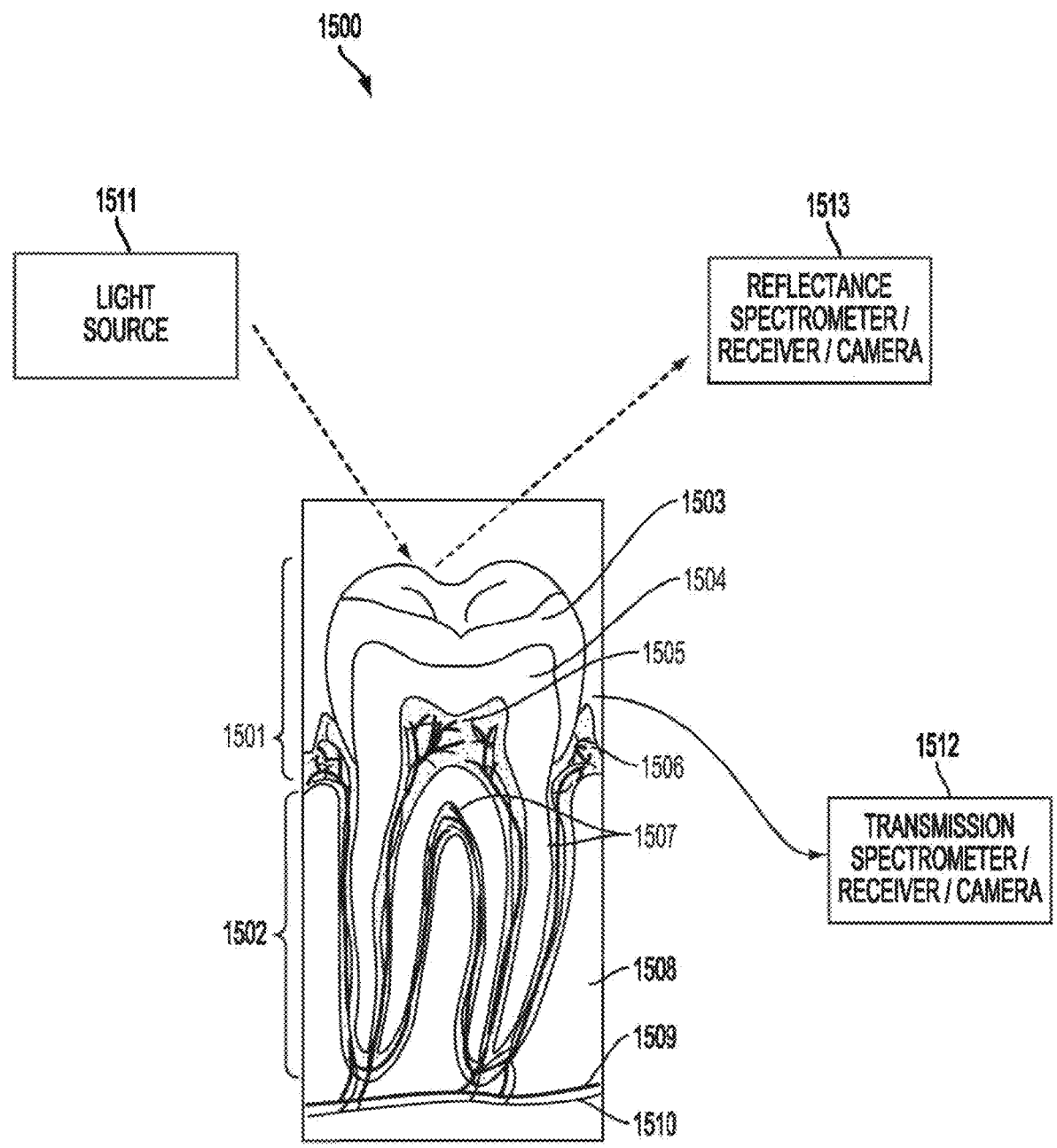
FIG. 15 illustrates the structure of a tooth.

Yet another embodiment may observe the transmittance or reflectance through teeth to measure blood constituents or analytes. FIG. 15 illustrates an exemplary structure of a tooth 1500. The tooth 1500 has a top layer called the crown 1501 and below that a root 1502 that reaches well into the gum 1506 and bone 1508 of the mouth. The exterior of the crown 1501 is an enamel layer 1503, and below the enamel is a layer of dentine 1504 that sits atop a layer of cementum 1507. Below the dentine 1504 is a pulp region 1505, which comprises within it blood vessels 1509 and nerves 1510. If the light can penetrate the enamel 1503 and dentine 1504, then the blood flow and blood constituents can be measured through the blood vessels in the dental pulp 1505. While it may be true that the amount of blood flow in the dental pulp 1505 may be less since it comprises capillaries, the smaller blood flow could still be advantageous if there is less interfering spectral features from the tooth.

Figure 16A:
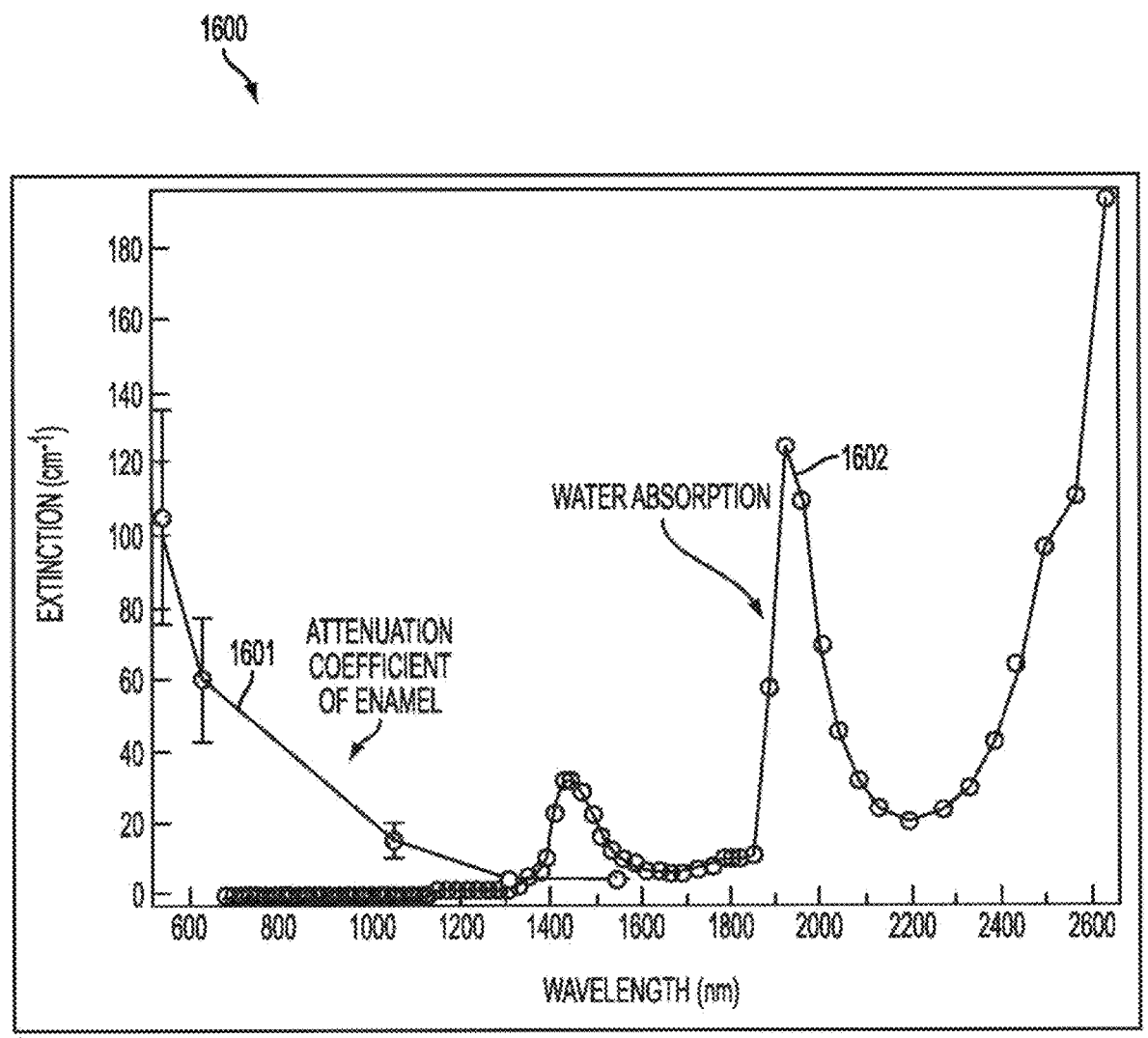
FIG. 16A shows the attenuation coefficient for dental enamel and water versus wavelength from approximately 600 nm to 2600 nm.

The transmission, absorption and reflection from teeth has been studied in the near infrared, and, although there are some features, the enamel and dentine appear to be fairly transparent in the near infrared (particularly wavelengths between 1500 and 2500 nm). For example, the absorption or extinction ratio for light transmission has been studied. FIG. 16A illustrates the attenuation coefficient 1600 for dental enamel 1601 (filled circles) and the absorption coefficient of water 1602 (open circles) versus wavelength. Near-infrared light may penetrate much further without scattering through all the tooth enamel, due to the reduced scattering coefficient in normal enamel. Scattering in enamel may be fairly strong in the visible, but decreases as approximately 1/(wavelength)3 [i.e., inverse of the cube of the wavelength] with increasing wavelength to a value of only 2-3 cm-1 at 1310 nm and 1550 nm in the near infrared. Therefore, enamel may be virtually transparent in the near infrared with optical attenuation 1-2 orders of magnitude less than in the visible range.

Figure 16B:
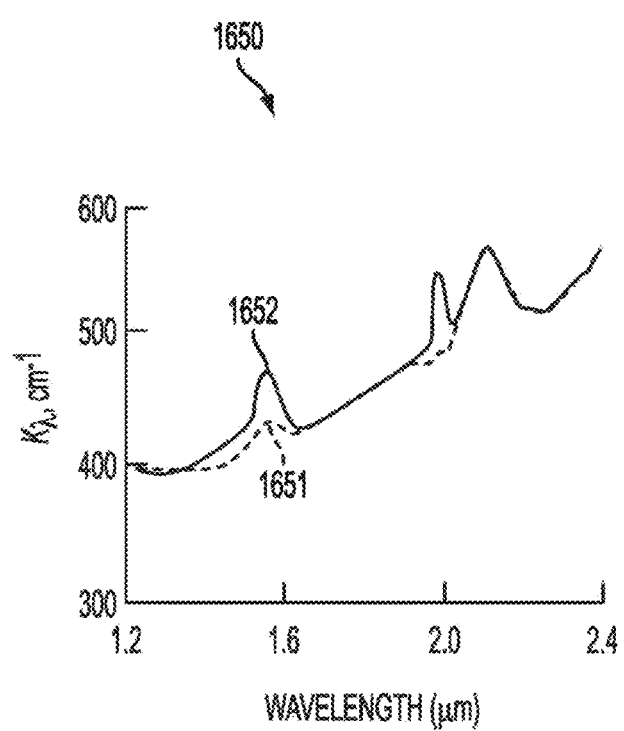
FIG. 16B illustrates the absorption spectrum of intact enamel and dentine in the wavelength range of approximately 1.2 to 2.4 microns.

As another example, FIG. 16B illustrates the absorption spectrum 1650 of intact enamel 1651 (dashed line) and dentine 1652 (solid line) in the wavelength range of approximately 1.2 to 2.4 microns. In the near infrared there are two absorption bands around 1.5 and 2 microns. The band with a peak around 1.57 microns may be attributed to the overtone of valent vibration of water present in both enamel and dentine. In this band, the absorption is greater for dentine than for enamel, which may be related to the large water content in this tissue. In the region of 2 microns, dentine may have two absorption bands, and enamel one. The band with a maximum near 2.1 microns may belong to the overtone of vibration of PO hydroxyapatite groups, which is the main substance of both enamel and dentine. Moreover, the band with a peak near 1.96 microns in dentine may correspond to water absorption (dentine may contain substantially higher water than enamel).

Figure 17:
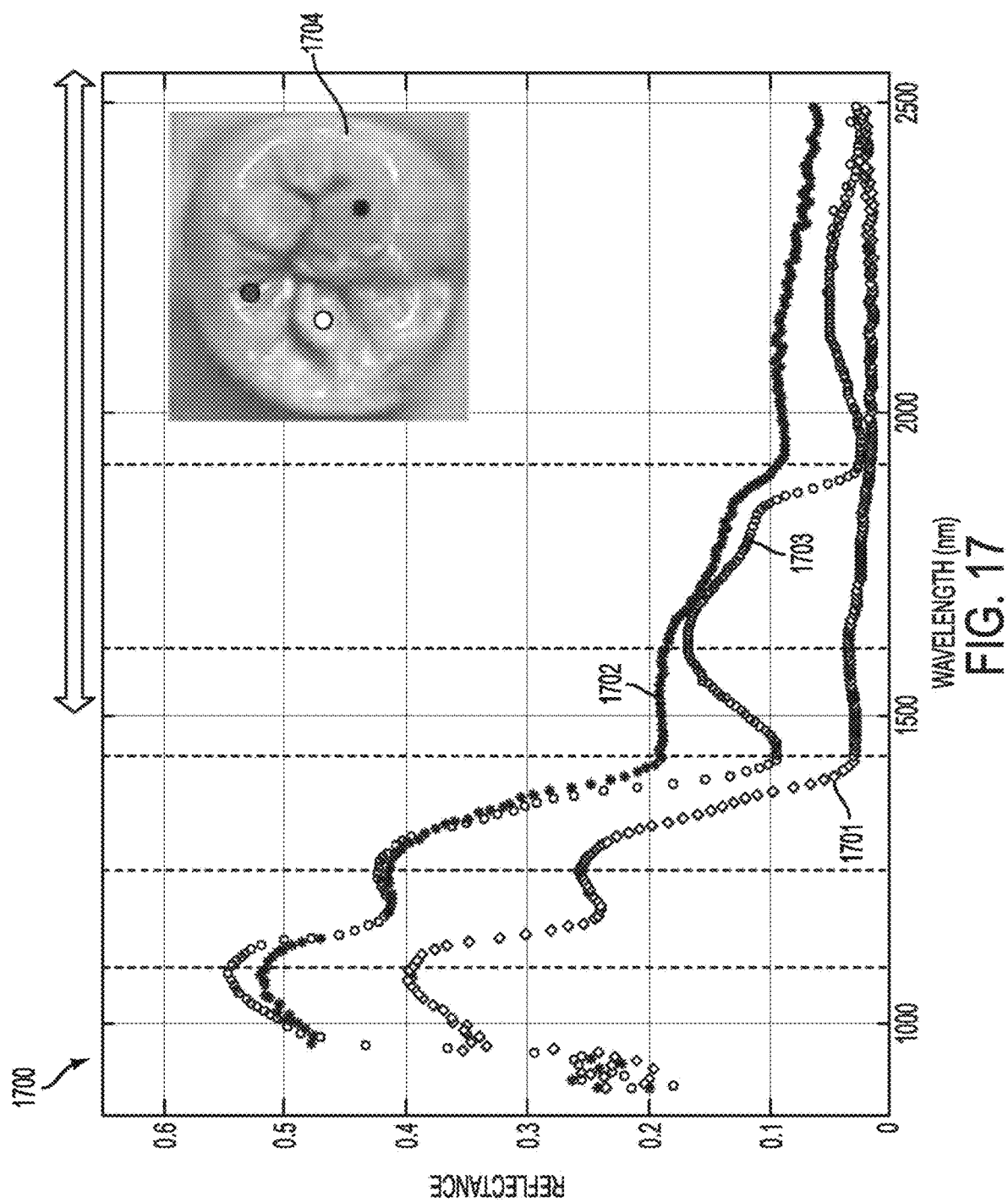
FIG. 17 shows the near infrared spectral reflectance over the wavelength range of approximately 800 nm to 2500 nm from an occlusal tooth surface. The black diamonds correspond to the reflectance from a sound, intact tooth section. The asterisks correspond to a tooth section with an enamel lesion. The circles correspond to a tooth section with a dentine lesion.

In addition to the absorption coefficient, the reflectance from intact teeth and teeth with dental caries (e.g., cavities) has been studied. In one embodiment, FIG. 17 shows the near infrared spectral reflectance 1700 over the wavelength range of approximately 800 nm to 2500 nm from an occlusal (e.g., top/bottom) tooth surface 1704. The curve with black diamonds 1701 corresponds to the reflectance from a sound, intact tooth section. The curve with asterisks * 1702 corresponds to a tooth section with an enamel lesion. The curve with circles 1703 corresponds to a tooth section with a dentine lesion. Thus, when there is a lesion, more scattering occurs and there may be an increase in the reflected light.

For wavelengths shorter than approximately 1400 nm, the shapes of the spectra remain similar, but the amplitude of the reflection changes with lesions. Between approximately 1400 nm and 2500 nm, an intact tooth 1701 has low reflectance (e.g., high transmission), and the reflectance appears to be more or less independent of wavelength. On the other hand, in the presence of lesions 1702 and 1703, there is increased scattering, and the scattering loss may be wavelength dependent. For example, the scattering loss may decrease as $1/(\text{wavelength})^3$—so, the scattering loss decreases with longer wavelengths. When there is a lesion in the dentine 1703, more water can accumulate in the area, so there is also increased water absorption. For example, the dips near 1450 nm and 1900 nm correspond to water absorption, and the reflectance dips are particularly pronounced in the dentine lesion 1703. One other benefit of the absorption, transmission or reflectance in the near infrared may be that stains and non-calcified plaque are not visible in this wavelength range, enabling better discrimination of defects, cracks, and demineralized areas.

Compared with the interference from skin 1000 in FIG. 10 or fingernails 1400 in FIG. 14, the teeth appear to introduce much less interference for non-invasive monitoring of blood constituents. The few features in FIG. 16B or 17 may be calibrated out of the measurement. Also, using an intact tooth 1701 may further minimize any interfering signals. Furthermore, since the tooth comprises relatively hard tissue, higher power from the light sources in the near infrared may be used without damaging the tissue, such as with skin.

Human Interface for Measurement System

A number of different types of measurements may be used to sample the blood in the dental pulp. The basic feature of the measurements should be that the optical properties are measured as a function of wavelength at a plurality of wavelengths. As further described below, the light source may output a plurality of wavelengths, or a continuous spectrum over a range of wavelengths. In a preferred embodiment, the light source may cover some or all of the wavelength range between approximately 1400 nm and 2500 nm. The signal may be received at a receiver, which may also comprise a spectrometer or filters to discriminate between different wavelengths. The signal may also be received at a camera, which may also comprise filters or a spectrometer. In an alternate embodiment, the spectral discrimination using filters or a spectrometer may be placed after the light source rather than at the receiver. The receiver usually comprises one or more detectors (optical-to-electrical conversion element) and electrical circuitry. The receiver may also be coupled to analog to digital converters, particularly if the signal is to be fed to a digital device.

Referring to FIG. 15, one or more light sources 1511 may be used for illumination. In one embodiment, a transmission measurement may be performed by directing the light source output 1511 to the region near the interface between the gum 1506 and dentine 1504. In one embodiment, the light may be directed using a light guide or a fiber optic. The light may then propagate through the dental pulp 1505 to the other side, where the light may be incident on one or more detectors or another light guide to transport the signal to a spectrometer, receiver or camera 1512. In another embodiment, the light source may be directed to one or more locations near the interface between the gum 1506 and dentine 1504 (in one example, could be from the two sides of the tooth). The transmitted light may then be detected in the occlusal surface above the tooth using a spectrometer, receiver, or camera 1512. In yet another embodiment, a reflectance measurement may be conducted by directing the light source output 1511 to, for example, the occlusal surface of the tooth, and then detecting the reflectance at a spectrometer, receiver or camera 1513. Although a few embodiments for measuring the blood constituents through a tooth are described, other embodiments and techniques may also be used and are intended to be covered by this disclosure.

Figure 18A:
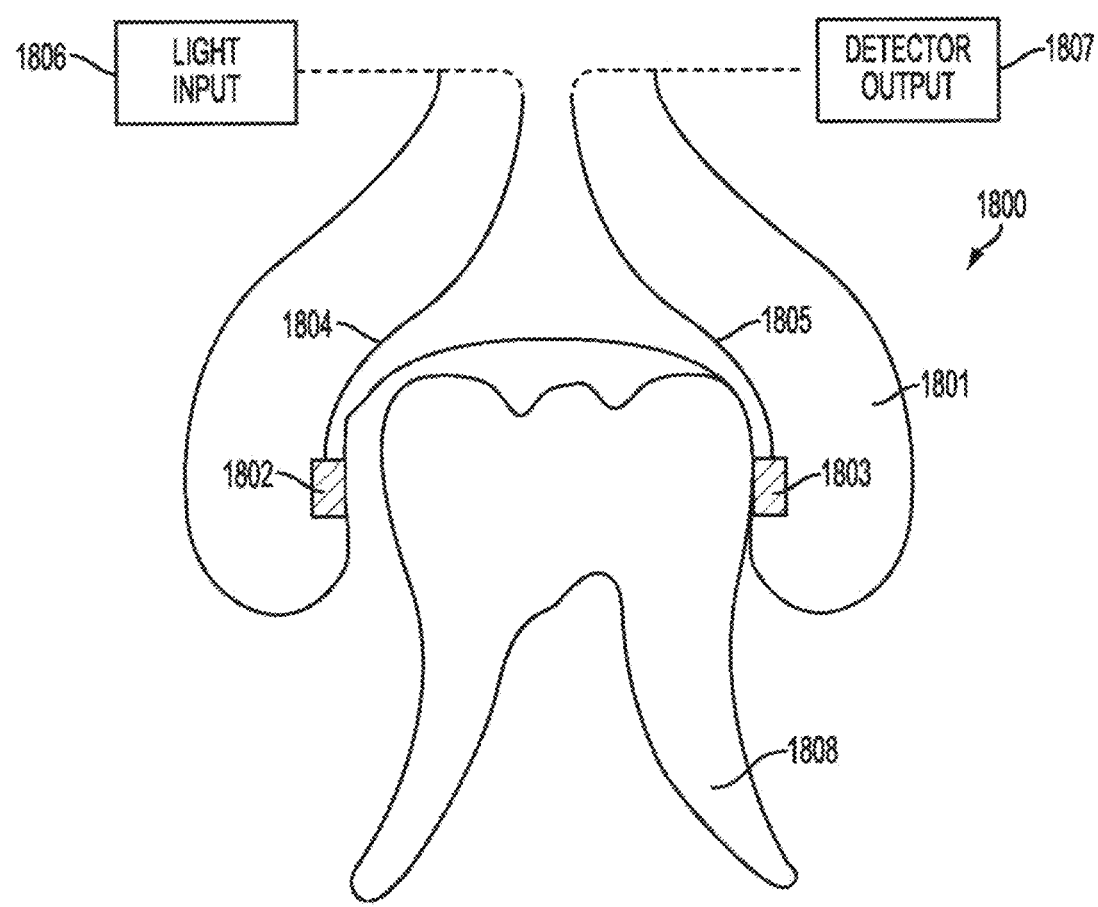
FIG. 18A illustrates a clamp design of a human interface to cap over one or more teeth and perform a non-invasive measurement of blood constituents.

The human interface for the non-invasive measurement of blood constituents may be of various forms. In one embodiment, a "clamp" design 1800 may be used to cap over one or more teeth, as illustrated in FIG. 18A. The clamp design may be different for different types of teeth, or it may be flexible enough to fit over different types of teeth. For example, different types of teeth include the molars (toward the back of the mouth), the premolars, the canine, and the incisors (toward the front of the mouth). One embodiment of the clamp-type design is illustrated in FIG. 18A for a molar tooth 1808. The C-clamp 1801 may be made of a plastic or rubber material, and it may comprise a light source input 1802 and a detector output 1803 on the front or back of the tooth.

The light source input 1802 may comprise a light source directly, or it may have light guided to it from an external light source. Also, the light source input 1802 may comprise a lens system to collimate or focus the light across the tooth. The detector output 1803 may comprise a detector directly, or it may have a light guide to transport the signal to an external detector element. The light source input 1802 may be coupled electrically or optically through 1804 to a light input 1806. For example, if the light source is external in 1806, then the coupling element 1804 may be a light guide, such as a fiber optic. Alternately, if the light source is contained in 1802, then the coupling element 1804 may be electrical wires connecting to a power supply in 1806. Similarly, the detector output 1803 may be coupled to a detector output unit 1807 with a coupling element 1805, which may be one or more electrical wires or a light guide, such as a fiber optic. This is just one example of a clamp over one or more teeth, but other embodiments may also be used and are intended to be covered by this disclosure.

Figure 18B:
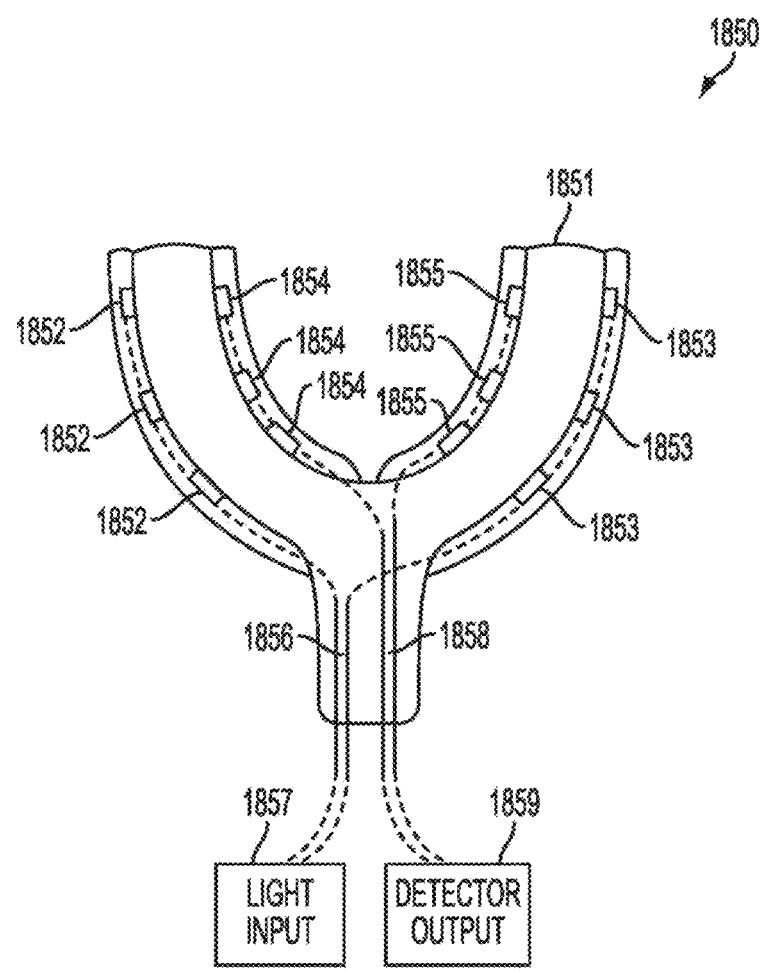
FIG. 18B shows a mouth guard design of a human interface to perform a non-invasive measurement of blood constituents.

In yet another embodiment, one or more light source ports and sensor ports may be used in a mouth-guard type design. For example, one embodiment of a dental mouth guard 1850 is illustrated in FIG. 18B. The structure of the mouth guard 1851 may be similar to mouth guards used in sports (e.g., when playing football or boxing) or in dental trays used for applying fluoride treatment, and the mouth guard may be made from plastic or rubber materials, for example. As an example, the mouth guard may have one or more light source input ports 1852, 1853 and one or more detector output ports 1854, 1855. Although six input and output ports are illustrated, any number of ports may be used.

Similar to the clamp design describe above, the light source inputs 1852, 1853 may comprise one or more light sources directly, or they may have light guided to them from an external light source. Also, the light source inputs 1852, 1853 may comprise lens systems to collimate or focus the light across the teeth. The detector outputs 1854, 1855 may comprise one or more detectors directly, or they may have one or more light guides to transport the signals to an external detector element. The light source inputs 1852, 1853 may be coupled electrically or optically through 1856 to a light input 1857. For example, if the light source is external in 1857, then the one or more coupling elements 1856 may be one or more light guides, such as a fiber optic. Alternately, if the light sources are contained in 1852, 1853, then the coupling element 1856 may be one or more electrical wires connecting to a power supply in 1857. Similarly, the detector outputs 1854, 1855 may be coupled to a detector output unit 1859 with one or more coupling elements 1858, which may be one or more electrical wires or one or more light guides, such as a fiber optic. This is just one example of a mouth guard design covering a plurality of teeth, but other embodiments may also be used and are intended to be covered by this disclosure. For instance, the position of the light source inputs and detector output ports could be exchanged, or some mixture of locations of light source inputs and detector output ports could be used.

Other elements may be added to the human interface designs of FIG. 18 and are also intended to be covered by this disclosure. For instance, in one embodiment it may be desirable to have replaceable inserts that may be disposable. Particularly in a doctor's office or hospital setting, the same instrument may be used with a plurality of patients. Rather than disinfecting the human interface after each use, it may be preferable to have disposable inserts that can be thrown away after each use. In one embodiment, a thin plastic coating material may enclose the clamp design of FIG. 18A or mouth guard design of FIG. 18B. The coating material may be inserted before each use, and then after the measurement is exercised the coating material may be peeled off and replaced. Such a design may save the physician or user considerable time, while at the same time provide the business venture with a recurring cost revenue source. Any coating material or other disposable device may be constructed of a material having suitable optical properties that may be considered during processing of the signals used to detect any anomalies in the teeth.

Light Sources for Near Infrared

There are a number of light sources that may be used in the near infrared. To be more specific, the discussion below will consider light sources operating in the so-called short wave infrared (SWIR), which may cover the wavelength range of approximately 1400 nm to 2500 nm. Other wavelength ranges may also be used for the applications described in this disclosure, so the discussion below is merely provided for exemplary types of light sources. The SWIR wavelength range may be valuable for a number of reasons. First, the SWIR corresponds to a transmission window through water and the atmosphere. For example, 302 in FIG. 3A and 1602 in FIG. 16A illustrate the water transmission windows. Also, through the atmosphere, wavelengths in the SWIR have similar transmission windows due to water vapor in the atmosphere. Second, the so-called "eye-safe" wavelengths are wavelengths longer than approximately 1400 nm. Third, the SWIR covers the wavelength range for nonlinear combinations of stretching and bending modes as well as the first overtone of C—H stretching modes. Thus, for example, glucose and ketones among other substances may have unique signatures in the SWIR. Moreover, many solids have distinct spectral signatures in the SWIR, so particular solids may be identified using stand-off detection or remote sensing. For instance, many explosives have unique signatures in the SWIR.

Different light sources may be selected for the SWIR based on the needs of the application. Some of the features for selecting a particular light source include power or intensity, wavelength range or bandwidth, spatial or temporal coherence, spatial beam quality for focusing or transmission over long distance, and pulse width or pulse repetition rate. Depending on the application, lamps, light emitting diodes (LEDs), laser diodes (LD's), tunable LD's, super-luminescent laser diodes (SLDs), fiber lasers or super-continuum sources (SC) may be advantageously used. Also, different fibers may be used for transporting the light, such as fused silica fibers, plastic fibers, mid-infrared fibers (e.g., tellurite, chalcogenides, fluorides, ZBLAN, etc), or a hybrid of these fibers.

Lamps may be used if low power or intensity of light is required in the SWIR, and if an incoherent beam is suitable. In one embodiment, in the SWIR an incandescent lamp that can be used is based on tungsten and halogen, which have an emission wavelength between approximately 500 nm to 2500 nm. For low intensity applications, it may also be possible to use thermal sources, where the SWIR radiation is based on the black body radiation from the hot object. Although the thermal and lamp based sources are broadband and have low intensity fluctuations, it may be difficult to achieve a high signal-to-noise ratio in a non-invasive blood constituent measurement due to the low power levels. Also, the lamp based sources tend to be energy inefficient.

In another embodiment, LED's can be used that have a higher power level in the SWIR wavelength range. LED's also produce an incoherent beam, but the power level can be higher than a lamp and with higher energy efficiency. Also, the LED output may more easily be modulated, and the LED provides the option of continuous wave or pulsed mode of operation. LED's are solid state components that emit a wavelength band that is of moderate width, typically between about 20 nm to 40 nm. There are also so-called super-luminescent LEDs that may even emit over a much wider wavelength range. In another embodiment, a wide band light source may be constructed by combining different LEDs that emit in different wavelength bands, some of which could preferably overlap in spectrum. One advantage of LEDs as well as other solid state components is the compact size that they may be packaged into.

In yet another embodiment, various types of laser diodes may be used in the SWIR wavelength range. Just as LEDs may be higher in power but narrower in wavelength emission than lamps and thermal sources, the LDs may be yet higher in power but yet narrower in wavelength emission than LEDs. Different kinds of LDs may be used, including Fabry-Perot LDs, distributed feedback (DFB) LDs, distributed Bragg reflector (DBR) LDs. Since the LDs have relatively narrow wavelength range (typically under 10 nm), in one embodiment a plurality of LDs may be used that are at different wavelengths in the SWIR. For example, in a preferred embodiment for non-invasive glucose monitoring, it may be advantageous to use LDs having emission spectra near some or all of the glucose spectral peaks (e.g., near 1587 nm, 1750 nm, 2120 nm, 2270 nm, and 2320 nm). The various LDs may be spatially multiplexed, polarization multiplexed, wavelength multiplexed, or a combination of these multiplexing methods. Also, the LDs may be fiber pig-tailed or have one or more lenses on the output to collimate or focus the light. Another advantage of LDs is that they may be packaged compactly and may have a spatially coherent beam output. Moreover, tunable LDs that can tune over a range of wavelengths are also available. The tuning may be done by varying the temperature, or electrical current may be used in particular structures, such as distributed Bragg reflector LDs. In another embodiment, external cavity LDs may be used that have a tuning element, such as a fiber grating or a bulk grating, in the external cavity.

In another embodiment, super-luminescent laser diodes may provide higher power as well as broad bandwidth. An SLD is typically an edge emitting semiconductor light source based on super-luminescence (e.g., this could be amplified spontaneous emission). SLDs combine the higher power and brightness of LDs with the low coherence of conventional LEDs, and the emission band for SLD's may be 5 to 100 nm wide, preferably in the 60 to 100 nm range. Although currently SLDs are commercially available in the wavelength range of approximately 400 nm to 1700 nm, SLDs could and may in the future be made to cover a broader region of the SWIR.

Figure 19:
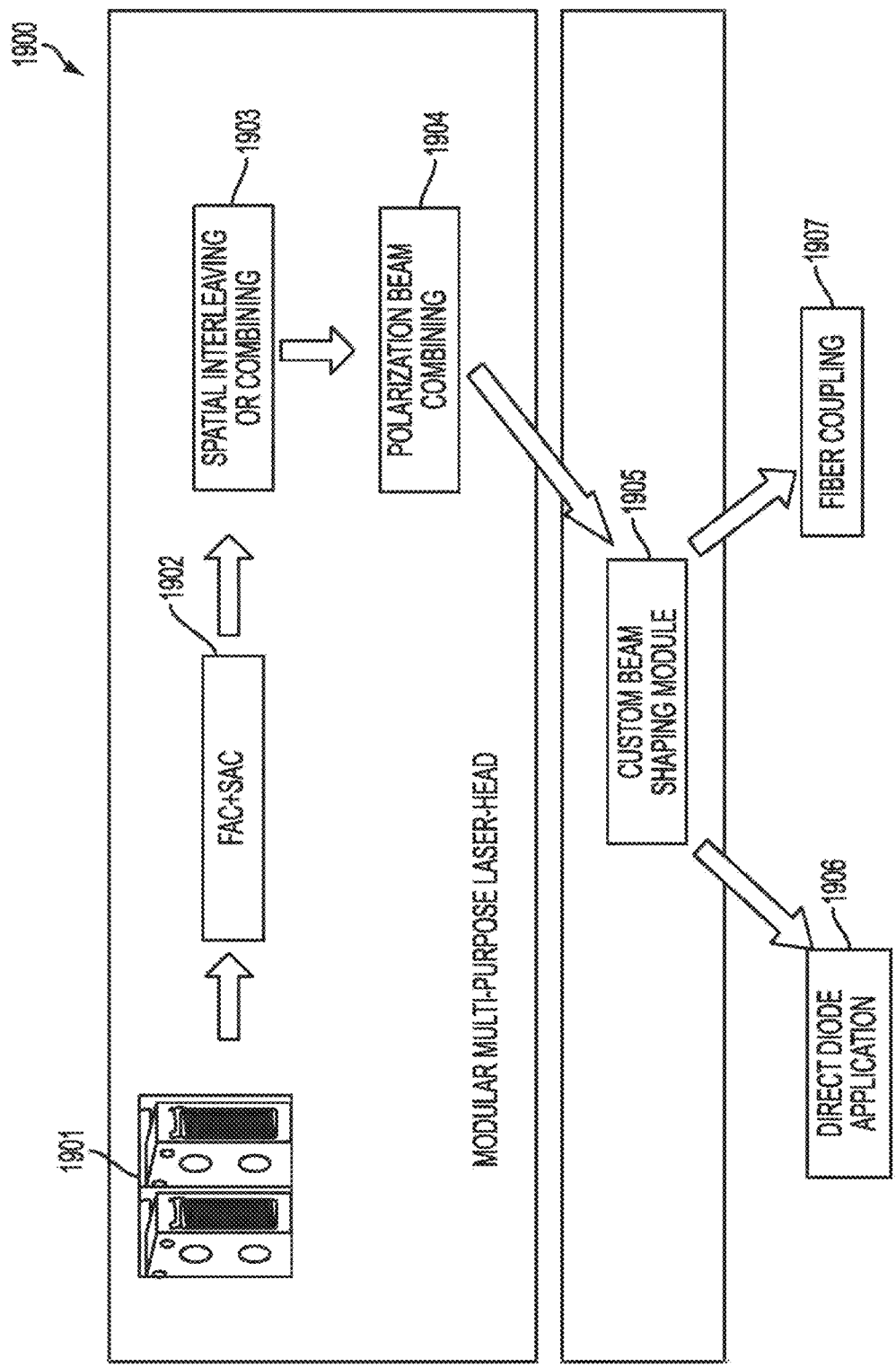
FIG. 19 illustrates a block diagram or building blocks for constructing high power laser diode assemblies.

In yet another embodiment, high power LDs for either direct excitation or to pump fiber lasers and SC light sources may be constructed using one or more laser diode bar stacks. As an example, FIG. 19 shows an example of the block diagram 1900 or building blocks for constructing the high power LDs. In this embodiment, one or more diode bar stacks 1901 may be used, where the diode bar stack may be an array of several single emitter LDs. Since the fast axis (e.g., vertical direction) may be nearly diffraction limited while the slow-axis (e.g., horizontal axis) may be far from diffraction limited, different collimators 1902 may be used for the two axes.

Then, the brightness may be increased by spatially combining the beams from multiple stacks 1903. The combiner may include spatial interleaving, it may include wavelength multiplexing, or it may involve a combination of the two. Different spatial interleaving schemes may be used, such as using an array of prisms or mirrors with spacers to bend one array of beams into the beam path of the other. In another embodiment, segmented mirrors with alternate high-reflection and anti-reflection coatings may be used. Moreover, the brightness may be increased by polarization beam combining 1904 the two orthogonal polarizations, such as by using a polarization beam splitter. In one embodiment, the output may then be focused or coupled into a large diameter core fiber. As an example, typical dimensions for the large diameter core fiber range from approximately 100 microns in diameter to 400 microns or more. Alternatively or in addition, a custom beam shaping module 1905 may be used, depending on the particular application. For example, the output of the high power LD may be used directly 1906, or it may be fiber coupled 1907 to combine, integrate, or transport the high power LD energy. These high power LDs may grow in importance because the LD powers can rapidly scale up. For example, instead of the power being limited by the power available from a single emitter, the power may increase in multiples depending on the number of diodes multiplexed and the size of the large diameter fiber. Although FIG. 19 is shown as one embodiment, some or all of the elements may be used in a high power LD, or additional elements may also be used.

SWIR Super-Continuum Lasers

Each of the light sources described above have particular strengths, but they also may have limitations. For example, there is typically a trade-off between wavelength range and power output. Also, sources such as lamps, thermal sources, and LEDs produce incoherent beams that may be difficult to focus to a small area and may have difficulty propagating for long distances. An alternative source that may overcome some of these limitations is an SC light source. Some of the advantages of the SC source may include high power and intensity, wide bandwidth, spatially coherent beam that can propagate nearly transform limited over long distances, and easy compatibility with fiber delivery.

Supercontinuum lasers may combine the broadband attributes of lamps with the spatial coherence and high brightness of lasers. By exploiting a modulational instability initiated supercontinuum (SC) mechanism, an all-fiber-integrated SC laser with no moving parts may be built using commercial-off-the-shelf (COTS) components. Moreover, the fiber laser architecture may be a platform where SC in the visible, near-infrared/SWIR, or mid-IR can be generated by appropriate selection of the amplifier technology and the SC generation fiber. But until now, SC lasers were used primarily in laboratory settings since typically large, table-top, mode-locked lasers were used to pump nonlinear media such as optical fibers to generate SC light. However, those large pump lasers may now be replaced with diode lasers and fiber amplifiers that gained maturity in the telecommunications industry.

Figure 20:
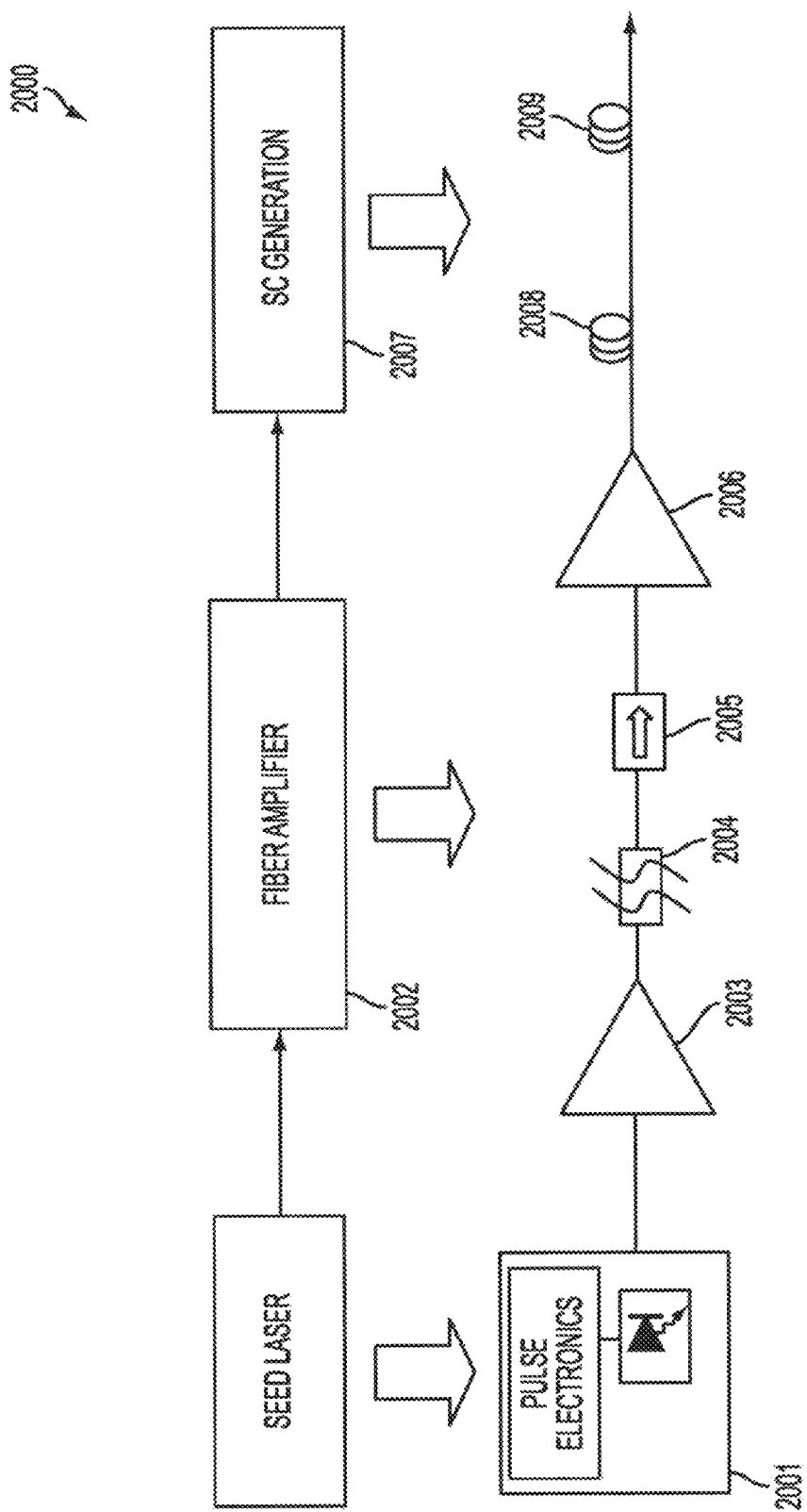
FIG. 20 shows a platform architecture for different wavelength ranges for an all-fiber-integrated, high powered, super-continuum light source.

In one embodiment, an all-fiber-integrated, high-powered SC light source 2000 may be elegant for its simplicity (FIG. 20). The light may be first generated from a seed laser diode 2001. For example, the seed LD 2001 may be a distributed feedback laser diode with a wavelength near 1542 or 1550 nm, with approximately 0.5-2.0 ns pulsed output, and with a pulse repetition rate between a kilohertz to about 100 MHz or more. The output from the seed laser diode may then be amplified in a multiple-stage fiber amplifier 2002 comprising one or more gain fiber segments. In one embodiment, the first stage pre-amplifier 2003 may be designed for optimal noise performance. For example, the pre-amplifier 2003 may be a standard erbium-doped fiber amplifier or an erbium/ytterbium doped cladding pumped fiber amplifier. Between amplifier stages 2003 and 2006, it may be advantageous to use band-pass filters 2004 to block amplified spontaneous emission and isolators 2005 to prevent spurious reflections. Then, the power amplifier stage 2006 may use a cladding-pumped fiber amplifier that may be optimized to minimize nonlinear distortion. The power amplifier fiber 2006 may also be an erbium-doped fiber amplifier, if only low or moderate power levels are to be generated.

The SC generation 2007 may occur in the relatively short lengths of fiber that follow the pump laser. In one exemplary embodiment, the SC fiber length may range from a few millimeters to 100 m or more. In one embodiment, the SC generation may occur in a first fiber 2008 where the modulational-instability initiated pulse break-up primarily occurs, followed by a second fiber 2009 where the SC generation and spectral broadening primarily occurs.

In one embodiment, one or two meters of standard single-mode fiber (SMF) after the power amplifier stage may be followed by several meters of SC generation fiber. For this example, in the SMF the peak power may be several kilowatts and the pump light may fall in the anomalous group-velocity dispersion regime-often called the soliton regime. For high peak powers in the dispersion regime, the nanosecond pulses may be unstable due to a phenomenon known as modulational instability, which is basically parametric amplification in which the fiber nonlinearity helps to phase match the pulses. As a consequence, the nanosecond pump pulses may be broken into many shorter pulses as the modulational instability tries to form soliton pulses from the quasi-continuous-wave background. Although the laser diode and amplification process starts with approximately nanosecond-long pulses, modulational instability in the short length of SMF fiber may form approximately 0.5 ps to several-picosecond-long pulses with high intensity. Thus, the few meters of SMF fiber may result in an output similar to that produced by mode-locked lasers, except in a much simpler and cost-effective manner.

The short pulses created through modulational instability may then be coupled into a nonlinear fiber for SC generation. The nonlinear mechanisms leading to broadband SC may include four-wave mixing or self-phase modulation along with the optical Raman effect. Since the Raman effect is self-phase-matched and shifts light to longer wavelengths by emission of optical photons, the SC may spread to longer wavelengths very efficiently. The short-wavelength edge may arise from four-wave mixing, and often times the short wavelength edge may be limited by increasing group-velocity dispersion in the fiber. In many instances, if the particular fiber used has sufficient peak power and SC fiber length, the SC generation process may fill the long-wavelength edge up to the transmission window.

Mature fiber amplifiers for the power amplifier stage 2006 include ytterbium-doped fibers (near 1060 nm), erbium-doped fibers (near 1550 nm), erbium/ytterbium-doped fibers (near 1550 nm), or thulium-doped fibers (near 2000 nm). In various embodiments, candidates for SC fiber 2009 include fused silica fibers (for generating SC between 0.8-2.7 µm), mid-IR fibers such as fluorides, chalcogenides, or tellurites (for generating SC out to 4.5 µm or longer), photonic crystal fibers (for generating SC between 0.4 and 1.7 µm), or combinations of these fibers. Therefore, by selecting the appropriate fiber-amplifier doping for 2006 and nonlinear fiber 2009, SC may be generated in the visible, near-IR/SWIR, or mid-IR wavelength region.

The configuration 2000 of FIG. 20 is just one particular example, and other configurations can be used and are intended to be covered by this disclosure. For example, further gain stages may be used, and different types of lossy elements or fiber taps may be used between the amplifier stages. In another embodiment, the SC generation may occur partially in the amplifier fiber and in the pig-tails from the pump combiner or other elements. In yet another embodiment, polarization maintaining fibers may be used, and a polarizer may also be used to enhance the polarization contrast between amplifier stages. Also, not discussed in detail are many accessories that may accompany this set-up, such as driver electronics, pump laser diodes, safety shut-offs, and thermal management and packaging.

Figure 21:
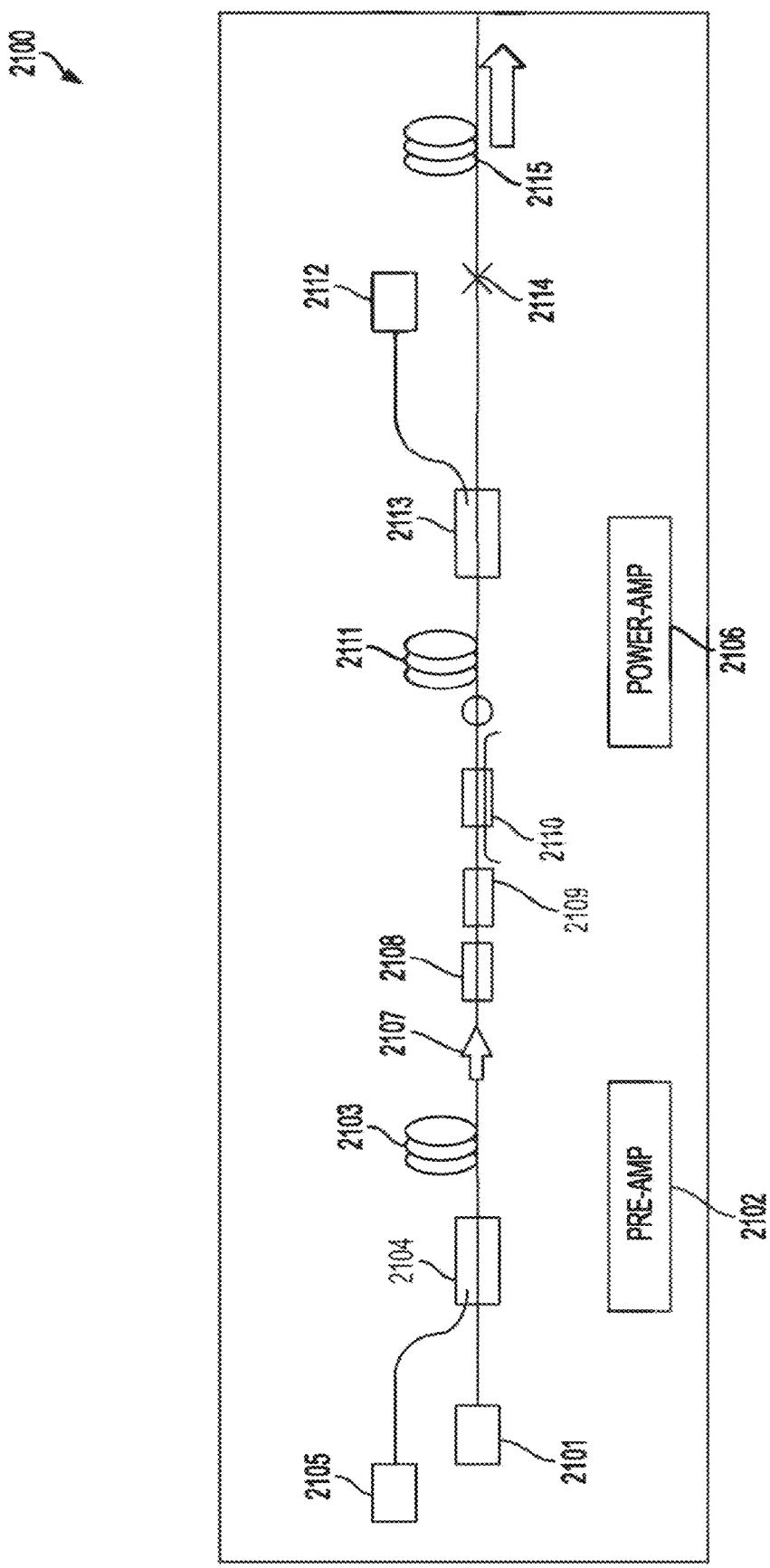
FIG. 21 illustrates one embodiment of a short-wave infrared (SWIR) super-continuum (SC) light source.

One example of an SC laser that operates in the SWIR used in one embodiment is illustrated in FIG. 21. This SWIR SC source 2100 produces an output of up to approximately 5 W over a spectral range of about 1.5 to 2.4 microns, and this particular laser is made out of polarization maintaining components. The seed laser 2101 is a distributed feedback (DFB) laser operating near 1542 nm producing approximately 0.5 nanosecond (ns) pulses at an about 8 MHz repetition rate. The pre-amplifier 2102 is forward pumped and uses about 2 m length of erbium/ytterbium cladding pumped fiber 2103 (often also called dual-core fiber) with an inner core diameter of 12 microns and outer core diameter of 130 microns. The pre-amplifier gain fiber 2103 is pumped using a 10 W 940 nm laser diode 2105 that is coupled in using a fiber combiner 2104.

In this particular 5 W unit, the mid-stage between amplifier stages 2102 and 2106 comprises an isolator 2107, a band-pass filter 2108, a polarizer 2109 and a fiber tap 2110. The power amplifier 2106 uses a 4 m length of the 12/130 micron erbium/ytterbium doped fiber 2111 that is counter-propagating pumped using one or more 30 W 940 nm laser diodes 2112 coupled in through a combiner 2113. An approximately 1-2 meter length of the combiner pig-tail helps to initiate the SC process, and then a length of PM-1550 fiber 2115 (polarization maintaining, single-mode, fused silica fiber optimized for 1550 nm) is spliced 2114 to the combiner output.

Figure 22:
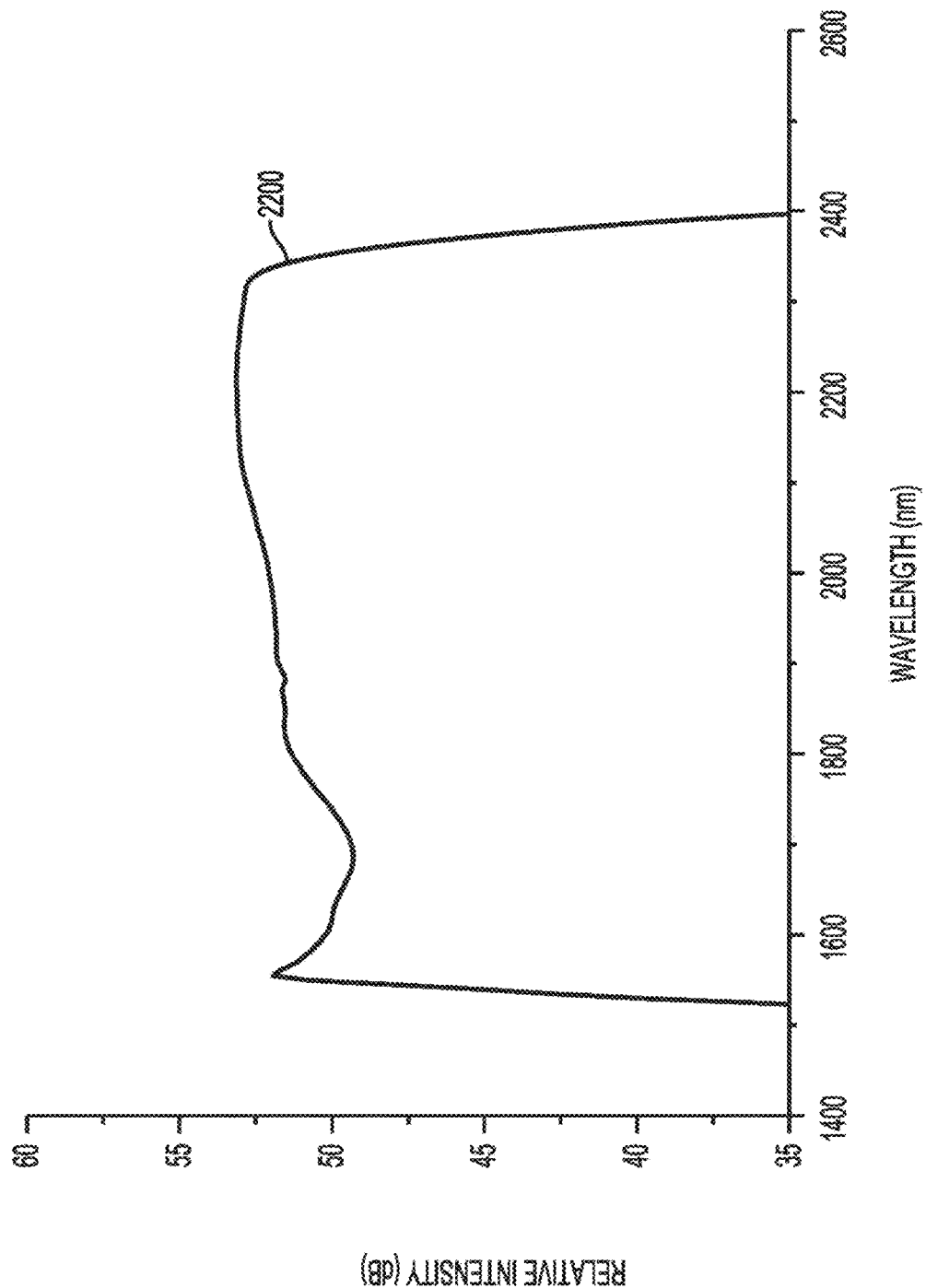
FIG. 22 shows the output spectrum from the SWIR SC laser of FIG. 21 when ~10 m length of fiber for SC generation is used. This fiber is a single-mode, non-dispersion shifted fiber that is optimized for operation near 1550 nm.

If an output fiber of about 10 m in length is used, then the resulting output spectrum 2200 is shown in FIG. 22. The details of the output spectrum 2200 depend on the peak power into the fiber, the fiber length, and properties of the fiber such as length and core size, as well as the zero dispersion wavelength and the dispersion properties. For example, if a shorter length of fiber is used, then the spectrum actually reaches to longer wavelengths (e.g., a 2 m length of SC fiber broadens the spectrum to ~2500 nm). Also, if extra-dry fibers are used with less O—H content, then the wavelength edge may also reach to a longer wavelength. To generate more spectrum toward the shorter wavelengths, the pump wavelength (in this case ~1542 nm) should be close to the zero dispersion wavelength in the fiber. For example, by using a dispersion shifted fiber or so-called non-zero dispersion shifted fiber, the short wavelength edge may shift to shorter wavelengths.

Although one particular example of a 5 W SWIR-SC has been described, different components, different fibers, and different configurations may also be used consistent with this disclosure. For instance, another embodiment of the similar configuration 2100 in FIG. 21 may be used to generate high powered SC between approximately 1060 and 1800 nm. For this embodiment, the seed laser 2101 may be a 1064 nm distributed feedback (DFB) laser diode, the pre-amplifier gain fiber 2103 may be a ytterbium-doped fiber amplifier with 10/125 microns dimensions, and the pump laser 2105 may be a 10 W 915 nm laser diode. In the mid-stage, a mode field adapter may be included in addition to the isolator 2107, band pass filter 2108, polarizer 2109 and tap 2110. The gain fiber 2111 in the power amplifier may be a 20 m length of ytterbium-doped fiber with 25/400 microns dimension for example. The pump 2112 for the power amplifier may be up to six pump diodes providing 30 W each near 915 nm, for example. For this much pump power, the output power in the SC may be as high as 50 W or more.

In another embodiment, it may be desirous to generate high power SWIR SC over 1.4-1.8 microns and separately 2-2.5 microns (the window between 1.8 and 2 microns may be less important due to the strong water and atmospheric absorption). For example, the top SC source of FIG. 23 can lead to bandwidths ranging from about 1400 nm to 1800 nm or broader, while the lower SC source of FIG. 23 can lead to bandwidths ranging from about 1900 nm to 2500 nm or broader. Since these wavelength ranges are shorter than about 2500 nm, the SC fiber can be based on fused silica fiber. Exemplary SC fibers include standard single-mode fiber SMF, high-nonlinearity fiber, high-NA fiber, dispersion shifted fiber, dispersion compensating fiber, and photonic crystal fibers. Non-fused-silica fibers can also be used for SC generation, including chalcogenides, fluorides, ZBLAN, tellurites, and germanium oxide fibers.

Figure 23:
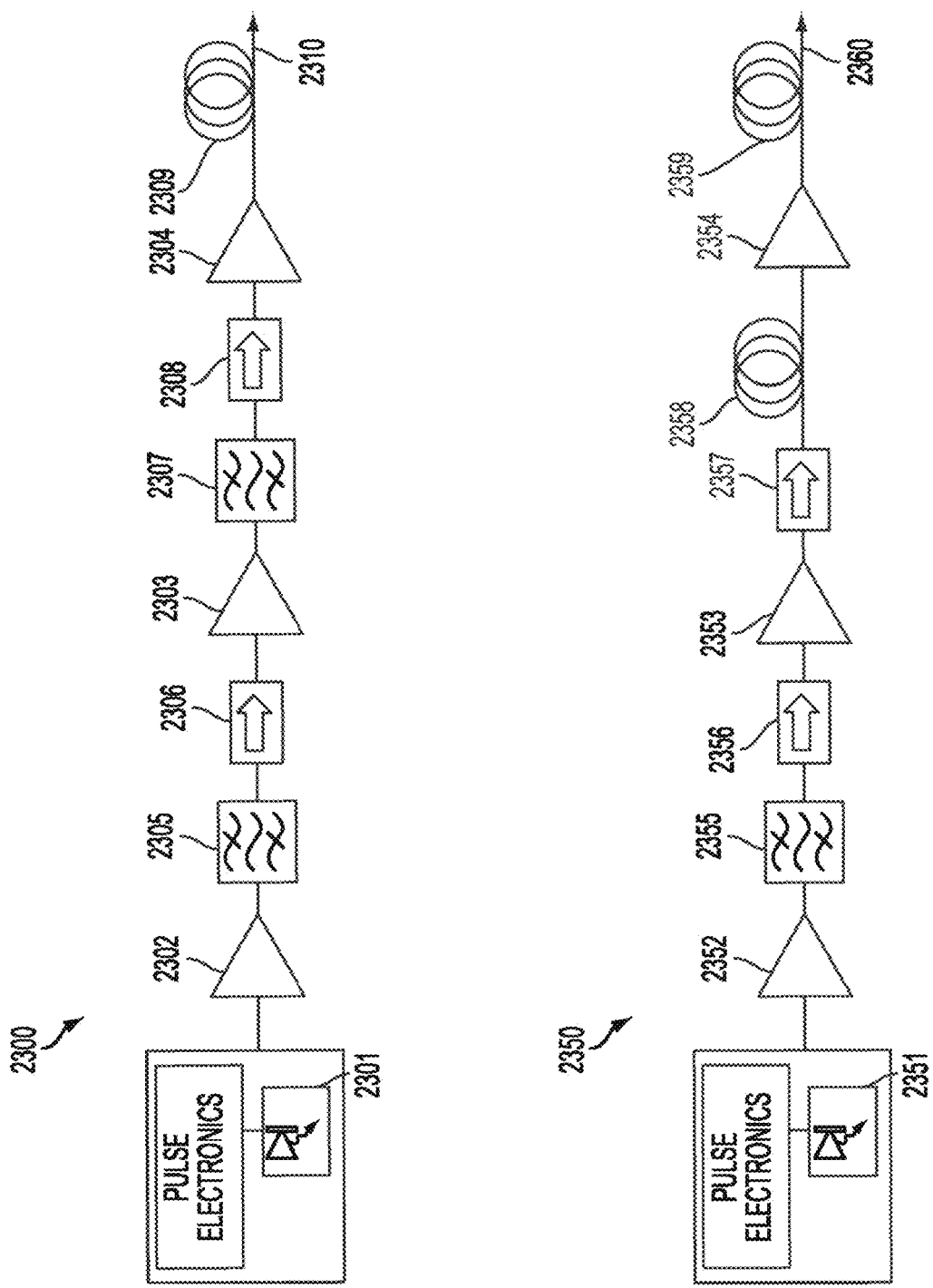
FIG. 23 illustrates high power SWIR-SC lasers that may generate light between approximately 1.4-1.8 microns (top) or approximately 2-2.5 microns (bottom).
Figure 24:
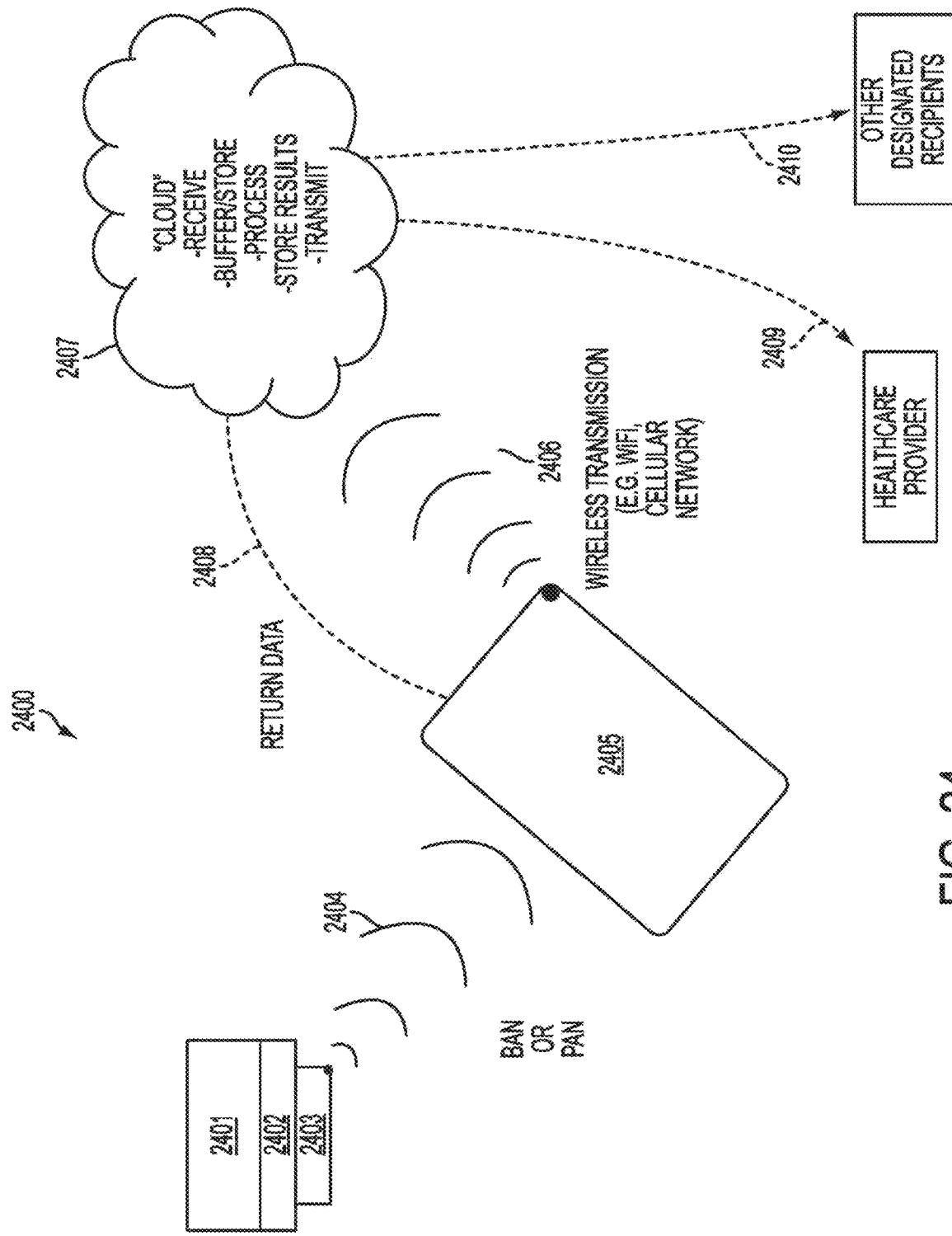
FIG. 24 schematically shows that the medical measurement device can be part of a personal or body area network that communicates with another device (e.g., smart phone or tablet) that communicates with the cloud. The cloud may in turn communicate information with the user, healthcare providers, or other designated recipients.

In one embodiment, the top of FIG. 23 illustrates a block diagram for an SC source 2300 capable of generating light between approximately 1400 and 1800 nm or broader. As an example, a pump fiber laser similar to FIG. 21 can be used as the input to a SC fiber 2309. The seed laser diode 2301 can comprise a DFB laser that generates, for example, several milliwatts of power around 1542 or 1553 nm. The fiber pre-amplifier 2302 can comprise an erbium-doped fiber amplifier or an erbium/ytterbium doped double clad fiber. In this example a mid-stage amplifier 2303 can be used, which can comprise an erbium/ytterbium doped double-clad fiber. A bandpass filter 2305 and isolator 2306 may be used between the pre-amplifier 2302 and mid-stage amplifier 2303. The power amplifier stage 2304 can comprise a larger core size erbium/ytterbium doped double-clad fiber, and another bandpass filter 2307 and isolator 2308 can be used before the power amplifier 2304. The output of the power amplifier can be coupled to the SC fiber 2309 to generate the SC output 2310. This is just one exemplary configuration for an SC source, and other configurations or elements may be used consistent with this disclosure.

In yet another embodiment, the bottom of FIG. 23 illustrates a block diagram for an SC source 2350 capable of generating light between approximately 1900 and 2500 nm or broader. As an example, the seed laser diode 2351 can comprise a DFB or DBR laser that generates, for example, several milliwatts of power around 1542 or 1553 nm. The fiber pre-amplifier 2352 can comprise an erbium-doped fiber amplifier or an erbium/ytterbium doped double-clad fiber. In this example a mid-stage amplifier 2353 can be used, which can comprise an erbium/ytterbium doped double-clad fiber. A bandpass filter 2355 and isolator 2356 may be used between the pre-amplifier 2352 and mid-stage amplifier 2353. The power amplifier stage 2354 can comprise a thulium doped double-clad fiber, and another isolator 2357 can be used before the power amplifier 2354. Note that the output of the mid-stage amplifier 2353 can be approximately near 1550 nm, while the thulium-doped fiber amplifier 2354 can amplify wavelengths longer than approximately 1900 nm and out to about 2100 nm. Therefore, for this configuration wavelength shifting may be required between 2353 and 2354. In one embodiment, the wavelength shifting can be accomplished using a length of standard single-mode fiber 2358, which can have a length between approximately 5 and 50 meters, for example. The output of the power amplifier 2354 can be coupled to the SC fiber 2359 to generate the SC output 2360. This is just one exemplary configuration for an SC source, and other configurations or elements can be used consistent with this disclosure. For example, the various amplifier stages can comprise different amplifier types, such as erbium doped fibers, ytterbium doped fibers, erbium/ytterbium co-doped fibers and thulium doped fibers. One advantage of the SC lasers illustrated in FIGS. 20-23 are that they may use all-fiber components, so that the SC laser can be all-fiber, monolithically integrated with no moving parts. The all-integrated configuration can consequently be robust and reliable.

FIGS. 20-23 are examples of SC light sources that may be advantageously used for SWIR light generation in various medical diagnostic and therapeutic applications. However, many other versions of the SC light sources may also be made that are intended to also be covered by this disclosure. For example, the SC generation fiber could be pumped by a mode-locked laser, a gain-switched semiconductor laser, an optically pumped semiconductor laser, a solid state laser, other fiber lasers, or a combination of these types of lasers. Also, rather than using a fiber for SC generation, either a liquid or a gas cell might be used as the nonlinear medium in which the spectrum is to be broadened.

Even within the all-fiber versions illustrated such as in FIG. 21, different configurations could be used consistent with the disclosure. In an alternate embodiment, it may be desirous to have a lower cost version of the SWIR SC laser of FIG. 21. One way to lower the cost could be to use a single stage of optical amplification, rather than two stages, which may be feasible if lower output power is required or the gain fiber is optimized. For example, the pre-amplifier stage 2102 might be removed, along with at least some of the mid-stage elements. In yet another embodiment, the gain fiber could be double passed to emulate a two stage amplifier. In this example, the pre-amplifier stage 2102 might be removed, and perhaps also some of the mid-stage elements. A mirror or fiber grating reflector could be placed after the power amplifier stage 2106 that may preferentially reflect light near the wavelength of the seed laser 2101. If the mirror or fiber grating reflector can transmit the pump light near 940 nm, then this could also be used instead of the pump combiner 2113 to bring in the pump light 2112. The SC fiber 2115 could be placed between the seed laser 2101 and the power amplifier stage 2106 (SC is only generated after the second pass through the amplifier, since the power level may be sufficiently high at that time). In addition, an output coupler may be placed between the seed laser diode 2101 and the SC fiber, which now may be in front of the power amplifier 2106. In a particular embodiment, the output coupler could be a power coupler or divider, a dichroic coupler (e.g., passing seed laser wavelength but outputting the SC wavelengths), or a wavelength division multiplexer coupler. This is just one further example, but a myriad of other combinations of components and architectures could also be used for SC light sources to generate SWIR light that are intended to be covered by this disclosure.

Wireless Link to the Cloud

The non-invasive blood constituent or analytes measurement device may also benefit from communicating the data output to the "cloud" (e.g., data servers and processors in the web remotely connected) via wired and/or wireless communication strategies. The non-invasive devices may be part of a series of biosensors applied to the patient, and collectively these devices form what might be called a body area network or a personal area network. The biosensors and non-invasive devices may communicate to a smart phone, tablet, personal data assistant, computer, and/or other microprocessor-based device, which may in turn wirelessly or over wire and/or fiber optically transmit some or all of the signal or processed data to the internet or cloud. The cloud or internet may in turn send the data to doctors or health care providers as well as the patients themselves. Thus, it may be possible to have a panoramic, high-definition, relatively comprehensive view of a patient that doctors can use to assess and manage disease, and that patients can use to help maintain their health and direct their own care.

In a particular embodiment 2400, the physiological measurement device or non-invasive blood constituent measurement device 2401 may comprise a transmitter 2403 to communicate over a first communication link 2404 in the body area network or personal area network to a receiver in a smart phone, tablet cell phone, PDA, or computer 2405. For the measurement device 2401, it may also be advantageous to have a processor 2402 to process some of the physiological data, since with processing the amount of data to transmit may be less (hence, more energy efficient). The first communication link 2404 may operate through the use of one of many wireless technologies such as Bluetooth, Zigbee, WiFi, IrDA (infrared data association), wireless USB, or Z-wave, to name a few. Alternatively, the communication link 2404 may occur in the wireless medical band between 2360 and 2390 MHz, which the FCC allocated for medical body area network devices, or in other designated medical device or WMTS bands. These are examples of devices that can be used in the body area network and surroundings, but other devices could also be used and are included in the scope of this disclosure.

The personal device 2405 may store, process, display, and transmit some of the data from the measurement device 2401. The device 2405 may comprise a receiver, transmitter, display, voice control and speakers, and one or more control buttons or knobs and a touch screen. Examples of the device 2405 include smart phones such as the Apple iPhones® or phones operating on the Android or Microsoft systems. In one embodiment, the device 2405 may have an application, software program, or firmware to receive and process the data from the measurement device 2401. The device 2405 may then transmit some or all of the data or the processed data over a second communication link 2406 to the internet or "cloud" 2407. The second communication link 2406 may advantageously comprise at least one segment of a wireless transmission link, which may operate using WiFi or the cellular network. The second communication link 2406 may additionally comprise lengths of fiber optic and/or communication over copper wires or cables.

The internet or cloud 2407 may add value to the measurement device 2401 by providing services that augment the physiological data collected. In a particular embodiment, some of the functions performed by the cloud include: (a) receive at least a fraction of the data from the device 2405; (b) buffer or store the data received; (c) process the data using software stored on the cloud; (d) store the resulting processed data; and (e) transmit some or all of the data either upon request or based on an alarm. As an example, the data or processed data may be transmitted 2408 back to the originator (e.g., patient or user), it may be transmitted 2409 to a health care provider or doctor, or it may be transmitted 2410 to other designated recipients.

The cloud 2407 may provide a number of value-add services. For example, the cloud application may store and process the physiological data for future reference or during a visit with the healthcare provider. If a patient has some sort of medical mishap or emergency, the physician can obtain the history of the physiological parameters over a specified period of time. In another embodiment, if the physiological parameters fall out of acceptable range, alarms may be delivered to the user 2408, the healthcare provider 2409, or other designated recipients 2410. These are just some of the features that may be offered, but many others may be possible and are intended to be covered by this disclosure. As an example, the device 2405 may also have a GPS sensor, so the cloud 2407 may be able to provide time, data and position along with the physiological parameters. Thus, if there is a medical emergency, the cloud 2407 could provide the location of the patient to the healthcare provider 2409 or other designated recipients 2410. Moreover, the digitized data in the cloud 2407 may help to move toward what is often called "personalized medicine." Based on the physiological parameter data history, medication or medical therapies may be prescribed that are customized to the particular patient.

Beyond the above benefits, the cloud application 2407 and application on the device 2405 may also have financial value for companies developing measurement devices 2401 such as a non-invasive blood constituent monitor. In the case of glucose monitors, the companies make the majority of their revenue on the measurement strips. However, with a non-invasive monitor, there is no need for strips, so there is less of an opportunity for recurring costs (e.g., the razor/razor blade model does not work for non-invasive devices). On the other hand, people may be willing to pay a periodic fee for the value-add services provided on the cloud 2407. Diabetic patients, for example, would probably be willing to pay a periodic fee for monitoring their glucose levels, storing the history of the glucose levels, and having alarm warnings when the glucose level falls out of range. Similarly, patients taking ketone bodies supplement for treatment of disorders characterized by impaired glucose metabolism (e.g., Alzheimer's, Parkinson's, Huntington's or ALS) may need to monitor their ketone bodies level. These patients would also probably be willing to pay a periodic fee for the value-add services provided on the cloud 2407. Thus, by leveraging the advances in wireless connectivity and the widespread use of handheld devices such as smart phones that can wirelessly connect to the cloud, businesses can build a recurring cost business model even using non-invasive measurement devices.

Described herein are just some examples of the beneficial use of near-infrared or SWIR lasers for non-invasive monitoring of glucose, ketones, HbA1c and other blood constituents. However, many other medical procedures can use the near-infrared or SWIR light consistent with this disclosure and are intended to be covered by the disclosure.

Section 2: Short-Wave Infrared Super-Continuum Lasers for Early Detection of Dental Caries Near-infrared (NIR) and SWIR light may be preferred for caries detection compared to visible light imaging because the NIR/SWIR wavelengths generally have lower absorption by stains and deeper penetration into teeth. Hence, NIR/SWIR light may provide a caries detection method that can be non-invasive, non-contact and relatively stain insensitive. Broadband light may provide further advantages because carious regions may demonstrate spectral signatures from water absorption and the wavelength dependence of porosity in the scattering of light.

In general, the near-infrared region of the electromagnetic spectrum covers between approximately 0.7 microns (700 nm) to about 2.5 microns (2500 nm). However, it may also be advantageous to use just the short-wave infrared between approximately 1.4 microns (1400 nm) and about 2.5 microns (2500 nm). One reason for preferring the SWIR over the entire NIR may be to operate in the so-called "eye safe" window, which corresponds to wavelengths longer than about 1400 nm. Therefore, for the remainder of the disclosure the SWIR will be used for illustrative purposes. However, it should be clear that the discussion that follows could also apply to using the NIR wavelength range, or other wavelength bands.

In particular, wavelengths in the eye safe window may not transmit down to the retina of the eye, and therefore, these wavelengths may be less likely to create permanent eye damage from inadvertent exposure. The near-infrared wavelengths have the potential to be dangerous, because the eye cannot see the wavelengths (as it can in the visible), yet they can penetrate and cause damage to the eye. Even if a practitioner is not looking directly at the laser beam, the practitioner's eyes may receive stray light from a reflection or scattering from some surface. Hence, it can always be a good practice to use eye protection when working around lasers. Since wavelengths longer than about 1400 nm are substantially not transmitted to the retina or substantially absorbed in the retina, this wavelength range is known as the eye safe window. For wavelengths longer than 1400 nm, in general only the cornea of the eye may receive or absorb the light radiation.

Figure 25:
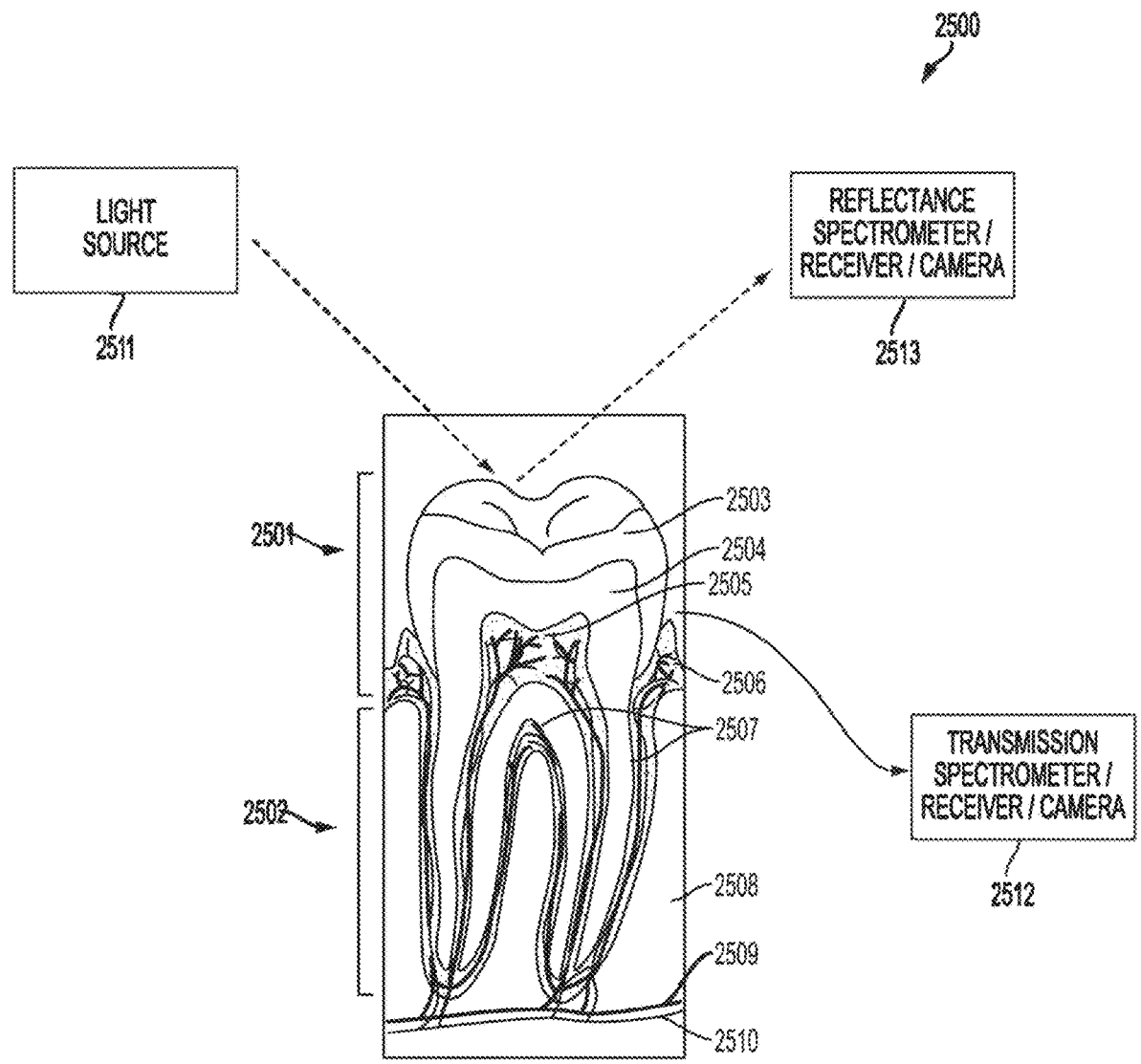
FIG. 25 illustrates the structure of a tooth.

FIG. 25 illustrates the structure of an exemplary cross-section of a tooth 2500. The tooth 2500 has a top layer called the crown 2501 and below that a root 2502 that reaches well into the gum 2506 and bone 2508 of the mouth. The exterior of the crown 2501 is an enamel layer 2503, and below the enamel is a layer of dentine 2504 that sits atop a layer of cementum 2507. Below the dentine 2504 is a pulp region 2505, which comprises within it blood vessels 2509 and nerves 2510. If the light can penetrate the enamel 2503 and dentine 2504, then the blood flow and blood constituents may be measured through the blood vessels in the dental pulp 2505. While the amount of blood flow in the capillaries of the dental pulp 2505 may be less than an artery or vein, the smaller blood flow could still be advantageous for detecting or measuring blood constituents as compared to detection through the skin if there is less interfering spectral features from the tooth.

As used throughout this document, the term "couple" and or "coupled" refers to any direct or indirect communication between two or more elements, whether or not those elements are physically connected to one another. As used throughout this disclosure, the term "spectroscopy" means that a tissue or sample is inspected by comparing different features, such as wavelength (or frequency), spatial location, transmission, absorption, reflectivity, scattering, refractive index, or opacity. In one embodiment, "spectroscopy" may mean that the wavelength of the light source is varied, and the transmission, absorption, or reflectivity of the tissue or sample is measured as a function of wavelength. In another embodiment, "spectroscopy" may mean that the wavelength dependence of the transmission, absorption or reflectivity is compared between different spatial locations on a tissue or sample. As an illustration, the "spectroscopy" may be performed by varying the wavelength of the light source, or by using a broadband light source and analyzing the signal using a spectrometer, wavemeter, or optical spectrum analyzer.

As used throughout this disclosure, the term "fiber laser" refers to a laser or oscillator that has as an output light or an optical beam, wherein at least a part of the laser comprises an optical fiber. For instance, the fiber in the "fiber laser" may comprise one of or a combination of a single mode fiber, a multi-mode fiber, a mid-infrared fiber, a photonic crystal fiber, a doped fiber, a gain fiber, or, more generally, an approximately cylindrically shaped waveguide or light-pipe. In one embodiment, the gain fiber may be doped with rare earth material, such as ytterbium, erbium, and/or thulium, for example. In another embodiment, the mid-infrared fiber may comprise one or a combination of fluoride fiber, ZBLAN fiber, chalcogenide fiber, tellurite fiber, or germanium doped fiber. In yet another embodiment, the single mode fiber may include standard single-mode fiber, dispersion shifted fiber, non-zero dispersion shifted fiber, high-nonlinearity fiber, and small core size fibers.

As used throughout this disclosure, the term "pump laser" refers to a laser or oscillator that has as an output light or an optical beam, wherein the output light or optical beam is coupled to a gain medium to excite the gain medium, which in turn may amplify another input optical signal or beam. In one particular example, the gain medium may be a doped fiber, such as a fiber doped with ytterbium, erbium, and/or thulium. In one embodiment, the "pump laser" may be a fiber laser, a solid state laser, a laser involving a nonlinear crystal, an optical parametric oscillator, a semiconductor laser, or a plurality of semiconductor lasers that may be multiplexed together. In another embodiment, the "pump laser" may be coupled to the gain medium by using a fiber coupler, a dichroic mirror, a multiplexer, a wavelength division multiplexer, a grating, or a fused fiber coupler.

As used throughout this document, the term "super-continuum" and or "supercontinuum" and or "SC" refers to a broadband light beam or output that comprises a plurality of wavelengths. In a particular example, the plurality of wavelengths may be adjacent to one-another, so that the spectrum of the light beam or output appears as a continuous band when measured with a spectrometer. In one embodiment, the broadband light beam may have a bandwidth or at least 10 nm. In another embodiment, the "super-continuum" may be generated through nonlinear optical interactions in a medium, such as an optical fiber or nonlinear crystal. For example, the "super-continuum" may be generated through one or a combination of nonlinear activities such as four-wave mixing, the Raman effect, modulational instability, and self-phase modulation.

As used throughout this disclosure, the terms "optical light" and or "optical beam" and or "light beam" refer to photons or light transmitted to a particular location in space. The "optical light" and or "optical beam" and or "light beam" may be modulated or unmodulated, which also means that they may or may not contain information. In one embodiment, the "optical light" and or "optical beam" and or "light beam" may originate from a fiber, a fiber laser, a laser, a light emitting diode, a lamp, a pump laser, or a light source.

Transmission or Reflection Through Teeth

Figure 26A:
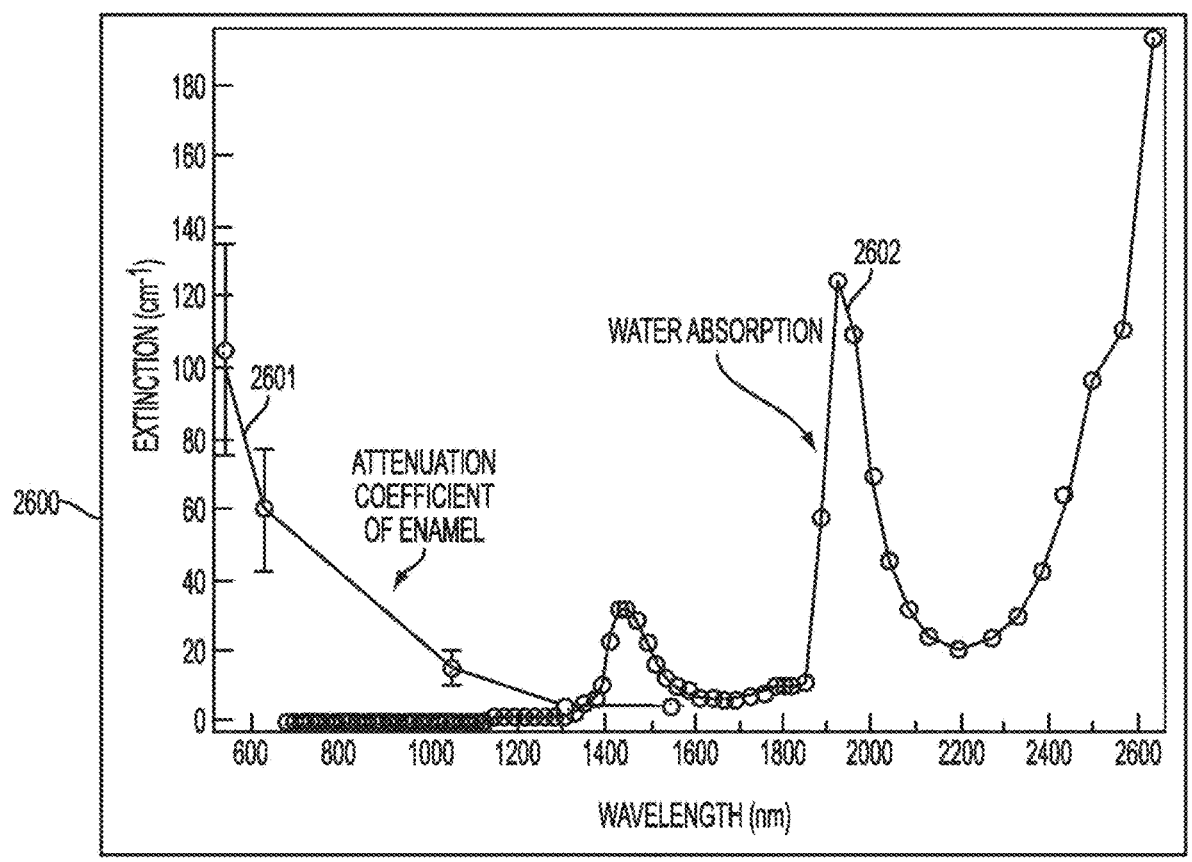
FIG. 26A shows the attenuation coefficient for dental enamel and water versus wavelength from approximately 600 nm to 2600 nm.

The transmission, absorption and reflection from teeth has been studied in the near infrared, and, although there are some features, the enamel and dentine appear to be fairly transparent in the near infrared (particularly SWIR wavelengths between about 1400 and 2500 nm). For example, the absorption or extinction ratio for light transmission has been studied. FIG. 26A illustrates the attenuation coefficient 2600 for dental enamel 2601 (filled circles) and the absorption coefficient of water 2602 (open circles) versus wavelength. Near-infrared light may penetrate much further without scattering through all the tooth enamel, due to the reduced scattering coefficient in normal enamel. Scattering in enamel may be fairly strong in the visible, but decreases as approximately 1/(wavelength)3 [i.e., inverse of the cube of the wavelength] with increasing wavelength to a value of only 2-3 cm-1 at 1310 nm and 1550 nm in the near infrared. Therefore, enamel may be virtually transparent in the near infrared with optical attenuation 1-2 orders of magnitude less than in the visible range.

Figure 26B:
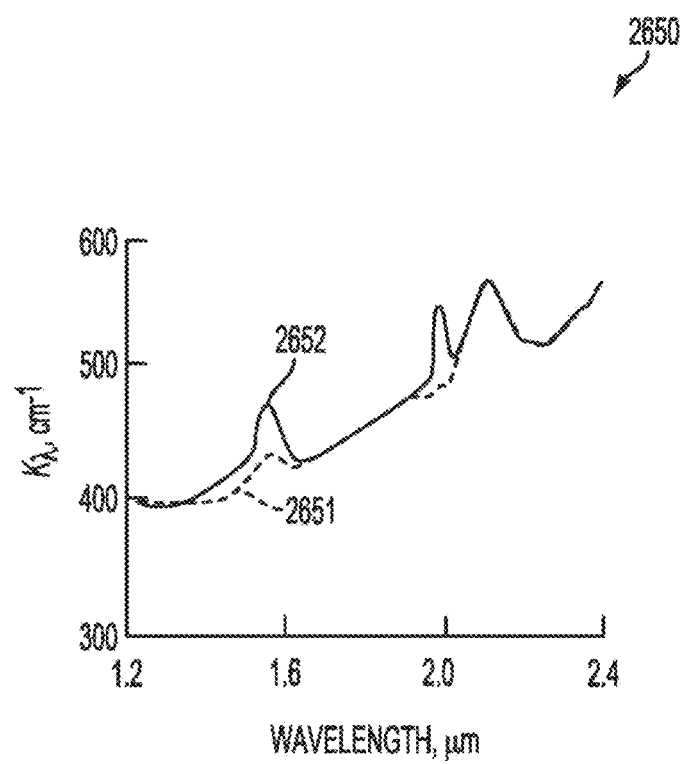
FIG. 26B illustrates the absorption spectrum of intact enamel and dentine in the wavelength range of approximately 1.2 to 2.4 microns.

As another example, FIG. 26B illustrates the absorption spectrum 2650 of intact enamel 2651 (dashed line) and dentine 2652 (solid line) in the wavelength range of approximately 1.2 to 2.4 microns. In the near infrared there are two absorption bands in the areas of about 1.5 and 2 microns. The band with a peak around 1.57 microns may be attributed to the overtone of valent vibration of water present in both enamel and dentine. In this band, the absorption is greater for dentine than for enamel, which may be related to the large water content in this tissue. In the region of 2 microns, dentine may have two absorption bands, and enamel one. The band with a maximum near 2.1 microns may belong to the overtone of vibration of PO hydroxyapatite groups, which is the main substance of both enamel and dentine. Moreover, the band with a peak near 1.96 microns in dentine may correspond to water absorption (dentine may contain substantially higher water than enamel).

Figure 27:
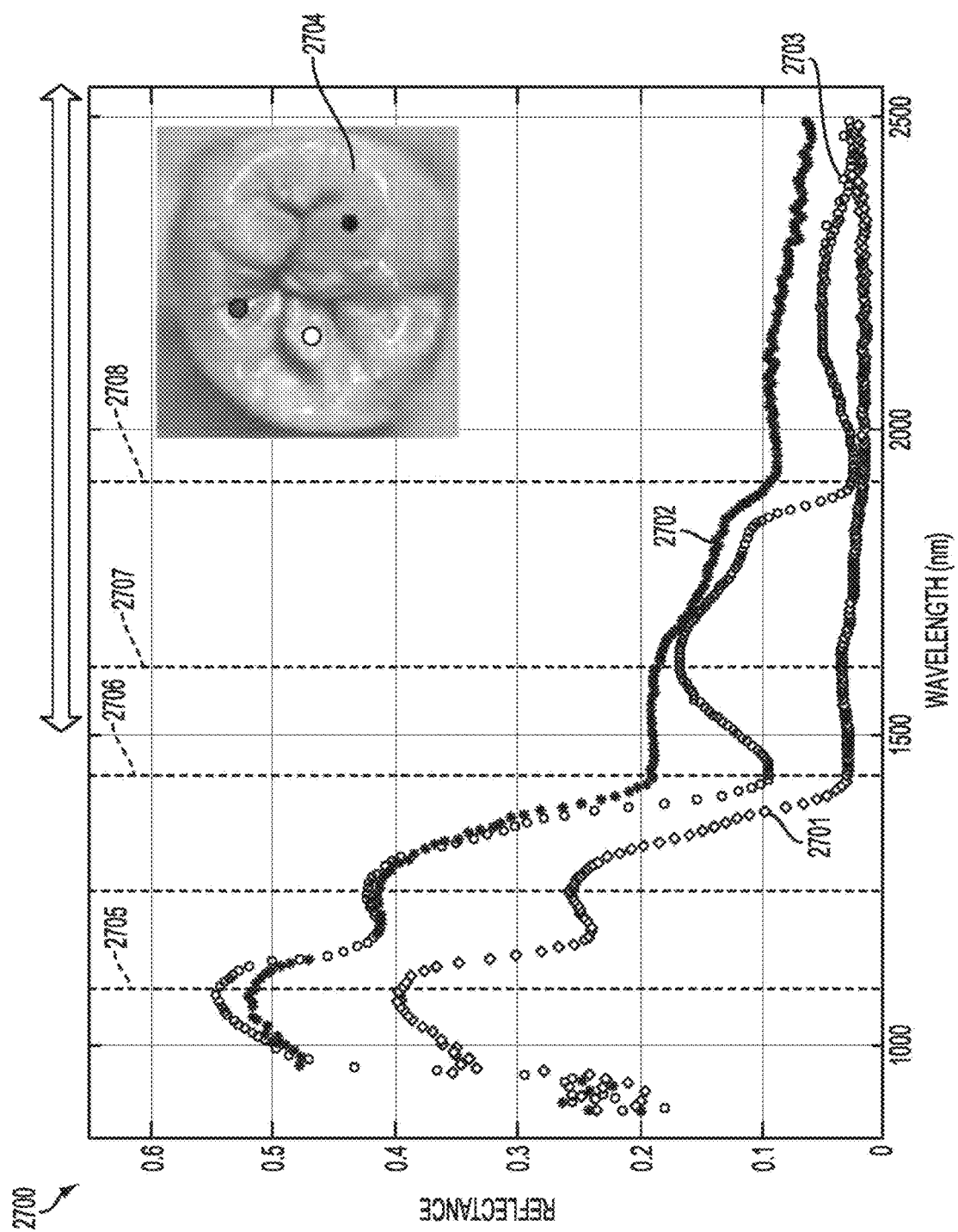
FIG. 27 shows the near infrared spectral reflectance over the wavelength range of approximately 800 nm to 2500 nm from an occlusal tooth surface. The black diamonds correspond to the reflectance from a sound, intact tooth section. The asterisks correspond to a tooth section with an enamel lesion. The circles correspond to a tooth section with a dentine lesion.

In addition to the absorption coefficient, the reflectance from intact teeth and teeth with dental caries (e.g., cavities) has been studied. In one embodiment, FIG. 27 shows the near infrared spectral reflectance 2700 over the wavelength range of approximately 800 nm to 2500 nm from an occlusal (e.g., top) tooth surface 2704. The curve with black diamonds 2701 corresponds to the reflectance from a sound, intact tooth section. The curve with asterisks (*) 2702 corresponds to a tooth section with an enamel lesion. The curve with circles 2703 corresponds to a tooth section with a dentine lesion. Thus, when there is a lesion, more scattering occurs and there may be an increase in the reflected light.

For wavelengths shorter than approximately 1400 nm, the shapes of the spectra remain similar, but the amplitude of the reflection changes with lesions. Between approximately 1400 nm and 2500 nm, an intact tooth 2701 has low reflectance (e.g., high transmission), and the reflectance appears to be more or less independent of wavelength. On the other hand, in the presence of lesions 2702 and 2703, there is increased scattering, and the scattering loss may be wavelength dependent. For example, the scattering loss may decrease as the inverse of some power of wavelength, such as 1/(wavelength)3—so, the scattering loss decreases with longer wavelengths. When there is a lesion in the dentine 2703, more water can accumulate in the area, so there is also increased water absorption. For example, the dips near 1450 nm and 1900 nm may correspond to water absorption, and the reflectance dips are particularly pronounced in the dentine lesion 2703.

FIG. 27 may point to several novel techniques for early detection and quantification of carious regions. One method may be to use a relatively narrow wavelength range (for example, from a laser diode or super-luminescent laser diode) in the wavelength window below 1400 nm. In one embodiment, wavelengths in the vicinity of 1310 nm may be used, which is a standard telecommunications wavelength where appropriate light sources are available. Also, it may be advantageous to use a super-luminescent laser diode rather than a laser diode, because the broader bandwidth may avoid the production of laser speckle that can produce interference patterns due to light's scattering after striking irregular surfaces. As FIG. 27 shows, the amplitude of the reflected light (which may also be proportional to the inverse of the transmission) may increase with dental caries. Hence, comparing the reflected light from a known intact region with a suspect region may help identify carious regions. However, one difficulty with using a relatively narrow wavelength range and relying on amplitude changes may be the calibration of the measurement. For example, the amplitude of the reflected light may depend on many factors, such as irregularities in the dental surface, placement of the light source and detector, distance of the measurement instrument from the tooth, etc.

In one embodiment, use of a plurality of wavelengths can help to better calibrate the dental caries measurement. For example, a plurality of laser diodes or super-luminescent laser diodes may be used at different center wavelengths. Alternately, a lamp or alternate broadband light source may be used followed by appropriate filters, which may be placed after the light source or before the detectors. In one example, wavelengths near 1090 nm, 1440 nm and 1610 nm may be employed. The reflection from the tooth 2705 appears to reach a local maximum near 1090 nm in the representative embodiment illustrated. Also, the reflectance near 1440 nm 2706 is higher for dental caries, with a distinct dip particularly for dentine caries 2703. Near 1610 nm 2707, the reflection is also higher for carious regions. By using a plurality of wavelengths, the values at different wavelengths may help quantify a caries score. In one embodiment, the degree of enamel lesions may be proportional to the ratio of the reflectance near 1610 nm divided by the reflectance near 1090 nm. Also, the degree of dentine lesion may be proportional to the difference between the reflectance near 1610 nm and 1440 nm, with the difference then divided by the reflectance near 1090 nm. Although one set of wavelengths has been described, other wavelengths may also be used and are intended to be covered by this disclosure.

In yet another embodiment, it may be further advantageous to use all of some fraction of the SWIR between approximately 1400 and 2500 nm. For example, a SWIR super-continuum light source could be used, or a lamp source could be used. On the receiver side, a spectrometer and/or dispersive element could be used to discriminate the various wavelengths. As FIG. 27 shows, an intact tooth 2701 has a relatively low and featureless reflectance over the SWIR. On the other hand, with a carious region there is more scattering, so the reflectance 2702, 2703 increases in amplitude. Since the scattering is inversely proportional to wavelength or some power of wavelength, the carious region reflectance 2702, 2703 also decreases with increasing wavelength. Moreover, the carious region may contain more water, so there are dips in the reflectance near the water absorption lines 2706 and 2708. The degree of caries or caries score may be quantified by the shape of the spectrum over the SWIR, taking ratios of different parts of the spectrum, or some combination of this and other spectral processing methods.

Although several methods of early caries detection using spectral reflectance have been described, other techniques could also be used and are intended to be covered by this disclosure. For example, transmittance may be used rather than reflectance, or a combination of the two could be used. Moreover, the transmittance, reflectance and/or absorbance could also be combined with other techniques, such as quantitative light-induced fluorescence or fiber-optic trans-illumination. Also, the SWIR could be advantageous, but other parts of the infrared, near-infrared or visible wavelengths may also be used consistent with this disclosure.

One other benefit of the absorption, transmission or reflectance in the near infrared and SWIR may be that stains and non-calcified plaque are not visible in this wavelength range, enabling better discrimination of defects, cracks, and demineralized areas. For example, dental calculus, accumulated plaque, and organic stains and debris may interfere significantly with visual diagnosis and fluorescence-based caries detection schemes in occlusal surfaces. In the case of using quantitative light-induced fluorescence, such confounding factors typically may need to be removed by prophylaxis (abrasive cleaning) before reliable measurements can be taken. Surface staining at visible wavelengths may further complicate the problem, and it may be difficult to determine whether pits and fissures are simply stained or demineralized. On the other hand, staining and pigmentation generally interfere less with NIR or SWIR imaging. For example, NIR and SWIR light may not be absorbed by melanin and porphyrins produced by bacteria and those found in food dyes that accumulate in dental plaque and are responsible for the pigmentation.

Human Interface for Measurement System

A number of different types of measurements may be used to image for dental caries, particularly early detection of dental caries. A basic feature of the measurements may be that the optical properties are measured as a function of wavelength at a plurality of wavelengths. As further described below, the light source may output a plurality of wavelengths, or a continuous spectrum over a range of wavelengths. In one embodiment, the light source may cover some or all of the wavelength range between approximately 1400 nm and 2500 nm. The signal may be received at a receiver, which may also comprise a spectrometer or filters to discriminate between different wavelengths. The signal may also be received at a camera, which may also comprise filters or a spectrometer. In one embodiment, the spectral discrimination using filters or a spectrometer may be placed after the light source rather than at the receiver. The receiver usually comprises one or more detectors (optical-to-electrical conversion element) and electrical circuitry. The receiver may also be coupled to analog to digital converters, particularly if the signal is to be fed to a digital device.

Referring to FIG. 25, one or more light sources 2511 may be used for illumination. In one embodiment, a transmission measurement may be performed by directing the light source output 2511 to the region near the interface between the gum 2506 and dentine 2504. In one embodiment, the light may be directed using a light guide or a fiber optic. The light may then propagate through the dental pulp 2505 to the other side, where the light may be incident on one or more detectors or another light guide to transport the signal to 2512 a spectrometer, receiver, and/or camera, for example. In one embodiment, the light source may be directed to one or more locations near the interface between the gum 2506 and dentine 2504 (in one example, could be from the two sides of the tooth). The transmitted light may then be detected in the occlusal surface above the tooth using a 2512 spectrometer, receiver, or camera, for example. In another embodiment, a reflectance measurement may be conducted by directing the light source output 2511 to, for example, the occlusal surface of the tooth, and then detecting the reflectance at a 2513 spectrometer, receiver or camera. Although a few embodiments for imaging the tooth are described, other embodiments and techniques may also be used and are intended to be covered by this disclosure. These optical techniques may measure optical properties such as reflectance, transmittance, absorption, or luminescence.

Figure 28:
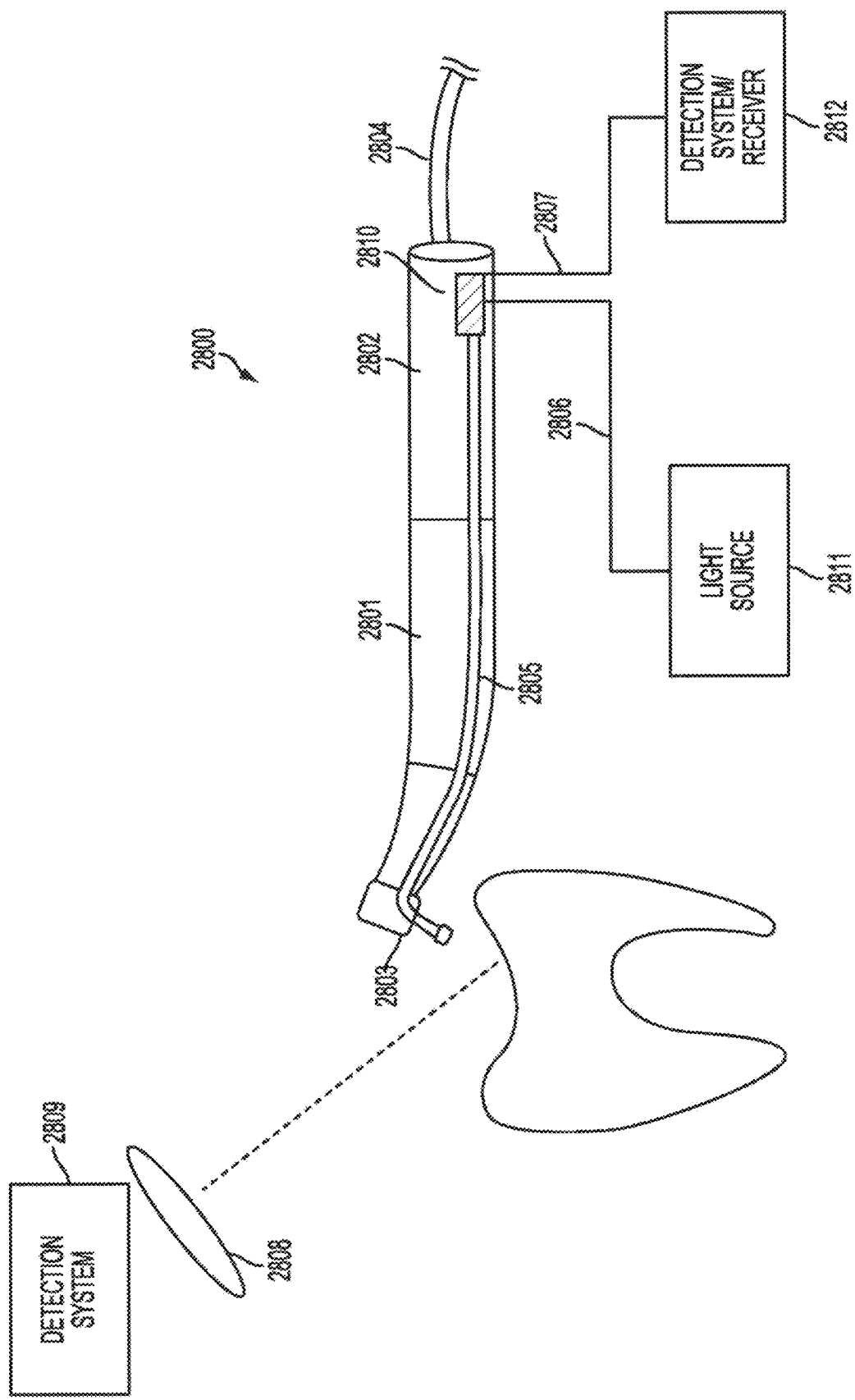
FIG. 28 illustrates a hand-held dental tool design of a human interface that may also be coupled with other dental tools.

In one embodiment, FIG. 28 shows that the light source and/or detection system may be integrated with a dental hand-piece 2800. The hand-piece 2800 may also include other dental equipment, such as a drill, pick, air spray or water cooling stream. The dental hand-piece 2800 may include a housing 2801 and a motor housing 2802 (in some embodiments such as with a drill, a motor may be placed in this section). The end of hand-piece 2803 that interfaces with the tooth may be detachable, and it may also have the light input and output end. The dental hand-piece 2800 may also have an umbilical cord 2804 for connecting to power supplies, diagnostics, or other equipment, for example.

A light guide 2805 may be integrated with the hand-piece 2800, either inside the housing 2801, 2802 or adjacent to the housing. In one embodiment, a light source 2810 may be contained within the housing 2801, 2802. In an alternative embodiment, the hand-piece 2800 may have a coupler 2810 to couple to an external light source 2811 and/or detection system or receiver 2812. The light source 2811 may be coupled to the hand-piece 2800 using a light guide or fiber optic cable 2806. In addition, the detection system or receiver 2812 may be coupled to the hand-piece 2800 using one or more light guides, fiber optic cable or a bundle of fibers 2807.

The light incident on the tooth may exit the hand-piece 2800 through the end 2803. The end 2803 may also have a lens system or curved mirror system to collimate or focus the light. In one embodiment, if the light source is integrated with a tool such as a drill, then the light may reach the tooth at the same point as the tip of the drill. The reflected or transmitted light from the tooth may then be observed externally and/or guided back through the light guide 405 in the hand-piece 2800. If observed externally, there may be a lens system 408 for collecting the light and a detection system 2809 that may have one or more detectors and electronics. If the light is to be guided back through the hand-piece 2800, then the reflected light may transmit through the light guide 2805 back to the detection system or receiver 2812. In one embodiment, the incident light may be guided by a fiber optic through the light guide 2805, and the reflected light may be captured by a series of fibers forming a bundle adjacent to or surrounding the incident light fiber.

Figure 29:
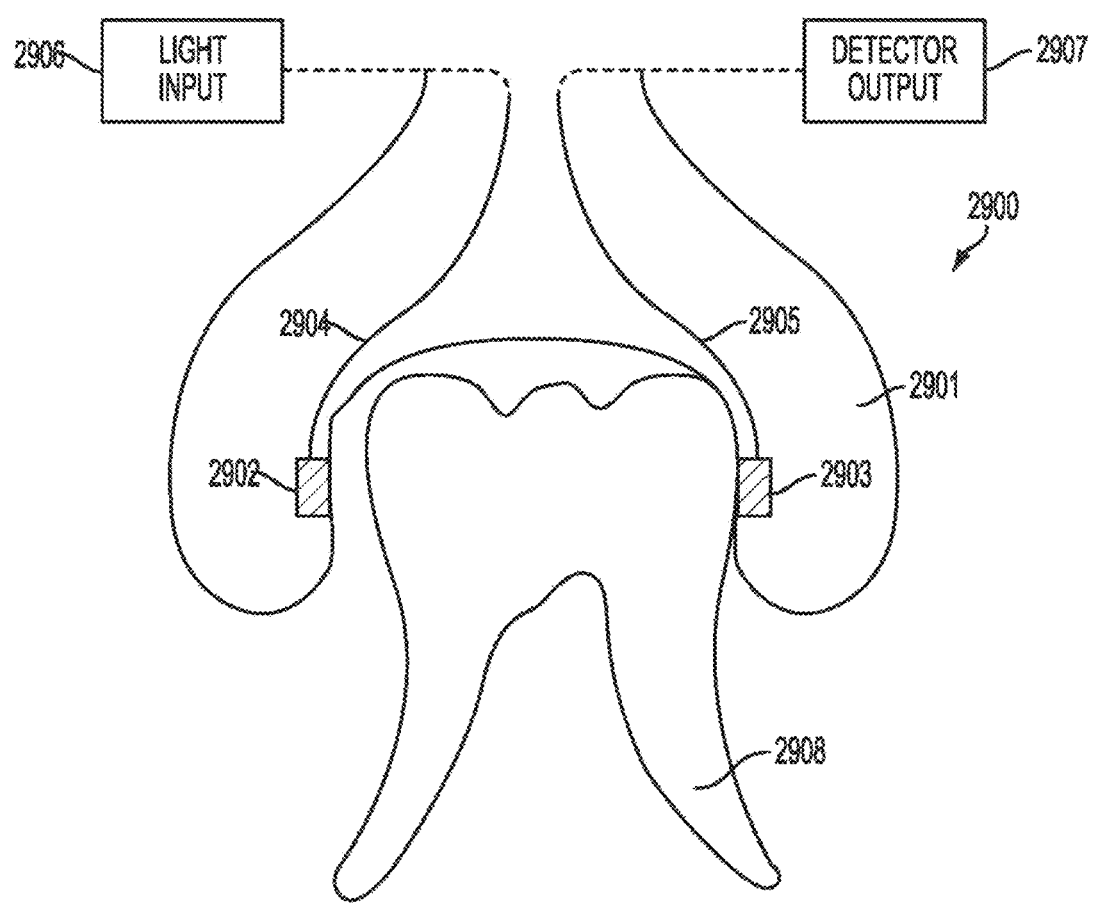
FIG. 29 illustrates a clamp design of a human interface to cap over one or more teeth and perform a non-invasive measurement for dental caries.

In another embodiment, a "clamp" design 2900 may be used as a cap over one or more teeth, as illustrated in FIG. 29. The clamp design may be different for different types of teeth, or it may be flexible enough to fit over different types of teeth. For example, different types of teeth include the molars (toward the back of the mouth), the premolars, the canine, and the incisors (toward the front of the mouth). One embodiment of the clamp-type design is illustrated in FIG. 29 for a molar tooth 2908. The C-clamp 2901 may be made of a plastic or rubber material, and it may comprise a light source input 2902 and a detector output 2903 on the front or back of the tooth, for example.

The light source input 2902 may comprise a light source directly, or it may have light guided to it from an external light source. Also, the light source input 2902 may comprise a lens system to collimate or focus the light across the tooth. The detector output 2903 may comprise a detector directly, or it may have a light guide to transport the signal to an external detector element. The light source input 2902 may be coupled electrically or optically through 2904 to a light input 2906. For example, if the light source is external in 2906, then the coupling element 2904 may be a light guide, such as a fiber optic. Alternately, if the light source is contained in 2902, then the coupling element 2904 may be electrical wires connecting to a power supply in 2906. Similarly, the detector output 2903 may be coupled to a detector output unit 2907 with a coupling element 2905, which may be one or more electrical wires or a light guide, such as a fiber optic. This is just one example of a clamp over one or more teeth, but other embodiments may also be used and are intended to be covered by this disclosure. For example, if reflectance from the teeth is to be used in the measurement, then the light input 2902 and detected light input 2903 may be on the same side of the tooth.

Figure 30:
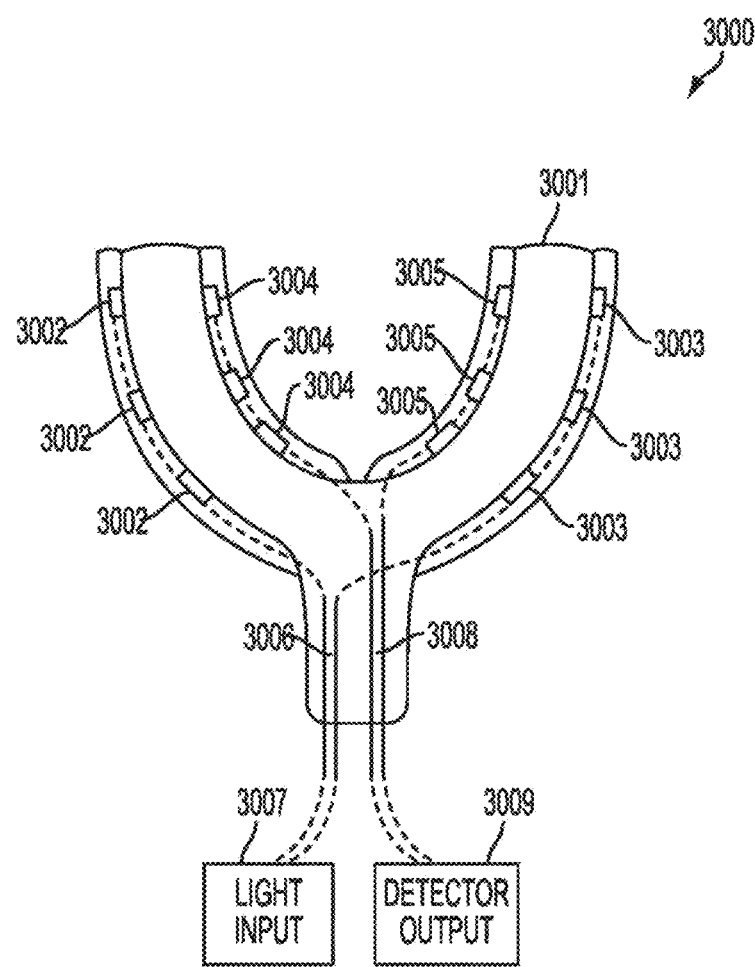
FIG. 30 shows a mouth guard design of a human interface to perform a non-invasive measurement for dental caries.
Figure 31:
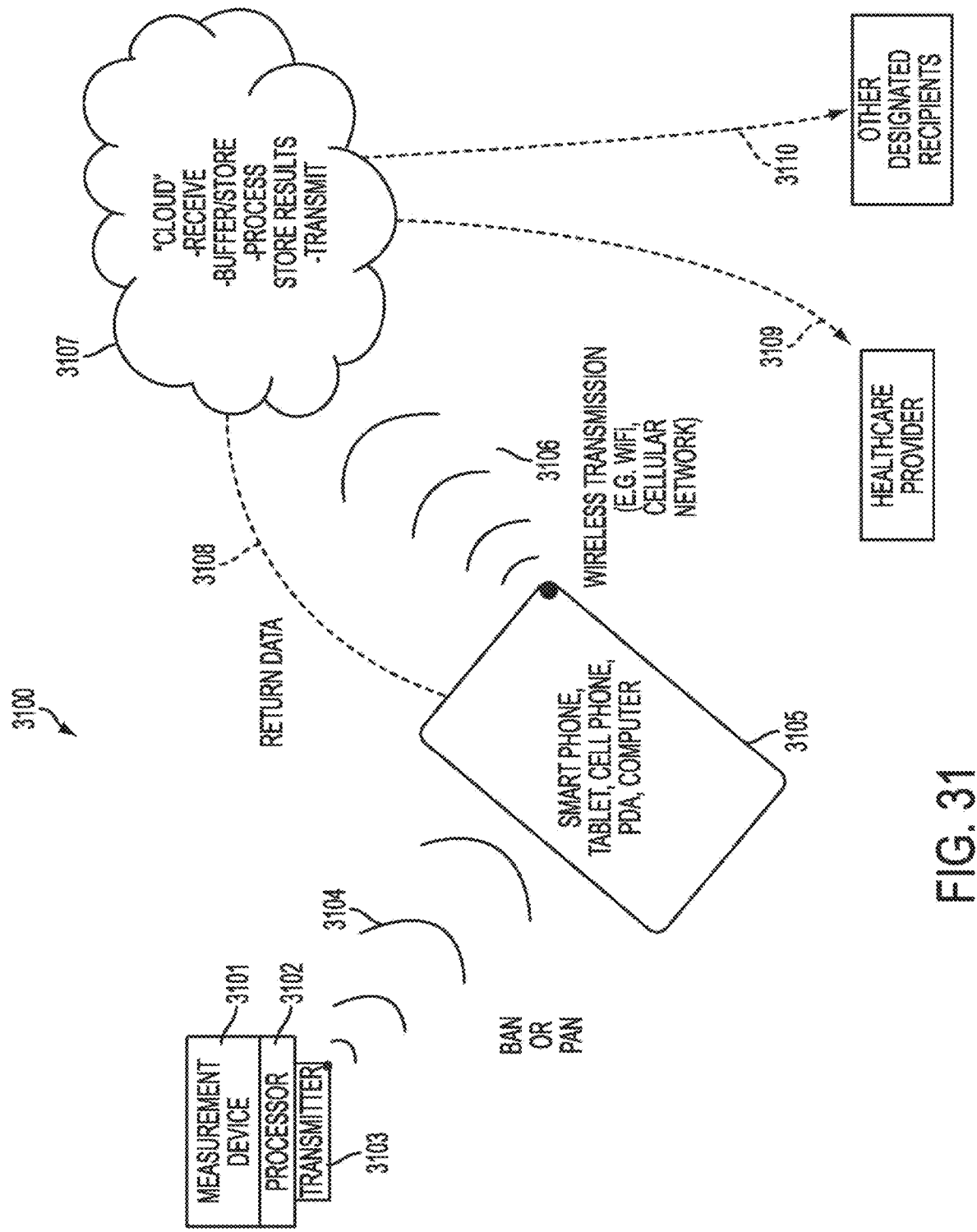
FIG. 31 schematically shows that the medical measurement device can be part of a personal or body area network that communicates with another device (e.g., smart phone or tablet) that communicates with the cloud. The cloud may in turn communicate information with the user, dental or healthcare providers, or other designated recipients.

In yet another embodiment, one or more light source ports and sensor ports may be used in a mouth-guard type design. For example, one embodiment of a dental mouth guard 3000 is illustrated in FIG. 30. The structure of the mouth guard 3001 may be similar to mouth guards used in sports (e.g., when playing football or boxing) or in dental trays used for applying fluoride treatment, and the mouth guard may be made from plastic, rubber, or any other suitable materials. As an example, the mouth guard may have one or more light source input ports 3002, 3003 and one or more detector output ports 3004, 3005. Although six input and output ports are illustrated, any number of ports may be used.

Similar to the clamp design described above, the light source inputs 3002, 3003 may comprise one or more light sources directly, or they may have light guided to them from an external light source. Also, the light source inputs 3002, 3003 may comprise lens systems to collimate or focus the light across the teeth. The detector outputs 3004, 3005 may comprise one or more detectors directly, or they may have one or more light guides to transport the signals to an external detector element. The light source inputs 3002, 3003 may be coupled electrically or optically through 3006 to a light input 3007. For example, if the light source is external in 3007, then the one or more coupling elements 3006 may be one or more light guides, such as a fiber optic. Alternately, if the light sources are contained in 3002, 3003, then the coupling element 3006 may be one or more electrical wires connecting to a power supply in 3007. Similarly, the detector outputs 3004, 3005 may be coupled to a detector output unit 3009 with one or more coupling elements 3008, which may be one or more electrical wires or one or more light guides, such as a fiber optic. This is just one example of a mouth guard design covering a plurality of teeth, but other embodiments may also be used and are intended to be covered by this disclosure. For instance, the position of the light source inputs and detector output ports could be exchanged, or some mixture of locations of light source inputs and detector output ports could be used. Also, if reflectance from the teeth is to be measured, then the light sources and detectors may be on the same side of the tooth. Moreover, it may be advantageous to pulse the light source with a particular pulse width and pulse repetition rate, and then the detection system can measure the pulsed light returned from or transmitted through the tooth. Using a lock-in type technique (e.g., detecting at the same frequency as the pulsed light source and also possibly phase locked to the same signal), the detection system may be able to reject background or spurious signals and increase the signal-to-noise ratio of the measurement.

Other elements may be added to the human interface designs of FIGS. 28-30 and are also intended to be covered by this disclosure. For instance, in one embodiment it may be desirable to have replaceable inserts that may be disposable. Particularly in a dentist's or doctor's office or hospital setting, the same instrument may be used with a plurality of patients. Rather than disinfecting the human interface after each use, it may be preferable to have disposable inserts that can be thrown away after each use. In one embodiment, a thin plastic coating material may enclose the clamp design of FIG. 29 or mouth guard design of FIG. 30. The coating material may be inserted before each use, and then after the measurement is exercised the coating material may be peeled off and replaced. The coating or covering material may be selected based on suitable optical properties that do not affect the measurement, or known optical properties that can be calibrated or compensated for during measurement. Such a design may save the dentist or physician or user considerable time, while at the same time provide the business venture with a recurring cost revenue source.

Wireless Link to the Cloud

The non-invasive dental caries measurement device may also benefit from communicating the data output to the "cloud" (e.g., data servers and processors in the web remotely connected) via wireless means. The non-invasive devices may be part of a series of biosensors applied to the patient, and collectively these devices form what might be called a body area network or a personal area network. The biosensors and non-invasive devices may communicate to a smart phone, tablet, personal data assistant, computer and/or other microprocessor-based device, which may in turn wirelessly or over wire and/or fiber optic transmit some or all of the signal or processed data to the internet or cloud. The cloud or internet may in turn send the data to dentists, doctors or health care providers as well as the patients themselves. Thus, it may be possible to have a panoramic, high-definition, relatively comprehensive view of a patient that doctors and dentists can use to assess and manage disease, and that patients can use to help maintain their health and direct their own care.

In a particular embodiment 3100, the non-invasive measurement device 3101 may comprise a transmitter 3103 to communicate over a first communication link 3104 in the body area network or personal area network to a receiver in a smart phone, tablet, cell phone, PDA, and/or computer 3105, for example. For the measurement device 3101, it may also be advantageous to have a processor 3102 to process some of the measured data, since with processing the amount of data to transmit may be less (hence, more energy efficient). The first communication link 3104 may operate through the use of one of many wireless technologies such as Bluetooth, Zigbee, WiFi, IrDA (infrared data association), wireless USB, or Z-wave, to name a few. Alternatively, the communication link 3104 may occur in the wireless medical band between 2360 MHz and 2390 MHz, which the FCC allocated for medical body area network devices, or in other designated medical device or WMTS bands. These are examples of devices that can be used in the body area network and surroundings, but other devices could also be used and are included in the scope of this disclosure.

The personal device 3105 may store, process, display, and transmit some of the data from the measurement device 3101. The device 3105 may comprise a receiver, transmitter, display, voice control and speakers, and one or more control buttons or knobs and a touch screen. Examples of the device 3105 include smart phones such as the Apple iPhones® or phones operating on the Android or Microsoft systems. In one embodiment, the device 3105 may have an application, software program, or firmware to receive and process the data from the measurement device 3101. The device 3105 may then transmit some or all of the data or the processed data over a second communication link 3106 to the internet or "cloud" 3107. The second communication link 3106 may advantageously comprise at least one segment of a wireless transmission link, which may operate using WiFi or the cellular network. The second communication link 3106 may additionally comprise lengths of fiber optic and/or communication over copper wires or cables.

The internet or cloud 3107 may add value to the measurement device 3101 by providing services that augment the measured data collected. In a particular embodiment, some of the functions performed by the cloud include: (a) receive at least a fraction of the data from the device 3105; (b) buffer or store the data received; (c) process the data using software stored on the cloud; (d) store the resulting processed data; and (e) transmit some or all of the data either upon request or based on an alarm. As an example, the data or processed data may be transmitted 3108 back to the originator (e.g., patient or user), it may be transmitted 3109 to a health care provider or doctor or dentist, or it may be transmitted 3110 to other designated recipients.

Service providers coupled to the cloud 3107 may provide a number of value-add services. For example, the cloud application may store and process the dental data for future reference or during a visit with the dentist or healthcare provider. If a patient has some sort of medical mishap or emergency, the physician can obtain the history of the dental or physiological parameters over a specified period of time. In another embodiment, alarms, warnings or reminders may be delivered to the user 3108, the healthcare provider 3109, or other designated recipients 3110. These are just some of the features that may be offered, but many others may be possible and are intended to be covered by this disclosure. As an example, the device 3105 may also have a GPS sensor, so the cloud 3107 may be able to provide time, date, and position along with the dental or physiological parameters. Thus, if there is a medical or dental emergency, the cloud 3107 could provide the location of the patient to the dental or healthcare provider 3109 or other designated recipients 3110. Moreover, the digitized data in the cloud 3107 may help to move toward what is often called "personalized medicine." Based on the dental or physiological parameter data history, medication or medical/dental therapies may be prescribed that are customized to the particular patient. Another advantage for commercial entities may be that by leveraging the advances in wireless connectivity and the widespread use of handheld devices such as smart phones that can wirelessly connect to the cloud, businesses can build a recurring cost business model even using non-invasive measurement devices.

Described herein are just some examples of the beneficial use of near-infrared or SWIR lasers for non-invasive measurements of dental caries and early detection of carious regions. However, many other dental or medical procedures can use the near-infrared or SWIR light consistent with this disclosure and are intended to be covered by the disclosure.

Section 3: Short-Wave Infrared Super-Continuum Lasers for Natural Gas Leak Detection, Exploration, and Other Active Remote Sensing Applications One advantage of optical systems is that they can perform non-contact, stand-off or remote sensing distance spectroscopy of various materials. For remote sensing particularly, it may also be necessary to operate in atmospheric transmission windows. For example, two windows in the SWIR that transmit through the atmosphere are approximately 1.4-1.8 microns and 2-2.5 microns. In general, the near-infrared region of the electromagnetic spectrum covers between approximately 0.7 microns (700 nm) to about 2.5 microns (2500 nm). However, it may also be advantageous to use just the short-wave infrared between approximately 1.4 microns (1400 nm) and about 2.5 microns (2500 nm). One reason for preferring the SWIR over the entire NIR may be to operate in the so-called "eye safe" window, which corresponds to wavelengths longer than about 1400 nm. Therefore, for the remainder of the disclosure the SWIR will be used for illustrative purposes. However, it should be clear that the discussion that follows could also apply to using the NIR wavelength range, or other wavelength bands.

In particular, wavelengths in the eye safe window may not transmit down to the retina of the eye, and therefore, these wavelengths may be less likely to create permanent eye damage from inadvertent exposure. The near-infrared wavelengths have the potential to be dangerous, because the eye cannot see the wavelengths (as it can in the visible), yet they can penetrate and cause damage to the eye. Even if a practitioner is not looking directly at the laser beam, the practitioner's eyes may receive stray light from a reflection or scattering from some surface. Hence, it can always be a good practice to use eye protection when working around lasers. Since wavelengths longer than about 1400 nm are substantially not transmitted to the retina or substantially absorbed in the retina, this wavelength range is known as the eye safe window. For wavelengths longer than 1400 nm, in general only the cornea of the eye may receive or absorb the light radiation.

Figure 32:
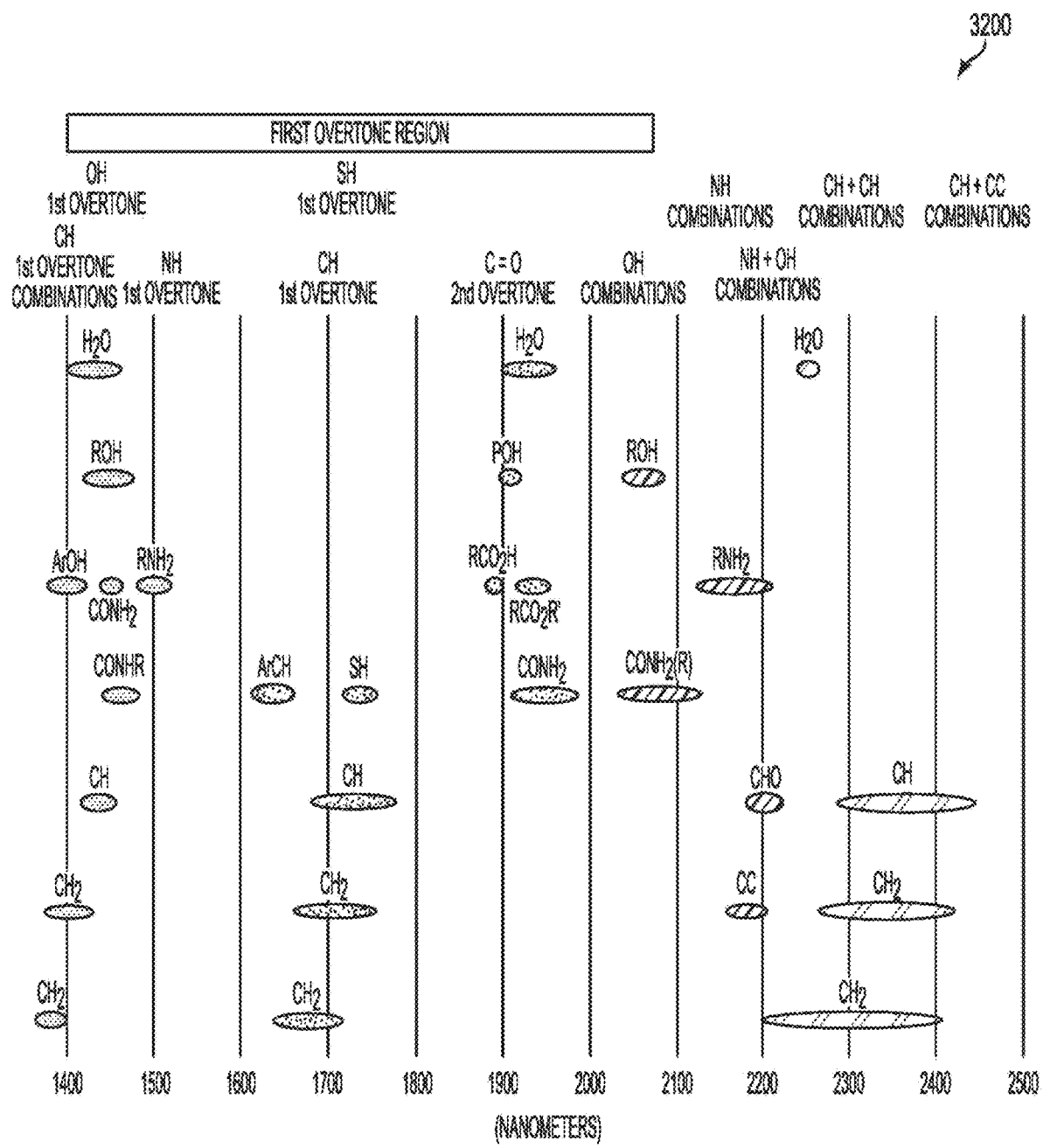
FIG. 32 illustrates wavelength bands for different chemical compounds over the SWIR wavelength range of approximately 1400 nm to 2500 nm. Also indicated are whether the bands are overtone or combination bands.

The SWIR wavelength range may be particularly valuable for identifying materials based on their chemical composition because the wavelength range comprises overtones and combination bands for numerous chemical bonds. As an example, FIG. 32 illustrates some of the wavelength bands for different chemical compositions. In 100 is plotted wavelength ranges in the SWIR (between 1400 and 2500 nm) for different chemical compounds that have vibrational or rotational resonances, along with whether the bands are overtone or combination bands. Numerous hydro-carbons are represented, along with oxygen-hydrogen and carbon-oxygen bonds. Thus, gases, liquids and solids that comprise these chemical compounds may exhibit spectral features in the SWIR wavelength range. In a particular embodiment, the spectra of organic compounds may be dominated by the C—H stretch. The C—H stretch fundamental occurs near 3.4 microns, the first overtone is near 1.7 microns, and a combination band occurs near 2.3 microns.

One embodiment of remote sensing that is used to identify and classify various materials is so-called "hyper-spectral imaging." Hyper-spectral sensors may collect information as a set of images, where each image represents a range of wavelengths over a spectral band. Hyper-spectral imaging may deal with imaging narrow spectral bands over an approximately continuous spectral range. As an example, in hyper-spectral imaging the sun may be used as the illumination source, and the daytime illumination may comprise direct solar illumination as well as scattered solar (skylight), which is caused by the presence of the atmosphere. However, the sun illumination changes with time of day, clouds or inclement weather may block the sun light, and the sun light is not accessible in the night time. Therefore, it would be advantageous to have a broadband light source covering the SWIR that may be used in place of the sun to identify or classify materials in remote sensing or stand-off detection applications.

As used throughout this document, the term "couple" and or "coupled" refers to any direct or indirect communication between two or more elements, whether or not those elements are physically connected to one another. As used throughout this disclosure, the term "spectroscopy" means that a tissue or sample is inspected by comparing different features, such as wavelength (or frequency), spatial location, transmission, absorption, reflectivity, scattering, refractive index, or opacity. In one embodiment, "spectroscopy" may mean that the wavelength of the light source is varied, and the transmission, absorption or reflectivity of the tissue or sample is measured as a function of wavelength. In another embodiment, "spectroscopy" may mean that the wavelength dependence of the transmission, absorption or reflectivity is compared between different spatial locations on a tissue or sample. As an illustration, the "spectroscopy" may be performed by varying the wavelength of the light source, or by using a broadband light source and analyzing the signal using a spectrometer, wavemeter, or optical spectrum analyzer.

As used throughout this document, the term "fiber laser" refers to a laser or oscillator that has as an output light or an optical beam, wherein at least a part of the laser comprises an optical fiber. For instance, the fiber in the "fiber laser" may comprise one of or a combination of a single mode fiber, a multi-mode fiber, a mid-infrared fiber, a photonic crystal fiber, a doped fiber, a gain fiber, or, more generally, an approximately cylindrically shaped waveguide or lightpipe. In one embodiment, the gain fiber may be doped with rare earth material, such as ytterbium, erbium, and/or thulium. In another embodiment, the mid-infrared fiber may comprise one or a combination of fluoride fiber, ZBLAN fiber, chalcogenide fiber, tellurite fiber, or germanium doped fiber. In yet another embodiment, the single mode fiber may include standard single-mode fiber, dispersion shifted fiber, non-zero dispersion shifted fiber, high-nonlinearity fiber, and small core size fibers.

As used throughout this disclosure, the term "pump laser" refers to a laser or oscillator that has as an output light or an optical beam, wherein the output light or optical beam is coupled to a gain medium to excite the gain medium, which in turn may amplify another input optical signal or beam. In one particular example, the gain medium may be a doped fiber, such as a fiber doped with ytterbium, erbium and/or thulium. In one embodiment, the "pump laser" may be a fiber laser, a solid state laser, a laser involving a nonlinear crystal, an optical parametric oscillator, a semiconductor laser, or a plurality of semiconductor lasers that may be multiplexed together. In another embodiment, the "pump laser" may be coupled to the gain medium by using a fiber coupler, a dichroic mirror, a multiplexer, a wavelength division multiplexer, a grating, or a fused fiber coupler.

As used throughout this document, the term "super-continuum" and or "supercontinuum" and or "SC" refers to a broadband light beam or output that comprises a plurality of wavelengths. In a particular example, the plurality of wavelengths may be adjacent to one-another, so that the spectrum of the light beam or output appears as a continuous band when measured with a spectrometer. In one embodiment, the broadband light beam may have a bandwidth of at least 10 nm. In another embodiment, the "super-continuum" may be generated through nonlinear optical interactions in a medium, such as an optical fiber or nonlinear crystal. For example, the "super-continuum" may be generated through one or a combination of nonlinear activities such as four-wave mixing, parametric amplification, the Raman effect, modulational instability, and self-phase modulation.

As used throughout this disclosure, the terms "optical light" and or "optical beam" and or "light beam" refer to photons or light transmitted to a particular location in space. The "optical light" and or "optical beam" and or "light beam" may be modulated or unmodulated, which also means that they may or may not contain information. In one embodiment, the "optical light" and or "optical beam" and or "light beam" may originate from a fiber, a fiber laser, a laser, a light emitting diode, a lamp, a pump laser, or a light source.

As used throughout this disclosure, the term "remote sensing" may include the measuring of properties of an object from a distance, without physically sampling the object, for example by detection of the interactions of the object with an electromagnetic field. In one embodiment, the electromagnetic field may be in the optical wavelength range, including the infrared or SWIR. One particular form of remote sensing may be stand-off detection, which may range from non-contact up to hundreds of meters away, for example.

Remote Sensing of Natural Gas Leaks

Natural gas may be a hydro-carbon gas mixture comprising primarily methane, with other hydro-carbons, carbon dioxide, nitrogen and hydrogen sulfide. Natural gas is important because it is an important energy source to provide heating and electricity. Moreover, it may also be used as fuel for vehicles and as a chemical feedstock in the manufacture of plastics and other commercially important organic chemicals. Although methane is the primary component of natural gas, to uniquely identify natural gas through spectroscopy requires monitoring of both methane and ethane. If only methane is used, then areas like cow pastures could be mistaken for natural gas fields or leaks. More specifically, the typical composition of natural gas is as follows:

| Component | Range (mole %) |
| --- | --- |
| Methane | 87.0-96.0 |
| Ethane | 1.5-5.1 |
| Propane | 0.1-1.5 |
| Iso-butane | 0.01-0.3 |
| Normal-butane | 0.01-0.3 |
| Iso-pentane | Trace-0.14 |
| Normal-pentane | Trace-0.04 |
| Hexanes plus | Trace-0.06 |
| Nitrogen | 0.7-5.6 |
| Carbon dioxide | 0.1-1.0 |
| Oxygen | 0.01-0.1 |
| Hydrogen | Trace-0.02 |

As one example of remote sensing of natural gas, a helicopter or aircraft may be flown at some elevation. The light source for remote sensing may direct the light beam toward the ground, and the diffuse reflected light may then be measured using a detection system on the aircraft. Thus, the helicopter or aircraft may be sampling a column area below it for natural gas, or whatever the material of interest is. In yet another embodiment, the column may sense aerosols of various sorts, as an example. Various kinds of SWIR light sources will be discussed later in this disclosure. The detection system may comprise, in one embodiment, a spectrometer followed by one or more detectors. In another embodiment, the detection system may be a dispersive element (examples include prisms, gratings, or other wavelength separators) followed by one or more detectors or detector arrays. In yet another embodiment, the detection system may comprise a gas-filter correlation radiometer. These are merely specific examples of the detection system, but combinations of these or other detection systems may also be used and are contemplated within the scope of this disclosure. Also, the use of aircraft is one particular example of a remote sensing system, but other system configurations may also be used and are included in the scope of this disclosure. For example, the light source and detection system may be placed in a fixed location, and for reflection the light source and detectors may be close to one another, while for transmission the light source and detectors may be at different locations. In yet another embodiment, the system could be placed on a vehicle such as an automobile or a truck, or the light source could be placed on one vehicle, while the detection system is on another vehicle. If the light source and detection system are compact and lightweight, they might even be carried by a person in the field, either in their hands or in a backpack.

Both methane and ethane are hydro-carbons with unique spectral signatures. For example, ethane is C2H6, while methane is CH4. Also, methane and ethane have infrared absorption bands near 1.6 microns, 2.4 microns, 3.3 microns and 7 microns. It should be noted that the approximately 7 micron lines cannot be observed generally due to atmospheric absorption. Although the fundamental lines near 3.3 microns are stronger absorption features, the light sources and detectors in the mid-infrared may be more difficult to implement. Hence, the focus here is on observing the SWIR lines that fall in atmospheric transparency windows.

Figure 33A:
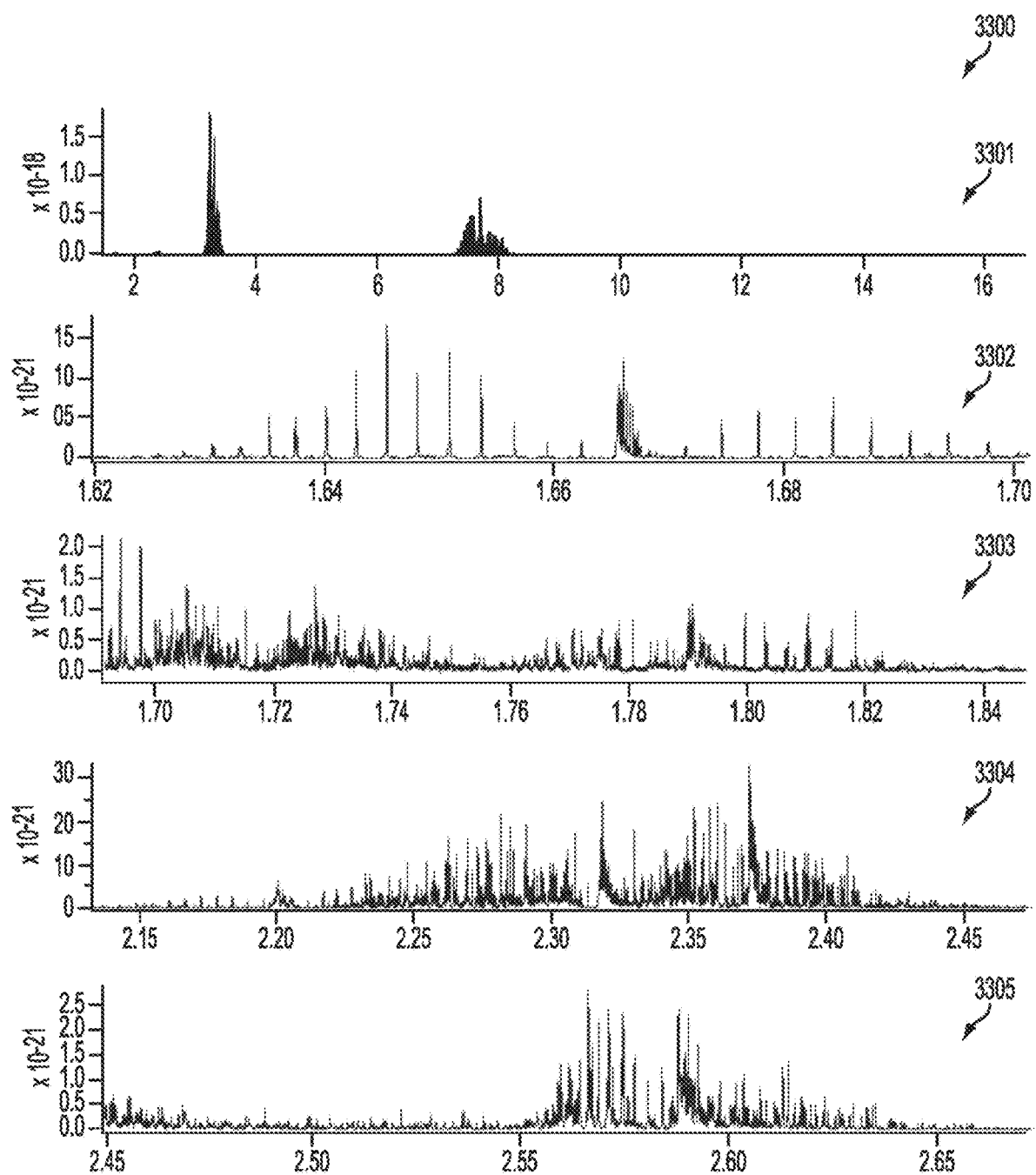
FIG. 33A shows the absorption spectra for methane.
Figure 33B:
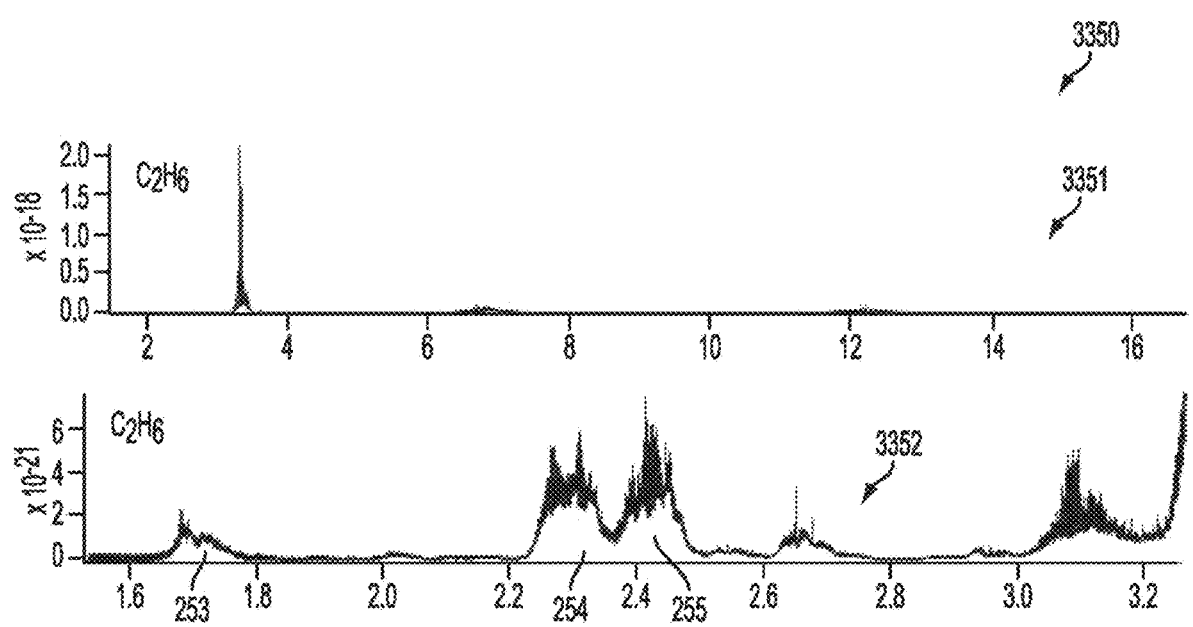
FIG. 33B shows the absorption spectra for ethane.

FIG. 33 illustrates the absorption spectra for methane (FIG. 33A) and ethane (FIG. 33B) (from http://vpl.astro.washington.edu/spectra). The curves 3300 plot on a linear scale the absorption cross-section versus wavelength (in microns) for various methane lines. The curve 3301 covers the wavelength range between approximately 1.5-16 microns, while the curves below provide blown-up views of different wavelength ranges (3302 for approximately 1.62-1.7 microns, 3303 for approximately 1.7-1.84 microns, 3304 for approximately 2.15-2.45 microns, and 3305 for approximately 2.45-2.65 microns). The curves 3302 and 3303 fall within about the first SWIR atmospheric transmission window between approximately 1.4-1.8 microns, while the curves 3304 and 3305 fall within the second SWIR atmospheric transmission window between approximately 2-2.5 microns. As can be seen, there are numerous spectral features for identifying methane in the SWIR. In addition, there are even stronger features near 3.4-3.6 microns and around 7-8 microns, although these require different light sources and detection systems.

FIG. 33B illustrates the absorption spectra for ethane. The curves 3350 plot on a linear scale the absorption cross-section versus wavelength (in microns) for various ethane lines. The curve 3351 covers the wavelength range between approximately 1.5-16 microns, while the curve 3352 expands the scale between about 1.6-3.2 microns. The features 3353 fall within about the first SWIR atmospheric transmission window between approximately 1.4-1.8 microns, while the features 3354 and 3355 fall within the second SWIR atmospheric transmission window between approximately 2-2.5 microns. There are distinct spectral features for identifying ethane as well in the SWIR. In addition, there are even stronger features near 3.4-3.6 microns and around 7 microns.

For detecting natural gas leaks, a SWIR light source and a detection system could be used in transmission or reflection. The area surrounding the source or natural gas pipeline may be surveyed, and the detection system may monitor the methane and ethane concentration, or even the presence of these two gases. The region may be scanned to cover an area larger than the laser beam. Also, if a certain quantity of natural gas is detected, an alarm may be set-off to alert the operator or people nearby. This is just one example of the natural gas leak detection, but other configurations and techniques may be used and are intended to be covered by this disclosure.

Natural gas leak detection is one example where active remote sensing or hyper-spectral imaging can be used to detect hydro-carbons or organic compounds. However, there are many other examples where the technique may be used to perform reflectance spectroscopy of organic compounds, and these are also intended to be covered by this disclosure. In one particular embodiment, alkanes may be detected, where alkanes are hydro-carbon molecules comprising single carbon-carbon bonds. Alkanes have the general formula CnH2n+2 and are open chain, aliphatic or non-cyclic molecules. Below are examples of some of the alkanes, which include methane and ethane, as well as more complicated compounds.

|  | Formula |
| --- | --- |
| Methane | $CH_4$ |
| Ethane | $C_2H_6$ |
| Propane | $C_3H_8$ |
| Butane | $C_4H_{10}$ |
| Pentane | $C_5H_{12}$ |
| Hexane | $C_6H_{14}$ |
| Heptane | $C_7H_{16}$ |
| Octane | $C_8H_{18}$ |
| Nonane | $C_9H_{20}$ |
| Decane | $C_{10}H_{22}$ |
| Paraffin | $C_{20+}H_{42+}$ |
| Polyethylene (LDPE, HDPE) | $(C_2H_4)_n$ or $(CH_2CH_2)_n$ |
| Polyvinylchloride (PVC) | $(C_2H_3Cl)_n$ or $(CHClCH_2)_n$ |
| Polypropylene | $(C_3H_5)_n$ or $\{CH(CH_3)CH_2\}_n$ |
| Polyethylene terephthalate (PETE) | $C_{10}H_8O_4$ or $\{(CO_2)_2C_6H_4(CH_2)_2\}_n$ |
| Nylon (polyamide) | $C_{12}H_{24}O_4N_2$ or $\{C_{10}H_{22}(CO_2)_2(NH)_2\}_n$ |

Figure 34:
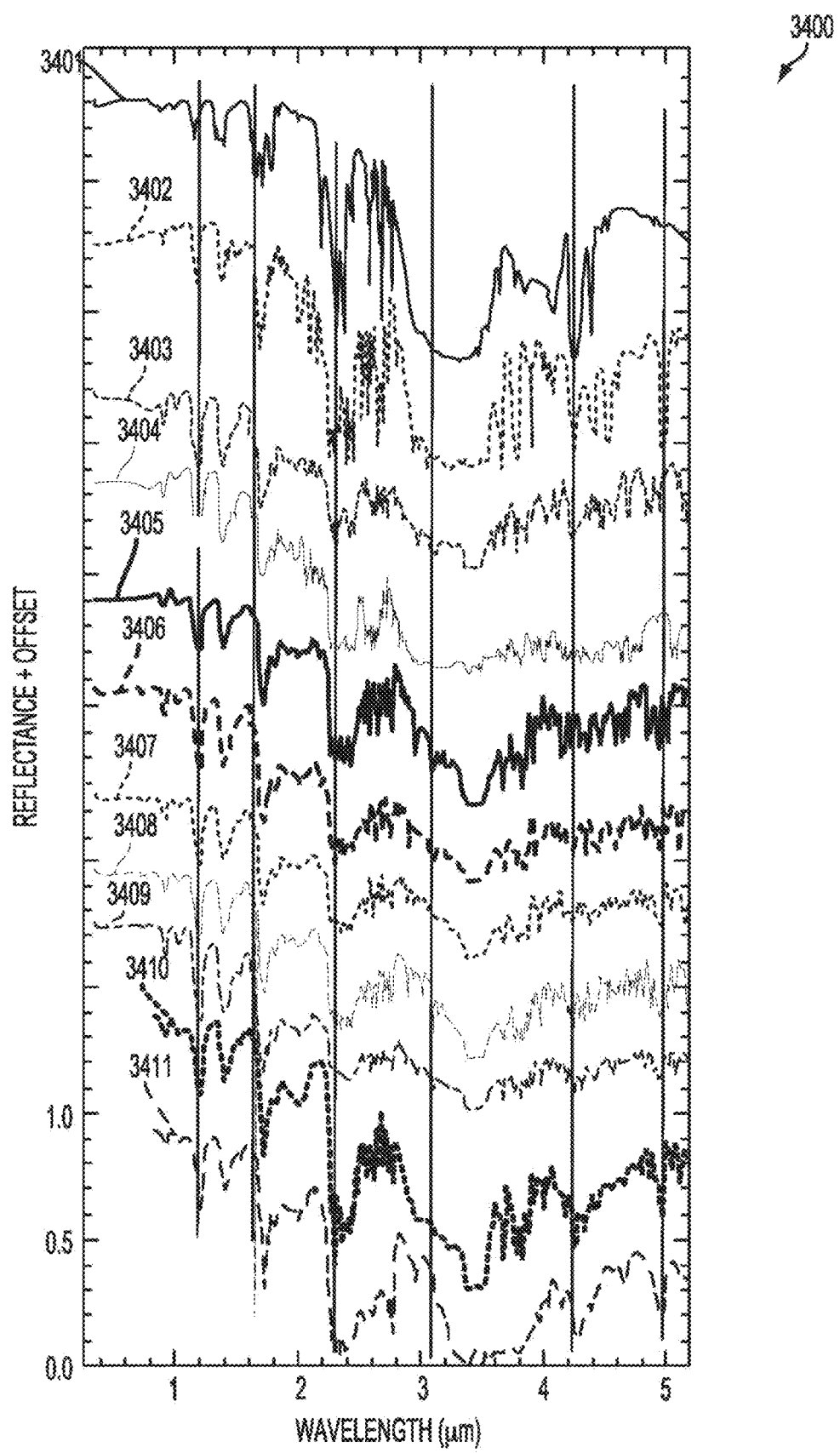
FIG. 34 illustrates the reflectance spectra for some members of the alkane family plus paraffin.

FIG. 34 illustrates the reflectance spectra 3400 for some members of the alkane family plus paraffin. The vertical lines indicate positions of constant wavelength and are aligned with apparent absorptions in the methane spectrum at 1.19, 1.67, 2.32, 3.1, 4.23 and 4.99 microns. The spectra ore offset to enable easier viewing, and the offsets are of the following amounts: 3401 methane 4.1; 3402 ethane 3.6; 3403 propane 3.3; 3404 butane 2.8; 3405 pentane 2.3; 3406 hexane 2.0; 3407 heptane 1.5; 3408 octane 1.2; 3409 nonane 0.85; 3410 decane 0.4; and 3411 paraffin 0.05. The reflectance of alkanes in the near-infrared may be dominated by absorptions due to combinations and overtones of bands at longer wavelengths. Although this wavelength range is mostly unexplored by organic spectroscopists, the near-infrared may be valuable for terrestrial and planetary remote sensing studies. Alkanes may have the fundamental absorptions due to a variety of C—H stretches between approximately 3.3-3.5 microns. The first overtone may be a relatively deep triplet near 1.7 microns. This triplet appears in most of the series, but the exact wavelength position may move. Another absorption band may be present near 1.2 microns, and this is likely the second overtone of the C—H stretch. The third C—H stretch overtone is near 0.9 microns. There is yet another near-infrared feature near 1.396 microns, which may correspond to the combinations of the first overtone of the C—H stretch with each of the two C—H band positions at approximately 1.35 microns and 1.37 microns. Moreover, there may be complex absorptions between 2.2-2.5 microns. For example, there may be a number of narrow individual absorption bands atop an overall absorption suite about 0.3 microns wide. A few absorption lines retain their location for most of the series 300, notably the 2.311 micron and 2.355 micron absorptions. This wavelength window may have multiple combinations and overtones, including contributions from the C—H stretch, CH3 asymmetric bend combination, and C—H stretch/CH3 symmetric bend combination.

Remote Sensing for Natural Gas Exploration

In addition to remote sensing to detect natural gas leaks, the same or similar system could also be used to explore for natural gas fields, whether under land or under water. Whereas a natural gas leak from a pipeline or building may be above the ground or only a few meters below the ground, natural gas exploration may occur for gas and oil that are much further below the ground, or under the water in a bay, lake, sea or ocean. For example, the exploration for natural gas and oil may be performed by determining the reflectance spectra of surface anomalies. The surface manifestations of oil and gas reservoirs may be used to map the petroleum potential of an area, particularly related to the seepage of oil and gas to the surface along faults or imperfect reservoir seals. The visible products of such seepage (e.g., oil and tar deposits) are generally referred to as macro-seeps, whereas the invisible gaseous products may be referred to as micro-seeps.

Figures 35A, 35B:
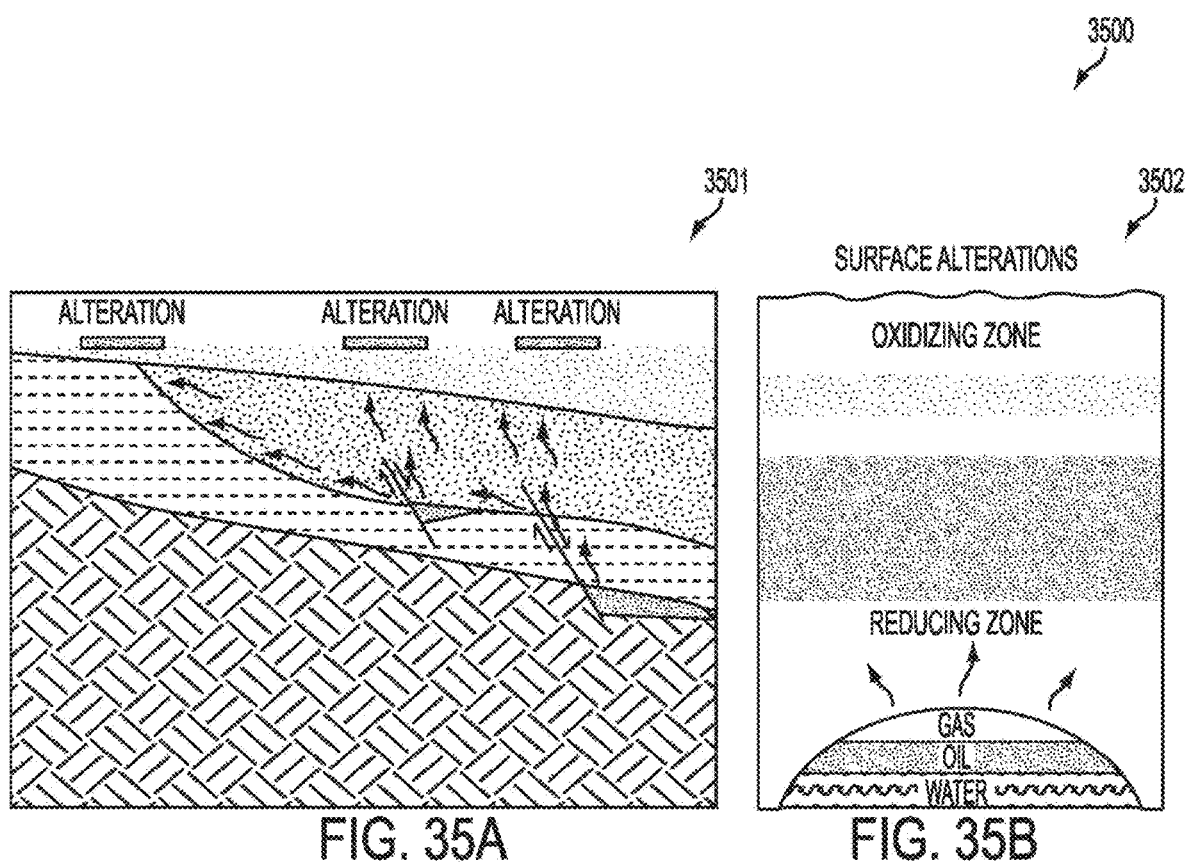
FIG. 35A depicts that micro-seepages may result from the vertical movement of hydro-carbons from their respective reservoirs to the surface. It is assumed that the rock column, including the seal rock, comprises interconnected fractures or micro-fracture systems.
FIG. 35B illustrates that surface alterations may occur because leaking hydro-carbons set up near-surface oxidation and/or reduction zones that favor the development of a diverse array of chemical and mineralogical changes.

As illustrated by 3500 in FIG. 35, micro-seepages may result from the vertical movement of hydrocarbons 3501 from their respective reservoirs to the surface. These hydrocarbon micro-seepages involve buoyant, relatively rapid, vertical ascent of ultra-small bubbles of light hydrocarbons (primarily methane through the butanes) through a network of interconnected, groundwater-filled joints and bedding planes (3501). One of the assumptions required for micro-seepage to occur is that a rock column, including the seal rock, comprises extensive interconnected fractures or micro-fracture systems.

Direct detection methods may involve measurements of hydrocarbons, either in the form of oil accumulations or concentrations of escaping vapors, such as methane through butane. In addition, there are also indirect methods that may involve the measurement of secondary alternations that arise from the seepage of the hydrocarbons. For instance, hydrocarbon-induced alterations may include microbial anomalies, mineralogical changes, bleaching of red beds, clay mineral alterations, and electrochemical changes. These alterations occur because leaking hydrocarbons set up near-surface oxidation and/or reduction zones that favor the development of a diverse array of chemical and mineralogical changes, c.f. 3502 in FIG. 35. Such alterations 3502 may be distinct from adjacent rocks and, thus, may in some instance be detectable by various remote sensing techniques.

The diagnostic spectral features of methane and crude oil may comprise four distinct hydrocarbon absorption bands. For example, two bands near 1.18 microns and 1.38 microns may be narrow and sharply defined, although they may also be fairly weak. The other two spectral features may be near 1.68-1.72 microns and 2.3-2.45 microns; these bands may be broader, but they are also stronger than the previous two bands. The bands near 1.7 microns and 2.3 microns are spectral overtones or combinations of C—H vibrational modes. Moreover, hydrocarbon induced alterations associated with indirect detection may express themselves in a variety of spectral changes, such as mineralogical changes (calcium carbonate mineralization, near 2.35 microns), bleaching of red beds (near 1 micron), and clay minerals alterations (near 2.2 microns), among other changes.

Figure 36A:
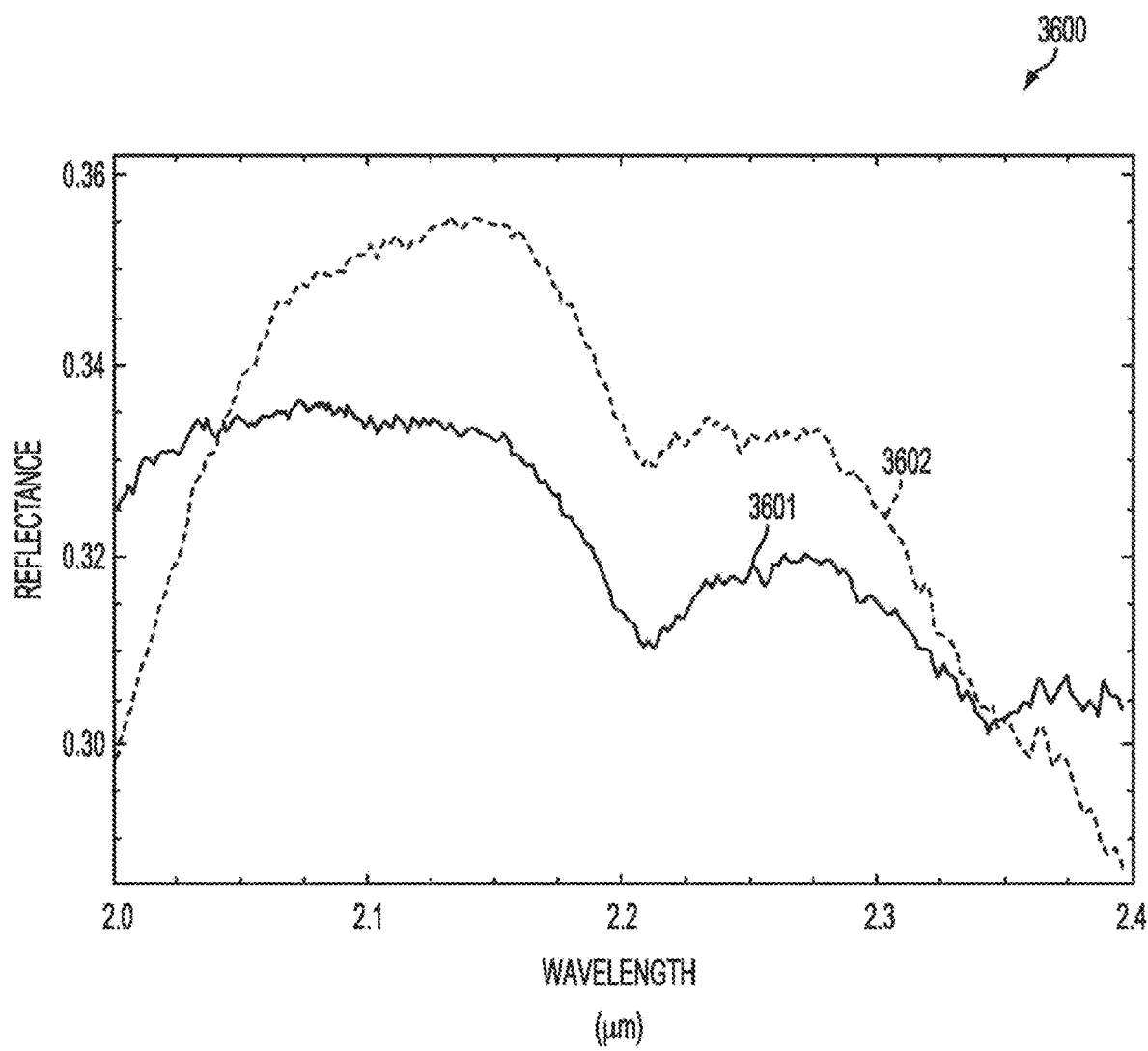
FIG. 36A shows the reflectance spectra for locations with natural gas fields (3601) and locations without natural gas fields (3602).

Various field tests have been conducted that verify the spectral signatures associated with natural gas fields, either land-based or water-based (e.g., in bays). In one example shown in FIG. 36A, the reflectance spectra 3600 was collected for different locations between approximately 2 microns and 2.4 microns. In 3601 the reflectance is plotted versus wavelength for locations with gas fields, while in 3602 the reflectance is plotted for locations without gas fields. The macroscopic features of the reflectance spectra of surface soils show two broad absorption bands near 2.2 microns and 2.33 microns with complex shapes. The slightly positive slope in the region of 2.3-2.4 microns with natural gas suggests that hydrocarbons are overriding the spectral signature of clays in this region.

Figure 36B:
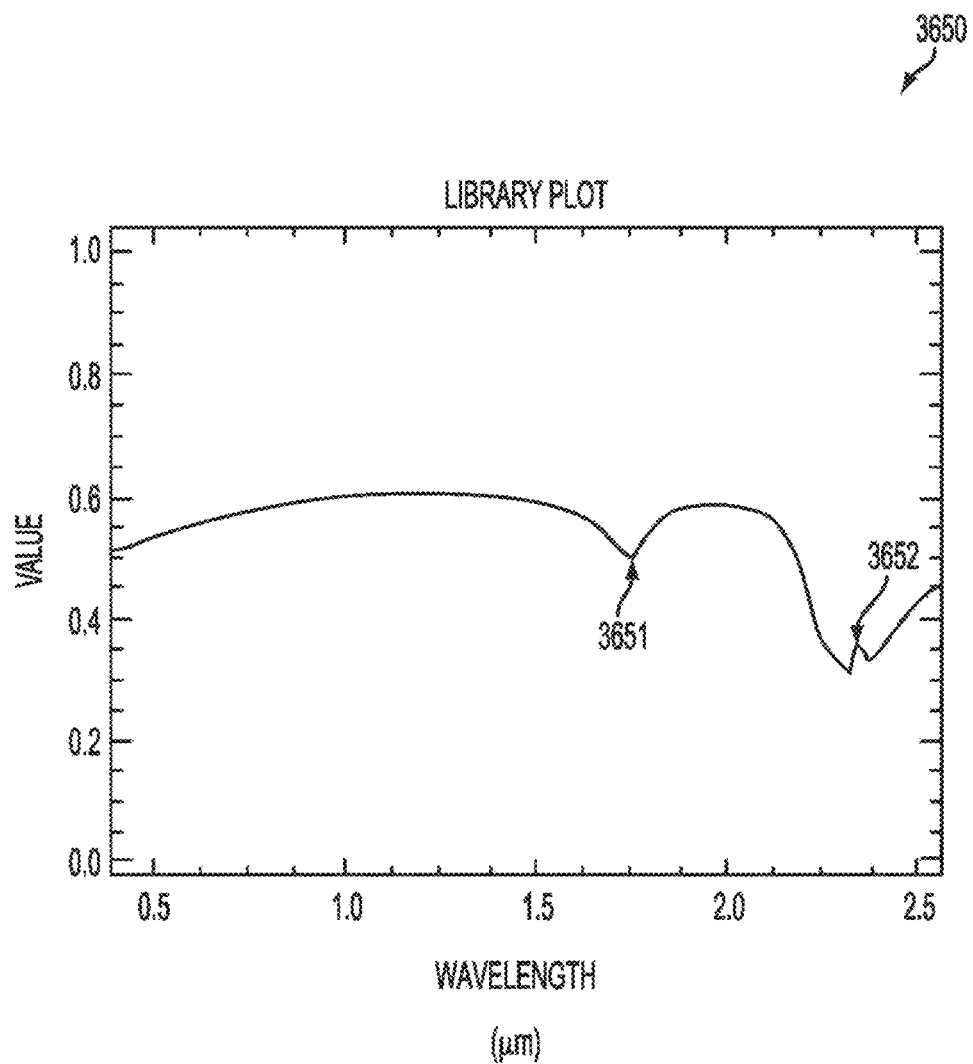
FIG. 36B illustrates spectra from field tests over regions with natural gas, which show two spectral features: one near 1.725 microns and another doublet between about 2.311 microns and 2.36 microns.

In yet another embodiment, field tests were conducted over a wider spectra range from approximately 0.5 microns to 2.5 microns (FIG. 36B). As the curve 3650 illustrates, two absorption features are found for the hydrocarbon spectral reflectance curve: one near 1.725 microns 3651 and a double absorption at approximately 2.311-2.36 microns 3652. Thus, in these two field trial examples, oil-gas reservoir areas were identifiable using feature bands of 1650-1750 nm and 2000-2400 nm. In addition, the remote sensing method may be used for off-shore oil and gas exploration and marine pollution investigation, to name just a few examples.

Other Uses of Active Remote Sensing or Hyperspectral Imaging

Active and/or hyper-spectral remote sensing may be used in a wide array of applications. Although originally developed for mining and geology (the ability of spectral imaging to identify various minerals may be ideal for the mining and oil industries, where it can be used to look for ore and oil), hyper-spectral remote sensing has spread to fields as diverse as ecology and surveillance. The table below illustrates some of the applications that can benefit from hyper-spectral remote sensing.

| Atmosphere | Water vapor, cloud properties, aerosols |
| Ecology | Chlorophyll, leaf water, cellulose, pigments, lignin |
| Geology | Mineral and soil types |
| Coastal Waters | Chlorophyll, phytoplankton, dissolved organic materials, suspended sediments |
| Snow/Ice | Snow cover fraction, grainsize, melting |
| Biomass Burning | Subpixel temperatures, smoke |
| Commercial | Mineral (oil) exploration, agriculture and forest production |

Figure 37:
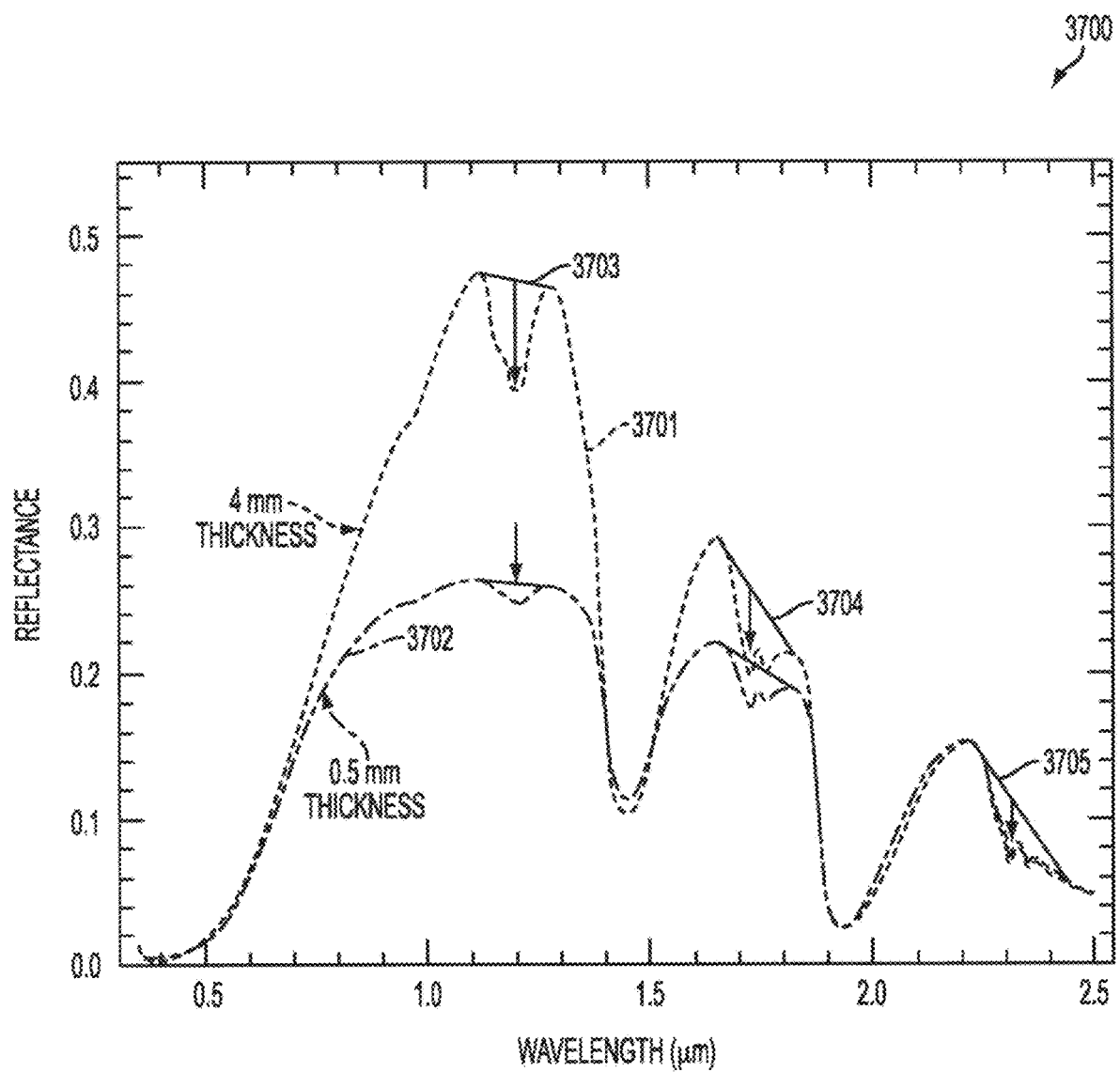
FIG. 37 shows the reflectance spectra of a sample of oil emulsion from the Gulf of Mexico 2010 oil spill (different thicknesses of oil).

In one embodiment, near-infrared imaging spectroscopy data may be used to create qualitative images of thick oil or oil spills on water. This may provide a rapid remote sensing method to map the locations of thick parts of an oil spill. While color imagery may show locations of thick oil, it is difficult to assess relative thickness or volume with just color imagery. As an example, FIG. 37 illustrates the reflectance spectra 3700 of a sample of oil emulsion from the Gulf of Mexico 2010 oil spill. Curve 3701 is a 4 mm thickness of oil, while curve 3702 is a 0.5 mm thickness. Whereas the data in the visible hardly changes with oil thickness, in the near-infrared the change in reflectance spectra is much more dependent on the oil thickness. The data shows, for example, the C—H features near 1.2 microns 3703, 1.73 microns 3704, and 2.3 microns 3705. Thus, in the infrared wavelengths, both the reflectance levels and absorption features due to organic compounds may vary in strength with oil thickness.

Figure 38:
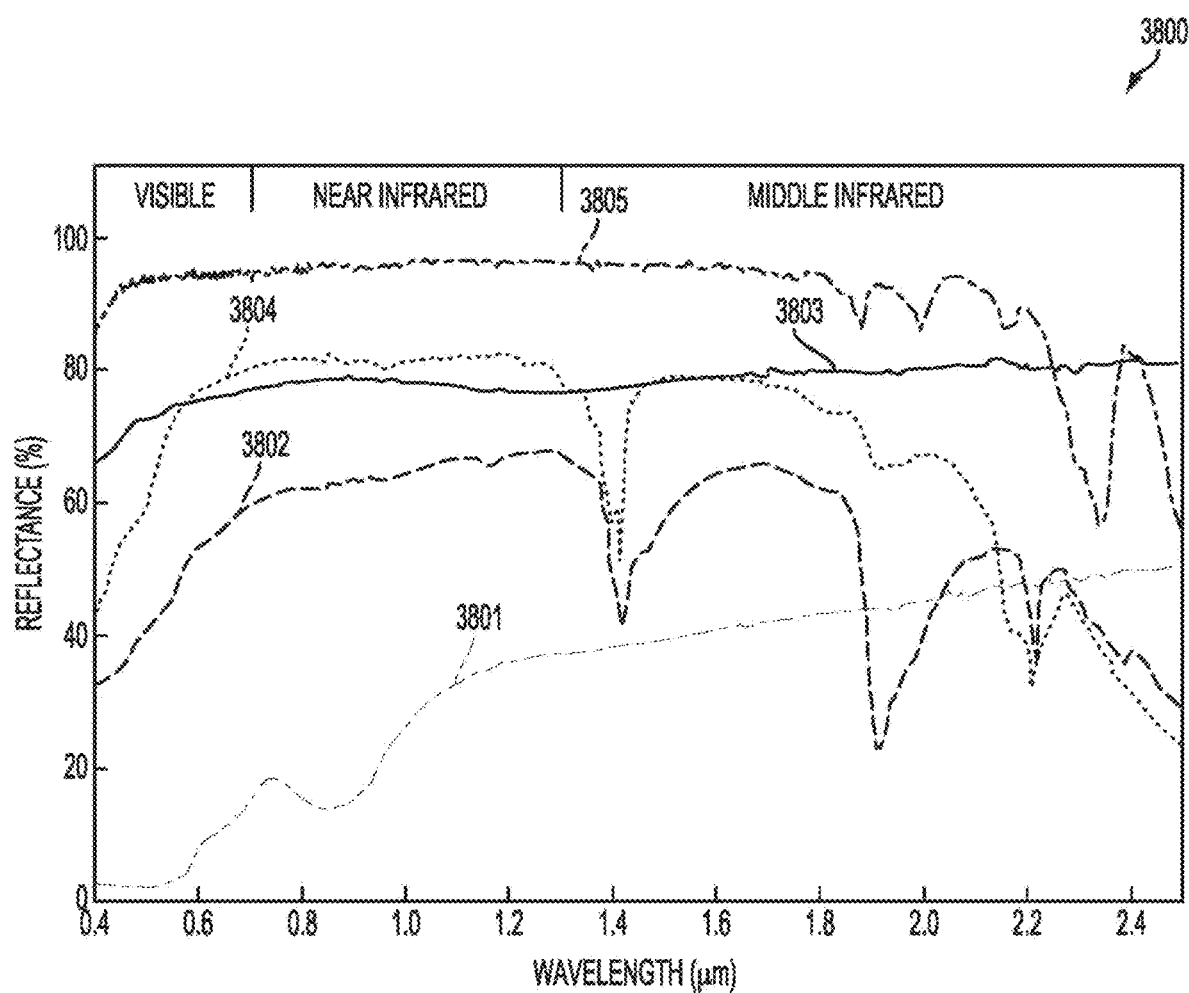
FIG. 38 illustrates the reflectance spectra of some representative minerals that may be major components of rocks and soils.

Remote sensing may also be used for geology and mineralogy mapping or inspection. FIG. 38 shows the reflectance spectra 3800 for some representative minerals that are major components of rocks and soils. In inorganic materials such as minerals, chemical composition and crystalline structure may control the shape of the spectral curve and the locations of absorption bands. Wavelength-specific absorption may arise from particular chemical elements or ions and the geometry of chemical bonds between elements, which is related to the crystal structure. In hematite 3801, the strong absorption in the visible may be caused by ferric iron. In calcite 3805, the carbonate ion may be responsible for the series of absorption bands between 1.8 and 2.4 microns. Kaolinite 3804 and montmorillonite 3802 are clay minerals common in soils. The strong absorption near 1.4 microns in both spectra, along with a weak 1.9 micron band in kaolinite arise from the hydroxide ions, while the stronger 1.9 micron band in montmorillonite may be caused by bound water molecules in the hydrous clay. In contrast to these spectra, orthoclase feldspar 3803, a dominant mineral in granite, shows very little absorption features in the visible or infrared.

Figure 39:
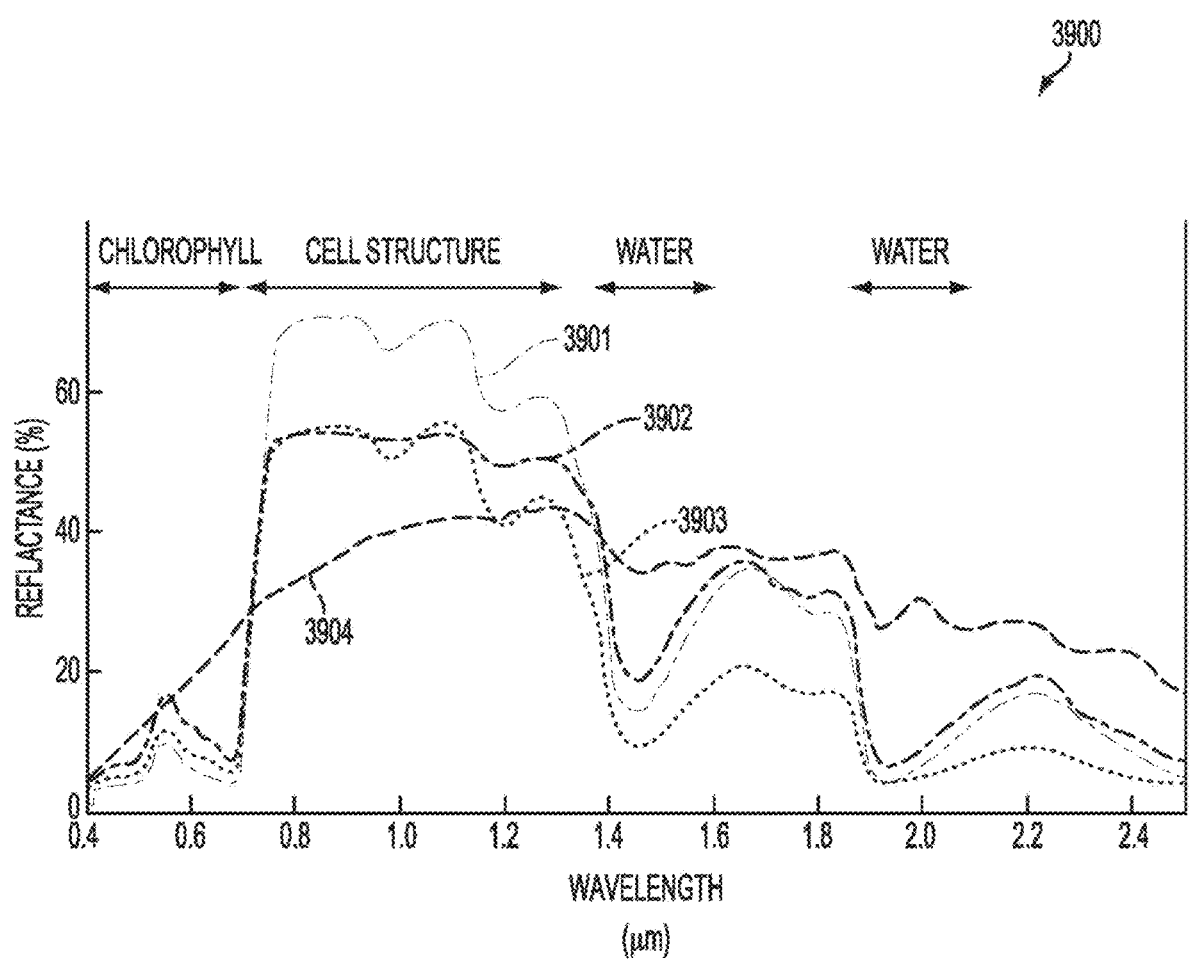
FIG. 39 shows the reflectance spectra of different types of green vegetation compared with dry, yellowed grass.

Remote sensing or hyper-spectral imaging may also be used for agriculture as well as vegetation monitoring. For example, hyper-spectral data may be used to detect the chemical composition of plants, which can be used to detect the nutrient and water status of crops. FIG. 39 illustrates the reflectance spectra 3900 of different types of green vegetation compared with dry, yellowed grass. In the visible spectra, the shape may be determined by absorption effects from chlorophyll and other leaf pigments. The reflectance rises rapidly across the boundary between red and infrared wavelengths, which may be due to interactions with the internal cellular structure of leaves. Leaf structure may vary significantly between plant species, as well as from plant stress. Beyond 1.3 microns the reflectance decreases with increasing wavelength, except for two water absorption bands near 1.4 microns and 1.9 microns. Illustrated in FIG. 39 are the reflectance for green grass 3901, walnut tree canopy 3902, fir tree 3903 and senescent 3904, which is dry, yellowed grass.

Figure 40:
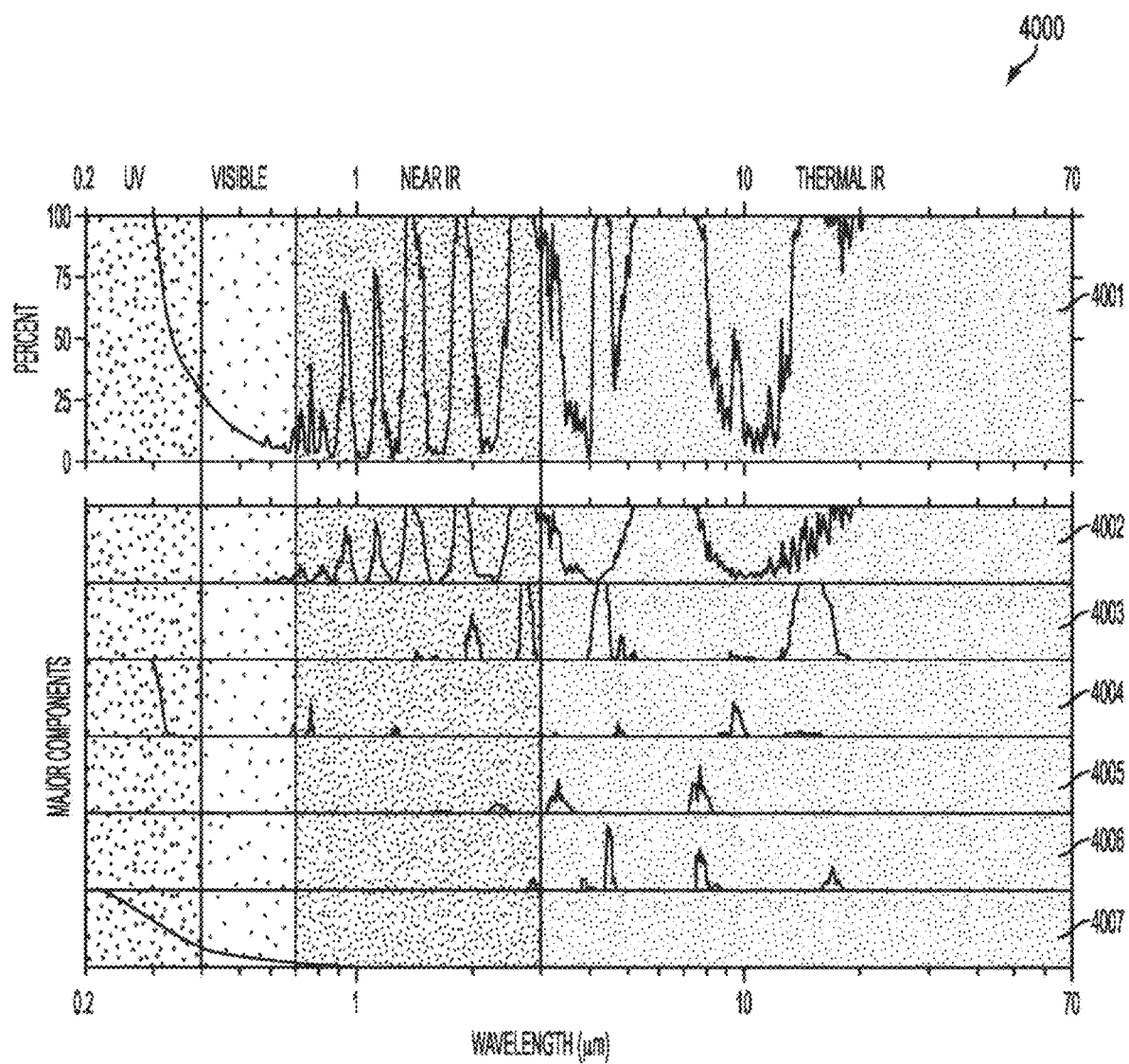
FIG. 40 illustrates the atmospheric absorption and scattering of greenhouse gases at different wavelengths.

Active remote sensing may also be used to measure or monitor gases in the earth's atmosphere, including greenhouse gases, environmental pollutants and aerosols. For instance, greenhouse gases are those that can absorb and emit infrared radiation: In order, the most abundant greenhouse gasses in the Earth's atmosphere are: water vapor (H2O), carbon dioxide (CO2), methane (CH4), nitrous oxide (N2O) and ozone (O3). FIG. 40 shows the atmospheric absorption and scattering of greenhouse gases 4000 at different wavelengths. Included in this figure are the total absorption and scattering 4001, along with the breakdown by major components: water vapor 4002, carbon dioxide 4003, oxygen and ozone 4004, methane 4005, and nitrous oxide 4006. Also shown is the Rayleigh scattering 4007 through the atmosphere, which dominates at shorter wavelengths, particularly wavelengths shorter than about 1 micron. In one embodiment, environmental concerns of climate change have led to the need to monitor the level of carbon dioxide in the atmosphere, and this may be achieved, for example, by performing spectroscopy in the vicinity of 1.6 microns and 2 microns.

Figure 41:
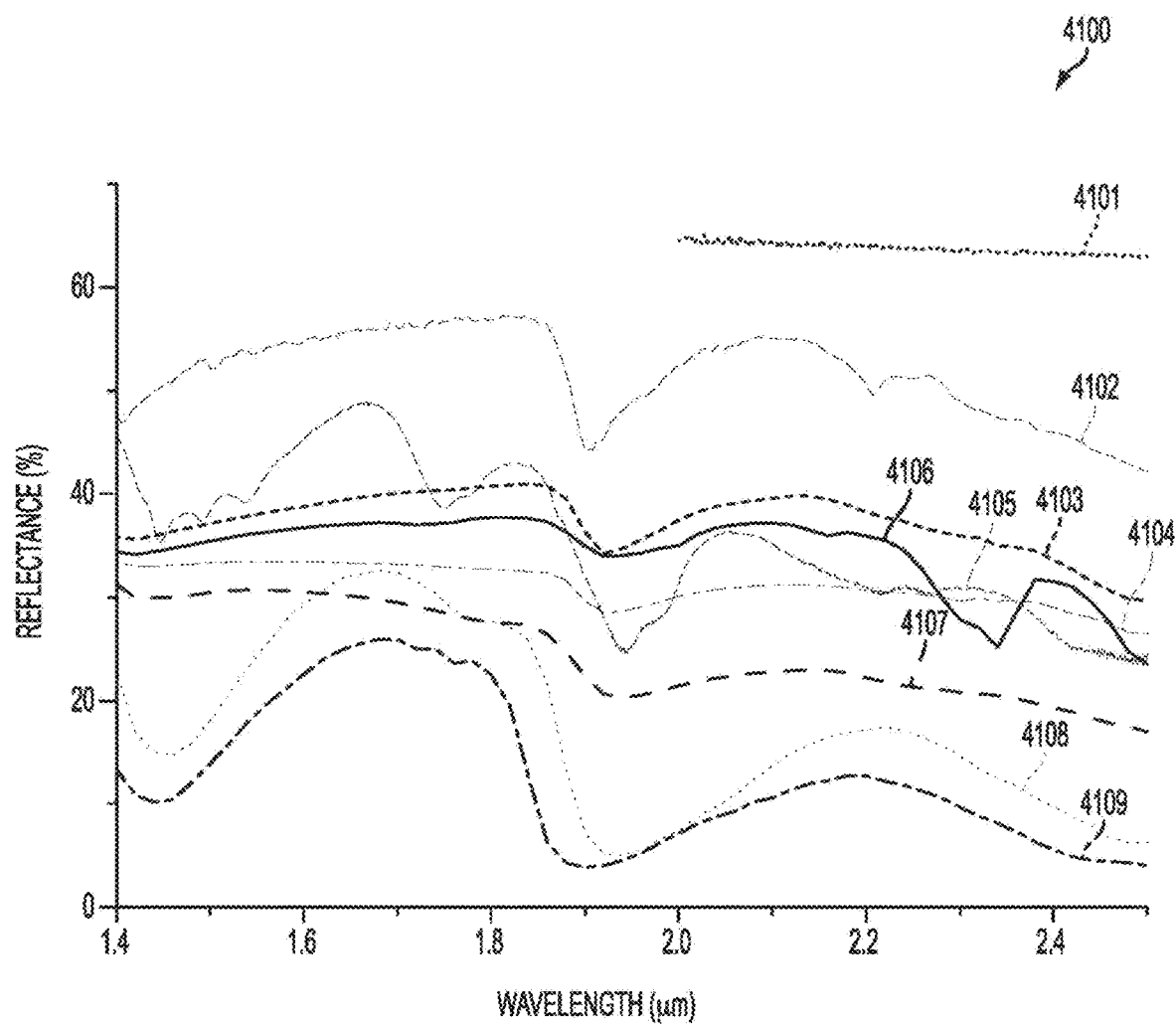
FIG. 41 overlays the reflectance for different building materials from the ASTER spectra library.

In yet another embodiment, different building materials may be identified and distinguished from surrounding vegetation and forestry. FIG. 41 overlays different reflectance data 4100 for samples cataloged in the ASTER spectra library (http://speclib.jpl.nasa.gov). This library has been made available by NASA as part of the Advanced Spaceborne Thermal Emission and Reflection Radiometer, ASTER, imaging instrumentation program. Included in this and other libraries are reflection spectra of natural and man-made materials, including minerals, rocks, soils, water and snow. In FIG. 41 several spectra are included over the SWIR atmospheric transmission bands, and the water absorption between approximately 1.8 and 2 microns has been blocked out (features in there are either due to water or would be masked by the atmospheric moisture). Included in the graph are the spectra for silver metallic paint 4101, light brown loamy sand 4102, construction concrete-1 4103, construction concrete-cement 4104, gypsum 4105, asphaltic concrete 4106, construction concrete-bridges 4107, grass 4108 and conifer trees 4109. As an example, active remote sensing can be used to distinguish different concrete structures, including roadways, buildings, and reinforced structures such as bridges. Also, building materials such as gypsum, painted structures, plywood, and concrete of various sorts, may be distinguished from plant life, soil and trees. Thus, beyond three dimensional imaging, this can add a fourth dimension-namely, identification of objects based on their chemical signature.

Figure 42:
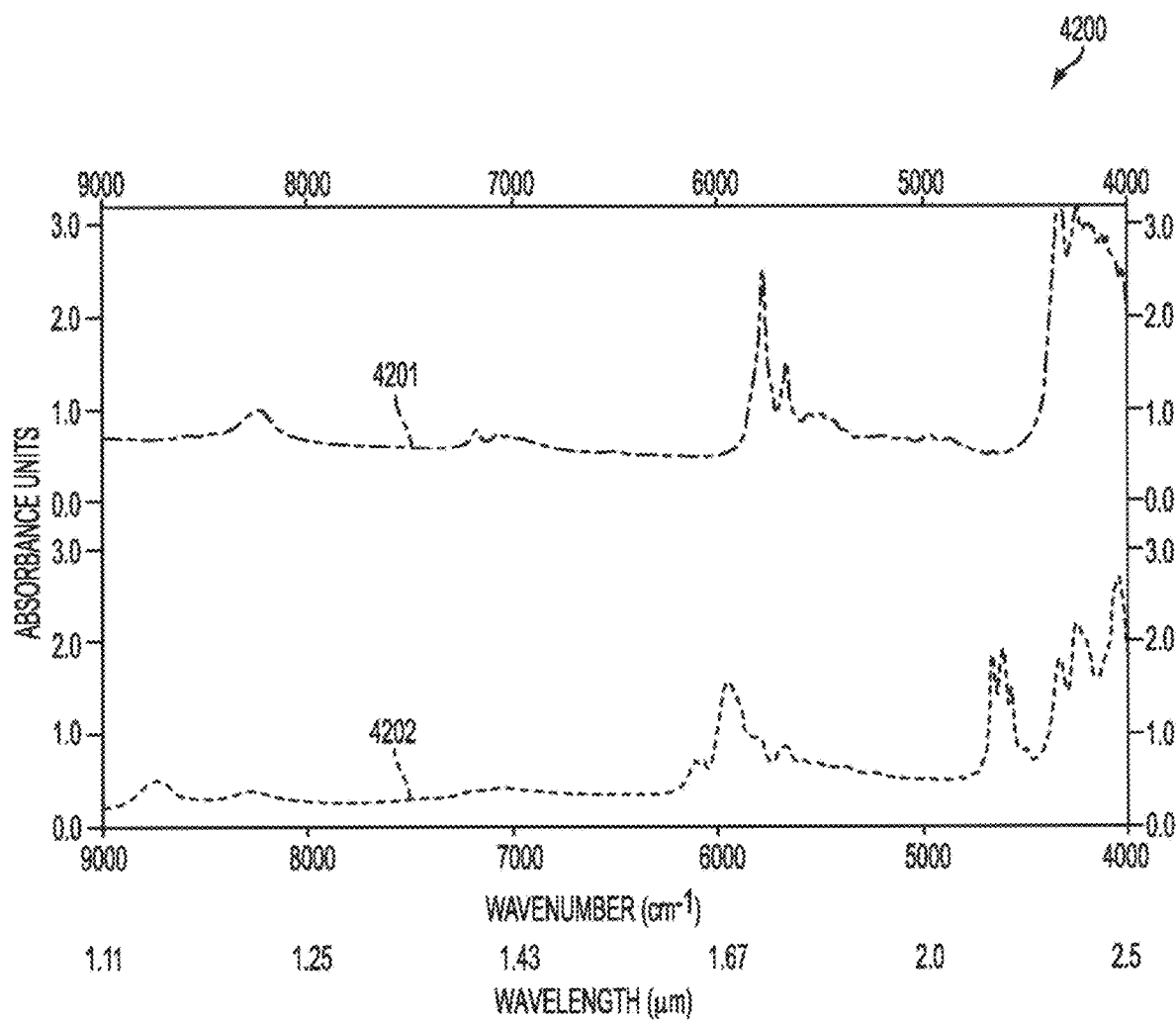
FIG. 42 shows the absorbance for two common plastics, polyethylene and polystyrene.

In a further embodiment, remote sensing or hyper-spectral imaging might be used for process control in a factory or manufacturing setting, particularly when the measurements are to be made at some stand-off or remote distance. As an example, plastics show distinct signatures in the SWIR, and process control may be used for monitoring the manufacture of plastics. Alternately, SWIR light could be used to see through plastics, since the signature for plastics can be subtracted off and there are large wavelength windows where the plastics are transparent. FIG. 42 illustrates the absorbance 4200 for two common plastics: polyethylene 4201 and polystyrene 4202. Because of the hydro-carbon bonds, there are absorption features near 1.7 microns and 2.2-2.5 microns (c.f., discussion on alkanes). In general, the absorption bands in the near infrared are due to overtones and combination bands for various functional group vibrations, including signals from C—H, O—H, C=O, N—H, —COOH, and aromatic C—H groups. It may be difficult to assign an absorption band to a specific functional group due to overlapping of several combinations and overtones. However, with advancements in computational power and chemometrics or multivariate analysis methods, complex systems may be better analyzed. In one embodiment, using software analysis tools the absorption spectrum may be converted to its second derivative equivalent. The spectral differences may permit a fast, accurate, non-destructive and reliable identification of materials. Although particular derivatives are discussed, other mathematical manipulations may be used in the analysis, and these other techniques are also intended to be covered by this disclosure.

Figure 43:
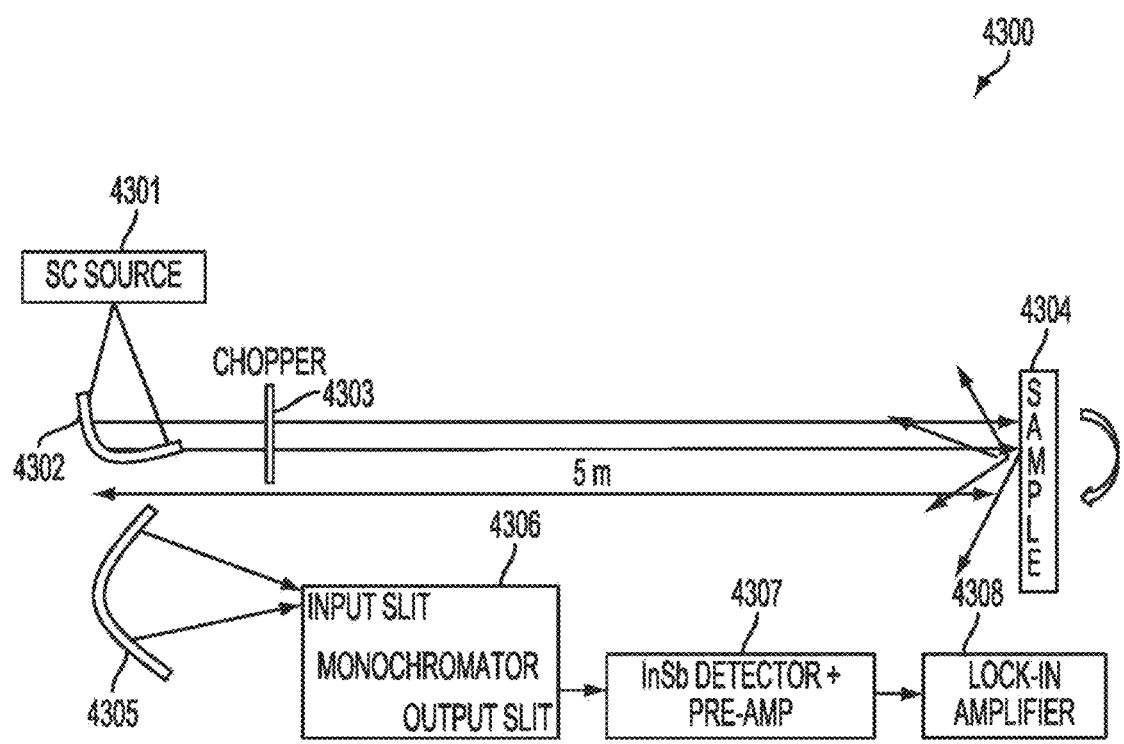
FIG. 43 shows the experimental set-up for a reflection-spectroscopy based stand-off detection system.

In another specific embodiment, experiments have been performed for stand-off detection of solid targets with diffuse reflection spectroscopy using a fiber-based super-continuum source (further described herein). In particular, the diffuse reflection spectrum of solid samples such as explosives (TNT, RDX, PETN), fertilizers (ammonium nitrate, urea), and paints (automotive and military grade) have been measured at stand-off distances of 5 m. Although the measurements were done at 5 m, calculations show that the distance could be anywhere from a few meters to over 150 m. These are specific samples that have been tested, but more generally other materials (particularly comprising hydro-carbons) could also be tested and identified using similar methods. The experimental set-up 4300 for the reflection-spectroscopy-based stand-off detection system is shown in FIG. 43, while details of the SC source 4301 are described later in this disclosure (c.f. FIGS. 20,21, and 23). First, the diverging SC output is collimated to a 1 cm diameter beam using a 25 mm focal length, 90 degrees off-axis, gold coated, parabolic mirror 4302. To reduce the effects of chromatic aberration, refractive optics are avoided in the setup. All focusing and collimation is done using metallic mirrors that have almost constant reflectivity and focal length over the entire SC output spectrum. The sample 4304 is kept at a distance of 5 m from the collimating mirror 4302, which corresponds to a total round trip path length of 10 m before reaching the collection optics 4305. A 12 cm diameter silver coated concave mirror 4305 with a 75 cm focal length is kept 20 cm to the side of the collimation mirror 4302. The mirror 4305 is used to collect a fraction of the diffusely reflected light from the sample, and focus it into the input slit of a monochromator 4306. Thus, the beam is incident normally on the sample 4304, but detected at a reflection angle of tan-1 (0.2/5) or about 2.3 degrees. Appropriate long wavelength pass filters mounted in a motorized rotating filter wheel are placed in the beam path before the input slit 4306 to avoid contribution from higher wavelength orders from the grating (300 grooves/mm, 2 µm blaze). The output slit width is set to 2 mm corresponding to a spectral resolution of 10.8 nm, and the light is detected by a 2 mm×2 mm liquid nitrogen cooled (77K) indium antimonide (InSb) detector 4307. The detected output is amplified using a trans-impedance pre-amplifier 4307 with a gain of about 105V/A and connected to a lock-in amplifier 4308 setup for high sensitivity detection. The chopper frequency is 400 Hz, and the lock-in time constant is set to 100 ms corresponding to a noise bandwidth of about 1 Hz. These are exemplary elements and parameter values, but other or different optical elements may be used consistent with this disclosure.

Three sets of solid samples are chosen to demonstrate the stand-off diffuse reflection spectra measurement in the laboratory. The first set comprises 'Non-hazardous Explosives for Security Training and Testing' (NESTT) manufactured by the XM Division of VanAken International. These samples contain small amounts of explosives deposited on an inert fused silica powder substrate. The experiments are conduced with the following samples-trinitrotoluene (TNT), research department explosive (RDX), Pentaerythritol tetranitrate (PETN), and potassium nitrate. The TNT, RDX and potassium nitrate NESTT samples have 8% (by weight) explosives, while the PETN sample has 4%.

The second sample set consists of ammonium nitrate, urea, gypsum, and pinewood. Ammonium nitrate and urea are common fertilizers, but are also often used as explosives. These samples are ground to a fine powder in a mortar and pestle, and filled to a depth of about 5 mm in a shallow glass container. We also measure the reflection spectrum of a 10 cm diameter×0.5 cm thick Gypsum (CaSO4.2H2O) disk and a 5 cm×5 cm×0.5 m piece of pine wood, since these samples are relevant for the remote sensing community (minerals and vegetation).

The final set of samples is selected to distinguish between commercial automotive and military vehicle paints based on their reflection signatures. Red, black, and green acrylic based spray paints are obtained from an auto supply store and sprayed 3 coats on different areas of a sanded Aluminum block to make the automotive paint samples. The sample of the military paint consisted of an Aluminum block coated with a chemical agent resistant coating (CARC) green paint.

The chemical structure and molecular formula of the 4 NESTT samples are shown in FIG. 44 (4401, 4402, 4403, 4404), while the absorbance spectra obtained using the SC source are shown below in the same FIG. 4405, 4406, 4407, 4408). For each sample, the positions of the strongest/unique peaks have been labeled for clarity. TNT 4401, 4405 belongs to a class of compounds known as nitro-aromatics, in which the carbon directly attached to the nitro (NO2) group is part of an aromatic ring. The strongest peaks in the spectrum observed at 3230 nm and 3270 nm are due to the fundamental C—H stretching vibrations in the aromatic ring. There are also features between 2200-2600 nm, which may arise from the combination between the C—H stretch and C—H bend vibrations. RDX 4402, 4406 belongs to the nitramines class containing the N—NO2 bond and also has multiple features in the 3200-3500 nm band due to the C—H stretch vibrations. This spectrum also contains the C—H combination bands from 2200-2600 nm. PETN 4403, 4407 is classified as a nitrate ester containing the C—O—NO2 bond, and its reflection spectrum is characterized by a triplet of peaks at 3310 nm, 3350 nm and 3440 nm due to the C—H stretch vibration from the aliphatic groups. The C—H combination band is also present from 2200-2600 nm. Potassium nitrate 4404, 4408 being an inorganic compound does not contain any absorption features due to the C—H bond present in the other three samples. Instead, the unique spectral feature for this sample is a pair of peaks at 3590 nm and 3650 nm, which arise due to the first overtone of the asymmetric N—O stretching vibration of the nitrate ion (NO3-).

Figure 45A:
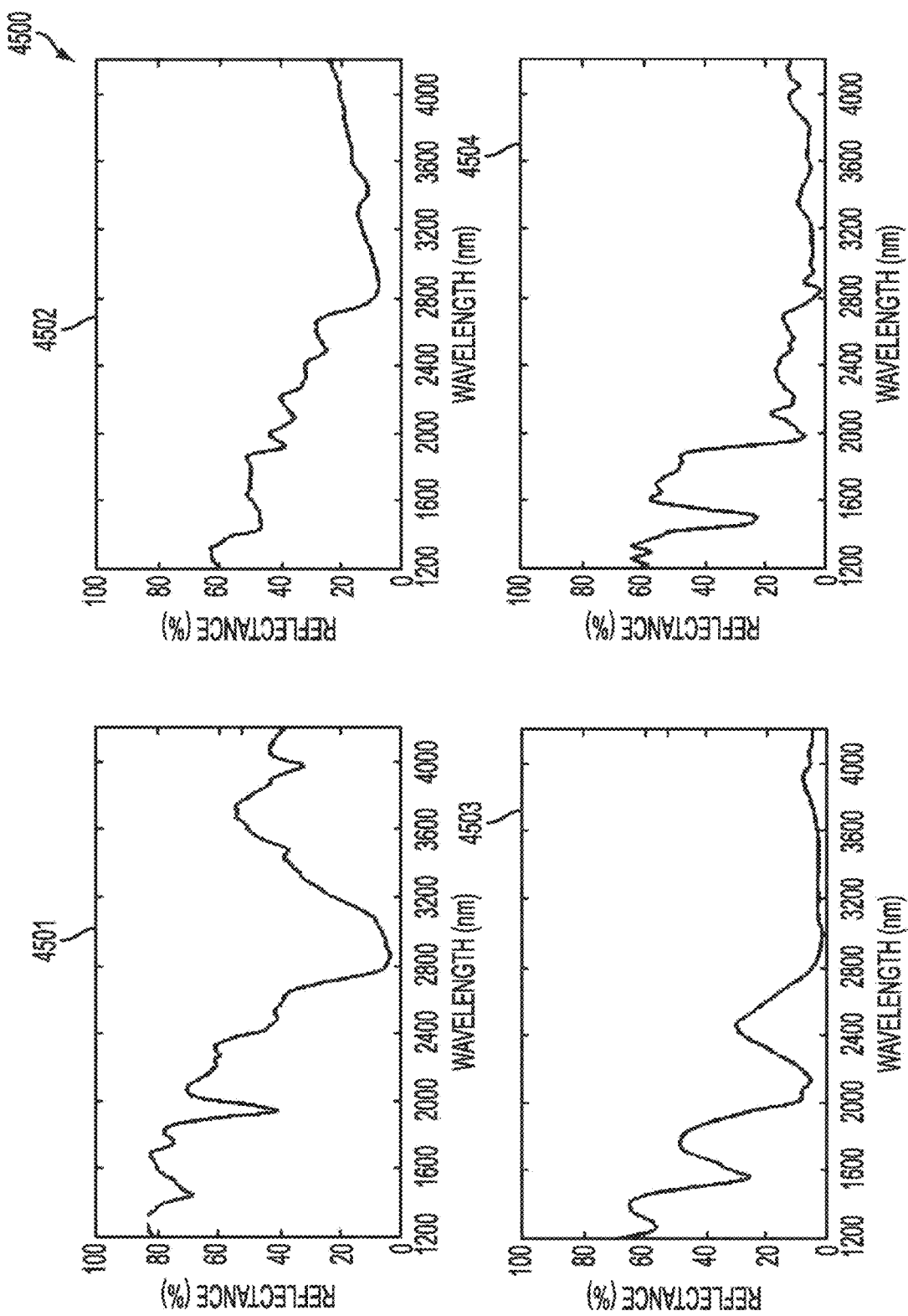
FIG. 45A shows the reflection spectra for gypsum, pine wood, ammonium nitrate and urea.

FIG. 45A illustrates the reflection spectra 4500 for gypsum 4501, pinewood 4502, ammonium nitrate 4503 and urea 4504. The predominant spectral features in the gypsum 4501 (CaSO4.2H2O) reflectance occur due to the fundamental as well as combination bands of the water molecule near 1450 nm, 1750 nm, 1940 nm and 2860 nm. In addition, small dips in the spectrum at 2220, 2260 and 2480 nm which arise due to the first overtone of the S—O bending vibration. Moreover, the valley at 3970 nm occurs due to the first overtone of the —O—S—O stretching vibration of the sulfate (SO42-) ion. The pine wood spectrum 4502 comprises of bands due to its main constituents-cellulose, lignin and water. The valleys at 1450 nm, 1920 nm and 2860 nm are attributed to water. The dip at 2100 nm is due to the first overtone of the C—O asymmetric stretch, the one at 2270 nm due to the combination band of O—H and C—H, and the one at 2490 nm due to combination band of C—H and C—O. Finally, the broad feature around 3450 nm is due to the C—H stretching vibration. The ammonium nitrate (NH4NO3) spectrum 4503 has three prominent features in the near-IR region. The dip at 1270 nm is due to the combination of N—H stretching and N—H bending vibrations, while the dip at 1570 nm is due to the first overtone of N—H stretch. The doublet at 2050 nm and 2140 nm is possibly due to the second overtone of the N—H bending vibrations, while the fundamental N—H stretch appears as a broad feature around 3000 nm. Urea (NH2)2CO 4504 has two amide (—NH2) groups joined by a carbonyl (C=O) functional group. The absorption line at 1490 nm occurs due to the third overtone of the C=O stretching vibration while the line at 1990 nm is due to the second overtone of the same.

Figure 45B:
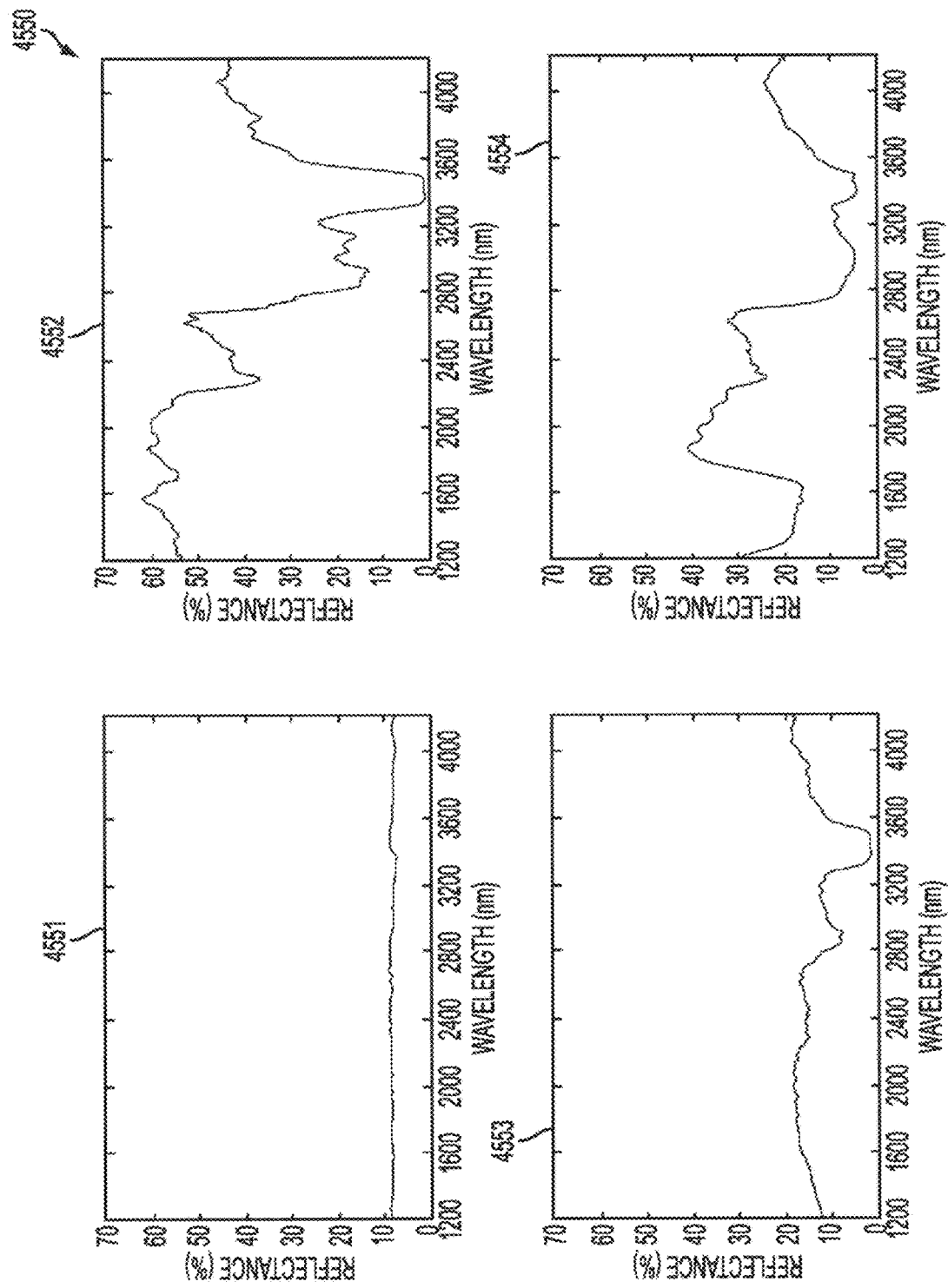
FIG. 45B illustrates the reflection spectra for three commercial automotive paints and military grade CARC paint (chemical agent resistant coating) (reflectance in this case are in arbitrary units).

FIG. 45B shows the reflection spectra 4550 for three commercial automotive paints 4551, 4552, 4553 and military grade CARC (chemical agent resistant coating) paint 4554. The paints consist of a complex mixture of many different chemicals, and, hence, it is very difficult to identify individual absorption lines. Since all four paints contain a variety of organic compounds, features are observed between 3200-3500 nm from the C—H stretch and from 2200-2600 nm due to the C—H stretch and C—H bond combination band. However, the primary difference between the automotive 45451, 4552, 4553 and CARC paint 4554 is the presence of a strong dip between 1200-1850 nm in the latter, which might be attributed to the absorption from Cobalt chromite—a green pigment found in CARC-green.

Figure 46:
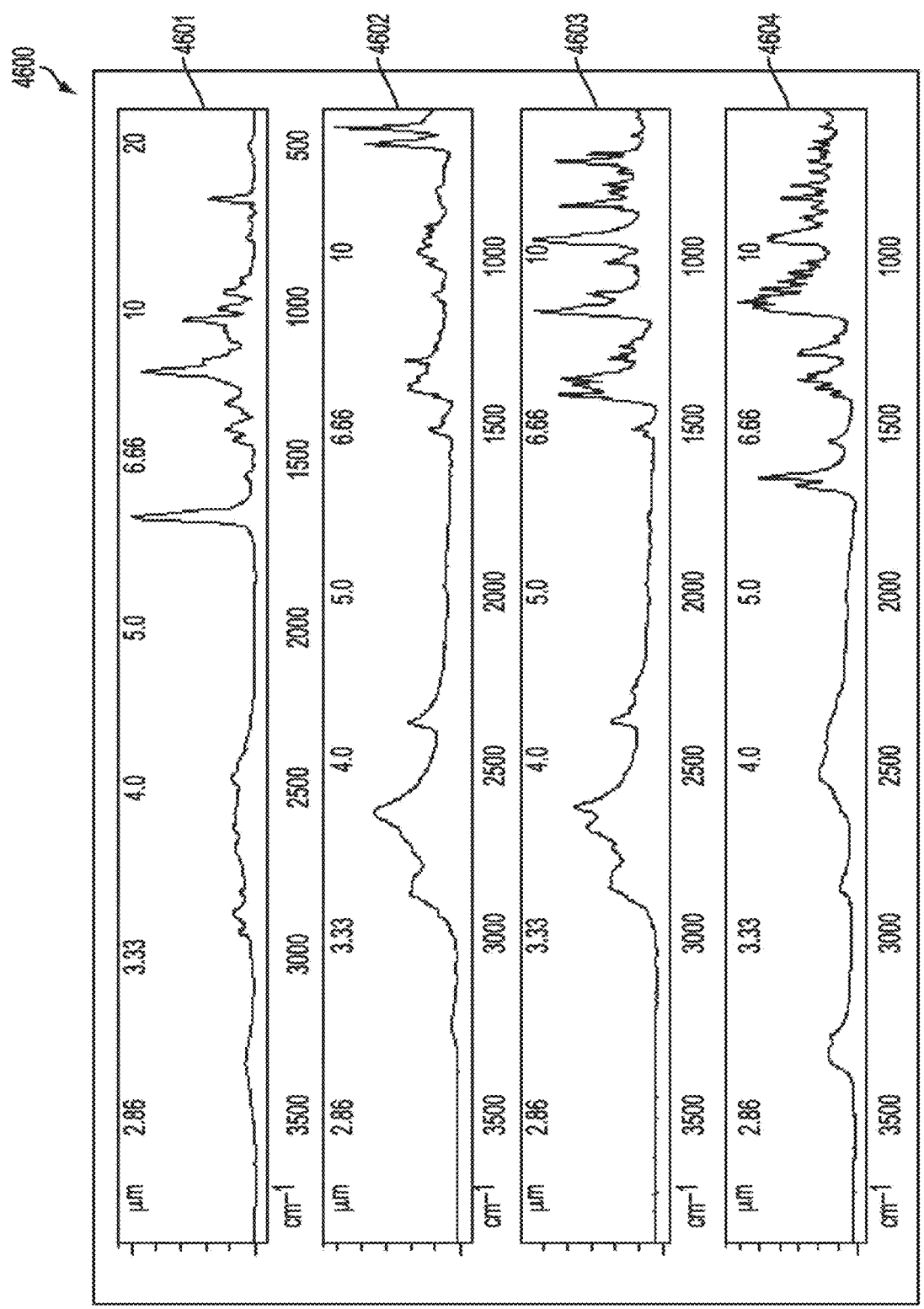
FIG. 46 shows the mid-wave infrared and long-wave infrared absorption spectra for various illicit drugs. It is expected that overtone and combination bands should be evident in the SWIR and near-infrared wavelength bands.

Thus, FIGS. 44 and 45 show that various materials, including explosives, fertilizers, vegetation, and paints have features in the near-infrared and SWIR that can be used to identify the various samples. Although stronger features are found in the mid-infrared, the near-infrared may be easier to measure due to higher quality detection systems, more mature fiber optics and light sources, and transmission through atmospheric transmission windows. Because of these distinct spectral signatures, these materials could also be detected using active remote sensing or hyper-spectral imaging, as described in this disclosure. These are just particular samples that have been tested at stand-off distances, but other materials and samples may also be identified using the SWIR remote sensing or hyper-spectral imaging methods, and these samples are also intended to be covered within this disclosure. As just another example, illicit drugs may be detectable using remote sensing or hyper-spectral imaging. FIG. 46 shows the mid-wave infrared and long-wave infrared absorption spectra 1500 for various illicit drugs. The absorbance for cocaine 4601, methamphetamine 4602, MDMA (ecstasy) 4603, and heroin 4604 are plotted versus wavelength from approximately 2.5-20 microns. Although the fundamental resonances for these drugs may lie in the longer wavelength regions, there are corresponding overtones and combination bands in the SWIR and near-infrared wavelength range. Therefore, the active remote sensing or hyper-spectral imaging techniques described herein may also be applicable to detecting illicit drugs from aircraft, vehicles, or hand held devices.

Detection Systems

As discussed earlier, the active remote sensing system or hyper-spectral imaging system may be on an airborne platform, mounted on a vehicle, a stationary transmission or reflection set-up, or even held by a human for a compact system. For such a system, there are fundamentally two hardware parts: the transmitter or light source and the detection system. Between the two, perhaps in a transmission or reflection setting, may be the sample being tested or measured. Moreover, the output from the detection system may go to a computational system, comprising computers or other processing equipment. The output from the computational system may be displayed graphically as well as with numerical tables and perhaps an identification of the material composition. These are just some of the parts of the systems, but other elements may be added or be eliminated, and these modified configurations are also intended to be covered by this disclosure.

By use of an active illuminator, a number of advantages may be achieved. First, the variations due to sunlight and time-of-day may be factored out. The effects of the weather, such as clouds and rain, might also be reduced. Also, higher signal-to-noise ratios may be achieved. For example, one way to improve the signal-to-noise ratio would be to use modulation and lock-in techniques. In one embodiment, the light source may be modulated, and then the detection system would be synchronized with the light source. In a particular embodiment, the techniques from lock-in detection may be used, where narrow band filtering around the modulation frequency may be used to reject noise outside the modulation frequency. In an alternate embodiment, change detection schemes may be used, where the detection system captures the signal with the light source on and with the light source off. Again, for this system the light source may be modulated. Then, the signal with and without the light source is differenced. This may enable the sun light changes to be subtracted out. In addition, change detection may help to identify objects that change in the field of view. In the following some exemplary detection systems are described.

In one embodiment, a SWIR camera or infrared camera system may be used to capture the images. The camera may include one or more lenses on the input, which may be adjustable. The focal plane assemblies may be made from mercury cadmium telluride material (HgCdTe), and the detectors may also include thermo-electric coolers. Alternately, the image sensors may be made from indium gallium arsenide (InGaAs), and CMOS transistors may be connected to each pixel of the InGaAs photodiode array. The camera may interface wirelessly or with a cable (e.g., USB, Ethernet cable, or fiber optics cable) to a computer or tablet or smart phone, where the images may be captured and processed. These are a few examples of infrared cameras, but other SWIR or infrared cameras may be used and are intended to be covered by this disclosure.

Figure 47A:
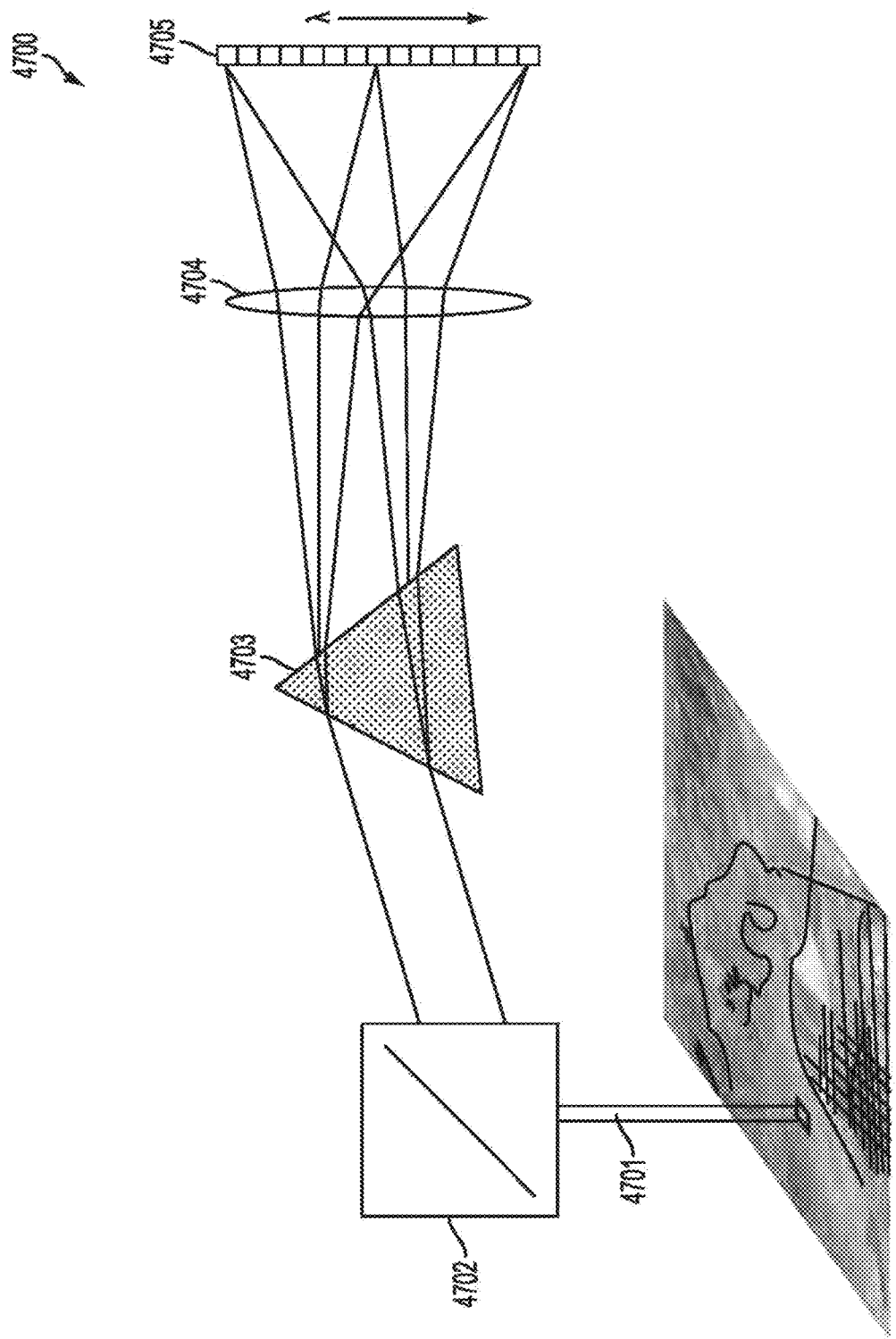
FIG. 47A is a schematic diagram of the basic elements of an imaging spectrometer.

In another embodiment, an imaging spectrometer may be used to detect the light received from the sample. For example, FIG. 47A shows a schematic diagram 4700 of the basic elements of an imaging spectrometer. The input light 4701 from the sample may first be directed by a scanning mirror and/or other optics 4702. An optical dispersing element 4703, such as a grating or prism, in the spectrometer may split the light into many narrow, adjacent wavelength bands, which may then be passed through imaging optics 4704 onto one or more detectors or detector arrays 4705. Some sensors may use multiple detector arrays to measure hundreds of narrow wavelength bands.

Figure 47B:
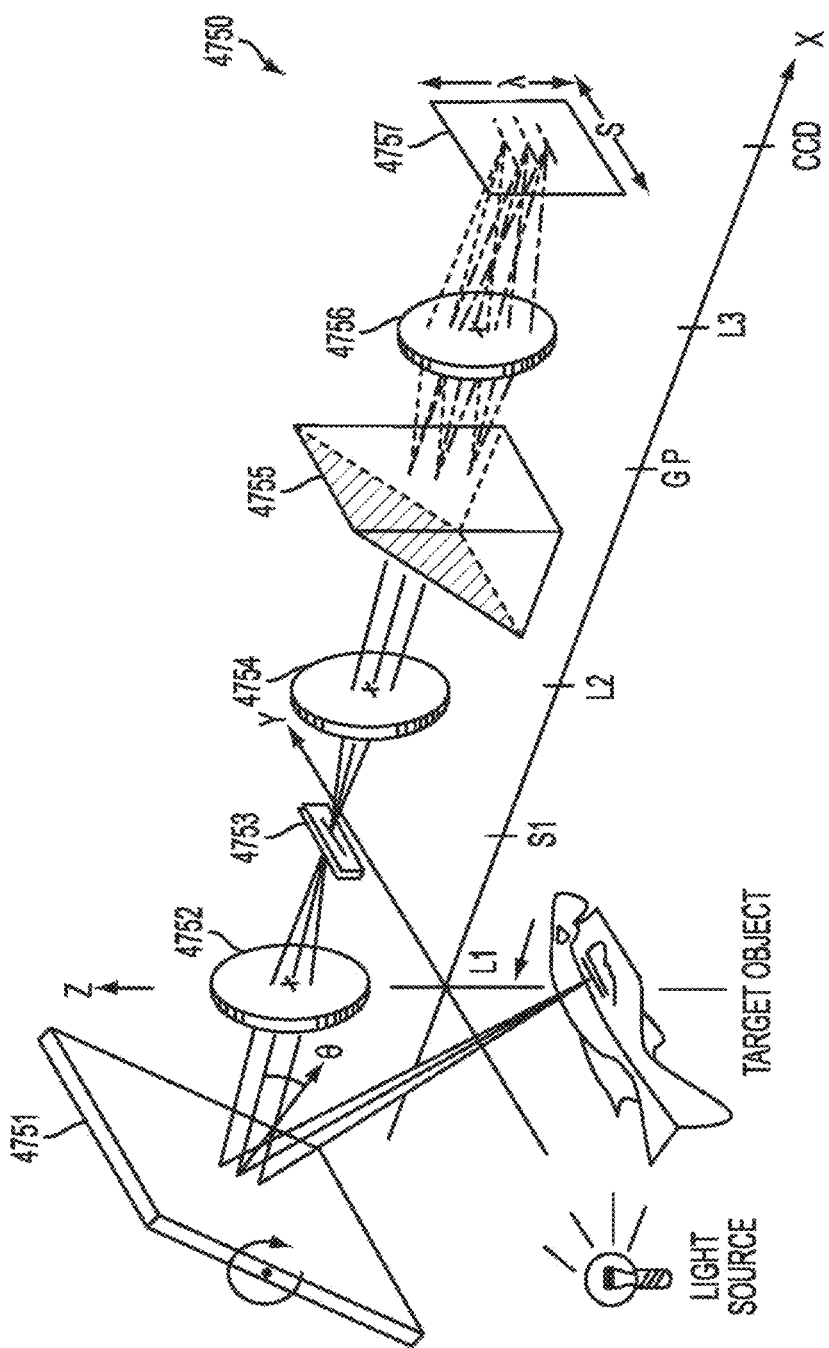
FIG. 47B illustrates one example of a typical imaging spectrometer used in hyper-spectral imaging systems.

An example of a typical imaging spectrometer 4750 used in hyper-spectral imaging systems is illustrated in FIG. 47B. In this particular embodiment, the input light may be directed first by a tunable mirror 4751. A front lens 4752 may be placed before the entrance slit 4753 and the collector lens 4754. In this embodiment, the dispersing element is a holographic grating with a prism 4755, which separates the different wavelength bands. Then, a camera lens 4756 may be used to image the wavelengths onto a detector or camera 4757.

FIGS. 47A and 47B provide particular examples, but some of the elements may not be used, or other elements may be added, and these embodiments are also intended to be covered by this disclosure. For instance, a scanning spectrometer may be used before the detector, where a grating or dispersive element is scanned to vary the wavelength being measured by the detector. In yet another embodiment, filters may be used before one or more detectors to select the wavelengths or wavelength bands to be measured. This may be particularly useful if only a few bands or wavelengths are to be measured. The filters may be dielectric filters, Fabry-Perot filters, absorption or reflection filters, fiber gratings, or any other wavelength selective filter. In an alternate embodiment, a wavelength division multiplexer, WDM, may be used followed by one or more detectors or detector arrays. One example of a planar wavelength division multiplexer may be a waveguide grating router or an arrayed waveguide grating. The WDM may be fiber coupled, and detectors may be placed directly at the output or the detectors may be coupled through fibers to the WDM. Some of these components may also be combined with the configurations in FIGS. 47A and 47B.

Figure 48:
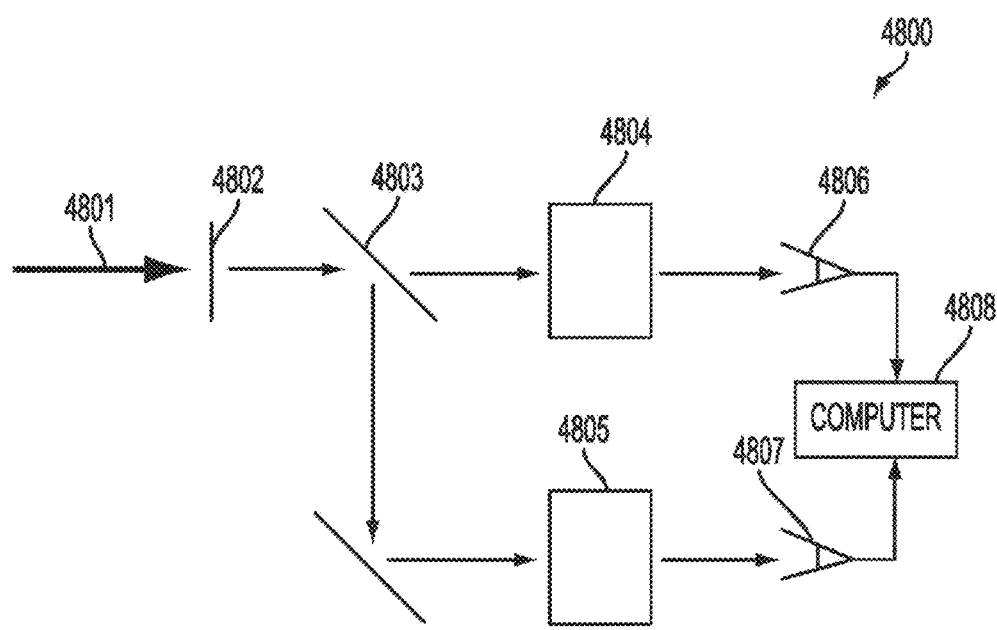
FIG. 48 shows one example of a gas-filter correlation radiometer, which is a detection system that uses a sample of the gas of interest as a spectral filter for the gas.

While the above detection systems could be categorized as single path detection systems, it may be advantageous in some cases to use multi-path detection systems. In one embodiment, when the aim is to measure particular gases or material (rather than identify out of a library of materials), it may be advantageous to use gas-filter correlation radiometry (GFCR), such as 4800 in FIG. 48. A GFCR is a detection system that uses a sample of the gas of interest as a spectral filter for the gas. As shown in FIG. 48, the incoming radiation 4801 may first be passed through a narrow band pass filter 4802. The beam may then be split by a beam splitter 4803 along two paths; one path comprising a gas cell filled with the gas of interest 4804 (known as the correlation cell) and the other path comprising no gas 4805. The light from each path may then be measured using two detectors 4806, 4807, and the signals may then be analyzed 4808. The difference in the transmission along the two paths may correspond primarily to the absorption of the gas along the correlation cell path. This GFCR configuration may be advantageous, for example, in the detection of natural gas. Since the goal is to measure methane and ethane, the correlation cells may contain these gases, either in combination or separately. Although a particular configuration for the GFCR has been described, variations of this configuration as well as addition of other components may also be used and are intended to be covered by this disclosure. For example, collection optics and lenses may be used with this configuration, and various modulation techniques may also be used to increase the signal to noise ratio.

Figure 49:
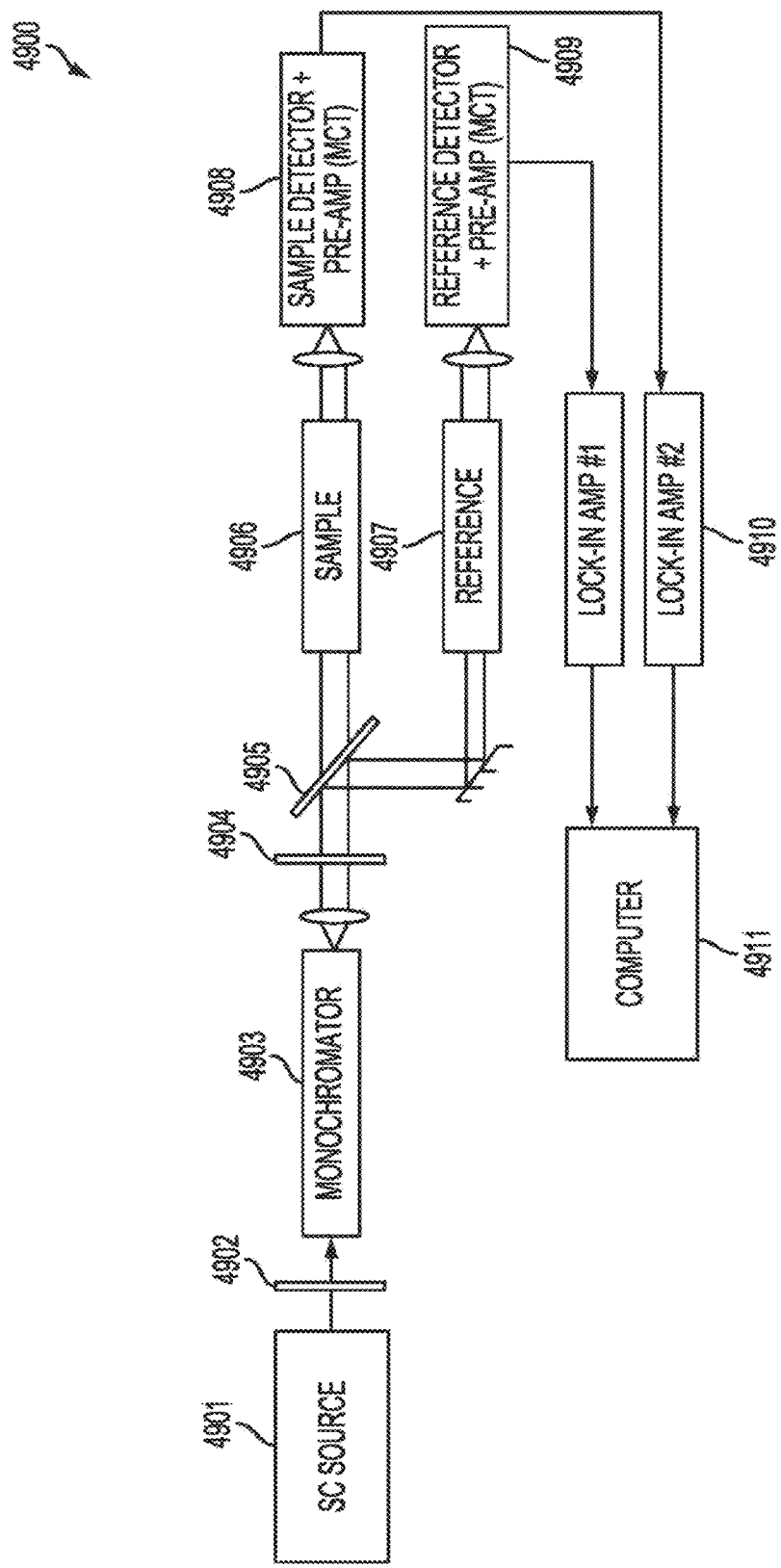
FIG. 49 exemplifies a dual-beam experimental set-up that may be used to subtract out (or at least minimize the adverse effects of) light source fluctuations.

In yet another example of multi-beam detection systems, a dual-beam set-up 4900 such as in FIG. 49 may be used to subtract out (or at least minimize the adverse effects of) light source fluctuations. In one embodiment, the output from an SC source 4901 may be collimated using a calcium fluoride (CaF2) lens 4902 and then focused into the entrance slit of the monochromator 4903. At the exit slit, light at the selected wavelength is collimated again and may be passed through a polarizer 4904 before being incident on a calcium fluoride beam splitter 4905. After passing through the beam splitter 4905, the light is split into a sample 4906 and reference 4907 arm to enable ratiometric detection that may cancel out effects of intensity fluctuations in the SC source 4901. The light in the sample arm 4906 passes through the sample of interest and is then focused onto a HgCdTe detector 4908 connected to a pre-amp. A chopper 4902 and lock-in amplifier 4910 setup enable low noise detection of the sample arm signal. The light in the reference arm 4907 passes through an empty container (cuvette, gas cell etc.) of the same kind as used in the sample arm. A substantially identical detector 4909, pre-amp and lock-in amplifier 4910 is used for detection of the reference arm signal. The signal may then be analyzed using a computer system 4911. This is one particular example of a method to remove fluctuations from the light source, but other components may be added and other configurations may be used, and these are also intended to be covered by this disclosure.

Although particular examples of detection systems have been described, combinations of these systems or other systems may also be used, and these are also within the scope of this disclosure. As one example, environmental fluctuations (such as turbulence or winds) may lead to fluctuations in the beam for active remote sensing or hyperspectral imaging. A configuration such as illustrated in the representative embodiment of FIG. 49 may be able to remove the effect of environmental fluctuations. Yet another technique may be to "wobble" the light beam after the light source using a vibrating mirror. The motion may lead to the beam moving enough to wash out spatial fluctuations within the beam waist at the sample or detection system. If the vibrating mirror is scanned faster than the integration time of the detectors, then the spatial fluctuations in the beam may be integrated out. Alternately, some sort of synchronous detection system may be used, where the detection is synchronized to the vibrating frequency.

Described herein are just some examples of the beneficial use of near-infrared or SWIR lasers for active remote sensing or hyper-spectral imaging. However, many other spectroscopy and identification procedures can use the near-infrared or SWIR light consistent with this disclosure and are intended to be covered by the disclosure. As one example, the fiber-based super-continuum lasers may have a pulsed output with pulse durations of approximately 0.5-2 nsec and pulse repetition rates of several Megahertz. Therefore, the active remote sensing or hyper-spectral imaging applications may also be combined with LIDAR-type applications. Namely, the distance or time axis can be added to the information based on time-of-flight measurements. For this type of information to be used, the detection system would also have to be time-gated to be able to measure the time difference between the pulses sent and the pulses received. By calculating the round-trip time for the signal, the distance of the object may be judged. In another embodiment, GPS (global positioning system) information may be added, so the active remote sensing or hyper-spectral imagery would also have a location tag on the data. Moreover, the active remote sensing or hyper-spectral imaging information could also be combined with two-dimensional or three-dimensional images to provide a physical picture as well as a chemical composition identification of the materials. These are just some modifications of the active remote sensing or hyper-spectral imaging system described in this disclosure, but other techniques may also be added or combinations of these techniques may be added, and these are also intended to be covered by this disclosure.

Section 4: Short-Wave Infrared Super-Continuum Lasers for Detecting Counterfeit or Illicit Drugs and Pharmaceutical Process Control One advantage of optical systems is that they can perform non-contact, stand-off or remote sensing distance spectroscopy of various materials. As an example, optical systems can be used for identification of counterfeit drugs, detection of illicit drugs, or process control in the pharmaceutical industry, especially when the sensing is to be done at remote or stand-off distances in a non-contact, rapid manner. In general, the near-infrared region of the electromagnetic spectrum covers between approximately 0.7 microns (700 nm) to about 2.5 microns (2500 nm). However, it may also be advantageous to use just the short-wave infrared (SWIR) between approximately 1.4 microns (1400 nm) and about 2.5 microns (2500 nm). One reason for preferring the SWIR over the entire NIR may be to operate in the so-called "eye safe" window, which corresponds to wavelengths longer than about 1400 nm. Therefore, for the remainder of the disclosure the SWIR will be used for illustrative purposes. However, it should be clear that the discussion that follows could also apply to using the near infrared-NIR—wavelength range, or other wavelength bands.

In particular, wavelengths in the eye safe window may not transmit down to the retina of the eye, and therefore, these wavelengths may be less likely to create permanent eye damage from inadvertent exposure. The near-infrared wavelengths have the potential to be dangerous, because the eye cannot see the wavelengths (as it can in the visible), yet they can penetrate and cause damage to the eye. Even if a practitioner is not looking directly at the laser beam, the practitioner's eyes may receive stray light from a reflection or scattering some surface. Hence, it can always be a good practice to use eye protection when working around lasers. Since wavelengths longer than about 1400 nm are substantially not transmitted to the retina or substantially absorbed in the retina, this wavelength range is known as the eye safe window. For wavelengths longer than 1400 nm, in general only the cornea of the eye may receive or absorb the light radiation.

The SWIR wavelength range may be particularly valuable for identifying materials based on their chemical composition because the wavelength range comprises overtones and combination bands for numerous chemical bonds. For example, in the SWIR numerous hydro-carbon chemical compounds have overtone and combinational bands, along with oxygen-hydrogen and carbon-oxygen compounds. Thus, gases, liquids and solids that comprise these chemical compounds may exhibit spectral features in the SWIR wavelength range. In a particular embodiment, the spectra of organic compounds may be dominated by the C—H stretch. The C—H stretch fundamental occurs near 3.4 microns, the first overtone is near 1.7 microns, and a combination band occurs near 2.3 microns.

One embodiment of remote sensing that is used to identify and classify various materials is so-called "hyper-spectral imaging." Hyper-spectral sensors may collect information as a set of images, where each image represents a range of wavelengths over a spectral band. Hyper-spectral imaging may deal with imaging narrow spectral bands over an approximately continuous spectral range. As an example, in hyper-spectral imaging a lamp may be used as the light source. However, the incoherent light from a lamp may spatially diffract rapidly, thereby making it difficult to perform spectroscopy at stand-off distances or remote distances. Therefore, it would be advantageous to have a broadband light source covering the SWIR that may be used in place of a lamp to identify or classify materials in remote sensing or stand-off detection applications.

As used throughout this document, the term "couple" and or "coupled" refers to any direct or indirect communication between two or more elements, whether or not those elements are physically connected to one another. As used throughout this disclosure, the term "spectroscopy" means that a tissue or sample is inspected by comparing different features, such as wavelength (or frequency), spatial location, transmission, absorption, reflectivity, scattering, fluorescence, refractive index, or opacity. In one embodiment, "spectroscopy" may mean that the wavelength of the light source is varied, and the transmission, absorption, fluorescence, or reflectivity of the tissue or sample is measured as a function of wavelength. In another embodiment, "spectroscopy" may mean that the wavelength dependence of the transmission, absorption, fluorescence or reflectivity is compared between different spatial locations on a tissue or sample. As an illustration, the "spectroscopy" may be performed by varying the wavelength of the light source, or by using a broadband light source and analyzing the signal using a spectrometer, wavemeter, or optical spectrum analyzer.

As used throughout this document, the term "fiber laser" refers to a laser or oscillator that has as an output light or an optical beam, wherein at least a part of the laser comprises an optical fiber. For instance, the fiber in the "fiber laser" may comprise one of or a combination of a single mode fiber, a multi-mode fiber, a mid-infrared fiber, a photonic crystal fiber, a doped fiber, a gain fiber, or, more generally, an approximately cylindrically shaped waveguide or light-pipe. In one embodiment, the gain fiber may be doped with rare earth material, such as ytterbium, erbium, and/or thulium. In another embodiment, the mid-infrared fiber may comprise one or a combination of fluoride fiber, ZBLAN fiber, chalcogenide fiber, tellurite fiber, or germanium doped fiber. In yet another embodiment, the single mode fiber may include standard single-mode fiber, dispersion shifted fiber, non-zero dispersion shifted fiber, high-nonlinearity fiber, and small core size fibers.

As used throughout this disclosure, the term "pump laser" refers to a laser or oscillator that has as an output light or an optical beam, wherein the output light or optical beam is coupled to a gain medium to excite the gain medium, which in turn may amplify another input optical signal or beam. In one particular example, the gain medium may be a doped fiber, such as a fiber doped with ytterbium, erbium and/or thulium. In one embodiment, the "pump laser" may be a fiber laser, a solid state laser, a laser involving a nonlinear crystal, an optical parametric oscillator, a semiconductor laser, or a plurality of semiconductor lasers that may be multiplexed together. In another embodiment, the "pump laser" may be coupled to the gain medium by using a fiber coupler, a dichroic mirror, a multiplexer, a wavelength division multiplexer, a grating, or a fused fiber coupler.

As used throughout this document, the term "super-continuum" and or "supercontinuum" and or "SC" refers to a broadband light beam or output that comprises a plurality of wavelengths. In a particular example, the plurality of wavelengths may be adjacent to one-another, so that the spectrum of the light beam or output appears as a continuous band when measured with a spectrometer. In one embodiment, the broadband light beam may have a bandwidth of at least 10 nm. In another embodiment, the "super-continuum" may be generated through nonlinear optical interactions in a medium, such as an optical fiber or nonlinear crystal. For example, the "super-continuum" may be generated through one or a combination of nonlinear activities such as four-wave mixing, parametric amplification, the Raman effect, modulational instability, and self-phase modulation.

As used throughout this disclosure, the terms "optical light" and or "optical beam" and or "light beam" refer to photons or light transmitted to a particular location in space. The "optical light" and or "optical beam" and or "light beam" may be modulated or unmodulated, which also means that they may or may not contain information. In one embodiment, the "optical light" and or "optical beam" and or "light beam" may originate from a fiber, a fiber laser, a laser, a light emitting diode, a lamp, a pump laser, or a light source.

As used throughout this disclosure, the term "remote sensing" may include the measuring of properties of an object from a distance, without physically sampling the object, for example by detection of the interactions of the object with an electromagnetic field. In one embodiment, the electromagnetic field may be in the optical wavelength range, including the infrared or SWIR. One particular form of remote sensing may be stand-off detection, which may range exemplary from non-contact up to hundreds of meters away.

Identification of Counterfeit Drugs

Pharmaceutical counterfeiting is a growing and significant issue for the healthcare community as well as the pharmaceutical industry worldwide. As a result of counterfeiting, users may be threatened by substandard drug quality or harmful ingredients, and legitimate companies may lose significant revenues. The definition for "counterfeit drug" by the World Health Organization was as follows: "A counterfeit medicine is one which is deliberately and fraudulently mislabeled with respect to identity and/or source. Counterfeiting can apply to both branded and generic products and counterfeit products may include products with the correct ingredients or with the wrong ingredients, without active ingredients, with insufficient active ingredient or with fake packaging." Later this definition was slightly modified, "Counterfeiting in relation to medicinal products means the deliberate and fraudulent mislabeling with respect to the identity, composition and/or source of a finished medicinal product, or ingredient for the preparation of a medicinal product."

A rapid screening technique such as near-infrared or SWIR spectroscopy could aid in the search for and identification of counterfeit drugs. In particular, using a non-lamp based light source could lead to contact-free control and analysis of drugs. In a particular embodiment, remote sensing, stand-off detection, or hyper-spectral imaging may be used for process control or counterfeit drug identification in a factory or manufacturing setting, or in a retail, wholesale, or warehouse setting. In one embodiment, the light source for remote sensing may direct the light beam toward the region of interest (e.g., conveyor belt, stocking shelves, boxes or cartons, etc), and the diffuse reflected light may then be measured using a detection system. Various kinds of SWIR light sources will be discussed later in this disclosure. The detection system may comprise, in one embodiment, a spectrometer followed by one or more detectors. In another embodiment, the detection system may be a dispersive element (examples include prisms, gratings, or other wavelength separators) followed by one or more detectors or detector arrays. In yet another embodiment, the detection system may comprise a Fourier transform infrared spectrometer. These are merely specific examples of the detection system, but combinations of these or other detection systems may also be used and are contemplated within the scope of this disclosure.

For monitoring drugs, the SWIR light source and the detection system could be used in transmission, reflection, fluorescence, or diffuse reflection. Also, different system configurations may also be used and are included in the scope of this disclosure. For example, the light source and detection system may be placed in a fixed location, and for reflection the light source and detectors may be close to one another, while for transmission the light source and detectors may be at different locations. The region of interest may be surveyed, and the light beam may also be scanned to cover an area larger than the light source beam. In yet another embodiment, the system could be placed on a vehicle such as an automobile or a truck, or the light source could be placed on one vehicle, while the detection system is on another vehicle. If the light source and detection system are compact and lightweight, they might even be carried by a person in the field, either in their hands or in a backpack.

Figure 50:
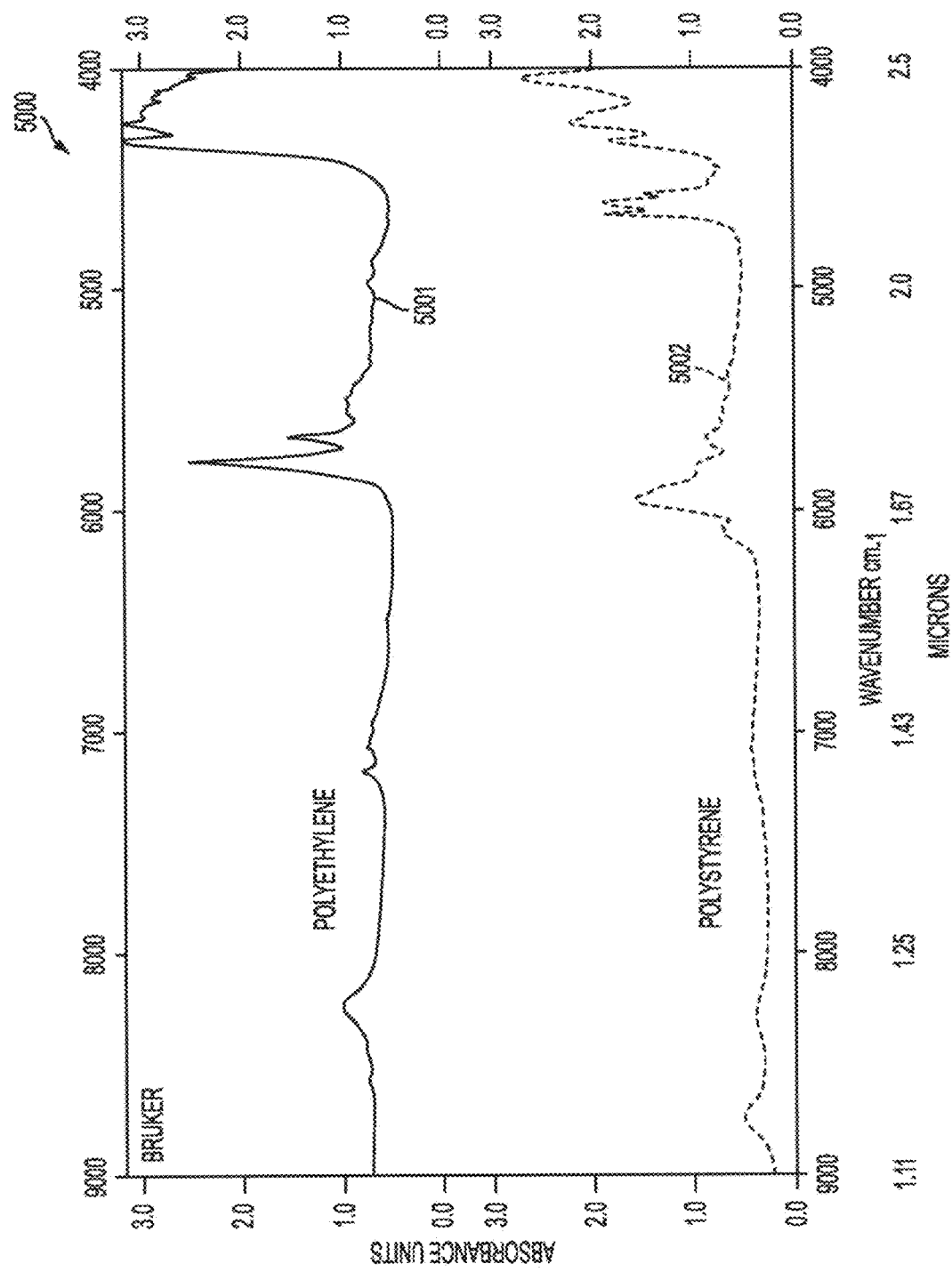
FIG. 50 shows the absorbance for two common plastics, polyethylene and polystyrene.

Another advantage of using the near-infrared or SWIR is that most drug packaging materials are at least partially transparent in this wavelength range, so that drug compositions may be detected and identified through the packaging non-destructively. As an example, SWIR light could be used to see through plastics, since the signature for plastics can be subtracted off and there are large wavelength windows where the plastics are transparent. FIG. 50 illustrates the absorbance 5000 for two common plastics: polyethylene 5001 and polystyrene 5002. Because of the hydro-carbon bonds, there are absorption features near 1.7 microns and 2.2-2.5 microns. In general, the absorption bands in the near infrared are due to overtones and combination bands for various functional group vibrations, including signals from C—H, O—H, C=O, N—H, —COOH, and aromatic C—H groups. It may be difficult to assign an absorption band to a specific functional group due to overlapping of several combinations and overtones. However, with advancements in computational power and chemometrics or multivariate analysis methods, complex systems may be better analyzed. In one embodiment, using software analysis tools the absorption spectrum may be converted to its second derivative equivalent. The spectral differences may permit a fast, accurate, non-destructive and reliable identification of materials. Although particular derivatives are discussed, other mathematical manipulations may be used in the analysis, and these other techniques are also intended to be covered by this disclosure.

Spectroscopy in the near-infrared or SWIR may be sensitive to both the chemical and physical nature of the sample composition and may be performed rapidly with minimal sample preparation. For example, near-infrared or SWIR spectroscopy may be used to study the homogeneity of powder samples, particle size determinations, product composition, the determination of the concentrations and distribution of components in solid tablets and content uniformity, among other applications. In yet other embodiments, applications include tablet identification, determination of moisture, residual solvents, active ingredient potency, the study of blending operations, and the detection of capsule tampering.

Figure 51:
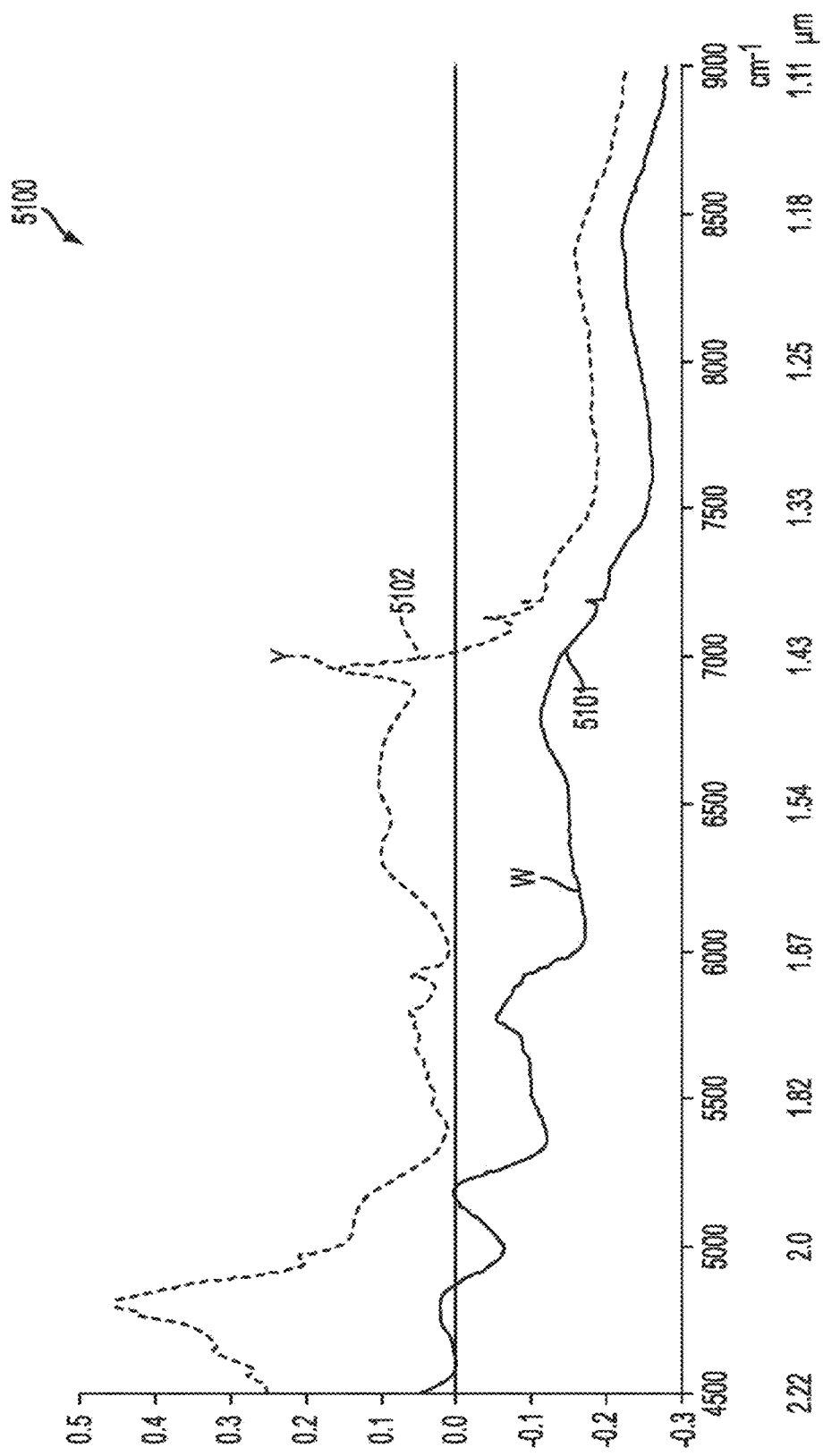
FIG. 51 illustrates one example of the difference in near-infrared spectrum between an authentic tablet and a counterfeit tablet.

FIG. 51 illustrates one example of the difference in near-infrared spectrum 5100 between an authentic tablet and a counterfeit tablet. Two grades of film coated tablets comprising drugs were investigated: curve 5101 is the genuine drug, while 5102 is a counterfeit drug. These two grades of capsules have noticeably different contents, and the differences are apparent in the near-infrared or SWIR spectra. In some cases the differences may not be as distinct. For these cases, more signal processing may be necessary to distinguish between samples.

Figure 52:
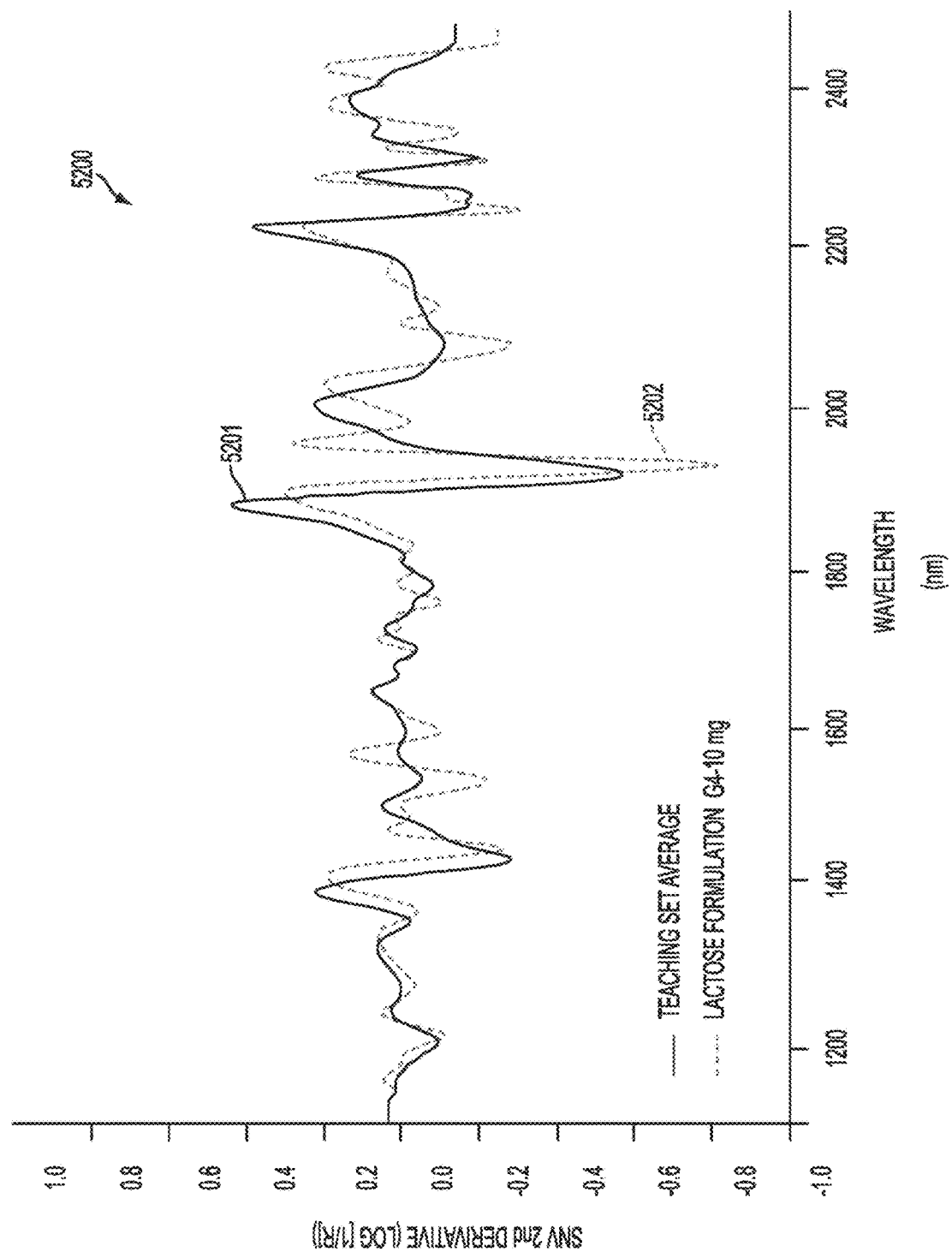
FIG. 52 shows the second derivative of the spectral comparison of Prozac and a similarly formulated generic.

In another embodiment, it may be advantageous to take a first, second or higher order derivative to elucidate the difference between real and counterfeit drugs. For example, FIG. 52 shows the second derivative 5200 of the spectral comparison of Prozac 5201 and a similarly formulated generic 5202, which had a fluoxetine hydrochloride (10 mg). Although the reflectance curves from the two samples are close and, therefore, difficult to distinguish, the second derivative of the data helps to bring out the differences more clearly. Although a second derivative is used in this example, any number of signal processing algorithms and methods may be used, and these are also intended to be covered by this disclosure. For example, partial least square algorithms, multivariate data analysis, principal component analysis, or chemometric software may be implemented without departing from the scope of this disclosure.

In yet another embodiment, near-infrared or SWIR spectroscopy may be used to measure and calibrate various pharmaceutical formulations based on the active pharmaceutical ingredients and excipients. An excipient may be a pharmacologically inactive substance used as a carrier for the active ingredients of a medication. In some cases, the active substance may not be easily administered and/or absorbed by the human body; in such cases the active ingredient may be dissolved into or mixed with an excipient. Also, excipients are also sometimes used to bulk up formulations that contain very potent active ingredients, to allow for convenient and accurate dosage. In addition to their use in the single-dosage quantity, excipients can be used in the manufacturing process to aid in the handling of the active substance concerned.

Figure 53:
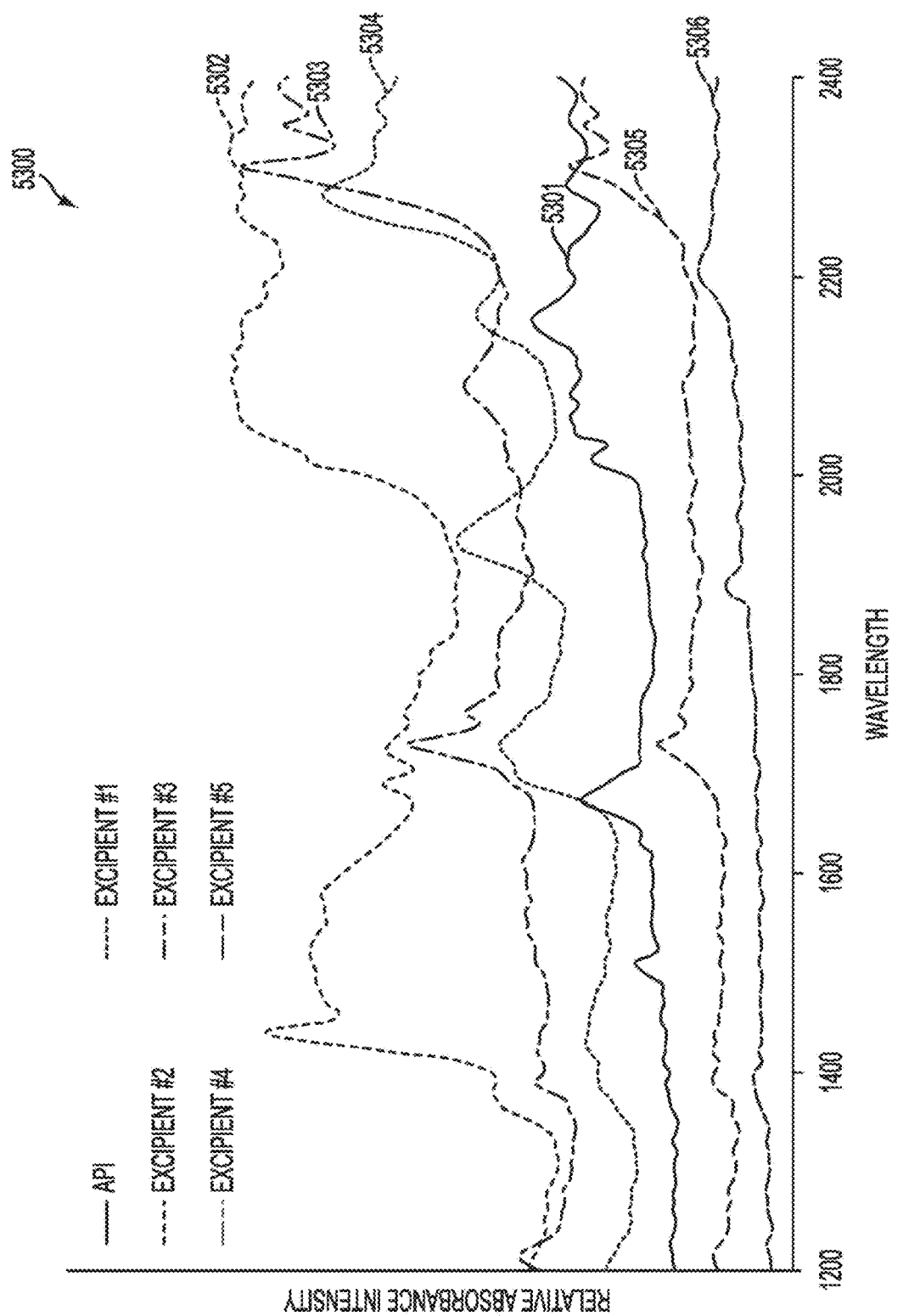
FIG. 53 illustrates an example of the near infrared spectra for different pure components of a studied drug.

FIG. 53 shows an example of the near-infrared spectra 5300 for different pure components of a studied drug. The spectrum for the active pharmaceutical ingredient (API) 5301 is plotted, along with the spectra for five different excipients 5302, 5303, 5304, 5305 and 5306. Each spectrum has been baseline shifted to avoid overlapping. The near-infrared spectra have been obtained by averaging the spectra of each pixel of an area of a hyper-spectral image. As FIG. 53 shows, each of the chemical compositions have a distinct spectrum, and the composition of a drug may be decomposed into its constitutive ingredients. These are just some examples of how near-infrared or SWIR spectroscopy may be applied to counterfeit drug detection, but other methods and analysis techniques may also be used without departing from the scope of this disclosure. As one other example, once the active pharmaceutical ingredient and the excipients spectral distribution of a drug formulation are understood, feedback may be provided of this information to the drug development stages.

Rapid Screening for Illicit Drugs

Figure 54:
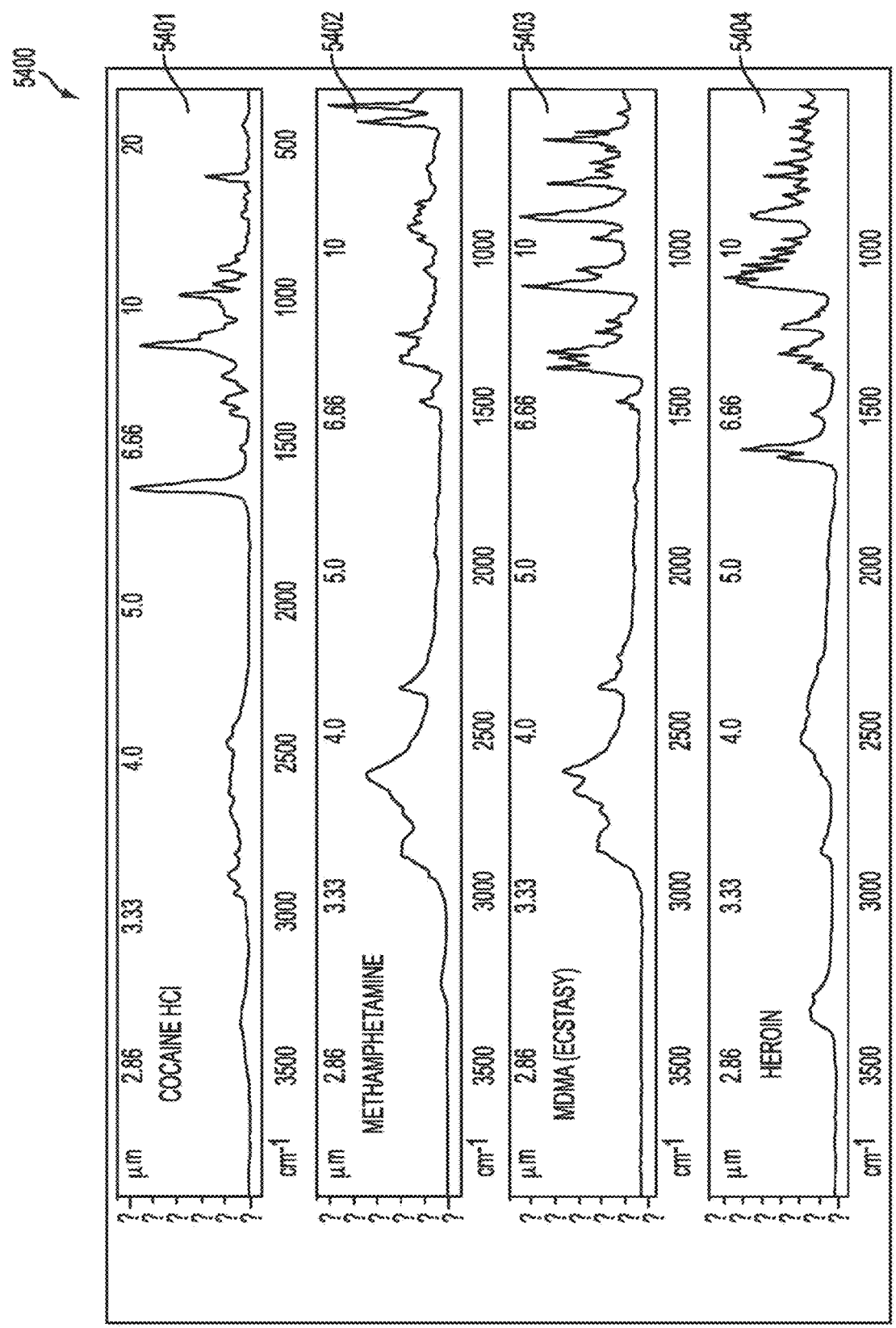
FIG. 54 shows the mid-wave infrared and long-wave infrared absorption spectra for various illicit drugs.

Thus, FIGS. 51-53 show that near-infrared or SWIR spectroscopy may be used to identify counterfeit drugs. More generally, various materials including illicit drugs, explosives, fertilizers, vegetation, and paints have features in the near-infrared and SWIR that can be used to identify the various samples, and these applications are also intended to be within the scope of this disclosure. Although stronger features may be found in the mid-infrared, the near-infrared may be easier to measure due to higher quality detection systems, more mature fiber optics and light sources, and transmission through atmospheric transmission windows. Because of these distinct spectral signatures, these materials could also be detected using active remote sensing, hyper-spectral imaging, or near-infrared or SWIR spectroscopy. As just another example, illicit drugs may be detectable using remote sensing, hyper-spectral imaging, or near-infrared spectroscopy. FIG. 54 shows the mid-wave infrared and long-wave infrared absorption spectra 5400 for various illicit drugs. The absorbance for cocaine 5401, methamphetamine 5402, MDMA (ecstasy) 5403, and heroin 5404 are plotted versus wavelength from approximately 2.5-20 microns. Although the fundamental resonances for these drugs may lie in the longer wavelength regions, there are corresponding overtones and combination bands in the SWIR and near-infrared wavelength range. Therefore, the active remote sensing, hyper-spectral imaging, or near-infrared or SWIR spectroscopy techniques described herein may also be applicable to detecting illicit drugs from aircraft, vehicles, or hand held devices.

Figure 55:
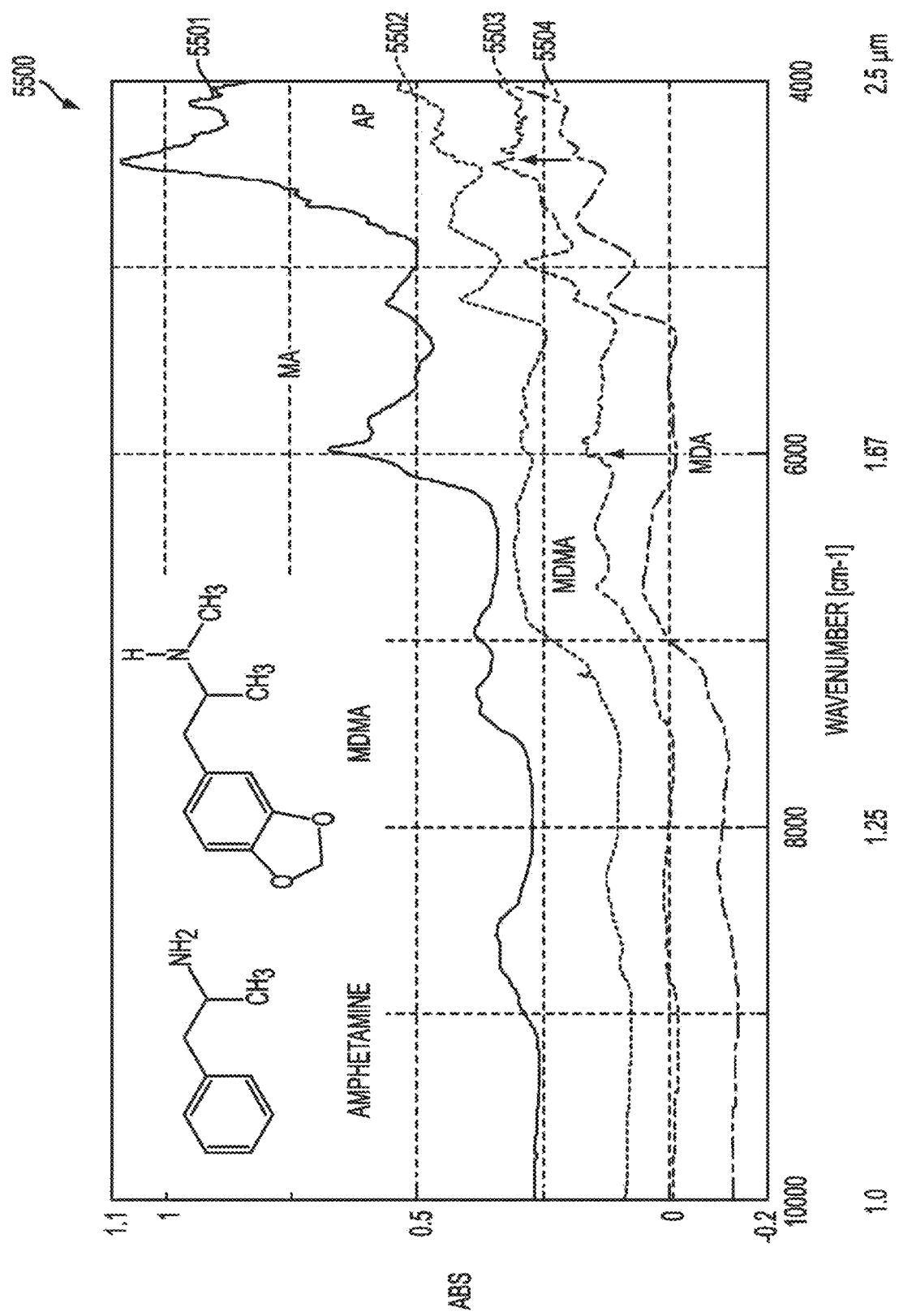
FIG. 55 shows the absorbance versus wavelength in the near-infrared region for four classes of illegal drugs.

The diffuse reflectance technique may be useful with near-infrared or SWIR spectroscopy for rapid identification of illegal drugs due to simple handling and simple use of a search data library created using near-infrared diffuse reflectance. For instance, FIG. 55 illustrates the absorbance 5500 versus wavelength in the near-infrared region for four classes of illegal drugs. In particular, the spectra are shown for methamphetamine (MA) 5501, amphetamine (AP) 5502, MDMA (street name: ecstasy) 5503, and MDA (street name: the love drug) 5504. Each of the illegal drugs have unique spectral features in the near-infrared and SWIR. Also, comparing the mid-infrared spectrum for MDMA (5403 in FIG. 54) with the near-infrared spectrum for MDMA (5503 in FIG. 55), it seems clear that the near-infrared region shows overtones and combination bands that should be discernible. Referring to FIG. 55, sample identification may be accomplished by using the region (indicated by the arrows) where the spectral absorptions may provide specific peaks depending on the drug component.

Figure 56:
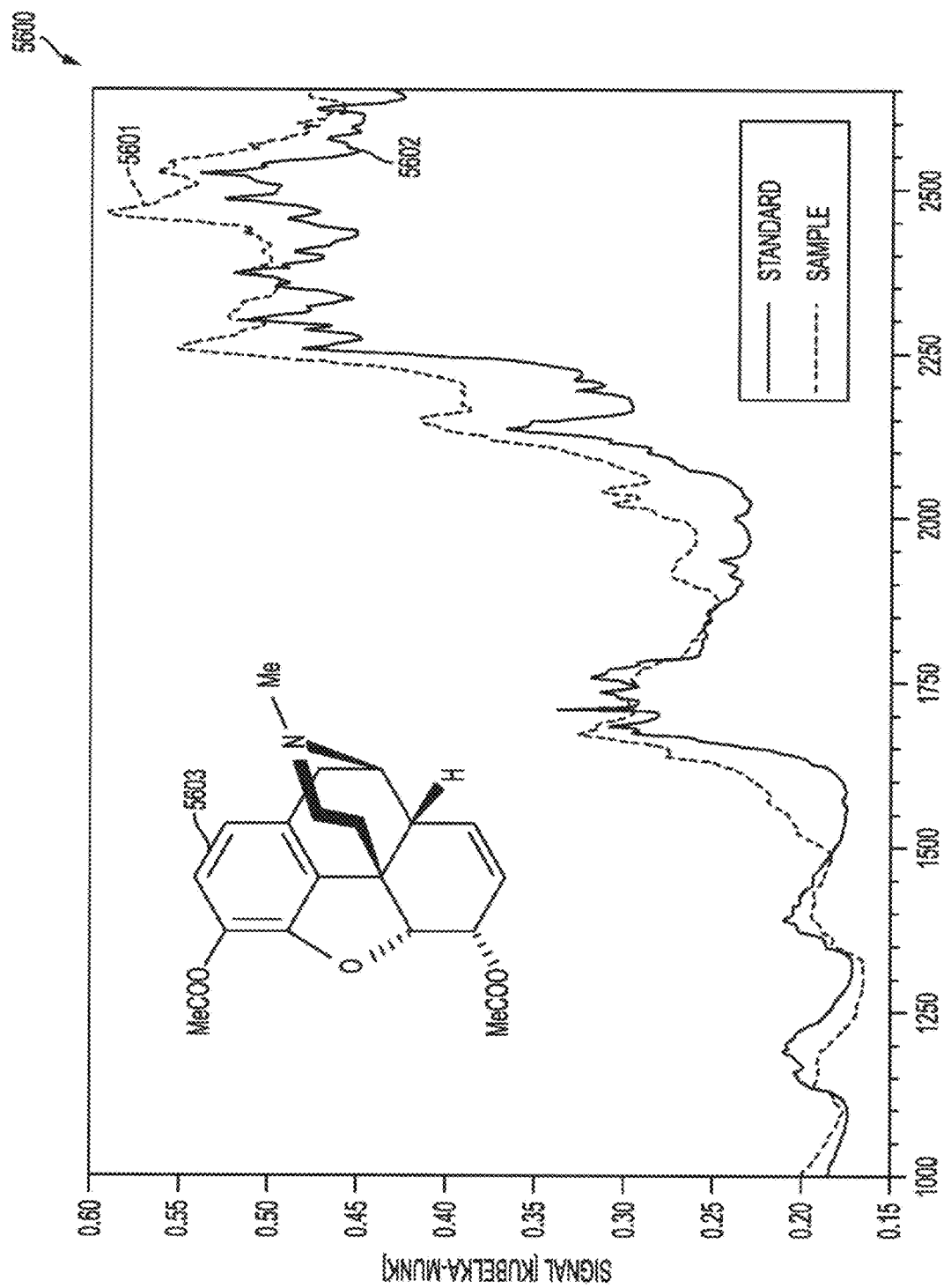
FIG. 56 illustrates the diffuse reflectance near-infrared spectrum of heroin samples.

In another embodiment, FIG. 56 shows the diffuse reflectance near-infrared spectrum 5600 of heroin samples. Heroin, the 3,6-diacetyl derivative of morphine (hence diacetyl-morphine) is an opiate drug synthesized from morphine, which is usually a naturally occurring substance extracted from the seedpod of certain varieties of poppy plants. In particular, 5601 is the near-infrared spectrum for an illicit street drug sample, while 5602 is the spectra for a pure heroin standard. The difference between the spectra may arise at least in part from cutting agents. The inset 5603 shows the molecular structure for heroin. As in the other examples, the absorption in the near-infrared range is caused by overtone and combination vibrations of O—H, C—H, N—H and C=O groups, which exhibit their fundamental molecular stretching and bending absorption in the mid-infrared range (c.f., the mid-infrared spectrum for heroin is shown 5404 in FIG. 54). These overtone and combination bands do not behave in a simple way, making the near-infrared spectra complex and harder to directly interpret. Also, although the near-infrared signatures may be weaker in magnitude, they are probably easier to detect in the near-infrared, and the sample preparation may also be much simpler in the near-infrared. Moreover, for remote sensing, the near-infrared may be preferable because of atmospheric transmission windows between approximately 1.4-1.8 microns and 2-2.5 microns.

Figure 57:
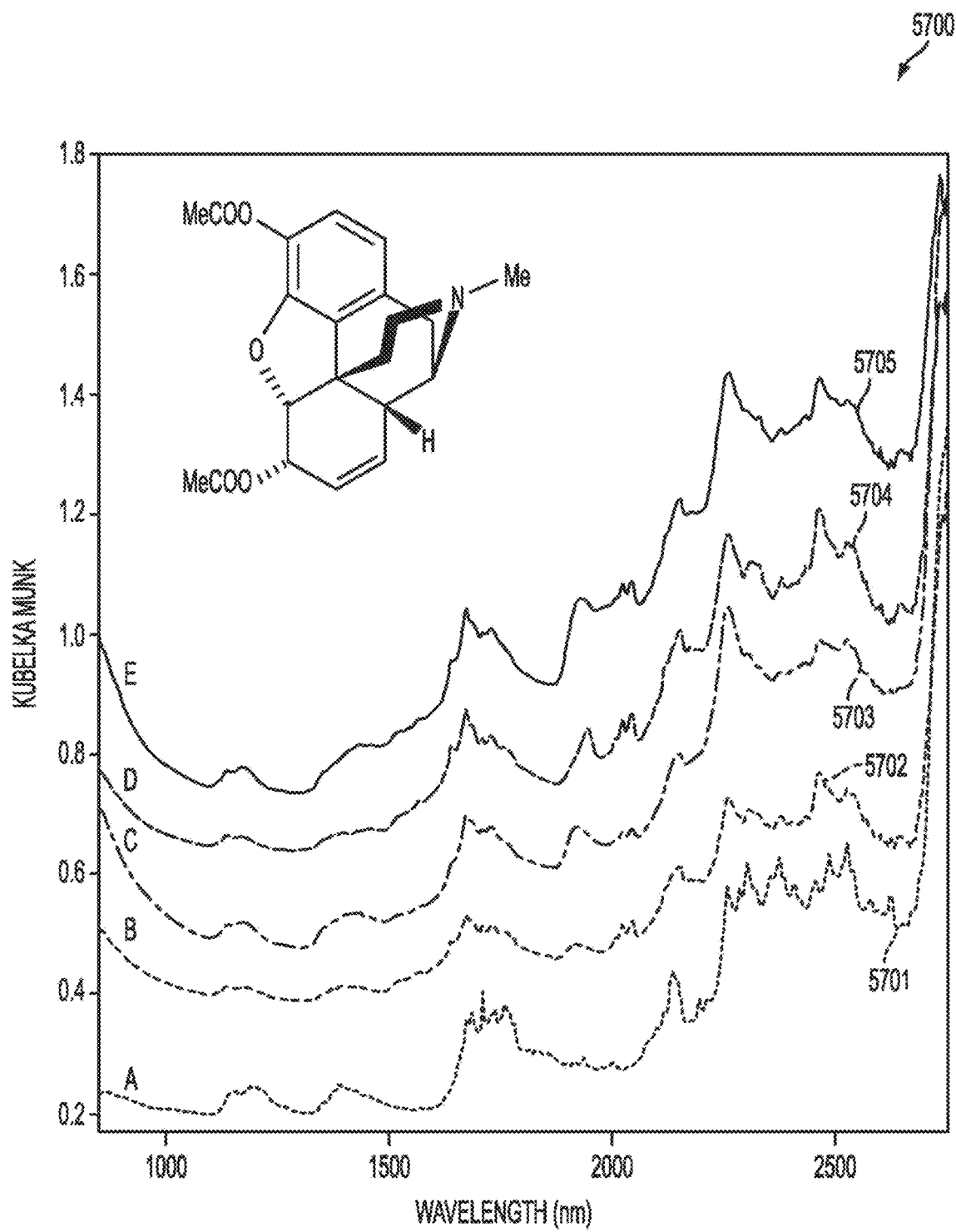
FIG. 57 illustrates the diffuse reflectance near-infrared spectra of different seized illicit drugs containing heroin of different concentrations, along with the spectrum for pure heroin.

Pure heroin may be a white powder with a bitter taste that is rarely sold on the streets, while illicit heroin may be a powder varying in color from white to dark brown due to impurities left from the manufacturing process or the presence of additives. The purity of street heroin may also vary widely, as the drug can be mixed with other white powders. The impurity of the drug may often make it difficult to gauge the strength of the dosage, which runs the risk of overdose. One nice feature of near-infrared or SWIR spectroscopy is that the technique may be used in a non-destructive, non-contact manner to determine rapidly the concentration of compounds present in complex samples at percentage levels with very little sample preparation. In a particular embodiment, FIG. 57 illustrates the diffuse reflectance near-infrared spectra 5700 of different seized illicit drugs containing heroin (between 10.7 and 21.8%) compared with the spectrum of pure heroin 5701. Curve 5702 is for 21.8% by weight, curve 5703 is 13.2% by weight, curve 5704 is 17% by weight, and curve 5705 is 10.7% by weight of heroin. The spectra have been shifted along the vertical axis to better illustrate the differences.

Although quite complex in the near-infrared, it may be possible to identify from the pure heroin near-infrared spectrum (5701 in FIG. 57 or 5602 in FIG. 56) the main wavelengths related to the most common functional groups in heroin. For example, FIG. 58 lists possible band assignments 5800 for the various spectral features in pure heroin. As can be seen from FIG. 58, the absorption in the near-infrared may be mainly due to overtone and combination bands associated with O—H, C—H, N—H and C=O groups.

Figure 59:
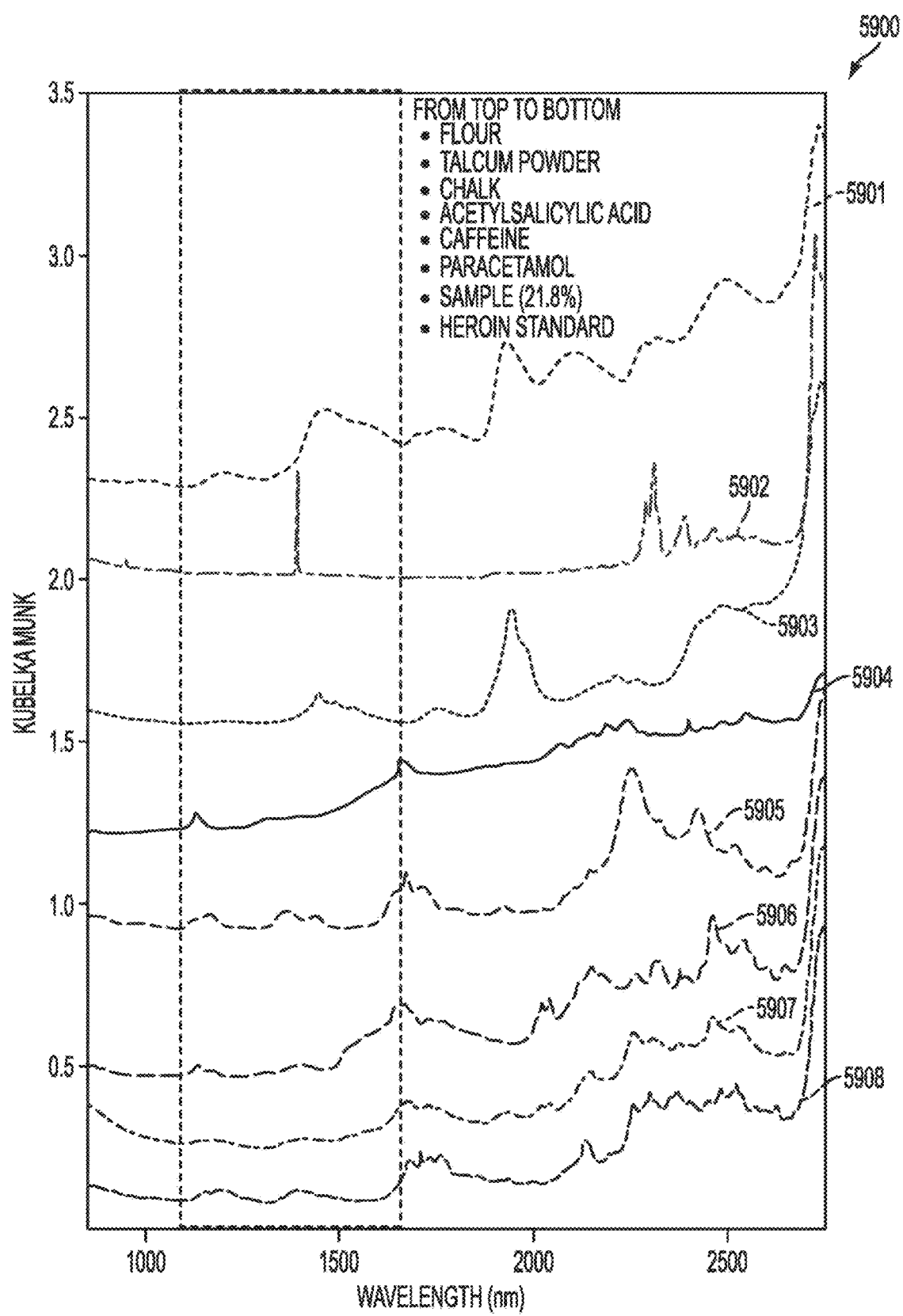
FIG. 59 shows the diffuse reflectance near-infrared spectra of different compounds that may be frequently employed as cutting agents.

As can be appreciated from FIG. 57, there may be significant differences between the spectrum of pure heroin and sample spectra. These differences may be due to the presence of different compounds used as cutting agents, which can affect the shape and intensity of the near-infrared signals. FIG. 59 illustrates the diffuse reflectance near-infrared spectra 5900 of different compounds that may be frequently employed as cutting agents. In the bottom of FIG. 59 are shown the spectra 5908 for pure heroin and the spectra 5907 for a seized illicit street drug sample comprising 21.8% of heroin. The spectra for various cutting agents include: 5901 for flour, 5902 for talcum powder, 5903 for chalk, 5904 for acetylsalicylic acid, 5905 for caffeine, and 5906 for paracetamol. Thus, near-infrared or SWIR spectroscopy may be used to work back to the composition of an unknown drug. Although particular examples of counterfeit and illicit drugs have been described, the near-infrared or SWIR spectroscopy (including diffuse reflectance, reflectance, fluorescence or transmission) may also be applied to the identification of other drugs and substances without departing from the scope of this disclosure. This spectroscopy may be used non-destructively and non-contact over stand-off distances or in remote sensing distances, whether from an airborne, vehicle, hand-held, or stationary platform.

Process Analytical Technology (PAT)

One definition of process analytical technology, PAT, is "a system for designing, analyzing and controlling manufacturing through timely evaluations (i.e., during processing) of significant quality and performance attributes of raw and in-process materials and processes, with the goal of ensuring final product quality." Near-infrared or SWIR spectroscopy may have applications in the PAT of the pharmaceutical industry by providing, for example, quantitative analysis of multiple components in a sample and in pack quantification of drugs in formulation, as well as quality of a drug and quality control of complex excipients used in formulation. The PAT process may benefit from near-infrared or SWIR spectroscopy for some steps, such as: raw material identification, active pharmaceutical ingredient applications, drying, granulation, blend uniformity and content uniformity. Some of the strengths of near-infrared or SWIR spectroscopy include: radiation has good penetration properties, and, thus, minimal sample preparation may be required; measurement results may be obtained rapidly, and simultaneous measurements may be obtained for several parameters; non-destructive methods with little or no chemical waste; and organic chemicals that comprise most pharmaceutical products have unique spectra in the near-infrared and SWIR ranges, for example.

Figure 60:
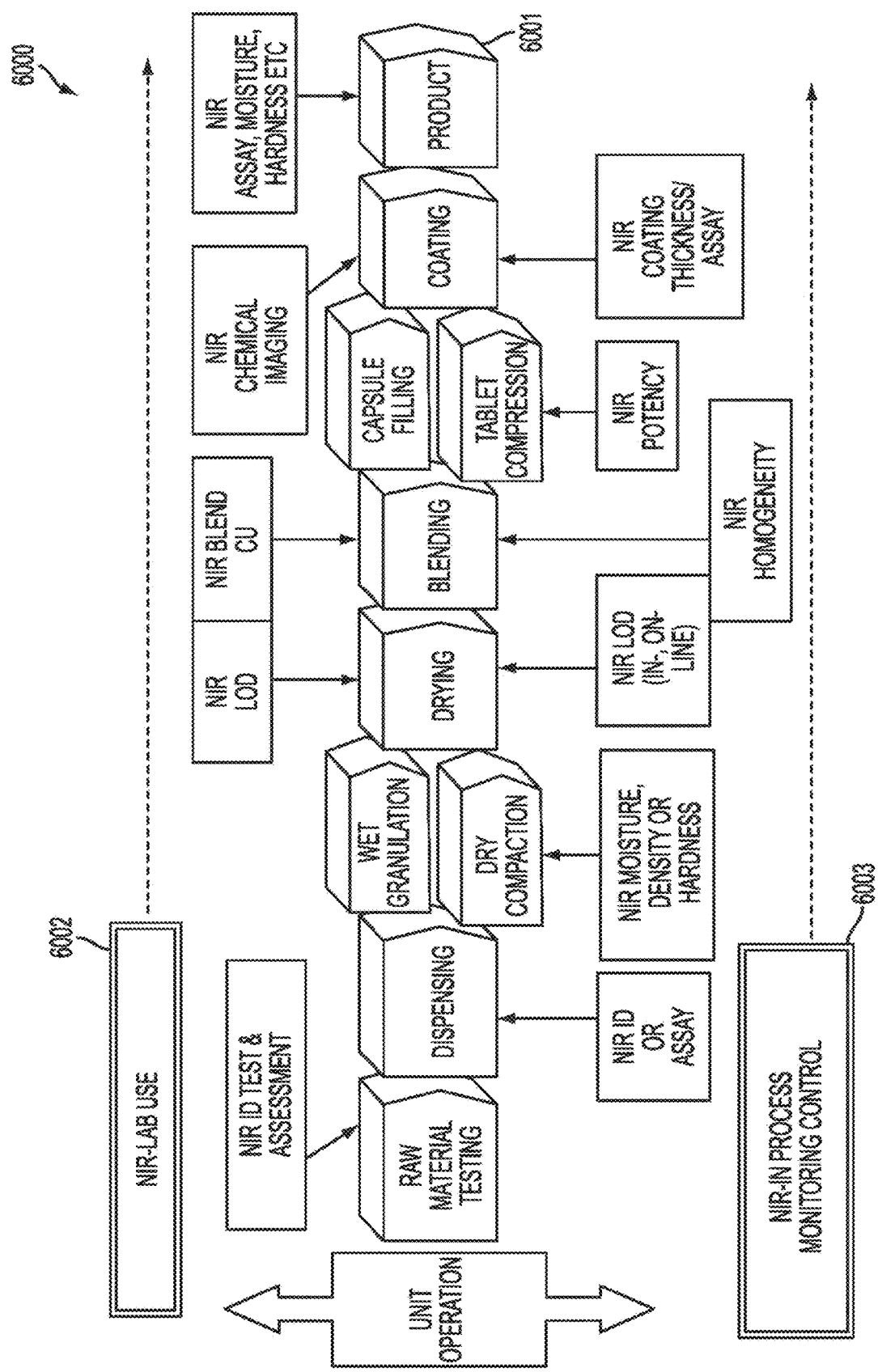
FIG. 60 provides one example of a flow-chart in the process analytical technology for the pharmaceutical industry.

FIG. 60 shows one example of a flow-chart 6000 in the PAT for the pharmaceutical industry. While the center shows the steps of the manufacturing process 6001, the top and bottom sides show where near-infrared spectroscopy could be applicable for lab use 6002 (top) or in process monitoring control 6003 (bottom). Indeed, near-infrared or SWIR spectroscopy has the potential to benefit almost every step in the manufacturing process. Just to provide a few examples of using near-infrared or SWIR spectroscopy in the PAT process, the raw material testing and blending process will be examined briefly.

Figure 61:
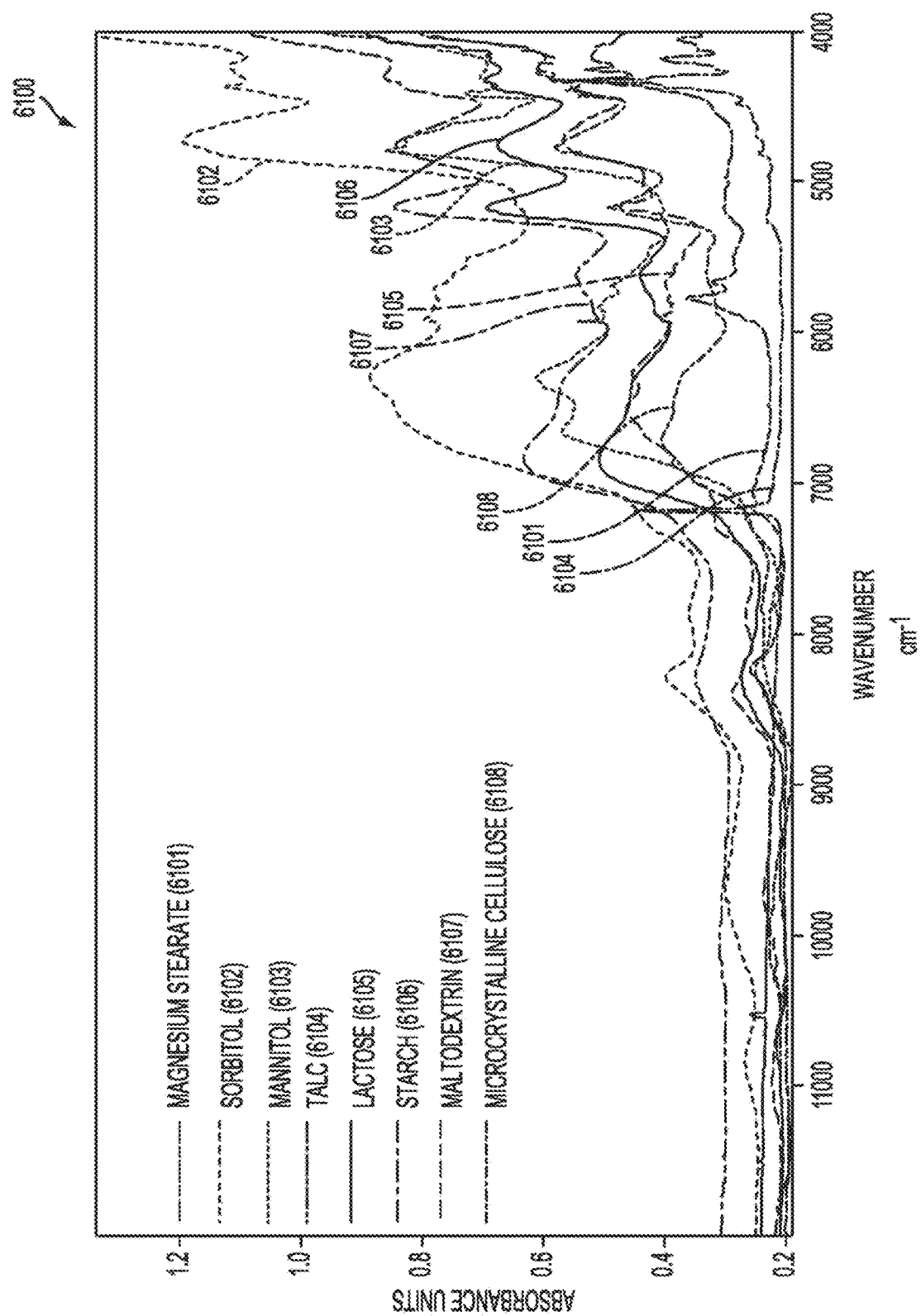
FIG. 61 illustrates the typical near-infrared spectra of a variety of excipients.

At the commencement of manufacture of a drug product, it may be required to identify the correct material and grade of the pharmaceutical excipients to be used in the formulation. FIG. 61 illustrates the typical near-infrared spectra 6100 for a variety of excipients. Included in the graph 6100 are spectra for: magnesium stearate 6101, sorbitol 6102, mannitol 6103, talc 6104, lactose 6105, starch 6106, maltodextrin 6107, and microcrystalline cellulose 6108. A suitable spectral database may be used to rapidly identify and qualify excipients. One nice aspect of the spectroscopy is that the near-infrared and SWIR are sensitive to both the physical and chemical characteristics of the samples.

Figure 62:
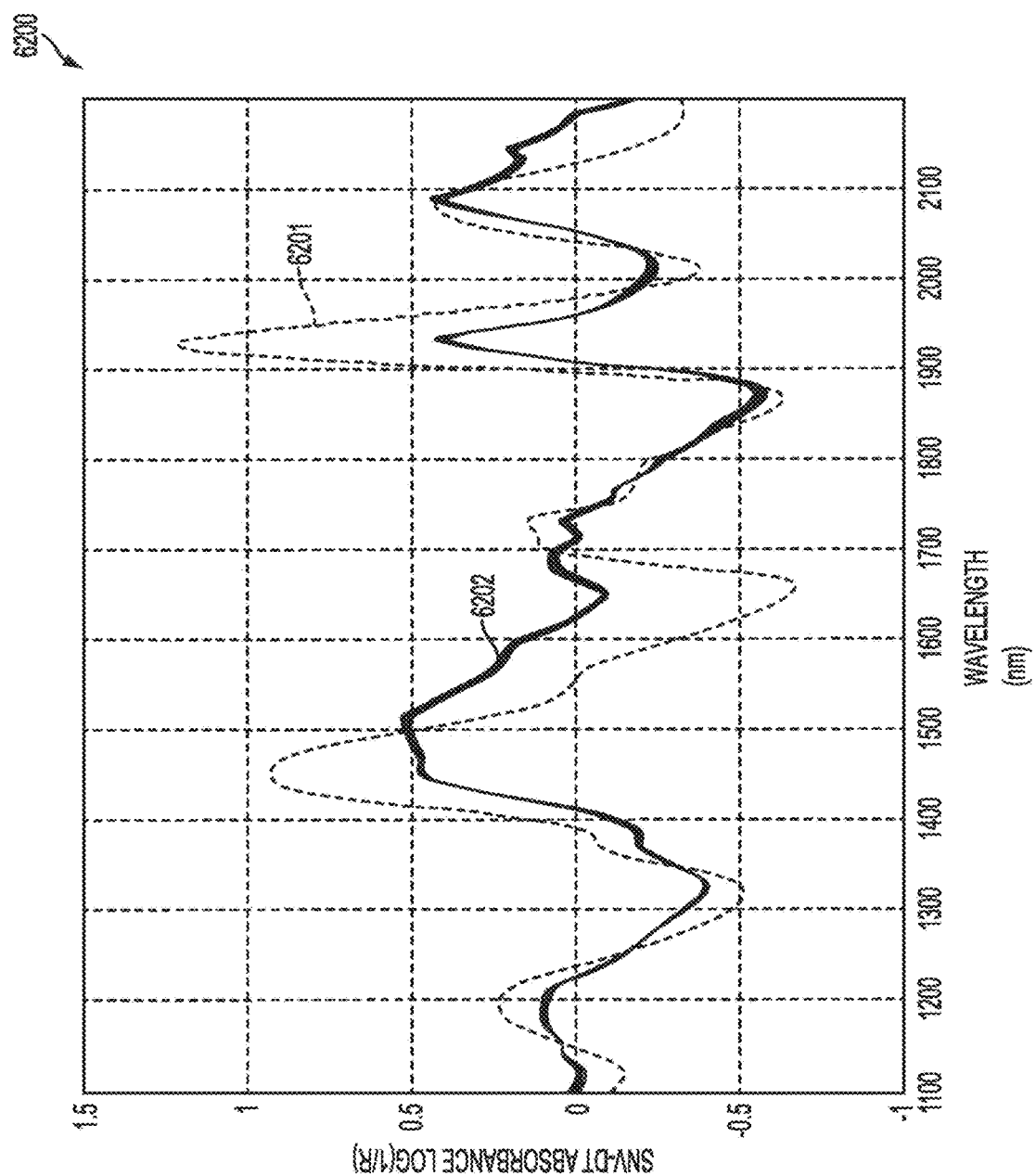
FIG. 62 exemplifies the absorbance from the blending process of a pharmaceutical compound.

One of the next steps in the manufacture of a dosage form is the blending together of the active component with the excipients to produce a homogeneous blend. In one embodiment, the near-infrared or SWIR spectroscopy apparatus may comprise a fiber-optic probe, which may, for example, interface with the blending vessel. For such a fiber-optic probe, near infrared or SWIR spectra may be collected in real-time from a blending process. FIG. 62 exemplifies the absorbance 6200 from the blending process. Although the initial spectra 6201 shows differences from the eventual spectra, as the process continues the blend converges to the final spectra 6202 and continues to overlap that spectra. Similar converging or overlapping spectra may also be used to check the product uniformity at the end of the process. The near-infrared spectra may be acquired in real-time; and, using appropriate data pre-processing and chemometric analysis, blend homogeneity plots may be derived, such as 6200.

One goal of the manufacturing process and PAT may be the concept of a "smart" manufacturing process, which may be a system or manufacturing operation responding to analytical data generated in real-time. Such a system may also have an in-built "artificial intelligence" as decisions may be made whether to continue a manufacturing operation. For example, with respect to the raw materials, integration of the quality measurement into smart manufacturing processes could be used to improve manufacturing operations by ensuring that the correct materials of the appropriate quality are used in the manufacture. Similarly, a smart blender would be under software control and would respond to the real-time spectral data collected.

Figure 63:
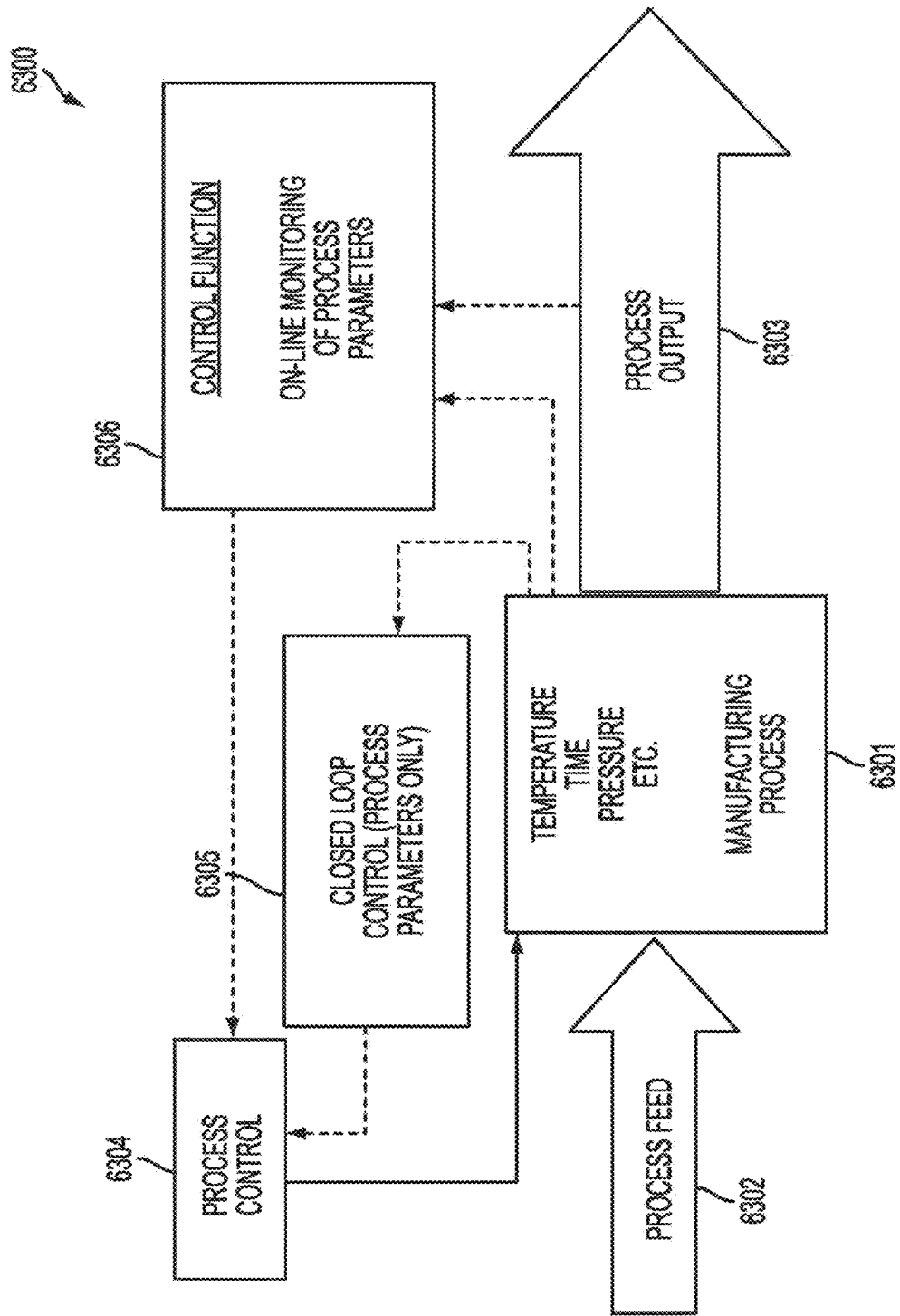
FIG. 63 shows what might be an eventual flow-chart of a smart manufacturing process.

FIG. 63 illustrates what might be an eventual flow-chart 6300 of a smart manufacturing process. The manufacturing process 6301 may have as input the process feed 6302 and result in a process output 6303. A process controller 6304 may at least partially control the manufacturing process 6301, and the controller 6304 may receive inputs from the closed loop control (process parameters) 6305 as well as the on-line monitoring of process parameters 6306. The feedback loops in the process could refine the manufacturing process 6301 and improve the quality of the process output 6303. These are particular embodiments of the use of near-infrared or SWIR spectroscopy in the PAT of the pharmaceutical industry, but other variations, combinations, and methods may also be used and are intended to be covered by this disclosure.

The discussion thus far has centered on use of near-infrared or SWIR spectroscopy in applications such as identification of counterfeit drugs, detection of illicit drugs, and pharmaceutical process control. Although drugs and pharmaceuticals are one example, many other fields and applications may also benefit from the use of near infrared or SWIR spectroscopy, and these may also be implemented without departing from the scope of this disclosure. As just another example, near-infrared or SWIR spectroscopy may also be used as an analytic tool for food quality and safety control. Applications in food safety and quality assessment include contaminant detection, defect identification, constituent analysis, and quality evaluation. The techniques described in this disclosure are particularly valuable when non-destructive testing is desired at stand-off or remote distances.

Figure 64A:
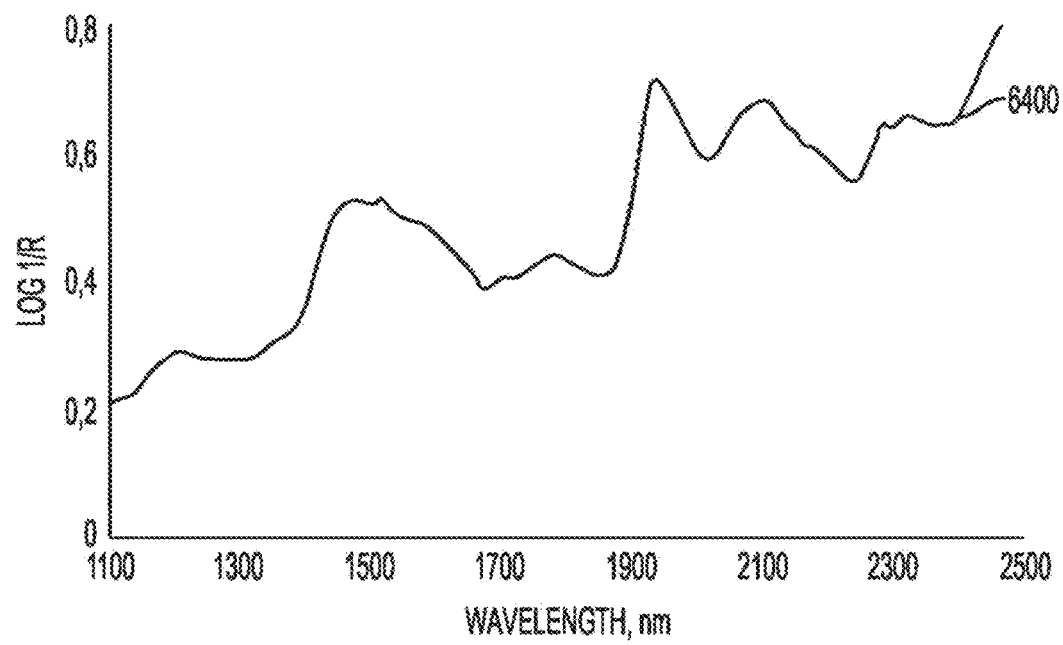
FIG. 64A illustrates the near-infrared reflectance spectrum of wheat flour.

In one example, near-infrared or SWIR spectroscopy may be used in cereal breeding. The breeding purposes may require knowledge on both composition and functional properties of grain, while the functionality of wheat grain is an issue for wheat breeders. Most of the wheat functionality parameters depend on the protein-proteinase complex of wheat grain, as well as the condition of the carbohydrate complex. FIG. 64A illustrates the near-infrared reflectance spectrum 6400 of wheat flour. Since these samples are complex in composition, several organic bonds involving hydrogen vibrate to produce overlapped spectral bands. Thus, the resulting spectrum 6400 appears like a wavy line without clearly defined features. Analytical methods based on this type of spectroscopy may have the potential to improve the quality of final cereal products by testing the products through the entire production process in the processing industry.

Figure 64B:
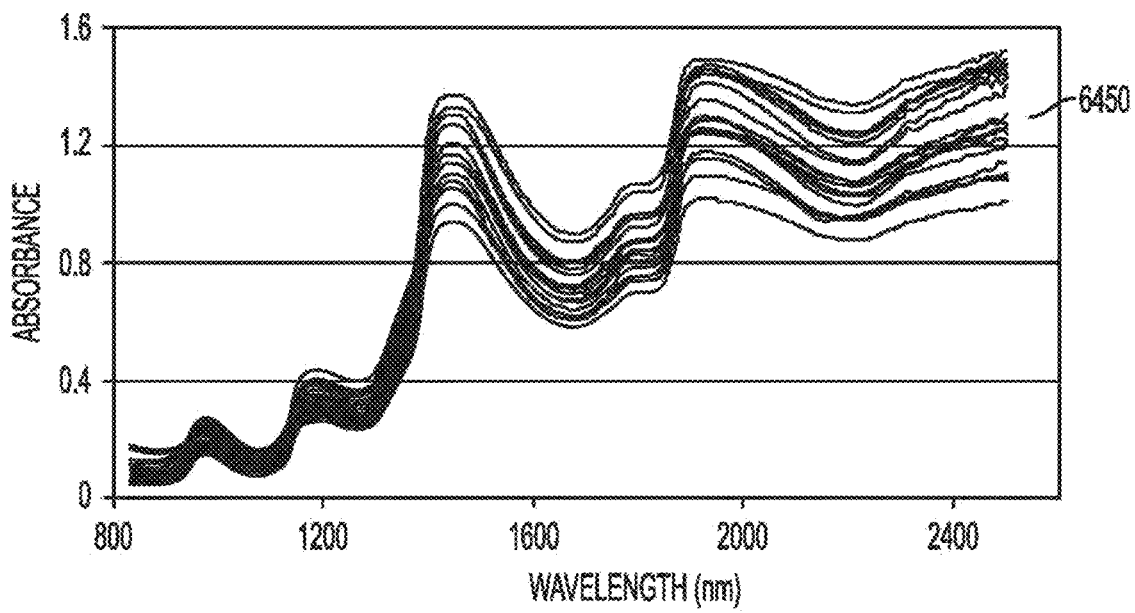
FIG. 64B shows the near-infrared absorbance spectra obtained in diffusion reflectance mode for a series of whole 'Hass' avocado fruit.

In yet another embodiment, near-infrared or SWIR spectroscopy may be used for the assessment of fruit and vegetable quality. Most commercial quality classification systems for fruit and vegetables are based on external features of the product, such as shape, color, size, weight and blemishes. However, the external appearance of most fruit is generally not an accurate guide to the internal eating quality of the fruit. As an example, for avocado fruit the external color is not a maturity characteristic, and its smell is too weak and appears later in its maturity stage. Analysis of the near-infrared or SWIR absorption spectra may provide qualitative and quantitative determination of many constituents and properties of horticulture produce, including oil, water, protein, pH, acidity, firmness, and soluble solids content or total soluble solids of fresh fruits. FIG. 64B shows the near-infrared absorbance spectra 6450 obtained in diffusion reflectance mode for a series of whole 'Hass' avocado fruit. Four oil absorption bands are near 2200-2400 nm (CH2 stretch bend and combinations), with weaker absorption around 750 nm, 1200 nm, and 900-930 nm ranges. On the other hand, near 1300-1750 nm range may be useful for determining the protein and oil content. The 900-920 nm absorbance band may be useful for sugar determination. Although described in the context of grains, fruits, and vegetables, the near-infrared or SWIR spectroscopy may also be valuable for other food quality control and assessment, such as measuring the properties of meats. These and other applications also fall within the scope of this disclosure.

Detection Systems

The near-infrared or SWIR spectroscopy system, remote sensing system or hyper-spectral imaging system may be on an airborne platform, mounted on a vehicle, a stationary transmission or reflection set-up, or even held by a human for a compact system. For such a system, there are fundamentally two hardware parts: the transmitter or light source and the detection system. Between the two, perhaps in a transmission or reflection setting, may be the sample being tested or measured. Moreover, the output from the detection system may go to a computational system, comprising computers or other processing equipment. The output from the computational system may be displayed graphically as well as with numerical tables and perhaps an identification of the material composition. These are just some of the parts of the systems, but other elements may be added or be eliminated, and these modified configurations are also intended to be covered by this disclosure.

By use of an active illuminator, a number of advantages may be achieved. First, stand-off or remote distances may be achieved if a non-lamp system is used—i.e., if the beam does not rapidly diffract. Also, higher signal-to-noise ratios may be achieved. For example, one way to improve the signal-to-noise ratio would be to use modulation and lock-in techniques. In one embodiment, the light source may be modulated, and then the detection system would be synchronized with the light source. In a particular embodiment, the techniques from lock-in detection may be used, where narrow band filtering around the modulation frequency may be used to reject noise outside the modulation frequency. In another embodiment, change detection schemes may be used, where the detection system captures the signal with the light source on and with the light source off. Again, for this system the light source may be modulated. Then, the signal with and without the light source is differenced. Change detection may help to identify objects that change in the field of view. In the following some exemplary detection systems are described.

In one embodiment, a SWIR camera or infrared camera system may be used to capture the images. The camera may include one or more lenses on the input, which may be adjustable. The focal plane assemblies may be made from mercury cadmium telluride material (HgCdTe), and the detectors may also include thermo-electric coolers. Alternately, the image sensors may be made from indium gallium arsenide (InGaAs), and CMOS transistors may be connected to each pixel of the InGaAs photodiode array. The camera may interface wirelessly or with a cable (e.g., USB, Ethernet cable, or fiber optics cable) to a computer or tablet or smart phone, where the images may be captured and processed. These are a few examples of infrared cameras, but other SWIR or infrared cameras may be used and are intended to be covered by this disclosure.

Figure 65A:
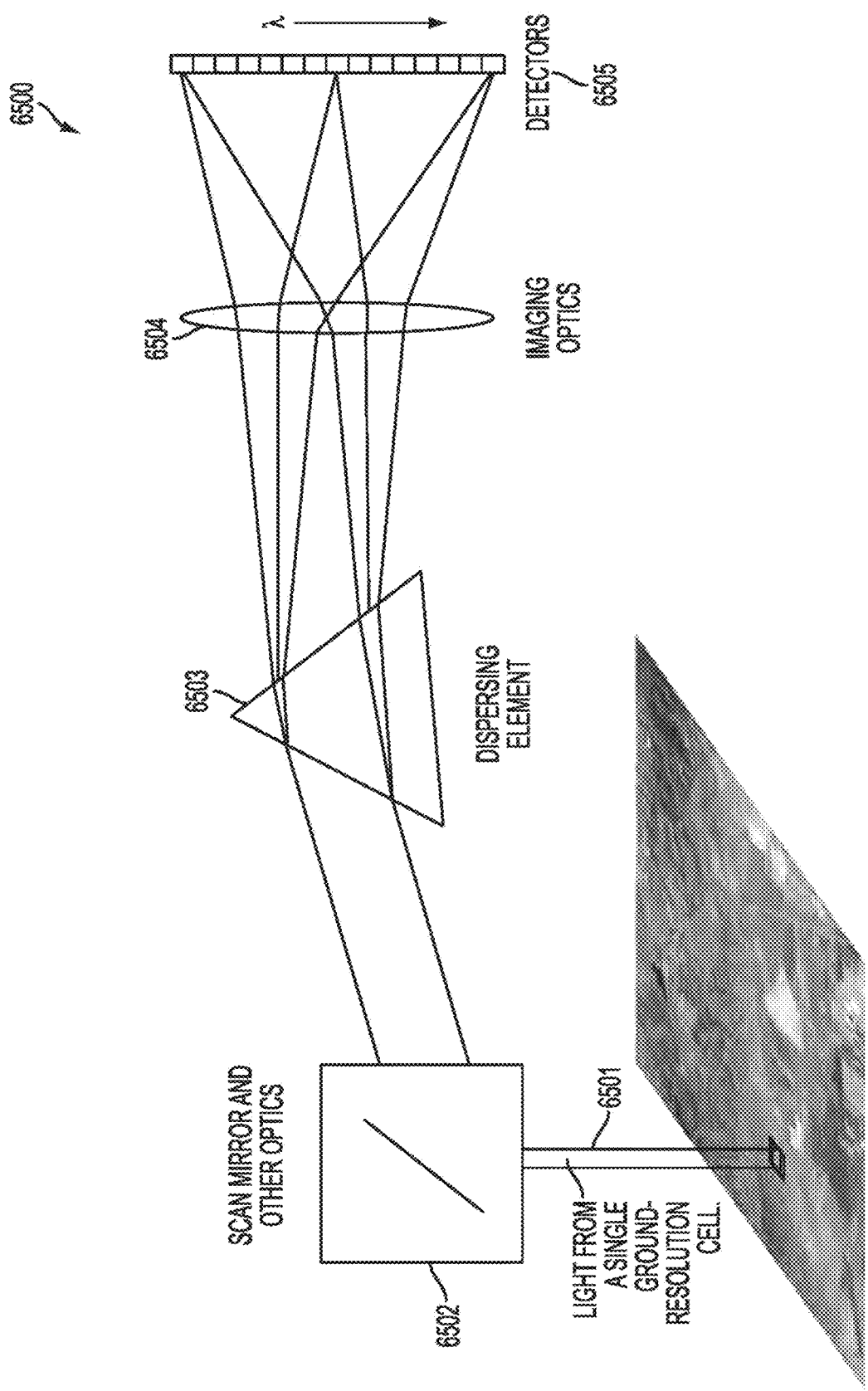
FIG. 65A is a schematic diagram of the basic elements of an imaging spectrometer.

In another embodiment, an imaging spectrometer may be used to detect the light received from the sample. For example, FIG. 65A shows a schematic diagram 6500 of the basic elements of an imaging spectrometer. The input light 6501 from the sample may first be directed by a scanning mirror and/or other optics 6502. An optical dispersing element 6503, such as a grating or prism, in the spectrometer may split the light into many narrow, adjacent wavelength bands, which may then be passed through imaging optics 6504 onto one or more detectors or detector arrays 6505. Some sensors may use multiple detector arrays to measure hundreds of narrow wavelength bands.

Figure 65B:
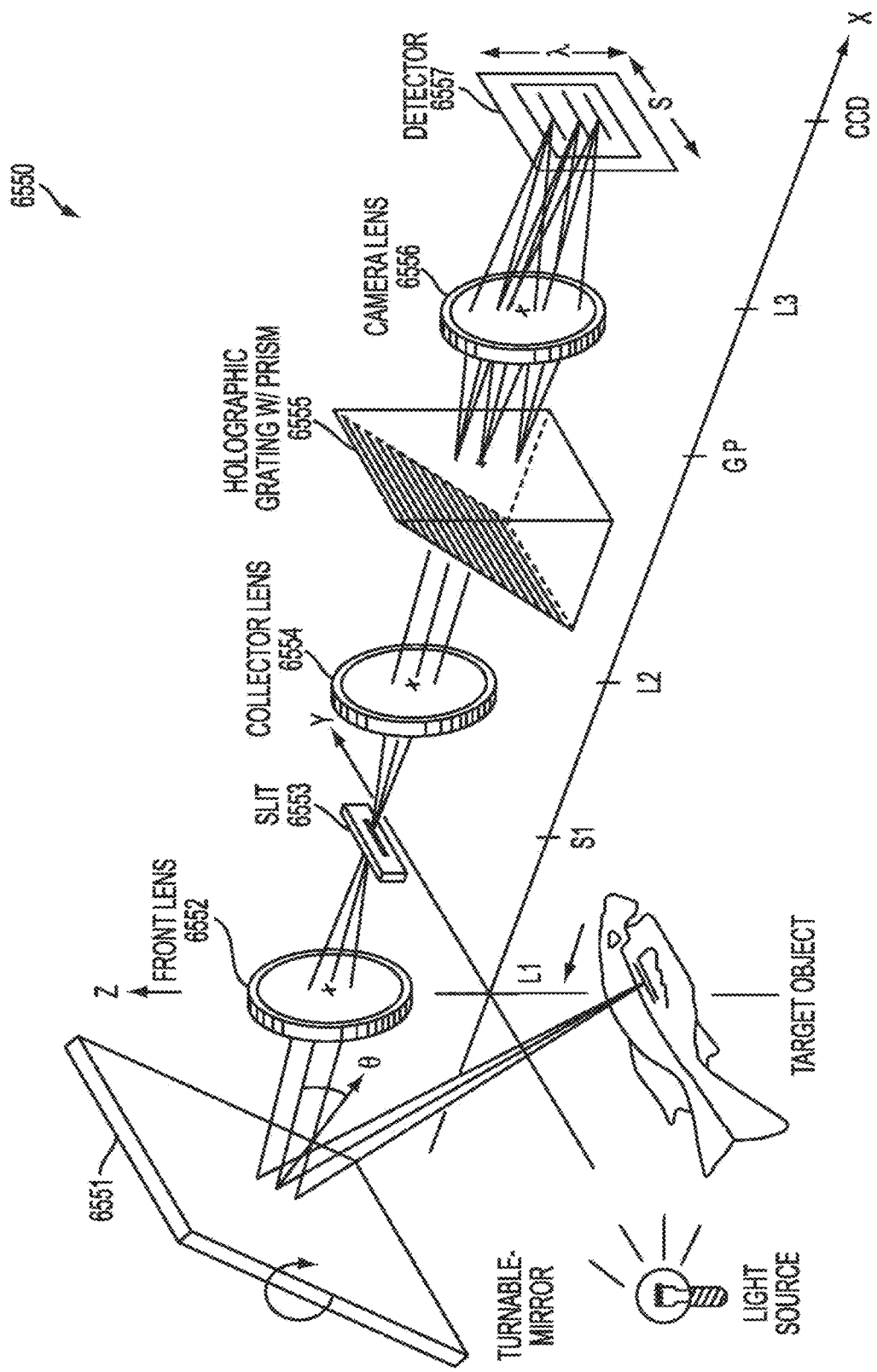
FIG. 65B illustrates one example of a typical imaging spectrometer used in hyper-spectral imaging systems.

An example of a typical imaging spectrometer 6550 used in hyper-spectral imaging systems is illustrated in FIG. 65B. In this particular embodiment, the input light may be directed first by a tunable mirror 6551. A front lens 6552 may be placed before the entrance slit 6553 and the collector lens 6554. In this embodiment, the dispersing element is a holographic grating with a prism 6555, which separates the different wavelength bands. Then, a camera lens 6556 may be used to image the wavelengths onto a detector or camera 6557.

FIG. 65 provide particular examples, but some of the elements may not be used, or other elements may be added, and these are also intended to be covered by this disclosure.

For instance, a scanning spectrometer may be used before the detector, where a grating or dispersive element is scanned to vary the wavelength being measured by the detector. In yet another embodiment, filters may be used before one or more detectors to select the wavelengths or wavelength bands to be measured. This may be particularly useful if only a few bands or wavelengths are to be measured. The filters may be dielectric filters, Fabry-Perot filters, absorption or reflection filters, fiber gratings, or any other wavelength selective filter. In one embodiment, a wavelength division multiplexer, WDM, may be used followed by one or more detectors or detector arrays. One example of a planar wavelength division multiplexer may be a waveguide grating router or an arrayed waveguide grating. The WDM may be fiber coupled, and detectors may be placed directly at the output or the detectors may be coupled through fibers to the WDM. Some of these components may also be combined with the configurations in FIG. 65.

While the above detection systems could be categorized as single path detection systems, it may be advantageous in some cases to use multi-path detection systems. In one embodiment, a detection system from a Fourier transform infrared spectrometer, FTIR, may be used. The received light may be incident on a particular configuration of mirrors, called a Michelson interferometer, that allows some wavelengths to pass through but blocks others due to wave interference. The beam may be modified for each new data point by moving one of the mirrors, which changes the set of wavelengths that pass through. This collected data is called an interferogram. The interferogram is then processed, typically on a computing system, using an algorithm called the Fourier transform. One advantageous feature of FTIR is that it may simultaneously collect spectral data in a wide spectral range.

Figure 66:
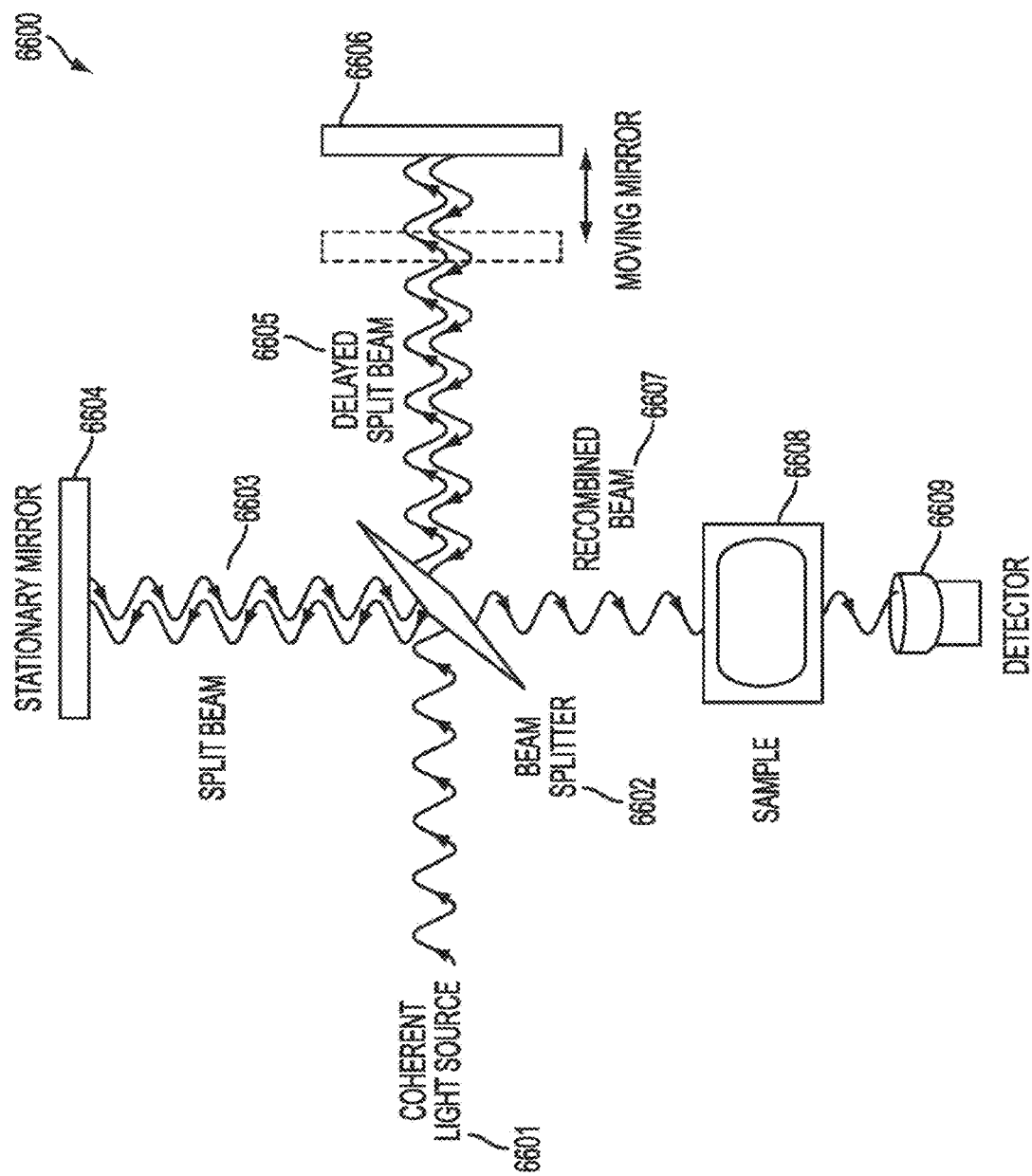
FIG. 66 shows one example of the Fourier transform infrared spectrometer.

FIG. 66 illustrates one example of the FTIR spectrometer 6600. Light from the near-infrared or SWIR light source 6601 may be collimated and directed to a beam splitter 6602. In one embodiment, the beam splitter 6602 may be a 50:50 beam splitter. One portion of the beam 6603 may be reflected toward a stationary mirror 6604, while the other portion of the beam 6605 may be transmitted towards a moving mirror 6606. Light may be reflected from the two mirrors 6604, 6606 back to the beam splitter 6602, and then a portion of the recombined beam 6607 may be directed toward the sample 6608. The recombined beam 6607 may be focused onto the sample 6608, in one embodiment. On leaving the sample 6608, the light may be refocused or at least collected at a detector 6609. A background interferogram may be obtained by using the set-up 6600 without a sample in the chamber 6608. When a sample is inserted into 6608, the background interferogram may be modulated by the presence of absorption bands in the sample. The FTIR spectrometer may have several advantages compared to a scanning (dispersive) spectrometer. Since all the wavelengths may be collected simultaneously, the FTIR may result in a higher signal-to-noise ratio for a given scan time or a shorter scan time for a given resolution. Moreover, unlike a spectrometer where a slit may limit the amount of the beam detected, the FTIR may accommodate the entire diameter of the beam coming from the light source 6601. The configuration 6600 is one example of an FTIR, but other configurations may also be used, and these are also intended to be covered by this disclosure.

Figure 67:
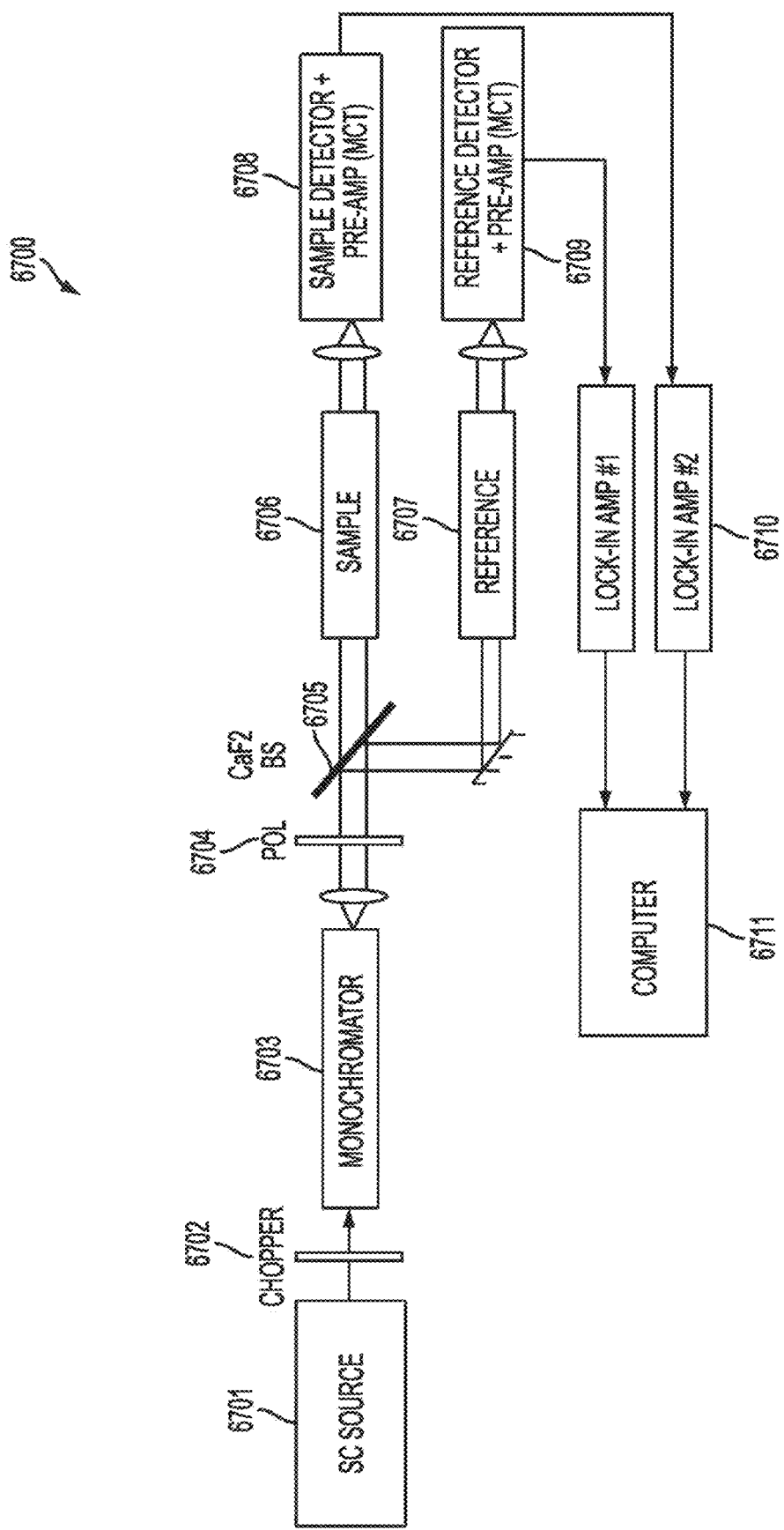
FIG. 67 exemplifies a dual-beam experimental set-up that may be used to subtract out (or at least minimize the adverse effects of) light source fluctuations.

In yet another example of multi-beam detection systems, a dual-beam set-up 6700 such as in FIG. 67 may be used to subtract out (or at least minimize the adverse effects of) light source fluctuations. In one embodiment, the output from an SC source 6701 may be collimated using a CaF2 lens 6702 and then focused into the entrance slit of the monochromator 6703. At the exit slit, light at the selected wavelength is collimated again and may be passed through a polarizer 6704 before being incident on a calcium fluoride beam splitter 6705. After passing through the beam splitter 6705, the light is split into a sample 6706 and reference 6707 arm to enable ratiometric detection that may cancel out effects of intensity fluctuations in the SC source 6701. The light in the sample arm 6706 passes through the sample of interest and is then focused onto a HgCdTe detector 6708 connected to a pre-amp. A chopper 6702 and lock-in amplifier 6710 setup enable low noise detection of the sample arm signal. The light in the reference arm 6707 passes through an empty container (cuvette, gas cell etc.) of the same kind as used in the sample arm. A substantially identical detector 6709, pre-amp and lock-in amplifier 6710 is used for detection of the reference arm signal. The signal may then be analyzed using a computer system 6711. This is one particular example of a method to remove fluctuations from the light source, but other components may be added and other configurations may be used, and these are also intended to be covered by this disclosure.

Although particular examples of detection systems have been described, combinations of these systems or other systems may also be used, and these are also within the scope of this disclosure. As one example, environmental fluctuations (such as turbulence or winds) may lead to fluctuations in the beam for active remote sensing or hyper-spectral imaging. A configuration such as FIG. 67 may be able to remove the effect of environmental fluctuations. Yet another technique may be to "wobble" the light beam after the light source using a vibrating mirror. The motion may lead to the beam moving enough to wash out spatial fluctuations within the beam waist at the sample or detection system. If the vibrating mirror is scanned faster than the integration time of the detectors, then the spatial fluctuations in the beam may be integrated out. Alternately, some sort of synchronous detection system may be used, where the detection is synchronized to the vibrating frequency.

Described herein are just some examples of the beneficial use of near-infrared or SWIR lasers for spectroscopy, active remote sensing or hyper-spectral imaging. However, many other spectroscopy and identification procedures can use the near-infrared or SWIR light consistent with this disclosure and are intended to be covered by the disclosure. As one example, the fiber-based super-continuum lasers may have a pulsed output with pulse durations of approximately 0.5-2 nsec and pulse repetition rates of several Megahertz. Therefore, the near-infrared or SWIR spectroscopy, active remote sensing or hyper-spectral imaging applications may also be combined with LIDAR-type applications. Namely, the distance or time axis can be added to the information based on time-of-flight measurements. For this type of information to be used, the detection system would also have to be time-gated to be able to measure the time difference between the pulses sent and the pulses received. By calculating the round-trip time for the signal, the distance of the object may be judged. In another embodiment, GPS (global positioning system) information may be added, so the near-infrared or SWIR spectroscopy, active remote sensing or hyper-spectral imagery would also have a location tag on the data. Moreover, the near-infrared or SWIR spectroscopy, active remote sensing or hyper-spectral imaging information could also be combined with two-dimensional or three-dimensional images to provide a physical picture as well as a chemical composition identification of the materials. These are just some modifications of the near-infrared or SWIR spectroscopy, active remote sensing or hyper-spectral imaging system described in this disclosure, but other techniques may also be added or combinations of these techniques may be added, and these are also intended to be covered by this disclosure.

Figure 68:
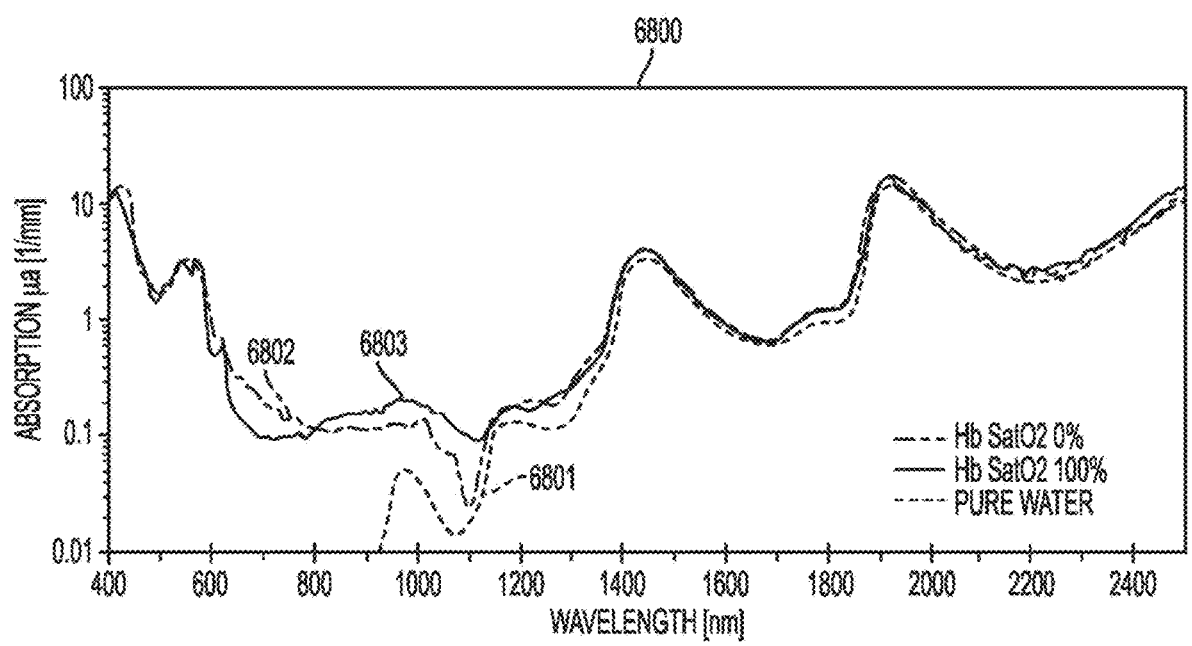
FIG. 68 illustrates the optical absorption of pure water, hemoglobin without oxygen, and hemoglobin saturated with oxygen.

Section 5: Near-Infrared Super-Continuum Lasers for Early Detection of Breast and Other Cancers To perform non-invasive optical mammography, one desired attribute is that the light may penetrate as far as possible into the breast tissue. In diffuse reflection spectroscopy, a broadband light spectrum may be emitted into the tissue, and the spectrum of the reflected or transmitted light may depend on the absorption and scattering interactions within the target tissue. Since breast tissue has significant water and hemoglobin content, it is valuable to examine the wavelength range over which deep penetration of light is possible. FIG. 68 illustrates the optical absorption 6800 of pure water (dotted line) 6801, hemoglobin without oxygen (thinner solid line) 6802, and hemoglobin saturated with oxygen (thicker solid line) 6803. It can be noted that above about 1100 nm, the absorption of hemoglobin is almost the same as water absorption. The penetration depth may be proportional to the inverse of the optical absorption. Therefore, the highest penetration depth will be at the absorption valley, approximately in the wavelength range between about 900 nm and about 1300 nm. Although not as low in absorption compared to the first window, another absorption valley lies between about 1600 nm and 1800 nm. Thus, non-invasive imaging preferably should use wavelengths that fall in one of these two absorption valleys.

Figure 69:
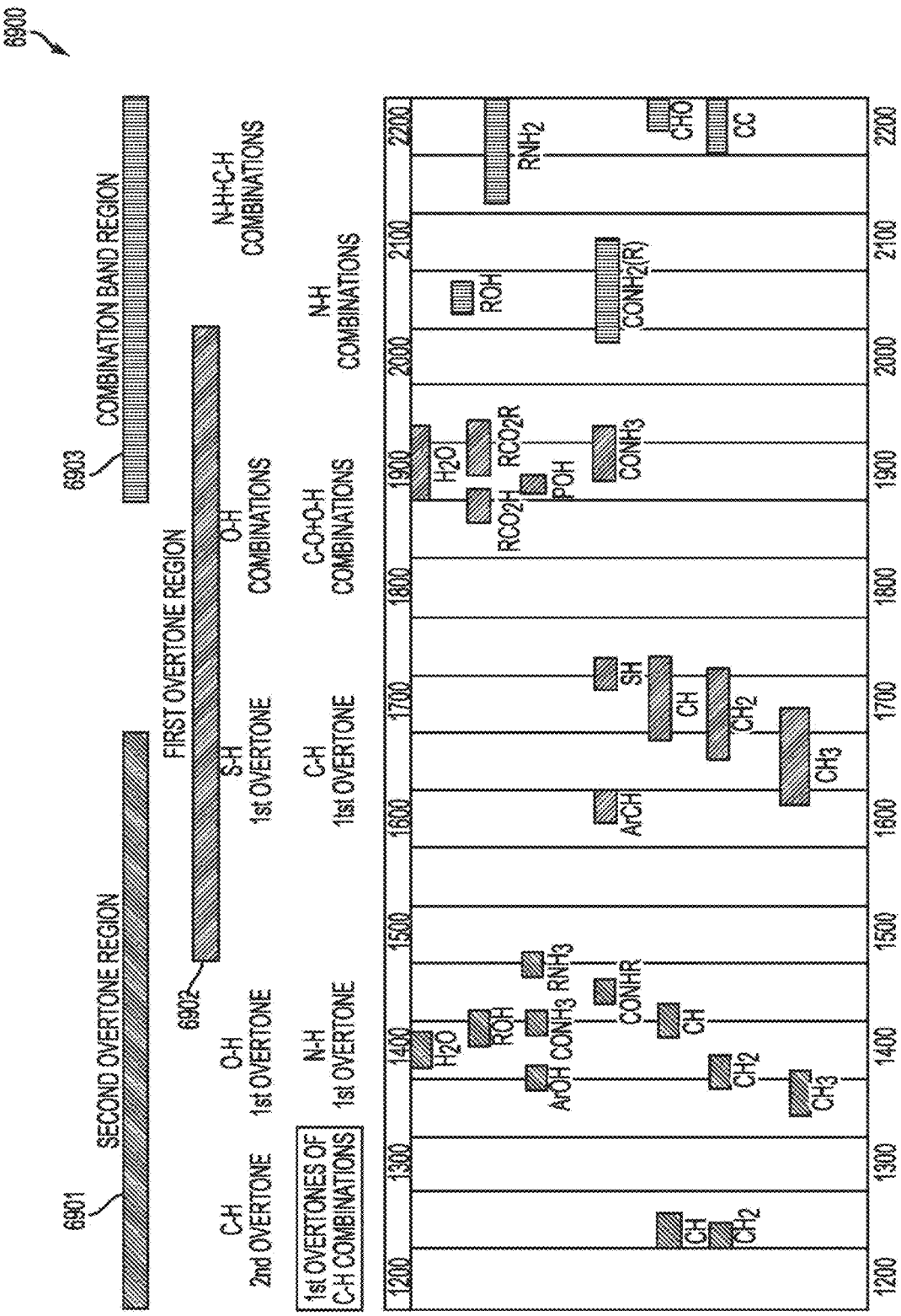
FIG. 69 shows examples of various absorption bands of chemical species in the wavelength range between about 1200-2200 nm.

FIG. 69 shows examples of various absorption bands of chemical species 6900 in the wavelength range between about 1200 nm and 2200 nm. Although the fundamental absorptions usually lie in the mid-infrared (e.g., wavelengths longer than about 3 microns), there are many absorption lines in the NIR corresponding to the second overtone region 6901 between about 1000 nm and 1700 nm, the first overtone region 6902 between about 1500 nm and 2050 nm, and the combination band region 6903 between about 1900 nm and 2300 nm. As an example, hydrocarbon bonds common in many biological substances have their fundamental absorption in the mid-IR near 3300-3600 nm, but they also have many combination band lines between 2000-2500 nm, and other lines at shorter wavelengths corresponding to the first and second overtones. Fortunately, there are spectral features of FIG. 69 that overlap with the absorption valleys in FIG. 68. These are likely to be the wavelengths of interest for spectroscopic analysis of cancerous regions.

Figure 70:
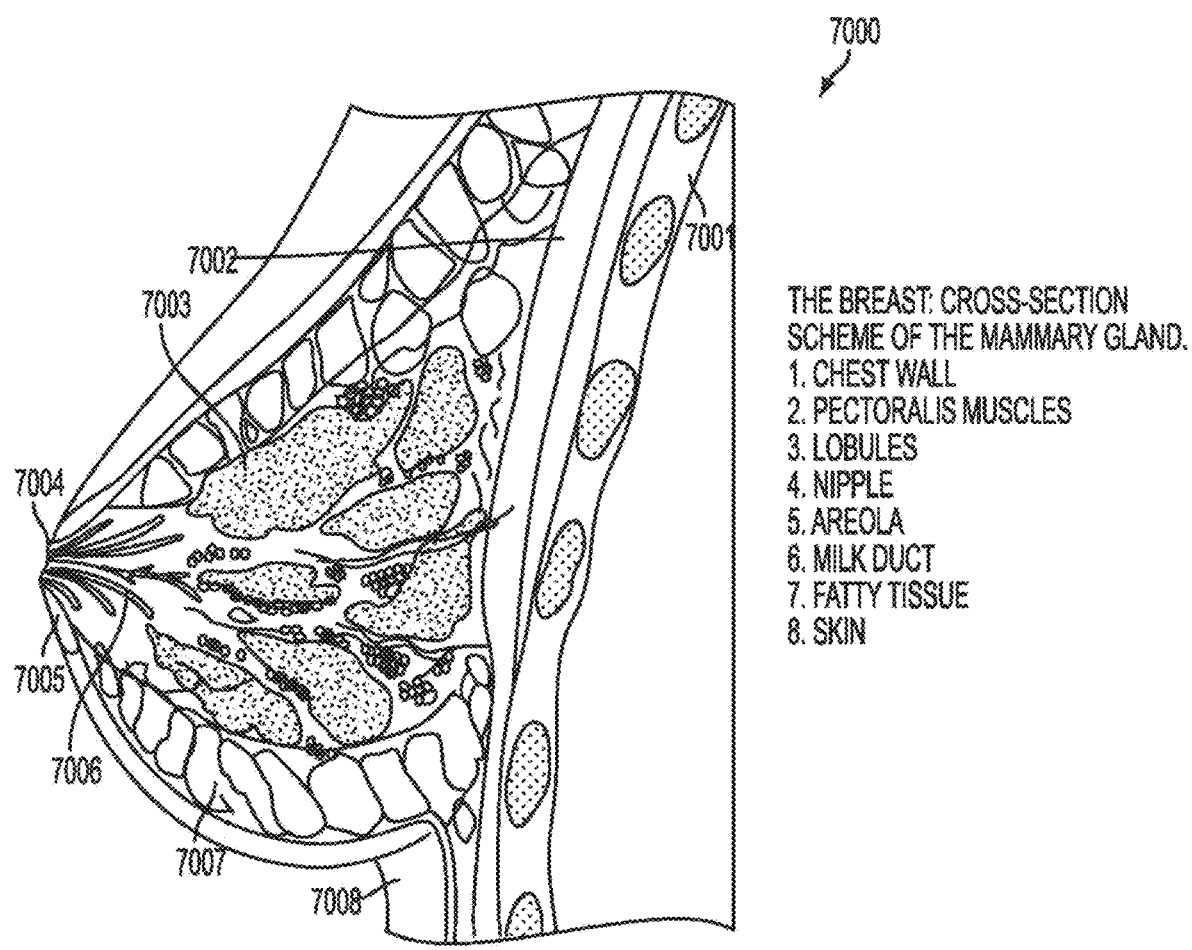
FIG. 70 depicts the structure of a female breast.

In women, the breasts (FIG. 70) 7000 overlay the pectoralis major muscles 7002 and cover much of the chest area and the chest walls 7001. The breast is an apocrine gland that produces milk to feed an infant child; the nipple 7004 of the breast is surrounded by an areola 7005, which has many sebaceous glands. The basic units of the breast are the terminal duct lobules 7003, which produce the fatty breast milk. They give the breast its function as a mammary gland. The lobules 7003 feed through the milk ducts 7006, and in turn these ducts drain to the nipple 7004. The superficial tissue layer (superficial fascia) may be separated from the skin 7008 by about 0.5-2.5 cm of adipose of fatty tissue 7007.

Breast cancer is a type of cancer originating from breast tissue, most commonly from the inner lining of milk ducts 7006, the lobules 7003 that supply the ducts with milk, and/or the connective tissue between the lobules. Cancers originating from ducts 7006 are known as ductal carcinomas, while those originating from lobules 7003 or their connective tissue are known as lobular carcinomas. While the overwhelming majority of human cases occur in women, male breast cancer may also occur.

Figure 71:
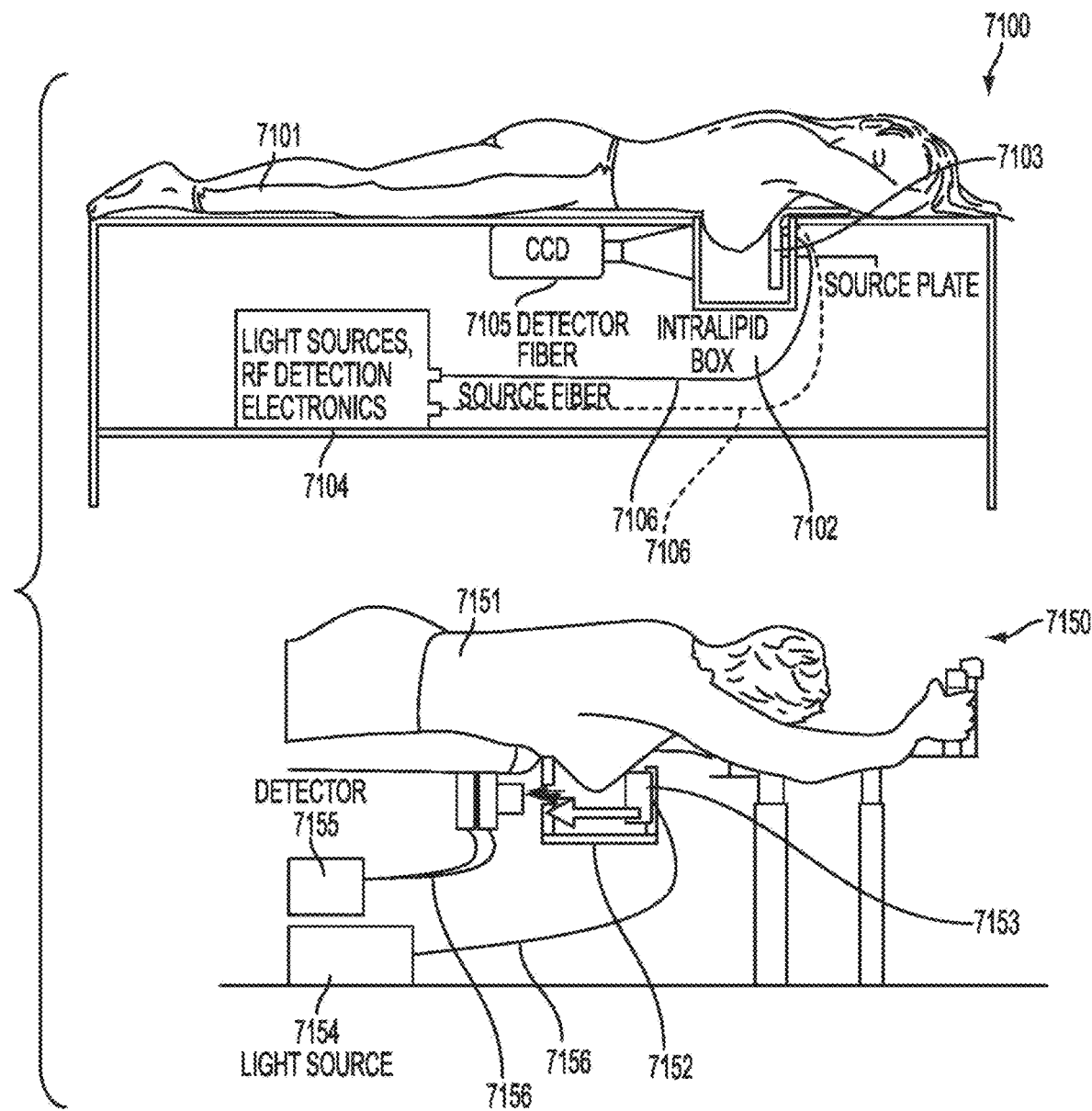
FIG. 71 illustrates particular embodiments of imaging systems for optically scanning a breast.

Several particular embodiments of imaging systems 7100, 7150 for optically scanning a breast are illustrated in FIG. 71. In these particular embodiments, the patient 7101, 7151 may lie in a prone position with her breasts inside a box 7102, 7152 with probably a transparent window on the detector side. A compression plate 7103, 7153 may hold the breast in place against the viewing window by mildly compressing the breast to a thickness between about 5.5 and 7.5 cm. The box 7102, 7152 may then be filled with a matching fluid with optical properties similar to human breast. In one instance, the matching fluid may comprise water, india ink for absorption, and a fat emulsion for scattering. The embodiments in FIG. 71 may also have one or more detectors 7104, 7155, one or more light sources 7104, 7154, various electronics, and even an imaging system based on charge coupled devices 7105. As illustrated in FIG. 71, the light sources 7104, 7154 and detectors 7104, 7155 may be coupled to the box 7102, 7152 through one or more fibers 7106, 7156. Also, the imaging may be in reflection mode (top of FIG. 71), transmission mode (bottom of FIG. 71), or some combination.

Beyond the geometry and apparatus of FIG. 71, the optical imaging system may use one or more of three different illumination methods: continuous wave, time-domain photon migration, and frequency-domain photon migration. In one embodiment, continuous-wave systems emit light at approximately constant intensity or modulated at low frequencies, such as 0.1-100 kHz. In another embodiment, the time-domain photon migration technique uses relatively short, such as 50-400 psec, light pulses to assess the temporal distribution of photons. Since scattering may increase the times of flight spent by photons migrating in tissues, the photons that arrive earliest at the detector probably encountered the fewest scattering events. In yet another embodiment, the frequency-domain photon migration devices modulate the amplitude of the light that may be continuously transmitted at relatively high frequencies, such as 10 MHz to 1 GHz. For example, by measuring the phase shift and amplitude decay of photons as compared to a reference signal, information may be acquired on the optical properties of tissue, and scattering and absorption may be distinguished. Beyond these three methods, other techniques or combinations of these methods may be used, and these other methods are also intended to fall within the scope of this disclosure.

Although particular embodiments of imaging architectures are illustrated in FIG. 71, other system architectures may also be used and are also intended to be covered by this disclosure. For example, in one embodiment several couples of optical fibers for light delivery and collection may be arranged along one or more rings placed at different distances from the nipple 7004. In an alternate embodiment a "cap" with fiber leads for light sources and detectors may be used that fits over the breast. In yet another embodiment, imaging optics and light sources and detectors may surround the nipple 7004 and areola 7005 regions of the breast. As yet another alternative, a minimally invasive procedure may involve inserting needles with fiber enclosure (to light sources and detectors or receivers) into the breast, so as to probe regions such as the lobules 7003 and connective tissue. Both non-invasive and minimally invasive optical imaging methods are intended to be covered by this disclosure.

Optical Wavelength Ranges for Cancer Detection

Figure 72:
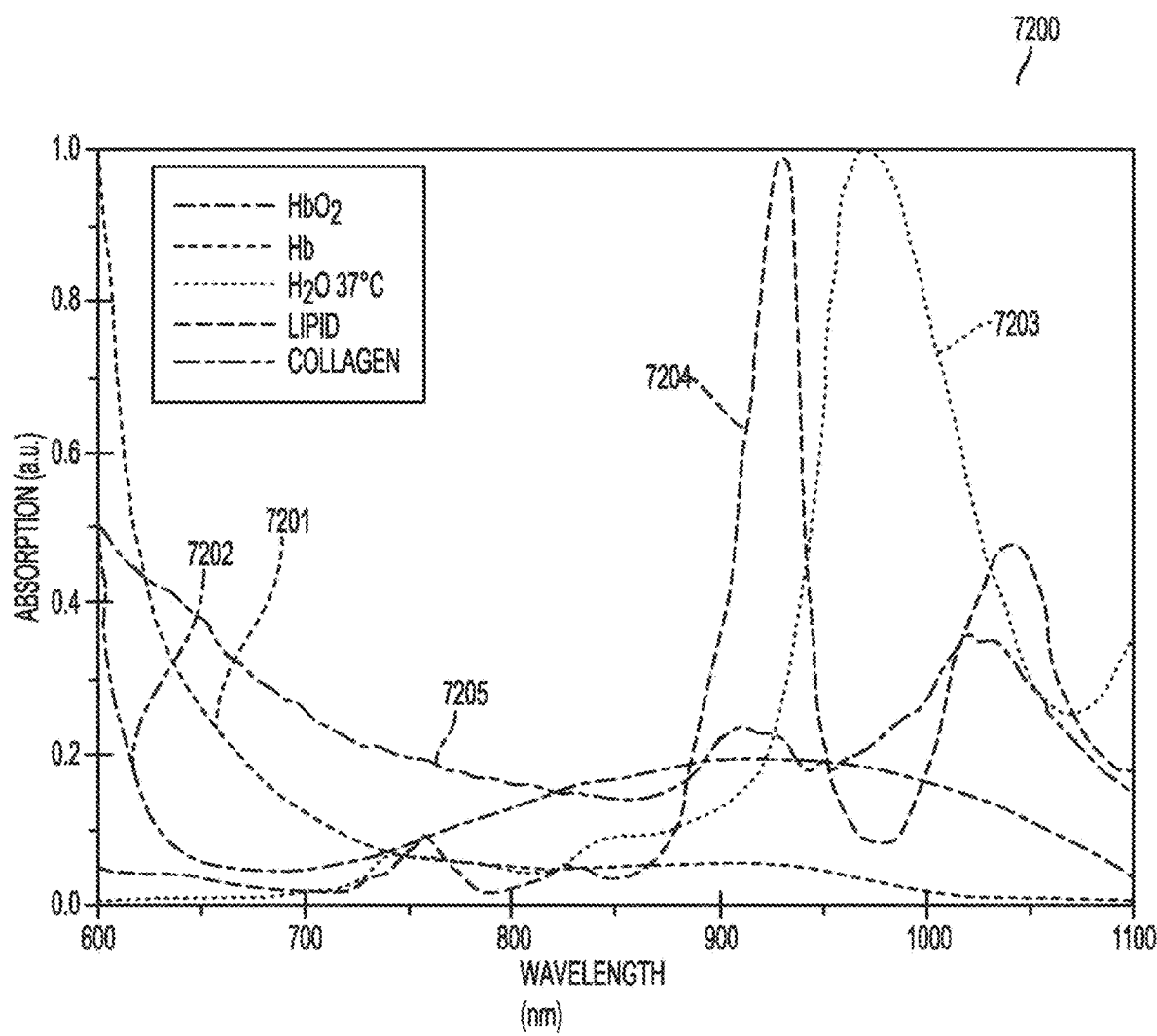
FIG. 72 shows the normalized absorption spectra of main tissue absorbers in the NIR for breast cancer, between about 600-1100 nm.

Many of the diffuse optical tomography studies previously have relied on using NIR in the wavelength range of about 600-1000 nm, where light absorption at these wavelengths may be minimal, allowing for sufficient tissue penetration (up to 15 cm). In these wavelength ranges, it has been claimed that concentrations of oxy- and deoxy-hemoglobin, water, and lipids can be determined. For example, FIG. 72 shows the normalized absorption spectra 7200 of main tissue absorbers in the NIR between about 600 nm and 1100 nm: deoxy-hemoglobin, Hb, 7201, oxy-hemoglobin, HbO2, 7202, water 7203, lipids 7204 and collagen 7205. It is speculated that in a malignant tumor, hemoglobin concentration may be directly related to angiogenesis, one of the main factors required for tumor growth and metastases. Moreover, the proportions of oxy- and deoxy-hemoglobin in a tumor may change due to its metabolism. Thus, by measuring concentrations of the breast components, discrimination of benign and malignant tumors may be possible with diffuse optical imaging. Experiment evidence suggests that cancerous tissue is associated with higher hemoglobin and water concentrations, and a lower lipid concentration with respect to normal breast tissue.

Based on FIG. 68 and the dynamics of carcinoma, it may be advantageous to perform spectroscopy in longer wavelengths, such as windows between 1000-1400 nm or 1600-1800 nm. For example, looking at the absorption curves 6800 in FIG. 68, the absorption between approximately 1000-1300 nm may be comparable to the 600-1000 nm window described in FIG. 72. However, the loss through the soft tissue medium (penetration depth may be inversely related to the loss) will be due to absorption and scattering. In fact, the scattering properties of tissue may also contain valuable information for lesion diagnosis. Since the scattering is inversely proportional to some power of wavelength (for example, in some tissue scattering is inversely proportional to the wavelength cubed), the scattering contribution to the loss may decrease at longer wavelengths. Moreover, these longer wavelength windows may contain diagnostic information on content of collagen and adipose, both of which may be significant indicators for breast cancer.

Figure 73:
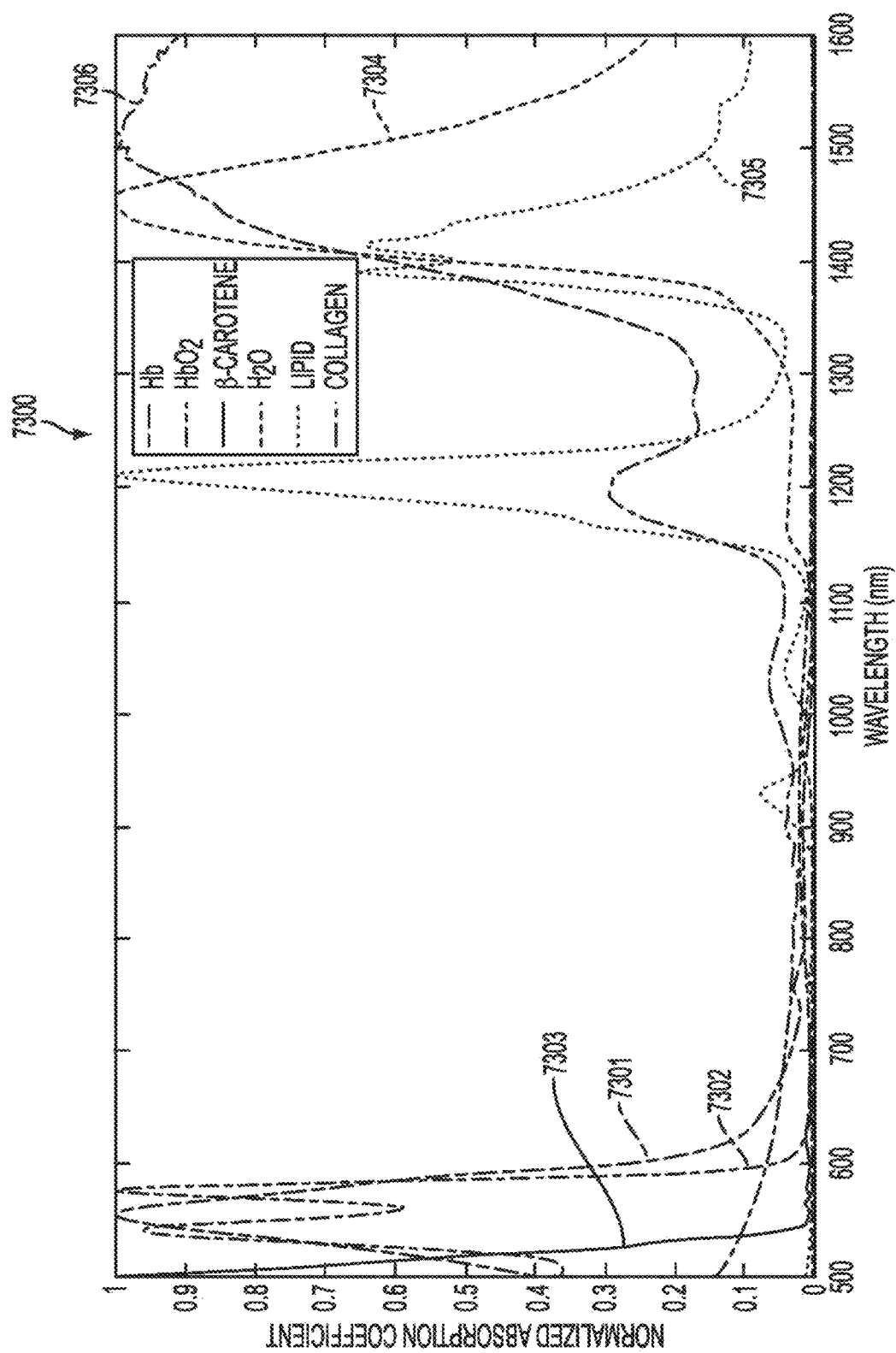
FIG. 73 illustrates the normalized absorption coefficient in the wavelength range between about 500-1600 nm for many of the components of breast tissue.

Breast cancer spectroscopy may benefit from the use of wavelengths longer than about 1000 nm for a number of reasons. As one example, the main absorbers in soft tissues of the visible spectrum of light may be oxy- and deoxygenated hemoglobin and beta-carotene. On the other hand, primary absorbers in the near-infrared spectrum of light may be water, adipose tissue and collagen. Particularly adipose and collagen content may be valuable for early detection of cancers. In one embodiment, increased levels of collagen in breast malignancies are thought to be due to increased vascularity of the tumors. Collagen type I may be an important component of artery walls. FIG. 73 illustrates the normalized absorption coefficient 7300 in the wavelength range between about 500 nm and 1600 nm for Hb 7301, HbO2 7302, beta-carotene 7303, water 7304, lipid 7305 and collagen 7306.

Collagen and Adipose Signatures in Near-IR

Examining the collagen content may be a valuable indicator for breast cancer detection. Collagen is one of the important extracellular matrix proteins, and fibrillar collagens help to determine stromal architecture. In turn, changes in the stromal architecture and composition are one of the aspects of both benign and malignant pathologies, and, therefore, may play an initial role in breast carcinogenesis. For example, collagen seems to be related to cancer development, because high mammographic density may be recognized as a risk factor for breast cancer. Moreover, collagen type in high-risk dense breasts may appear to be different from collagen in low-density breasts.

Experimental data also shows that malignant mammary gland tissues of animals and humans show a decrease in lipids when compared to normal tissues. The reduced amounts of lipids in the cancerous sites may be caused by a high metabolic demand of lipids in the malignant tumors. For example, due to the rapid proliferation of cancerous cells, there may be reduced lipid content in cancerous tissues. Thus, in addition to collagen, another valuable marker for breast cancer may be the lipid spectral features. It may also be possible to combine the markers from oxy- and deoxygenated hemoglobin and water with lipid and collagen lines to improve the diagnostics and/or therapeutics of optical imaging and/or treatment for breast and other types of cancer. Although specific examples of tissue constituents are discussed, other tissue constituents and related markers may also be associated with breast cancer and other cancers, and these other constituents are also intended to be covered by this disclosure.

Figure 74A:
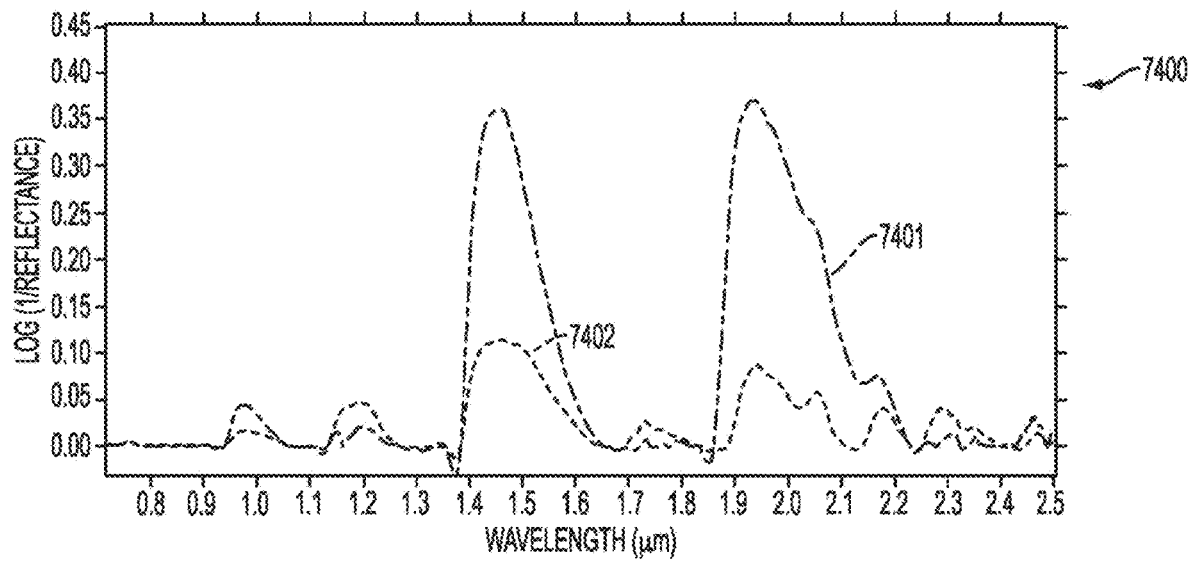
FIG. 74A shows the typical spectra of the cancerous site of a treated rat and the corresponding site of a normal rat and illustrates the logarithm of the inverse of reflection spectra.
Figure 74B:
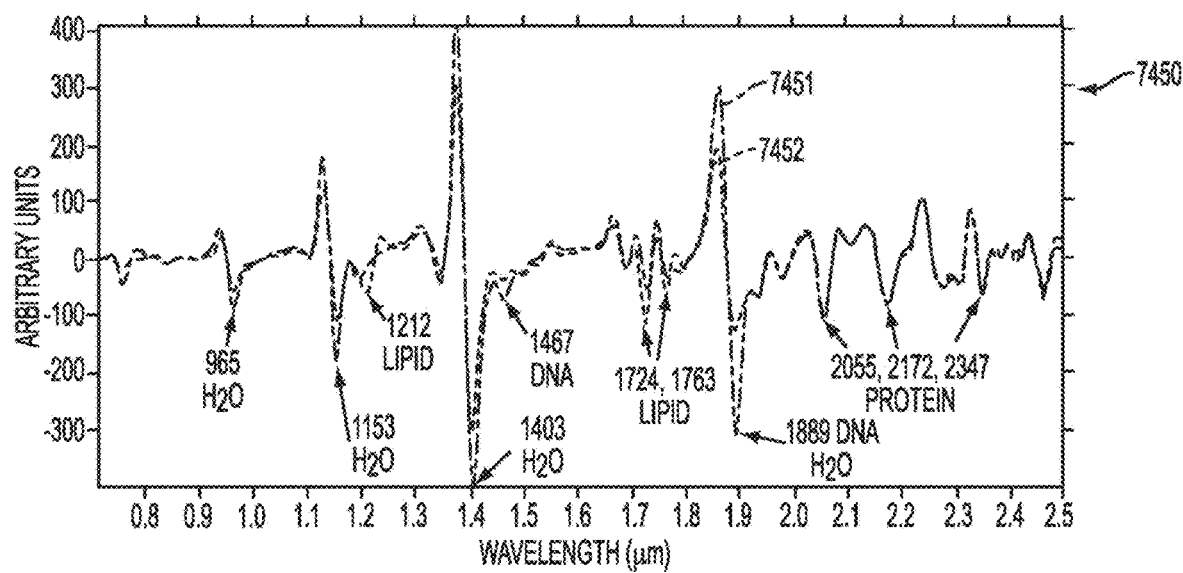
FIG. 74B shows the typical spectra of the cancerous site of a treated rat and the corresponding site of a normal rat and illustrates second derivative spectra.

As an example of the types of spectral signatures that may exist, in vivo investigations of progressive changes in rat mammary gland tumors were conducted using near-infrared spectroscopy with a Fourier-transform infrared spectrometer. In one embodiment, FIG. 74 shows the typical spectra of the cancerous site of the treated rat and the corresponding site of the normal rat. FIG. 74A shows the logarithm of the inverse of reflection spectra 7400, while FIG. 74B shows their second derivative spectra 7450. The curves 7401, 7451 correspond to the spectra of the cancerous sites, while 7402, 7452 correspond to the spectra of the normal sites. Since the second derivative techniques may be useful in the analyses of NIR spectra to minimize baseline offsets and to resolve overlapping absorption without compromising signal-to-noise, FIG. 74B may be used for interpretation of the spectral changes.

In FIG. 74B identification may be made of several of the spectral features. In particular, there are DNA bands near 1471 nm and 1911 nm, while there are water bands near 967 nm, 1154 nm, 1402 nm, and 1888 nm. Moreover, there are lipid bands near 1209 nm, 1721 nm and 1764 nm, and there are protein bands near 2055 nm, 2172 nm and 2347 nm. The NIR spectra of FIG. 74 show that the DNA and water contents in the cancerous site may be higher than those in normal tissues. On the other hand, the lipid content in the cancerous tissue may be less than the lipid content in normal tissues. With protein contents, however, little difference may be found between the normal and cancerous tissue.

Figure 75:
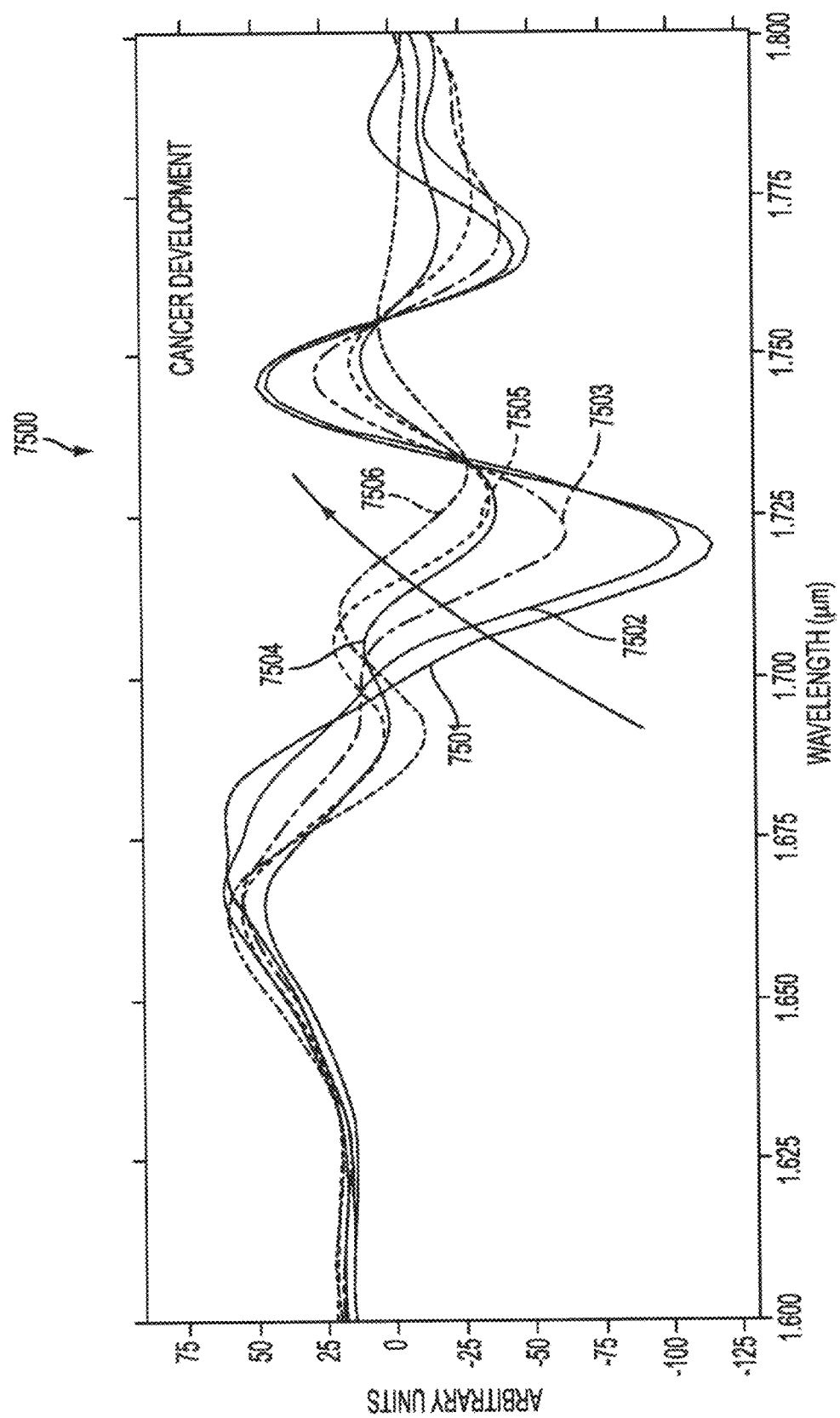
FIG. 75 shows the second derivative of spectral changes over several weeks between about 1600-1800 nm in rats with breast cancer.

These experiments on rats with breast cancer were also used to observe the temporal progression of the cancer. In this embodiment, as the cancer grew, the lipid band intensity decreased, and this band also shifted to higher wavelengths, and collagen peaks appeared in the tissues. In FIG. 75, the second derivative spectral changes 7500 were investigated in the 1600 nm to 1800 nm wavelength range over several weeks. An early cancer was detected in the 5th week, and then it grew rapidly from the 6th 7501 to the 7th 7502 week. The cancer's temporal progression through the 8th 7503, 9th 7504, 10th 7505 and 11th 7506 week are shown in the various curves in FIG. 75. With the cancer growth, the intensity of the lipid band in the vicinity of 1721 nm decreased, and this band shifted to higher wavelengths by 7 nm at the 11th week 7506 compared to the wavelength band at the 5th week. The higher wavelength shift may indicate that an order parameter of the lipids increases with progressive cancer growth.

Figure 78:
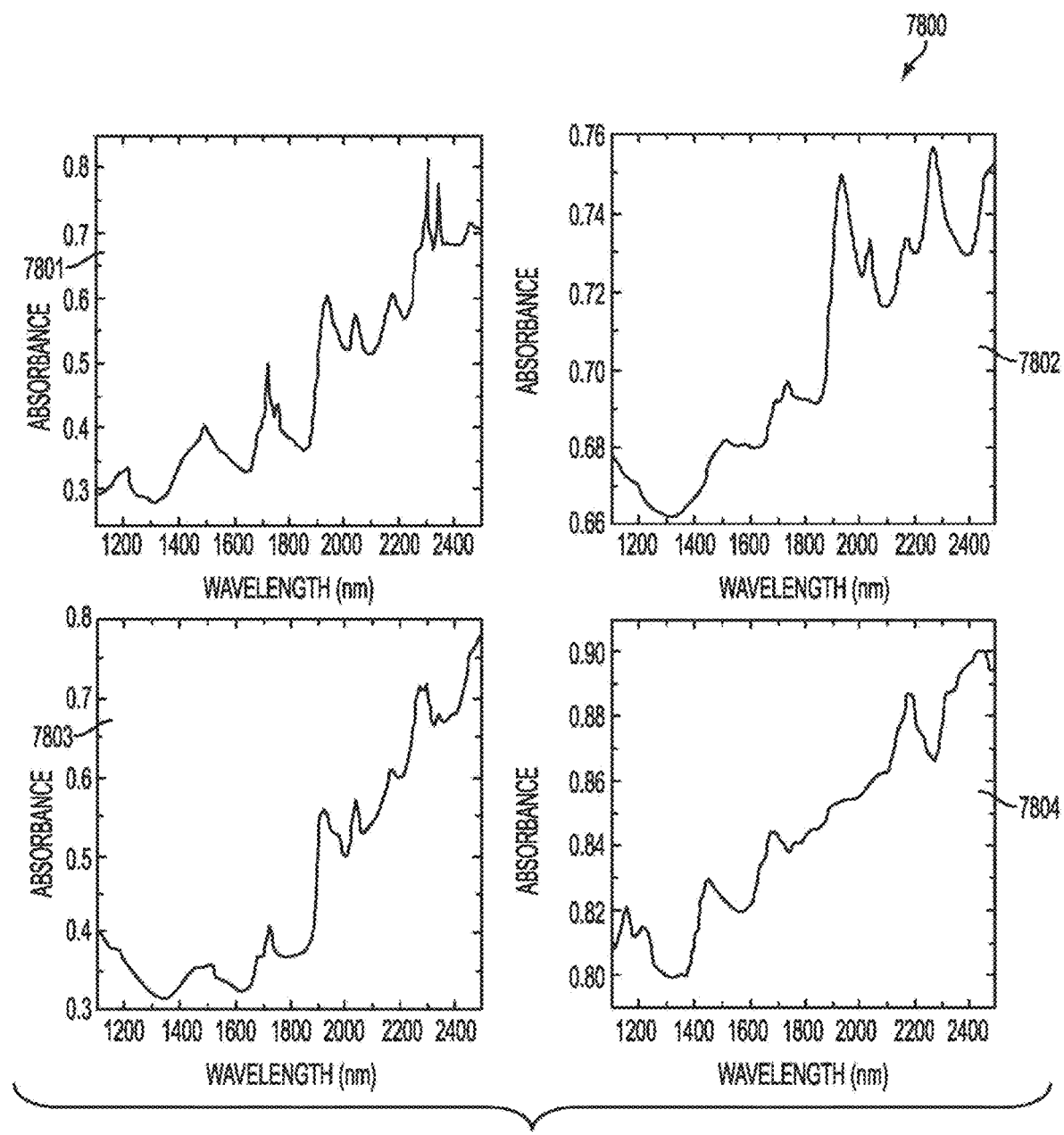
FIG. 78 illustrates the absorbance for four types of collagen: collagen I, collagen II, collagen III, and collagen IV.

Moreover, in the data of FIG. 75 is seen that a new peak appeared as the cancer grew around 1690 nm, which may be assigned to be a collagen absorption by comparison with the absorptions of standard collagen (c.f., FIG. 78). The higher wavelength shift may be attributable to the formation of elastic fibers in the lipid layer with collagen induced in the cancer tissues, thus leading to an increased order parameter of the lipids. Thus, it can be seen that significant information about breast cancer tissue compared with normal tissue may be obtained by spectroscopy at the longer wavelengths in the near-infrared.

Figure 76:
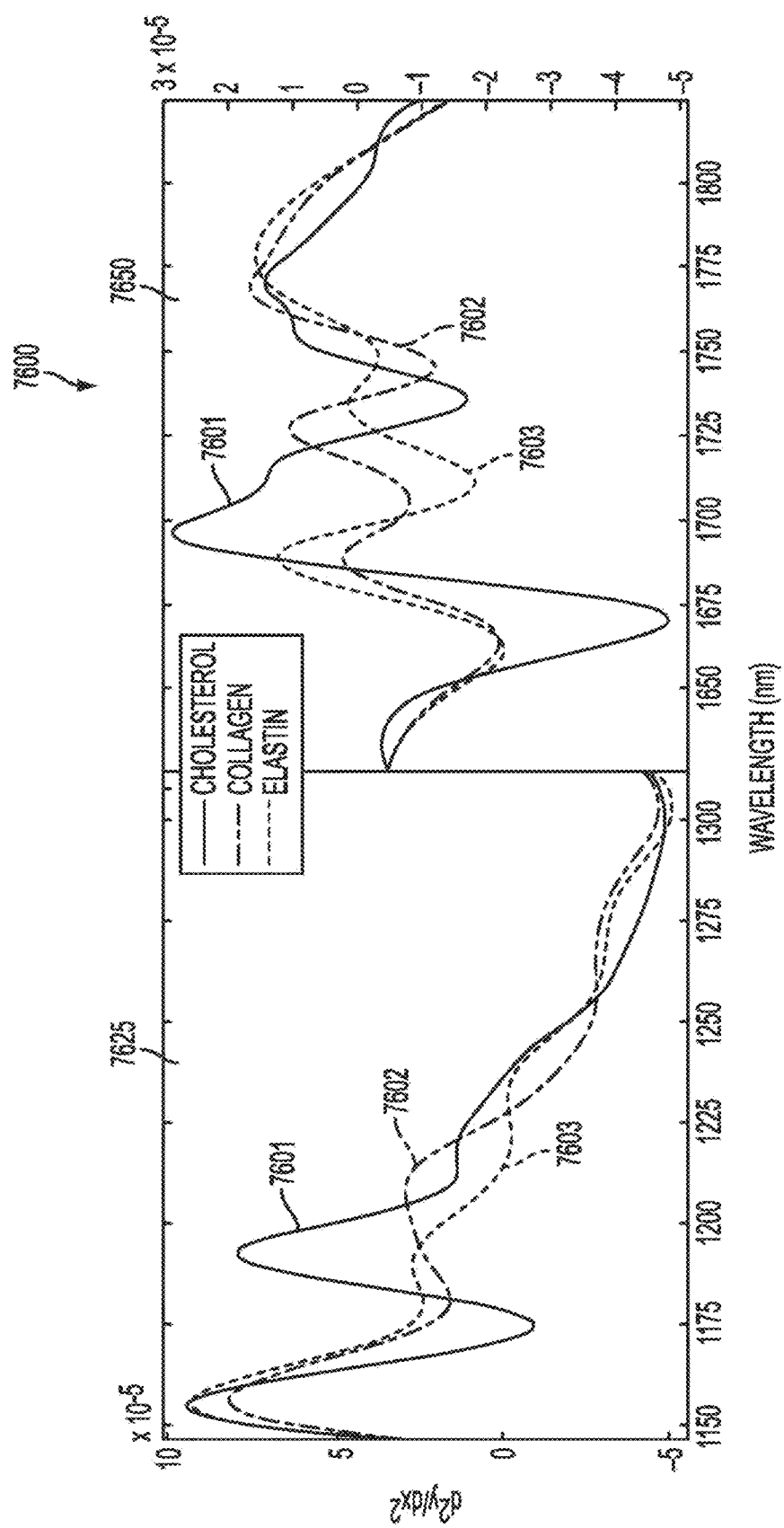
FIG. 76 illustrates the second derivative spectra for cholesterol, collagen and elastin.

The second derivative spectra may also be insightful for observing and monitoring changes in tissue as well as characterizing tissue in the near-infrared wavelength range. As an example, FIG. 76 illustrates the second derivative spectra 7600 for cholesterol (similar to one embodiment of lipids) 7601, collagen 7602, and elastin 7603. The left curve 7625 shows the second derivative data over the wavelength range of about 1150 nm to 1300 nm, while the right curve 7650 shows the second derivative data over the wavelength range of about 1600 nm to 1850 nm. These wavelengths show numerous features for cholesterol/lipid 7601, collagen 7602, and elastin 7603, which again emphasizes the added value of using wavelengths longer than about 1000 nm for cancer diagnostics.

Figure 77:
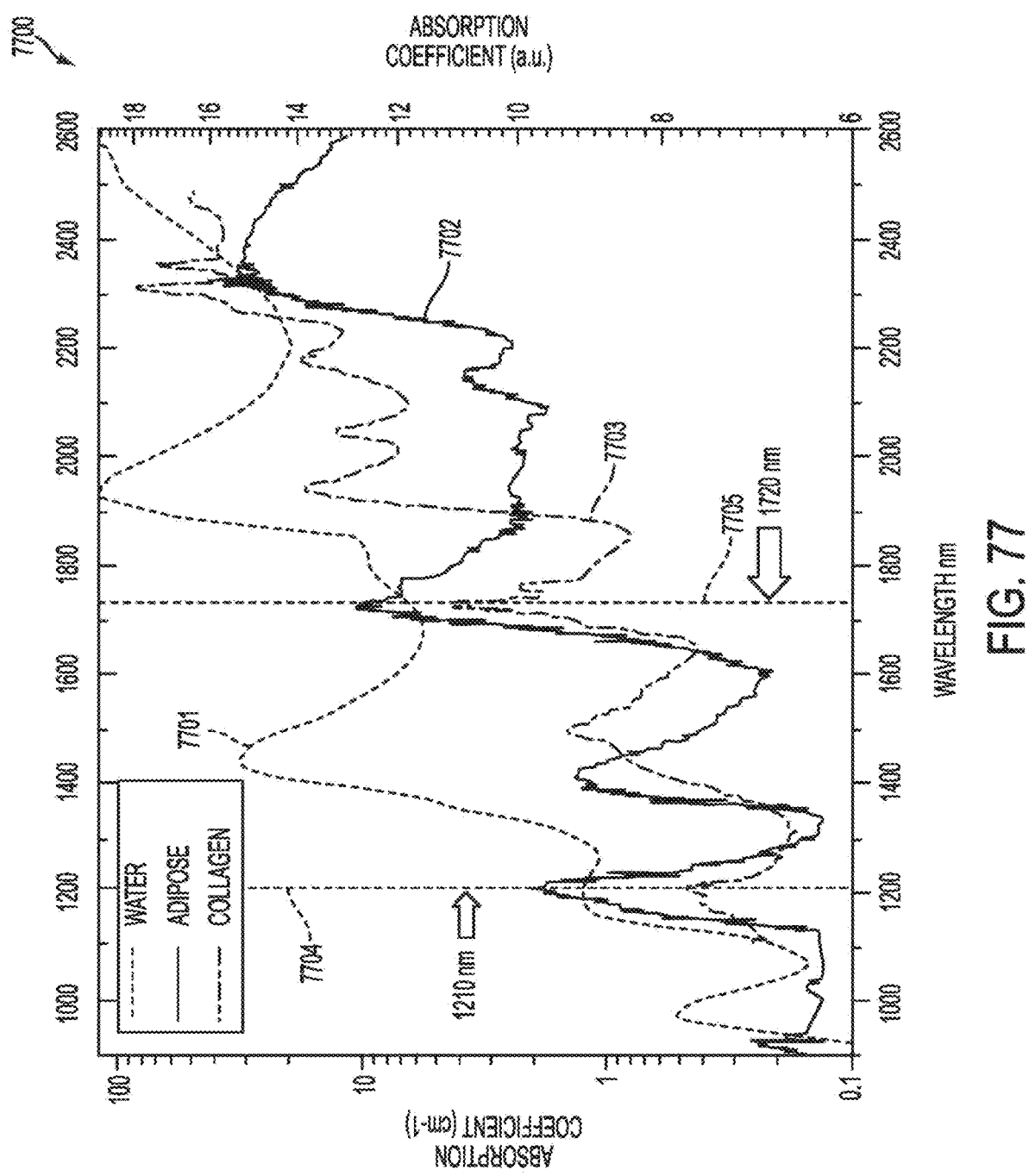
FIG. 77 shows the absorption coefficient as a function of wavelength between about 1000 nm and 2600 nm for water, adipose and collagen.

To further illustrate the value of using longer wavelengths in the NIR or SWIR for observing changes in breast cancer and other cancer markers, the spectra of in water, lipids/adipose and collagen of different varieties may be studied. As one embodiment, the absorption coefficients 7700 are shown in FIG. 77 as a function of wavelength between about 1000 nm and 2600 nm. FIG. 77 overlaps the absorption coefficient for water 7701, adipose 7702 (forms of adipose include fatty tissue and acids, lipids, and cholesterol), and collagen type I 7703. One may note that particular absorption peaks for adipose 7702 and collagen type I 7703 align at wavelengths near 1210 nm 7704 and 1720 nm 7705, which also correspond to local minima in water absorption.

Moreover, the NIR spectra for collagen also depend on the type of collagen. As an example, FIG. 78 illustrates the absorbance 7800 for four types of collagen: collagen I 7801, collagen II 7802, collagen III 7803, and collagen IV 7804. Collagen I, for instance, may be a major constituent of stroma. Also, collagen I and collagen III may be the principal collagens of the aorta. Since the spectra of the four collagens are distinctive, multicomponent analysis of collagens may possibly be used to distinguish the type of collagen involved.

The experimental results discussed thus far indicate that breast cancer detection may benefit from spectroscopy in the NIR and SWIR, particularly wavelengths between approximately 1000-1400 nm and 1600-1800 nm. These are wavelength windows that may have deep penetration into soft tissue, while still falling within lower absorption valleys of water. Moreover, the longer wavelengths lead to less scattering in tissue and water, again permitting deeper penetration of the light. In the NIR and SWIR wavelength range, the spectra of standard samples of cholesterol, protein, collagen, elastin and DNA were measured to obtain information on their characteristic bands in the spectra of mammary gland tissues. Absorption peaks in the standard samples occur at the following exemplary wavelengths:

Collagen: 1182 nm, 1360 nm, 1426 nm, 1496 nm, 1569 nm, 1690 nm, 1732 nm;
Lipids: 1157 nm, 1209 nm, 1404 nm, 1721 nm, 1764 nm;
Cholesterol: 918 nm, 1195 nm, 1376 nm, 1585 nm, 1711 nm, 1757 nm;
Protein: 910 nm, 1143 nm, 1186 nm, 1279 nm, 1420 nm, 1503 nm, 1579 nm, 1690 nm, 1739 nm, 1799 nm; and
DNA: 1414 nm, 1471 nm, 1626 nm, 1728 nm.

Comparing these absorption features with the data in FIGS. 73-78 shows that there are absorption features or signatures in the second derivatives that can be used to monitor changes in, for example, collagen and lipids. By using broadband light and performing spectroscopy in at least some part of the wavelength windows between about 1000-1400 nm and/or 1600-1800 nm, the collagen and lipid changes, or other constituent changes, may be monitored. In one embodiment, for breast cancer the decrease in lipid content, increase in collagen content, and possible shift in collagen peaks may be observed by performing broadband light spectroscopy and comparing normal regions to cancerous regions as well as the absorption strength as a function of wavelength. The spectroscopy may be in transmission, reflection, diffuse reflection, diffuse optical tomography, or some combination. Also, this spectroscopy may be augmented by fluorescence data, if particular tags or markers are added. Beyond looking at the absorbance, the data processing may involve also observing the first, second, or higher order derivatives.

Broadband spectroscopy is one example of the optical data that can be collected to study breast cancer and other types of cancer. However, other types of spectral analysis may also be performed to compare the collagen and lipid features between different wavelengths and different tissue regions (e.g., comparing normal regions to cancerous regions), and these methods also fall within the scope of this disclosure. For example, in one embodiment just a few discrete wavelengths may be monitored to see changes in lipid and collagen contents. In a particular embodiment, wavelengths near 1200 nm may be monitored in the second derivative data of FIG. 76 to measure the cholesterol/lipid peak below 1200 nm in 7601 versus the collagen peak above 1200 nm in 7602. In yet another embodiment, the absorption features in FIG. 73 may be relied upon to monitor the lipid content 7305 by measuring near 1200 nm and the collagen content 7306 by measuring near 1300 nm. Although these embodiments use only two wavelengths, any number of wavelengths may be used and are intended to be covered by this disclosure.

Thus, a breast cancer monitoring system, or a system to monitor different types of cancers, may comprise broadband light sources and detectors to permit spectroscopy in transmission, reflection, diffuse optical tomography, or some combination. In one particular embodiment, high signal-to-noise ratio may be achieved using a fiber-based super-continuum light source (described further herein). Other light sources may also be used, including a plurality of laser diodes, super-luminescent laser diodes, or fiber lasers.

Wavelength ranges that may be advantageous for cancer detection include the NIR and SWIR windows (or some part of these windows) between about 1000-1400 nm and 1600-1800 nm. These longer wavelengths fall within local minima of water absorption, and the scattering loss decreases with increasing wavelength. Thus, these wavelength windows may permit relatively high penetration depths. Moreover, these wavelength ranges contain information on the overtone and combination bands for various chemical bonds of interest, such as hydrocarbons.

These longer wavelength ranges may also permit monitoring levels and changes in levels of important cancer tissue constituents, such as lipids and collagen. Breast cancer tissue may be characterized by decreases in lipid content and increases in collagen content, possibly with a shift in the collagen peak wavelengths. The changes in collagen and lipids may also be augmented by monitoring the levels of oxy- and deoxy-hemoglobin and water, which are more traditionally monitored between 600-1000 nm. Other optical techniques may also be used, such as fluorescent microscopy.

To permit higher signal-to-noise levels and higher penetration depths, higher intensity or brightness of light sources may be used. With the higher intensities and brightness, there may be a higher risk of pain or skin damage. At least some of these risks may be mitigated by using surface cooling and focused infrared light, as further described herein.

Laser Experiments: Penetration Depth, Focusing, Skin Cooling

Some preliminary experiments show the feasibility of using focused infrared light for non-invasive procedures, or other procedures where relatively shallow vessels below the skin are to be thermally coagulated or occluded with minimum damage to the skin upper layers. In one embodiment, the penetration depth and optically induced thermal damage has been studied in chicken breast samples. Chicken breast may be a reasonable optical model for smooth muscle tissue, comprising water, collagen and proteins. Commercially available chicken breast samples were kept in a warm bath (~32 degree Celsius) for about an hour, and then about half an hour at room temperature in preparation for the measurements.

Figure 79:
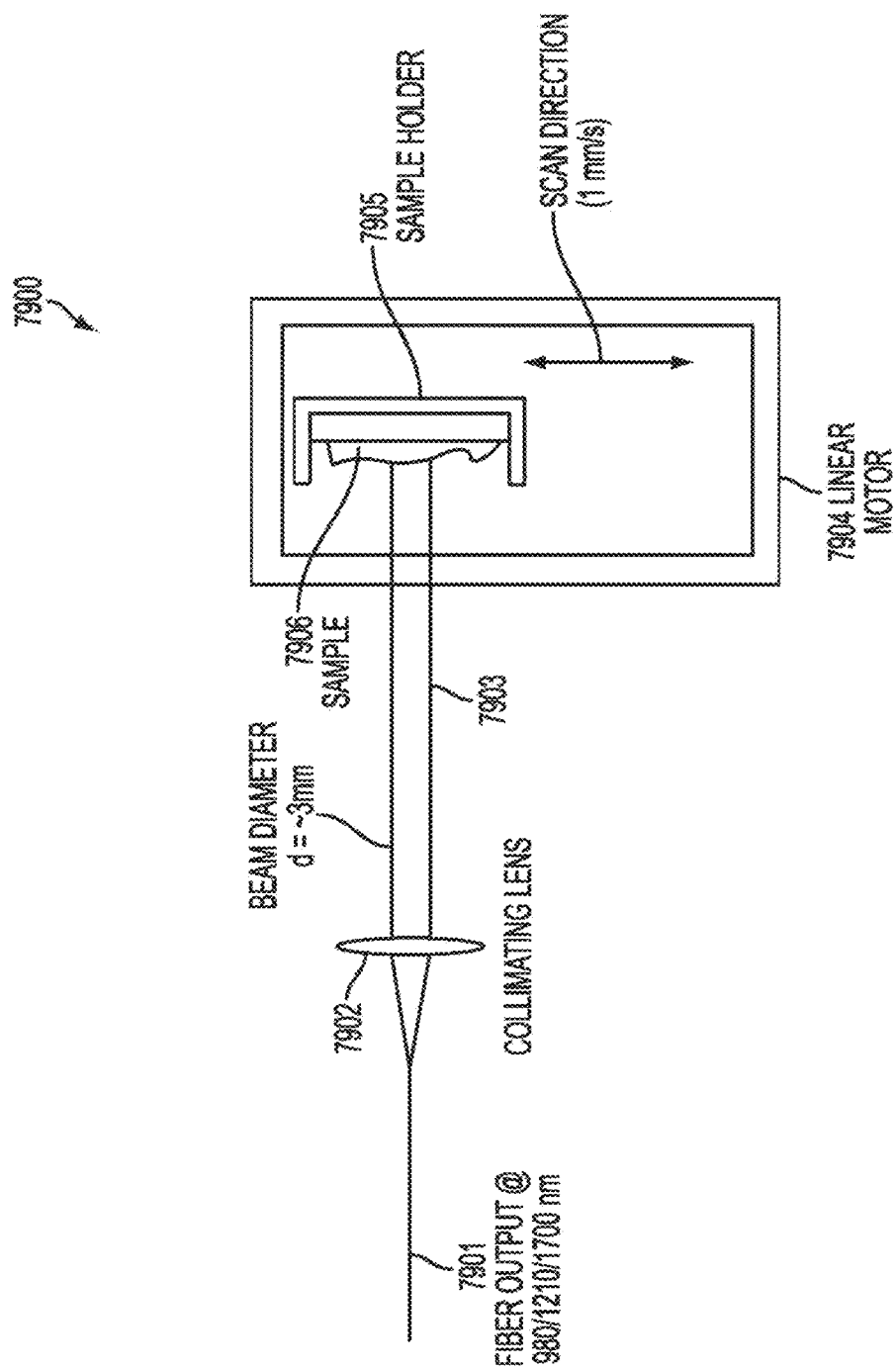
FIG. 79 shows an experimental set-up for testing chicken breast samples using collimated light. In this experiment, the collimated light has a beam diameter of about 3 mm.

An exemplary set-up 7900 for testing chicken breast samples using collimated light is illustrated in FIG. 79. The laser light 7901 near 980 nm, 1210 nm, or 1700 nm may be provided from one or more laser diodes or fiber lasers, as described further below. In this instance, laser diodes were used, which comprise a plurality of laser diode emitters that are combined using one or more multiplexers (particularly spatial multiplexers), and then the combined beam is coupled into a multi-mode fiber (typically 100 microns to 400 microns in diameter). The output from the laser diode fiber was then collimated using one or more lenses 7902. The resulting beam 7903 was approximately round with a beam diameter of about 3 mm. The beam diameter was verified by blade measurements (i.e., translating a blade across the beam). Also, the time-averaged power was measured in the nearly collimated section after the lens using a large power meter. The chicken breast samples 7906 were mounted in a sample holder 7905, and the sampler holder 7905 was mounted in turn on a translation stage 7904 with a linear motor that could move perpendicular to the incoming laser beam. Although particular details of the experiment are described, other elements may be added or eliminated, and these alternate embodiments are also intended to be covered by this disclosure.

Figure 80:
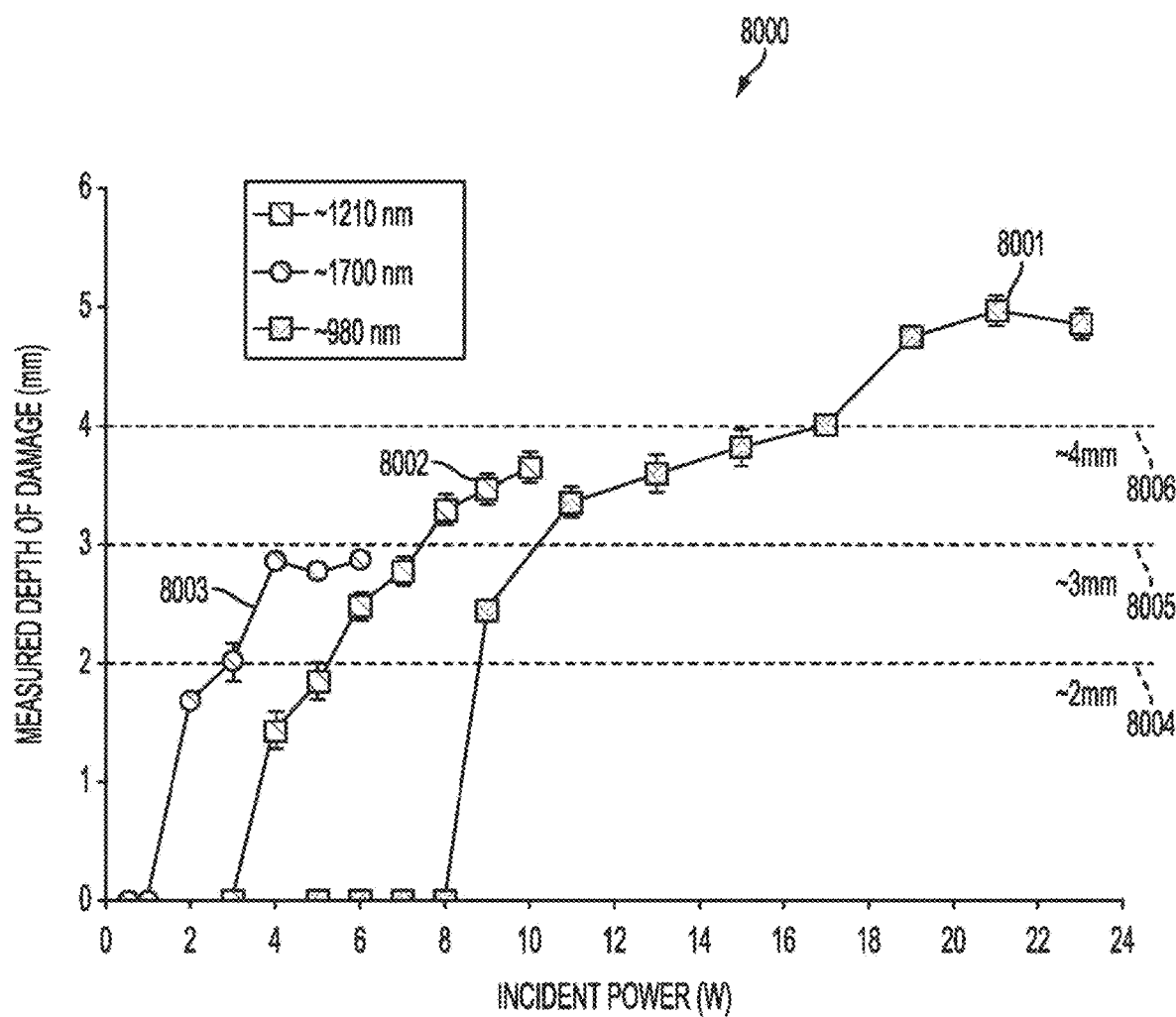
FIG. 80 plots the measured depth of damage (in millimeters) versus the time-averaged incident power (in Watts). Data is presented for laser wavelengths near 980 nm, 1210 nm and 1700 nm, and lines are drawn corresponding to penetration depths of approximately 2 mm, 3 mm, and 4 mm.

For these particular experiments, the measured depth of damage (in millimeters) versus the incident laser power (in Watts) is shown 8000 in FIG. 80. In this embodiment, laser diodes were used at wavelengths near 980 nm, 1210 nm and 1700 nm. The curve 8001 corresponds to about 980 nm, the curve 8002 corresponds to about 1210 nm, and the curve 8003 corresponds to about 1700 nm. It may be noted that there is a threshold power, above which the damage depth increases relatively rapidly. For example, the threshold power for wavelengths around 980 nm may be about 8 W, the threshold power for wavelengths around 1210 nm may be 3 W, and the threshold power for wavelengths around 1700 nm may be about 1 W. The threshold powers may be different at the different wavelengths because of the difference in water absorption (e.g., 7701 in FIG. 77). Part of the difference in threshold powers may also arise from the absorption of proteins such as collagen (e.g., 7703 in FIG. 77). After a certain power level, the damage depth appears to saturate: i.e., the slope flattens out as a function of increasing pump power.

In one embodiment, if the penetration depth is defined as the depth where damage begins to approximately saturate, then for wavelengths of about 980 nm 8001 the penetration depth 8006 may be defined as approximately 4 mm, for wavelengths of about 1210 nm 8002 the penetration depth 8005 may be defined as approximately 3 mm, and for wavelengths of about 1700 nm 8003 the penetration depth 8004 may be defined as approximately 2 mm. These are only approximate values, and other values and criteria may be used to define the penetration depth. It may also be noted that the level of damage at the highest power points differs at the different wavelengths. For example, at the highest power point of 8003 near 1700 nm, much more damage is observed, showing evidence of even boiling and cavitation. This may be due to the higher absorption level near 1700 nm (e.g., 7701 in FIG. 77). On the other hand, at the highest power point 8001 near 980 nm, the damage is not as catastrophic, but the spot size appears larger. The larger spot size may be due to the increased scattering at the shorter wavelengths (e.g., 7701 in FIG. 77). Based on data 8000 such as in FIG. 80, it may be possible to select the particular wavelength for the laser beam to be used in the non-invasive procedure.

Figure 81:
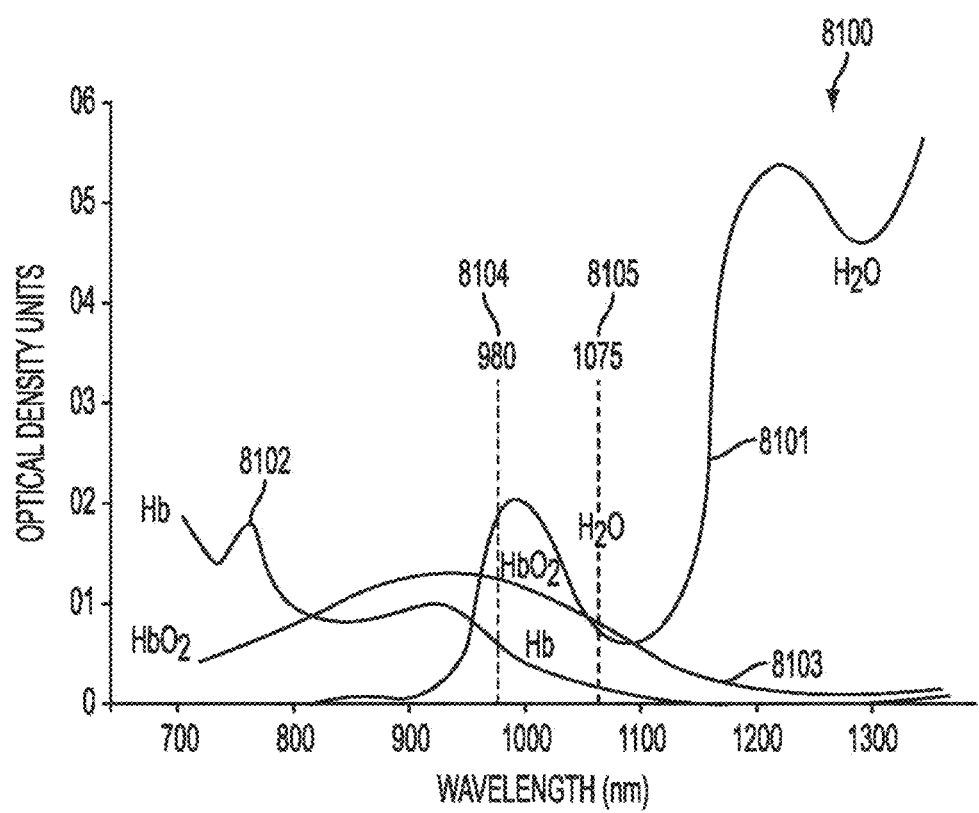
FIG. 81 illustrates the optical absorption or density as a function of wavelength between approximately 700 nm and 1300 nm for water, hemoglobin and oxygenated hemoglobin.

Even near wavelengths such as described in FIG. 80, the particular wavelength selected may be more specifically defined based on the target tissue of interest. In one particular embodiment, the vessel lumen may be modeled as water, and for this example assume that wavelengths in the vicinity of 980 nm are being selected to create thermal coagulation or occlusion. FIG. 81 shows the optical absorption or density as a function of wavelength 8100 between approximately 700 nm and 1300 nm. Curves are shown for the water absorption 8101, hemoglobin Hb absorption 8102, and oxygenated hemoglobin HbO2 8103. In this example, two particular wavelengths are compared: 980 nm 8104 and 1075 nm 8105. For instance, 980 nm may be generated using one or more laser diodes, while 1075 nm may be generated using an ytterbium-doped fiber laser. If maximizing the penetration depth is the significant problem, then 1075 nm 8105 may be preferred, since it falls near a local minimum in water 8101, hemoglobin 8102, and oxygenated hemoglobin 8103 absorption. On the other hand, if the penetration depth at 980 nm 8104 is adequate and the problem is to generate heat through water absorption, then 980 nm 8104 may be a preferred wavelength for the light source because of the higher water absorption. This wavelength range is only meant to be exemplary, but other wavelength ranges and particular criteria for selecting the wavelength may be used and are intended to be covered by this disclosure.

Figure 82:
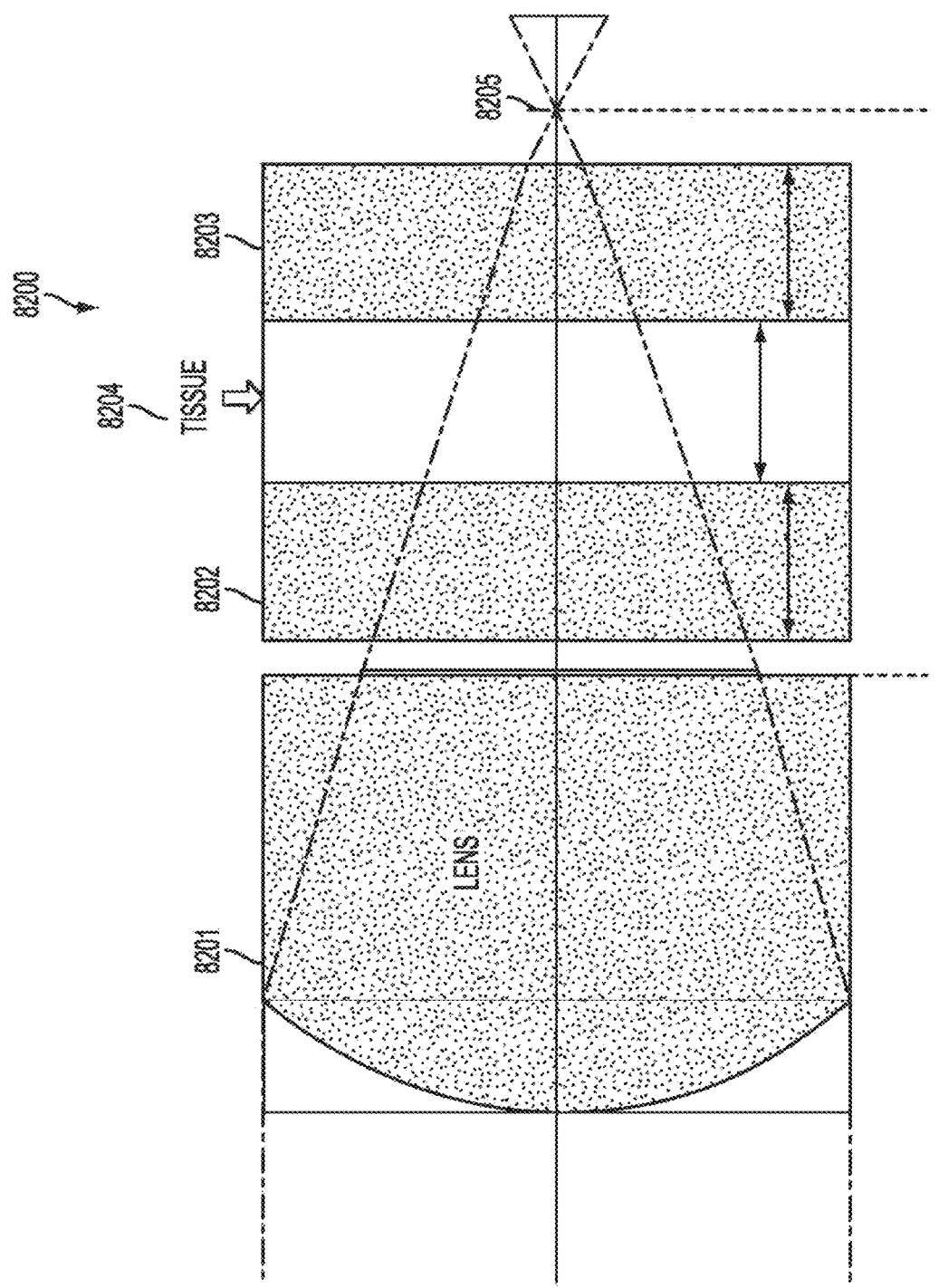
FIG. 82 shows a set-up used for in vitro damage experiments using focused infrared light. After a lens system, the tissue is placed between two microscope slides.

In another embodiment, focused infrared light has been used to preserve the top layer of a tissue while damaging nerves at a deeper level. For instance, FIG. 82 illustrates the set-up 8200 used for the focused infrared experiments. In this embodiment, a lens 8201 is used to focus the light. Although a single lens is shown, either multiple lenses, GRIN (gradient index) lenses, curved mirrors, or a combination of lenses and mirrors may be used. In this particular example, the tissue 8204 is placed between two microscope slides 8202 and 8203 for in vitro experiments. The tissue 8204 is renal artery wall either from porcine or bovine animals (about 1.2 mm thick sample)—i.e., this is the artery leading to the kidneys, and it is the artery where typically renal denervation may be performed to treat hypertension. For this example, the minimum beam waist 8205 falls behind the tissue, and the intensity contrast from the front of the tissue (closest to the lens) to the back of the tissue (furthest from the lens) is about 4:1. These are particular ranges used for this experiment, but other values and locations of minimum beam waist may also be used and intended to be covered by this disclosure.

Figure 83A:
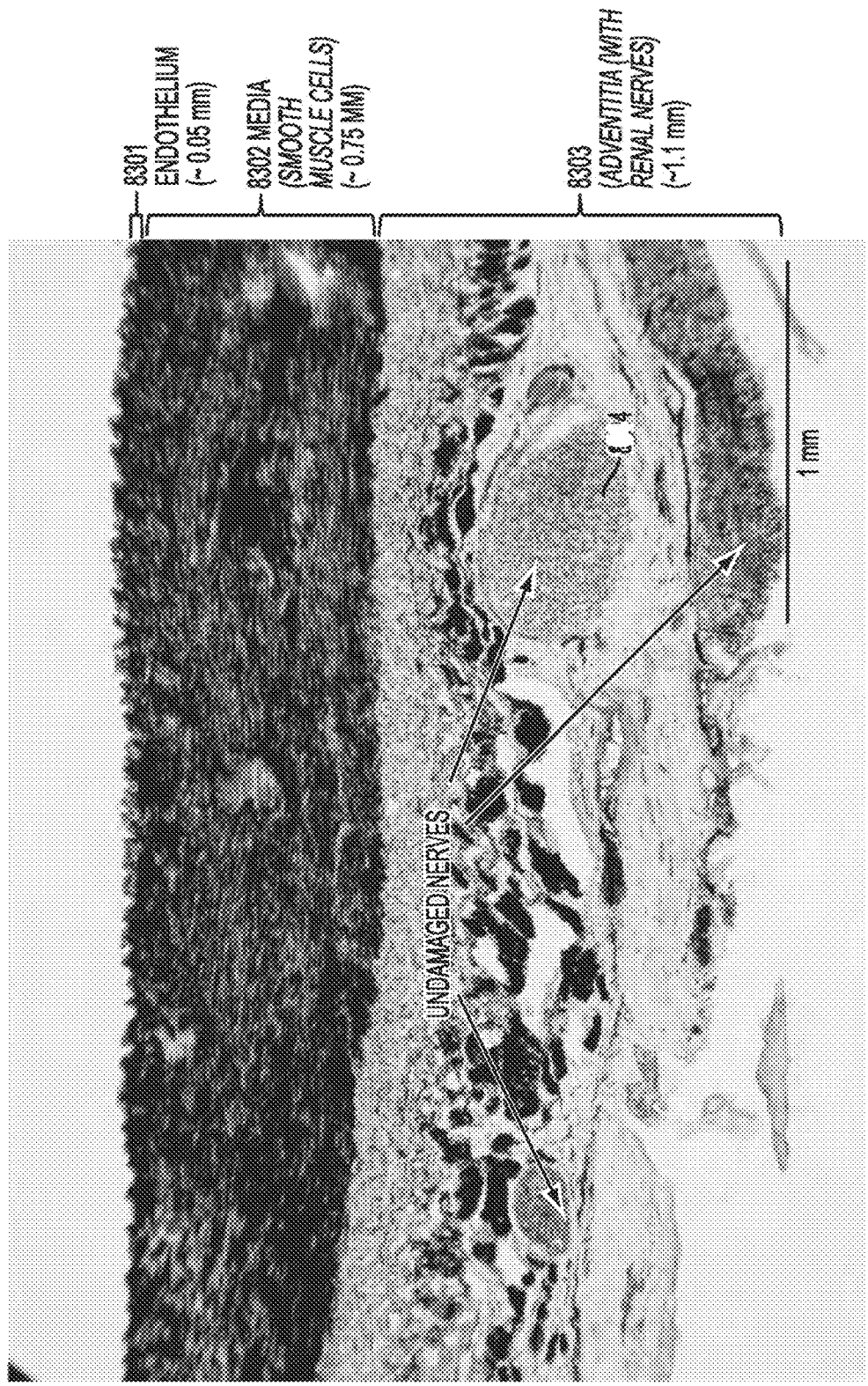
FIG. 83A presents histology of renal arteries comprising endothelium, media and adventitia layers and some renal nerves in or below the adventitia and illustrates renal arteries with no laser exposure.
Figure 83B:
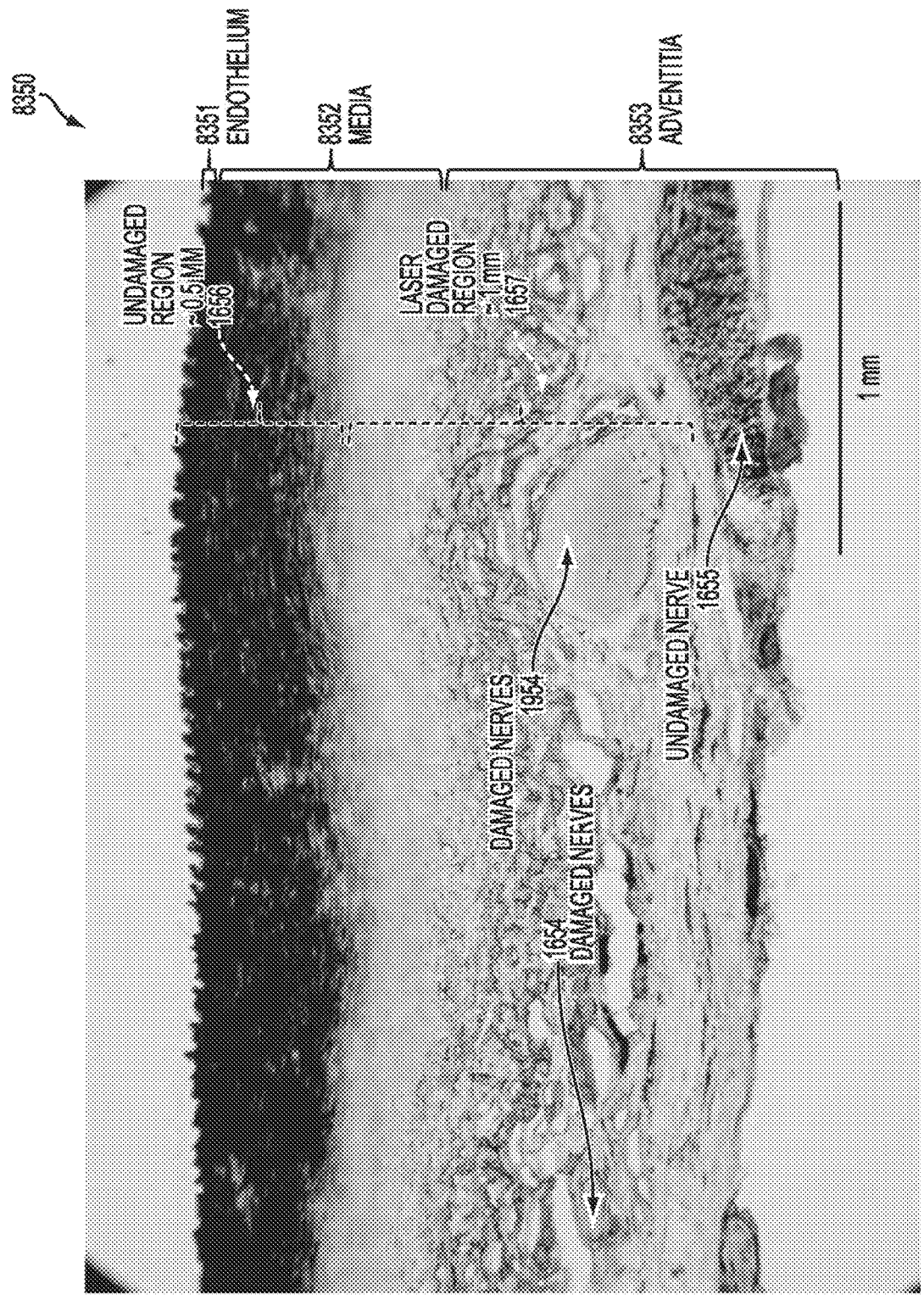
FIG. 83B presents histology of renal arteries comprising endothelium, media and adventitia layers and some renal nerves in or below the adventitia and illustrates renal arteries after focused laser exposure, with the laser light near 1708 nm.

For a particular embodiment, histology of the renal artery is shown in FIG. 83A for no laser exposure 8300 and shown in FIG. 83B with focused infrared laser exposure 8350. In this experiment, the beam diameter incident on the lens was about 4 mm, and the distance from the edge of the flat side of lens to the minimum beam waist was about 3.75 mm. The beam diameter on the front side of the renal artery (i.e., the endothelium side) was about 1.6 mm, and the beam diameter on the back side of the renal artery was about 0.8 mm. In FIG. 83A with no laser exposure, the layers of the artery wall may be identified: top layer of endothelium 8301 that is about 0.05 mm thick, the media comprising smooth muscle cells or tissue 8302 that is about 0.75 mm thick, and the adventitia 8303 comprising some of the renal nerves 8304 that is about 1.1 mm thick. These are particular values for this experiment, and other layers and thicknesses may also be used and are intended to be covered by this disclosure.

The histology with focused infrared light exposure 8350 is illustrated in FIG. 83B. The laser light used is near 1708 nm from a cascaded Raman oscillator (described in greater detail herein), and the power incident on the tissue is about 0.8 W and the beam is scanned across the tissue at a rate of approximately 0.4 mm/sec. The various layers are still observable: the endothelium 8351, the media 8352, and the adventitia 8353. With this type of histology, the non-damaged regions remain darker (similar to FIG. 83A), while the laser induced damaged regions turn lighter in color. In this example, the endothelium 8351 and top layer of the media 8352 remain undamaged—i.e., the top approximately 0.5 mm is the undamaged region 8356. The laser damaged region 8357 extends for about 1 mm, and it includes the bottom layer of the media 8352 and much of the adventitia 8353. The renal nerves 8354 that fall within the damage region 8357 are also damaged (i.e., lighter colored). On the other hand, the renal nerves beyond this depth, such as 8355, may remain undamaged.

Thus, by using focused infrared light near 1708 nm in this example, the top approximately 0.5 mm of the renal artery is spared from laser damage. It should be noted that when the same experiment is conducted with a collimated laser beam, the entire approximately 1.5 mm is damaged (i.e., including regions 8356 and 8357). Therefore, the cone of light with the lower intensity at the top and the higher intensity toward the bottom may, in fact, help preserve the top layer from damage. There should be a Beer's Law attenuation of the light intensity as the light propagates into the tissue. For example, the light intensity should reduce exponentially at a rate determined by the absorption coefficient. In these experiments it appears that the focused light is able to overcome the Beer's law attenuation and still provide contrast in intensity between the front and back surfaces.

Figure 84:
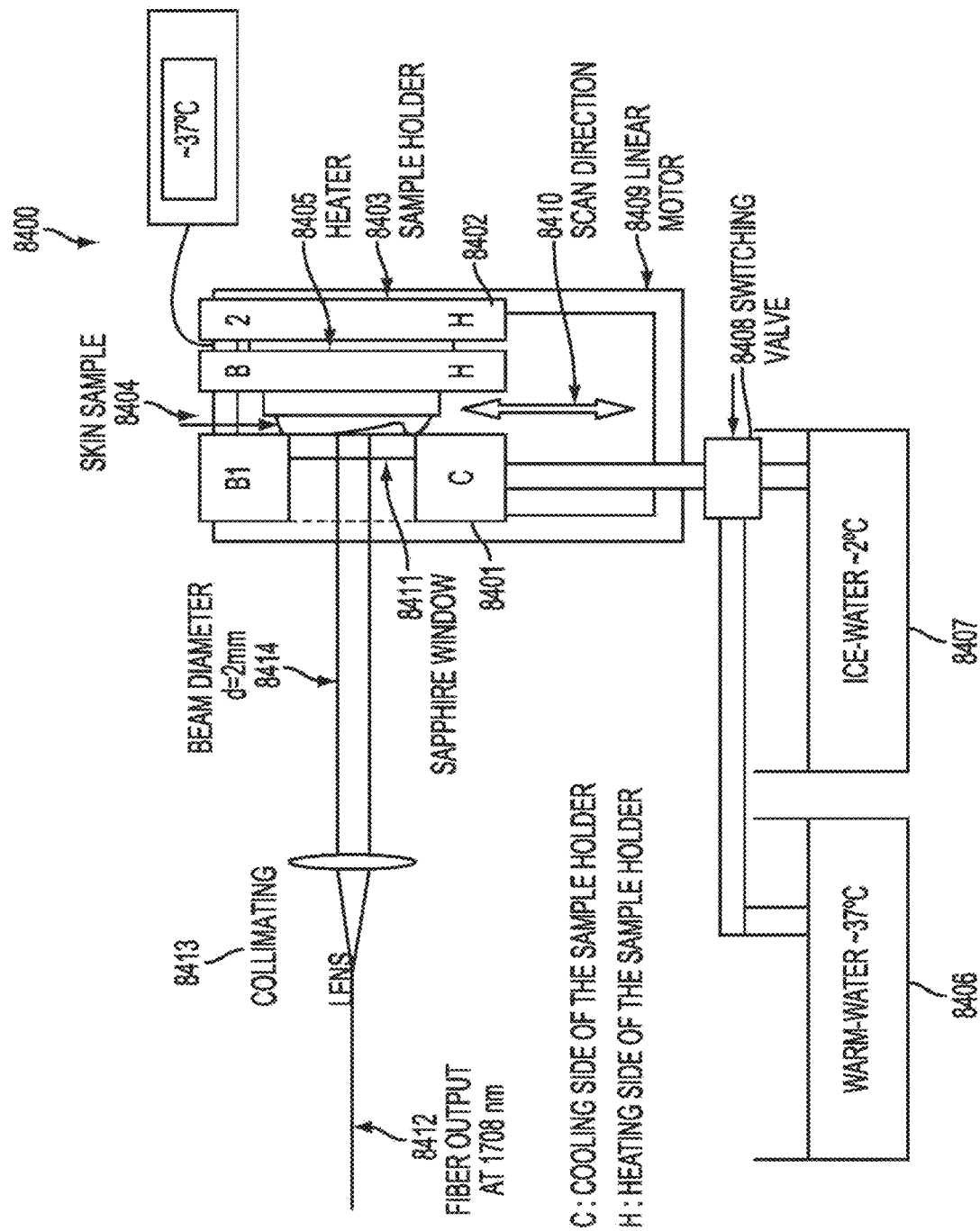
FIG. 84 illustrates the experimental set-up for ex vivo skin laser treatment with surface cooling to protect the epidermis and top layer of the dermis.
Figure 85A:
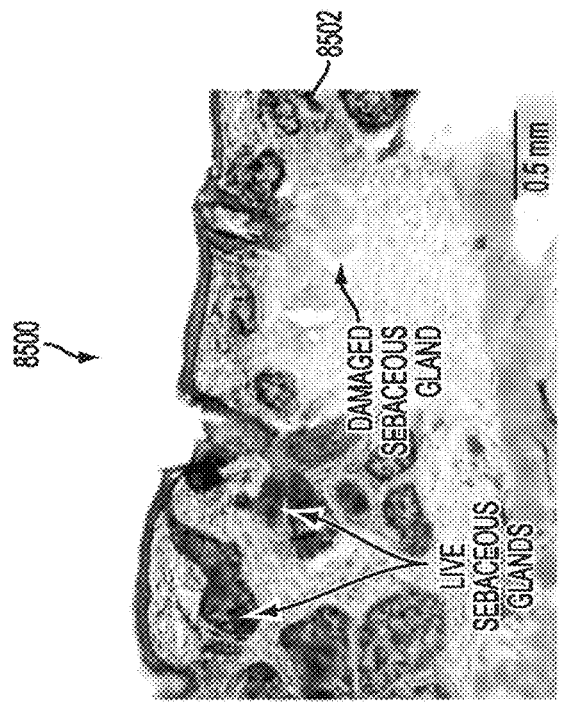
FIG. 85A shows MTT histo-chemistry of ex vivo human skin treated with ~1708 nm laser and cold window (5 seconds precool; 2 mm diameter spot exposure for 3 seconds) at 725 mW corresponding to ~70 J/cm2 average fluence.
Figure 85B:
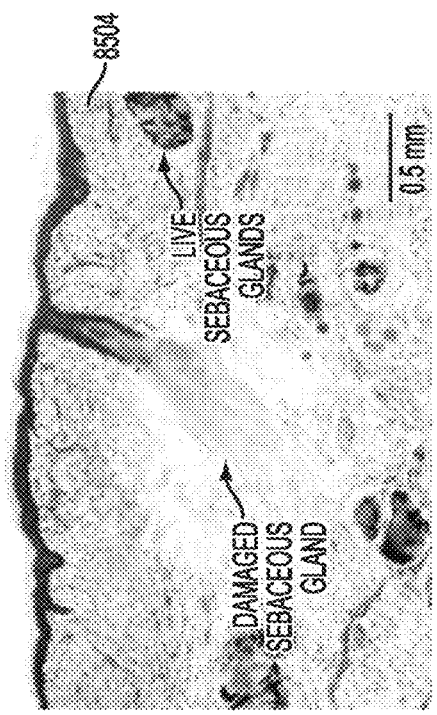
FIG. 85B also shows MTT histo-chemistry of ex vivo human skin treated with ~1708 nm laser and cold window (5 seconds precool; 2 mm diameter spot exposure for 3 seconds) at 725 mW corresponding to ~70 J/cm2 average fluence.
Figure 85C:
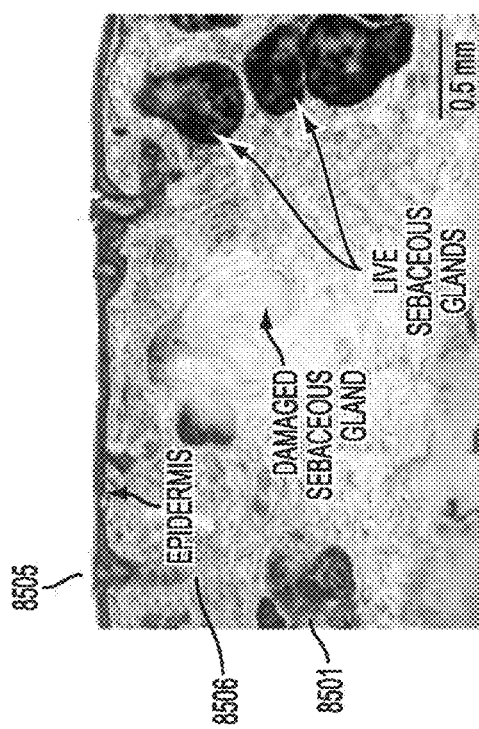
FIG. 85C shows MTT histo-chemistry of ex vivo human skin treated with ~1708 nm laser and cold window (5 seconds precool; 2 mm diameter spot exposure for 3 seconds) at 830 mW corresponding to ~80 J/cm2 average fluence.
Figure 85D:
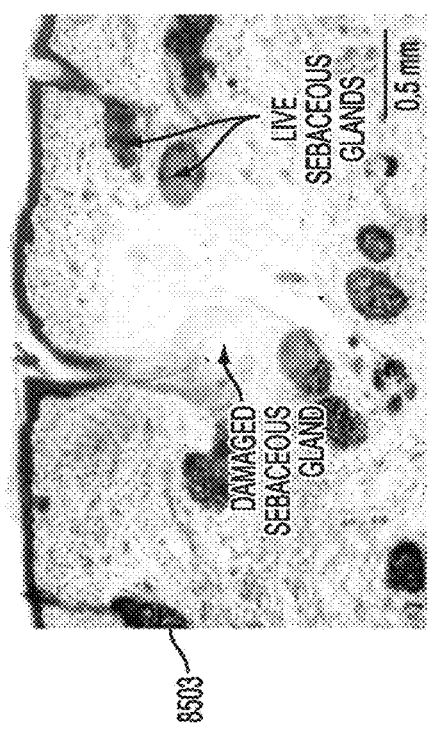
FIG. 85D also shows MTT histo-chemistry of ex vivo human skin treated with ~1708 nm laser and cold window (5 seconds precool; 2 mm diameter spot exposure for 3 seconds) at 830 mW corresponding to ~80 J/cm2 average fluence.

In another embodiment, experiments have also been conducted on dermatology samples with surface cooling, and surface cooling is shown to preserve the top layer of the skin during laser exposure. In this particular example, the experimental set-up 8400 is illustrated in FIG. 84. The skin sample 8404, or more generally sample under test, is placed in a sample holder 8403. The sample holder 8403 has a cooling side 8401 and a heating side 8402. The heating side 8402 comprises a heater 8405, which may be adjusted to operate around 37 degrees Celsius—i.e., close to body temperature. The cooling side 8401 is coupled to an ice-water bath 8407 (around 2 degrees Celsius) and a warm-water bath 8406 (around 37 degrees Celsius) through a switching valve 8408. The entire sample holder 8403 is mounted on a linear motor 8409, so the sample can be moved perpendicular 8410 to the incoming light beam.

In this embodiment, the light is incident on the sample 8404 through a sapphire window 8411. The sapphire material 8411 is selected because it is transparent to the infrared wavelengths, while also being a good thermal conductor. Thus, the top layer of the sample 8404 may be cooled by being approximately in contact with the sapphire window 8411. The laser light 8412 used is near 1708 nm from a cascaded Raman oscillator (described in greater detail herein), and one or more collimating lenses 8413 are used to create a beam with a diameter 8414 of approximately 2 mm. This is one particular embodiment of the sample surface cooling arrangement, but other apparatuses and methods may be used and are intended to be covered by this disclosure.

Experimental results obtained using the set-up of FIG. 84 are included in FIG. 18. In this example, FIG. 85 shows the MTT histochemistry of human skin 8500 treated with ~1708 nm laser (5 seconds pre-cool; 2 mm diameter spot exposure for 3 seconds) at 725 mW (A 8501, B 8502) corresponding to about 70 J/cm2 average fluence, and 830 mW (C 8503, D 8504) corresponding to about 80 J/cm2 average fluence. The images in FIG. 85 show that the application of a cold window was effective in protecting the epidermis 8505 (darker top layer) and the top approximately 0.4 or 0.5 mm of the dermis 8506. As before, the darker regions of the histology correspond to undamaged regions, while the lighter regions correspond to damaged regions. In contrast, when no surface cooling is applied, then thermal damage to the dermis occurs in the epidermis and dermis where the laser exposure occurs, and the thermal damage extends to about 1.3 or 1.4 mm or more from the skin surface. Thus, surface cooling applied to the skin may help to reduce or eliminate damage to the top layer of the skin under laser exposure.

In summary, experiments verify that infrared light, such as near 980 nm, 1210 nm, or 1700 nm, may achieve penetration depths between approximately 2 mm to 4 mm or more. The top layer of skin or tissue may be spared damage under laser exposure by focusing the light beyond the top layer, applying surface cooling, or some combination of the two. These are particular experimental results, but other wavelengths, methods and apparatuses may be used for achieving the penetration and minimizing damage to the top layer and are intended to be covered by this disclosure. In an alternate embodiment, it may be beneficial to use wavelengths near 1310 nm if the absorption from skin constituents (FIG. 77), such as collagen 7703, adipose 7702 and elastin 7704, are to be minimized. The water absorption 7701 near 1310 nm may still permit a penetration depth of approximately 1 cm, or perhaps less. In yet another embodiment, wavelengths near 1210 nm may be beneficial, if penetration depths on the order of 3 mm are adequate and less scattering loss (e.g. 7701 in FIG. 77) is desired. Any of FIG. 68, 73, 75, 77, or 78 may be used to select these or other wavelengths to achieve the desired penetration depth and to also perhaps target particular tissue of interest, and these alternate embodiments are also intended to be covered by this disclosure.

Laser Systems for Therapeutics or Diagnostics

Infrared light sources can be used for diagnostics and therapeutics in a number of medical applications. For example, broadband light sources can advantageously be used for diagnostics, while narrower band light sources can advantageously be used for therapeutics. In one embodiment, selective absorption or damage can be achieved by choosing the laser wavelength to lie approximately at an absorption peak of particular tissue types. Also, by using infrared wavelengths that minimize water absorption peaks and longer wavelengths that have lower tissue scattering, larger penetration depths into the biological tissue can be obtained. In this disclosure, infrared wavelengths include wavelengths in the range of approximately 0.9 microns to 10 microns, with wavelengths between about 0.98 microns and 2.5 microns more suitable for certain applications.

As used throughout this document, the term "couple" and or "coupled" refers to any direct or indirect communication between two or more elements, whether or not those elements are physically connected to one another. In this disclosure, the term "damage" refers to affecting a tissue or sample so as to render the tissue or sample inoperable. For instance, if a particular tissue normally emits certain signaling chemicals, then by "damaging" the tissue is meant that the tissue reduces or no longer emits that certain signaling chemical. The term "damage" and or "damaged" may include ablation, melting, charring, killing, or simply incapacitating the chemical emissions from the particular tissue or sample. In one embodiment, histology or histochemical analysis may be used to determine whether a tissue or sample has been damaged.

As used throughout this disclosure, the term "spectroscopy" means that a tissue or sample is inspected by comparing different features, such as wavelength (or frequency), spatial location, transmission, absorption, reflectivity, scattering, refractive index, or opacity. In one embodiment, "spectroscopy" may mean that the wavelength of the light source is varied, and the transmission, absorption or reflectivity of the tissue or sample is measured as a function of wavelength. In another embodiment, "spectroscopy" may mean that the wavelength dependence of the transmission, absorption or reflectivity is compared between different spatial locations on a tissue or sample. As an illustration, the "spectroscopy" may be performed by varying the wavelength of the light source, or by using a broadband light source and analyzing the signal using a spectrometer, wavemeter, or optical spectrum analyzer.

As used throughout this document, the term "fiber laser" refers to a laser or oscillator that has as an output light or an optical beam, wherein at least a part of the laser comprises an optical fiber. For instance, the fiber in the "fiber laser" may comprise one of or a combination of a single mode fiber, a multi-mode fiber, a mid-infrared fiber, a photonic crystal fiber, a doped fiber, a gain fiber, or, more generally, an approximately cylindrically shaped waveguide or light-pipe. In one embodiment, the gain fiber may be doped with rare earth material, such as ytterbium, erbium, and/or thulium. In another embodiment, the infrared fiber may comprise one or a combination of fluoride fiber, ZBLAN fiber, chalcogenide fiber, tellurite fiber, or germanium doped fiber. In yet another embodiment, the single mode fiber may include standard single-mode fiber, dispersion shifted fiber, non-zero dispersion shifted fiber, high-nonlinearity fiber, and small core size fibers.

As used throughout this disclosure, the term "pump laser" refers to a laser or oscillator that has as an output light or an optical beam, wherein the output light or optical beam may be coupled to a gain medium to excite the gain medium, which in turn may amplify another input optical signal or beam. In one particular example, the gain medium may be a doped fiber, such as a fiber doped with ytterbium, erbium, and/or thulium. In another embodiment, the gain medium may be a fused silica fiber or a fiber with a Raman effect from the glass. In one embodiment, the "pump laser" may be a fiber laser, a solid state laser, a laser involving a nonlinear crystal, an optical parametric oscillator, a semiconductor laser, or a plurality of semiconductor lasers that may be multiplexed together. In another embodiment, the "pump laser" may be coupled to the gain medium by using a fiber coupler, a dichroic mirror, a multiplexer, a wavelength division multiplexer, a grating, or a fused fiber coupler.

As used throughout this document, the term "super-continuum" and/or "supercontinuum" and/or "SC" refers to a broadband light beam or output that comprises a plurality of wavelengths. In a particular example, the plurality of wavelengths may be adjacent to one-another, so that the spectrum of the light beam or output appears as a continuous band when measured with a spectrometer. In one embodiment, the broadband light beam may have a bandwidth of at least 10 nm. In another embodiment, the "super-continuum" may be generated through nonlinear optical interactions in a medium, such as an optical fiber or nonlinear crystal. For example, the "super-continuum" may be generated through one or a combination of nonlinear activities such as four-wave mixing, the Raman effect, modulational instability, and self-phase modulation.

As used throughout this disclosure, the terms "optical light" and/or "optical beam" and or "light beam" refer to photons or light transmitted to a particular location in space. The "optical light" and or "optical beam" and/or "light beam" may be modulated or unmodulated, which also means that they may or may not contain information. In one embodiment, the "optical light" and/or "optical beam" and/ or "light beam" may originate from a fiber, a fiber laser, a laser, a light emitting diode, a lamp, a pump laser, or a light source.

As used throughout this document, the terms "near" or "about" or the symbol "~" refer to one or more wavelengths of light with wavelengths around the stated wavelength to accomplish the function described. For example, "near 1720 nm" may include wavelengths of between about 1680 nm and 1760 nm. In one embodiment, the term "near 1720 nm" refers to one or more wavelengths of light with a wavelength value anywhere between approximately 1700 nm and 1740 nm. Similarly, as used throughout this document, the term "near 1210 nm" refers to one or wavelengths of light with a wavelength value anywhere between approximately 1170 nm and 1250 nm. In one embodiment, the term "near 1210 nm" refers to one or more wavelengths of light with a wavelength value anywhere between approximately 1190 nm and 1230 nm.

While exemplary embodiments are described above, it is not intended that these embodiments describe all possible forms of the disclosure. Rather, the words used in the specification are words of description rather than limitation, and it is understood that various changes may be made without departing from the spirit and scope of the disclosure. Additionally, the features of various implementing embodiments may be combined to form further embodiments of the disclosure. While various embodiments may have been described as providing advantages or being preferred over other embodiments with respect to one or more desired characteristics, as one skilled in the art is aware, one or more characteristics may be compromised to achieve desired system attributes, which depend on the specific application and implementation. These attributes include, but are not limited to: cost, strength, durability, life cycle cost, marketability, appearance, packaging, size, serviceability, weight, manufacturability, ease of assembly, etc. The embodiments described herein that are described as less desirable than other embodiments or prior art implementations with respect to one or more characteristics are not outside the scope of the disclosure and may be desirable for particular applications.

What is claimed is:

1. An apparatus adapted to be worn by a user comprising:
   one or more biosensors adapted to be placed on the user, wherein one or more physiological parameters are measured, wherein measuring of the one or more physiological parameters comprises a differential measurement, and wherein the one or more physiological parameters comprises a pulse rate monitoring and a blood flow measurement;
   a light source comprising a plurality of light emitting diodes that are configured to generate an output optical light having one or more optical wavelengths;
   one or more lenses configured to receive at least a portion of the output optical light and to deliver a lens output light to tissue comprising skin;
   a detection system configured to receive at least a portion of the lens output light reflected from the tissue and to generate an output signal having a signal-to-noise ratio, wherein the detection system is configured to be synchronized to the light source, wherein the detection system comprises a plurality of detectors that are spatially separated from each other, and wherein at least one analog to digital converter is coupled to at least one of the plurality of detectors;
   wherein the output signal is indicative of the one or more physiological parameters;
   the apparatus being configured to increase the signal-to-noise ratio by increasing light intensity of at least one of the plurality of light emitting diodes from an initial light intensity; and
   the detection system further configured to:
      generate a first signal responsive to light received while the light emitting diodes are off,
      generate a second signal responsive to light received while at least one of the light emitting diodes is on, and
      increase the signal-to-noise ratio by comparing the first signal and the second signal; and
   wherein the apparatus is at least in part configured to determine, based at least in part on the output signal, that the apparatus is being worn by the user.

2. The apparatus of claim 1, wherein the tissue further comprises blood vessels and the one or more physiological parameters are related to hypertension, and wherein the blood flow measurement is affected by a temporal lag between different parts of the user.

3. The apparatus of claim 1, wherein the tissue further comprises blood vessels and the one or more physiological parameters are related to hypertension, and wherein the differential measurement comprises a comparison of at least two separate spatial locations on the user.

4. The apparatus of claim 1, wherein the one or more physiological parameters is configured to change in response to stretching of a hand of the user, movement of a finger of the user, or movement of a thumb of the user, and wherein the apparatus is further configured to combine at least a part of the output signal with data from at least some other of the one of more biosensors.

5. The apparatus of claim 1, wherein the apparatus further comprises a processor configured to be coupled to a non-transitory computer readable medium, and wherein the apparatus including the processor is configured to use artificial intelligence in making decisions associated with at least a portion of the output signal.

6. The apparatus of claim 1, wherein the plurality of light emitting diodes comprises six light emitting diodes, and wherein the detection system comprises the plurality of detectors arranged along an arc.

7. The apparatus of claim 6, wherein the apparatus is further configured to communicate with a smart phone or a tablet, the smart phone or the tablet comprising a wireless receiver, a wireless transmitter, a display, a speaker, a voice input module, one or more buttons or knobs, a microprocessor, and a touch screen.

8. A wearable device configured to be worn by a user, the wearable device comprising:
   a light source configured to be on or off, responsive to the light source being on, the light source generates an output light;
   a lens positioned to direct at least a portion of the output light towards a bodily tissue of the user;
   a detector; and
   a processor configured to:
      (i) responsive to the light source being on and the detector receiving at least a portion of the output light that is reflected from the bodily tissue of the user, generate a first output signal having a first signal-to-noise ratio; and
      (ii) responsive to the light source being off and the detector receiving ambient light, generate a second output signal having a second signal-to-noise ratio;
      (iii) generate a third output signal using at least a portion of the first output signal and at least a portion of the second output signal, the third output signal having a third signal-to-noise ratio that is greater than the first signal-to-noise ratio and greater than the second signal-to-noise ratio, the third output signal being associated with a physiological parameter of the user; and
      (iv) determine, based at least in part on the third output signal, that the wearable device is being worn by the user.

9. The wearable device of claim 8, wherein the generation of the third output signal is in response to movement of a thumb and a finger of the user.

10. The wearable device of claim 8, wherein the physiological parameter of the user changes in response to movement of a thumb and a finger of the user.

11. The wearable device of claim 8, wherein at least a portion of the output light has an optical wavelength between about 700 nanometers and about 2500 nanometers.

12. The wearable device of claim 8, wherein the physiological parameter of the user is associated with a blood constituent or a blood flow of the user.

13. The wearable device of claim 8, wherein the processor is further configured to modulate the light source with a modulation frequency.

14. The wearable device of claim 13, wherein the processor is further configured to cause the detector to apply narrow band filtering to the at least a portion of the output light that is reflected from the bodily tissue of the user around the modulation frequency.

15. A system for a device worn by a user comprising:
- a light source comprising a plurality of light emitting diodes that are configured to generate an output optical light having one or more optical wavelengths;
- one or more lenses configured to receive at least a portion of the output optical light and to direct a lens output light towards a bodily tissue of the user; and
- a detection system configured to receive at least a portion of the lens output light reflected from the bodily tissue and to generate an output signal having a signal-to-noise ratio, wherein the detection system is configured to be synchronized to the light source, wherein the signal-to-noise ratio of the output signal is increased by increasing light intensity of at least one of the plurality of light emitting diodes from an initial light intensity, wherein the detection system comprises a plurality of detectors that are spatially separated from each other, and wherein at least one analog to digital converter is coupled to at least one of the plurality of detectors;
- wherein the output signal is associated with one or more physiological parameters; and
- wherein the detection system configured to:
    - generate a first signal responsive to light received while the light emitting diodes are off,
    - generate a second signal responsive to light received while at least one of the light emitting diodes is on, and
    - increase the signal-to-noise ratio by comparing the first signal and the second signal; and
- measuring the one or more physiological parameters when worn by the user, wherein the one or more physiological parameters change in response to stretching of a hand of the user, movement of a finger of the user, or movement of a thumb of the user, and wherein the device is at least in part configured to determine, based at least in part on the output signal, that the device is being worn by the user.

16. The system of claim 15, wherein the plurality of light emitting diodes comprises six light emitting diodes, and wherein the detection system comprises the plurality of detectors arranged along an arc.

17. The system of claim 16, wherein the device is configured to use artificial intelligence in making decisions associated with at least a portion of the output signal.

18. The system of claim 17, wherein the device is further configured to combine at least a part of the output signal with data from other non-invasive devices or biosensors adapted to be placed on the user.

19. The system of claim 18, wherein the device is further configured to communicate with a smart phone or a tablet, the smart phone or the tablet comprising a wireless receiver, a wireless transmitter, a display, a speaker, a voice input module, a microprocessor, and a touch screen.

20. The system of claim 19, the device further configured to be coupled to an imaging system configured to remotely sense the user, the imaging system comprising:
- a laser diode configured to be pulsed and to generate laser light having a laser wavelength, wherein the laser wavelength is a near-infrared wavelength between 700 nanometers and 2500 nanometers, and wherein the laser diode comprises one or more Bragg reflectors;
- a beam splitter configured to receive at least part of received laser light from the laser diode and to split the received laser light into a sample arm light and a reference arm light, at least a portion of the sample arm light configured to be directed to the user;
- the imaging system further comprising a second plurality of detectors; and
- at least one of the second plurality of detectors configured to receive at least a portion of the reference arm light and configured to generate a reference detector output, and at least another of the second plurality of detectors configured to receive from the user at least a portion of reflected sample arm light and configured to generate a sample detector output; and
- wherein the imaging system is configured to measure time-of-flight based at least in part on the sample detector output.

* * * * *